(12) United States Patent
Konradi et al.

(10) Patent No.: US 10,016,354 B2
(45) Date of Patent: Jul. 10, 2018

(54) COMPOSITIONS CONTAINING POLYMERIC, IONIC COMPOUNDS COMPRISING IMIDAZOLIUM GROUPS

(75) Inventors: Rupert Konradi, Ladenburg (DE); Michael Siemer, Mannheim (DE); Bettina Sobotka, Mannheim (DE); Sebastian Koltzenburg, Neustadt (DE); Monika Haberecht, Ludwigshafen (DE); Jean-Pierre Berkan Lindner, Mannheim (DE); Claudia Rosenbaum, Einhausen (DE); Bernd Müller, Frankenthal (DE); Richard Riggs, Mannheim (DE); Erica May Wilson Lauterwasser, Mannheim (DE); Jurith Montag, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 8 days.

(21) Appl. No.: 13/427,287

(22) Filed: Mar. 22, 2012

(65) Prior Publication Data
US 2012/0244095 A1  Sep. 27, 2012

Related U.S. Application Data

(60) Provisional application No. 61/466,493, filed on Mar. 23, 2011.

(51) Int. Cl.
| | |
|---|---|
| *A61K 31/787* | (2006.01) |
| *A61K 8/84* | (2006.01) |
| *A61Q 17/00* | (2006.01) |
| *A61Q 19/00* | (2006.01) |
| *A01N 43/50* | (2006.01) |

(52) U.S. Cl.
CPC ............... *A61K 8/84* (2013.01); *A01N 43/50* (2013.01); *A61K 31/787* (2013.01); *A61Q 17/00* (2013.01); *A61Q 19/00* (2013.01)

(58) Field of Classification Search
CPC .......... A61Q 17/00; A61Q 19/00; A61K 8/84; A61K 31/787; A01N 43/50
See application file for complete search history.

(56) References Cited

U.S. PATENT DOCUMENTS

| | | | |
|---|---|---|---|
| 5,631,274 A * | 5/1997 | Austin et al. | 514/397 |
| 2008/0131391 A1 | 6/2008 | Ellington et al. | |
| 2009/0048132 A1 | 2/2009 | Paul et al. | |
| 2009/0074692 A1 | 3/2009 | Biganska et al. | |
| 2009/0226394 A1 | 9/2009 | Champ et al. | |
| 2011/0263810 A1 | 10/2011 | Siemer et al. | |

FOREIGN PATENT DOCUMENTS

| | | |
|---|---|---|
| EP | 0594329 A1 | 4/1994 |
| FR | 2910276 A1 | 6/2008 |
| FR | 2912908 A1 | 8/2008 |
| FR | 2920975 A1 | 3/2009 |
| GB | 2271718 A | 4/1994 |
| JP | 04202305 A | 7/1992 |
| WO | WO-94/08972 A1 | 4/1994 |
| WO | WO-98/49898 A1 | 11/1998 |
| WO | WO-03/000221 A1 | 1/2003 |
| WO | WO-2006117382 A1 | 11/2006 |
| WO | WO-2010/072571 A1 | 7/2010 |

OTHER PUBLICATIONS

Author: unknown,title: 1-propanol, PubChem, date published Mar. 26, 2005, downloaded from https://pubchem.ncbi.nih.gov/compound/1-propanol#section=Top on Jul. 21, 2017.*

Author: K. M. Gitis, et al.; title: The staged synthesis of 2-methylimidazole from ethylenediamine and acetic acid in the presence of a bifunctional aluminoplatinum catalyst; Bulletin of the Russian Academy of Sciences, Division of chemical science, vol. 41, Issue 9, pp. 1551-1554, Sep. 1992.*

Garg, et al., "Anion Effects on Anti-Microbial Activity of Poly[1-Vinyl-3-(2-Sulfoethyl Imidazolium Betaine", Journal of Colloid and Interface Science, vol. 344, (2010), pp. 90-96.

International Search Report for PCT/EP2012/055136.

* cited by examiner

*Primary Examiner* — Yanzhi Zhang

(74) *Attorney, Agent, or Firm* — Drinker Biddle & Reath LLP

(57) ABSTRACT

The present invention relates to compositions containing polymeric, ionic compounds comprising imidazolium groups. In particular, it relates to the use of polymeric, ionic compounds comprising imidazolium groups in personal care compositions and/or in biocide compositions.

39 Claims, No Drawings

COMPOSITIONS CONTAINING POLYMERIC, IONIC COMPOUNDS COMPRISING IMIDAZOLIUM GROUPS

CROSS-REFERENCE TO RELATED APPLICATIONS

This application claims benefit (under 35 USC 119(e)) of U.S. Provisional Application 61/466,493, filed Mar. 23, 2011, which is incorporated by reference.

BACKGROUND OF THE INVENTION

The present invention relates to compositions containing polymeric, ionic compounds comprising imidazolium groups. In particular, it relates to the use of polymeric, ionic compounds comprising imidazolium groups in personal care compositions and/or in biocide compositions and in particular in fungicide compositions.

DESCRIPTION OF THE RELATED ART

Cationic polymers are widely used in various technical fields. They are employed e.g. as the active component of biocide compositions for diversified applications. They are also widely used in personal care and household products to perform a function in the final product, ranging e.g. from thickening to conditioning of a substrate. Depending on the application, the substrate treated with a composition of a cationic polymer can be skin, hair, leather, a textile substrate, the surface of an object, etc. Cationic polymers can be used in haircare products to provide conditioning to the hair. In skincare products, the same polymers can provide conditioning effects to the skin. When incorporated into detergent and fabric softening formulations, the same polymers can provide conditioning, softening, and antistatic characteristics to fabrics. There is a continuing demand for cationic polymers having an overall good application profile for diverse areas of use.

According to German biocide law and the EU Biocidal Products Directive "biocides" are active substances or mixtures containing one or more active substances, intended to destroy, deter, render harmless, prevent the action of, or otherwise exert a controlling effect on any harmful organism by chemical or biological means. "Harmful organism" means organisms, including pathogenic agents, which have an unwanted presence or a detrimental effect on humans, their activities or the products they use or produce, or on animals, plants or the environment. According to the classification of the EU Biocidal Products Directive the classification of biocides, is broken down into 23 product types (i.e. application categories). They can be roughly categorised in the following main groups: general biocidal products, disinfectants, preservatives, pest control, anti-fouling products.

It is known to employ cationic oligomers and polymers as active components of biocide compositions. WO 2006/117382 A1 teaches the use of a cationic polymer selected from polyethylene imines and polyvinyl amines comprising 0.1 to 22 milliequivalent cationic groups per gram of polymer as active biocidal substances.

JP 04-202305 describes a resin having a polystyrene based main chain and a graft-chain attached to a benzene ring of the main chain comprising imidazolinium groups. Those resins are useful inter alia as antimicrobial agent.

G. Garg et al. describe in J. Colloid Interface Sci. 344 (2010), 90-96 anion effects on anti-microbial activity of poly[1-vinyl-3-(2-sulfoethyl imidazolium betaine)]. The employed polymers have a comb structure with a polyalkylene main chain and zwitterionic side chains comprising a cationic imidazolium group and an anionic sulfonate group.

GB 2271718 A describes polyquaternary ammonium compounds of the formula:

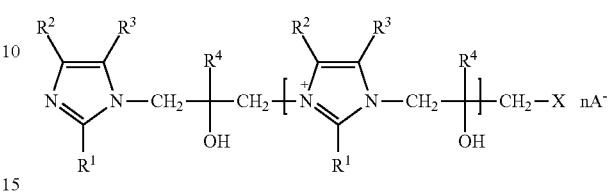

where $R^1$ is hydrogen, alkyl, or aryl, each of $R^2$ and $R^3$ is hydrogen or alkyl of 1 to 4 carbon atoms, $R^4$ is hydrogen or methyl, X is hydroxyl or halogen, and n is an integer, that are useful as antimicrobial agents, especially against fungi and bacteria.

WO 98/49898 describes biocidal agents comprising quaternary cationic surfactants having two imidazolinium groups.

WO 94/08972 describes inter alia the use of oligomeric imidazolium salts as swimming pool sanitizers having improved compatibility with chlorine. The oligomeric imidazolium salts comprise at the most 7 repeat units and the main chain is terminated by $C_1$-$C_{24}$-hydrocarbyl groups at both ends. The anion is especially halide, such as chloride, iodide and in particular bromide.

WO 03/000221 describes a composition for the treatment of acne and further skin problems that are accompanied by a hyperseborrhoea. The composition comprises at least one polymeric compound with quaternary ammonium groups in the main chain that are at least partly derived from imidazolium groups. In the concrete embodiments the main chain comprises in addition at least one 1,4-bound benzene ring and/or a quaternary ammonium ion derived from an acyclic amine.

WO 2010/072571 relates to a method for producing polymeric, ionic imidazolium compounds, characterized in that an α-dicarbonyl compound, an aldehyde, at least one amino compound having at least two primary amino groups, optionally an amino compound having only one primary amino group, and a hydracid are reacted with each other. It is not disclosed to employ the obtained imidazolium compounds as biocides.

There is a continuing demand for biocides that simultaneously meet the complex application requirements of various different uses.

In the field of personal care compositions, cationic polymers are used inter alia in detergent cosmetic compositions employed for cleansing and caring the hair or the skin. Detergent compositions may additionally comprise at least one cosmetically acceptable active ingredient that is beneficial to keratin materials.

US 2009/0048132 A1 (EP 2 011 477) describes a detergent and conditioning composition comprising, in a cosmetically acceptable aqueous medium, at least one cationic polymer, a mixture of 4 different surfactants and at least one beneficial agent other than the cationic polymer. The composition is used in particular for cleansing and caring the hair or the skin.

US 2009/0074692 A1 teaches to use a combination of at least one cationic polymer and at least one associative polymer in cosmetic conditioning compositions.

FR 2920975 A1 describes a composition for antidandruff treatment of hair and scalp that comprises selenium disulfide and one or more cationic polymers obtained by polymerization of a mixture of monomers comprising one or more vinyl monomers substituted by amino groups, one or more hydrophobic non-ionic vinyl monomers and one or more associative vinyl monomers.

FR 2912908 A1 describes a hair dye composition comprising a cationic dye and a cationic polymer.

US 2008/131391 A1 (EP 1 927 344) describes a composition for treating a keratinous substrate, comprising: a) at least one quaternary ammonium polymer, b) at least one fatty quaternary agent, c) at least one nonionic surfactant, and d) optionally, at least one ceramide.

FR 2910276 A1 describes a composition for treating a keratinous substrate, comprising a cationic polymer and alkoxysilanes with solubilizing functional groups, to avoid any degradation in hair feel on repeated application of the composition.

It has now been found, surprisingly, that polymeric, ionic compounds comprising imidazolium groups of the type described in WO 2010/072571 can be advantageously employed as biocides. Due to their unique application properties they are in particular suitable for a use in this technical field. It was also surprisingly found that irrespective of their biocidal activity those polymeric, ionic compounds comprising imidazolium groups can be advantageously employed as an alternative of known cationic polymers. They have an overall good application profile for diverse areas of use, e.g. in personal care compositions, home care compositions, compositions used for material protection, pharmaceutical compositions, plant protection compositions, etc. In particular, advantageous properties are obtained if conventional cationic polymers used in personal care compositions are replaced completely or partly by at least one polymeric, ionic compound comprising imidazolium groups.

SUMMARY OF THE INVENTION

In a first aspect, the invention provides a biocide composition, comprising at least one polymeric, ionic compound comprising imidazolium groups (imidazolium compound), obtainable by reacting
  a) at least one α-dicarbonyl compound,
  b) at least one aldehyde,
  c) at least one amino compound having at least two primary amino groups,
  d) optionally an amino compound having only one primary amino group and
  e) at least one protic acid,
and optionally subjecting the reaction product to an anion exchange,
where in the components a) and b) the aldehyde carbonyl groups may also be present as hemiacetal or acetal and the ketone carbonyl groups may also be present as hemiketal or ketal;
where the main chain of the at least one compound comprising imidazolium groups does not contain 1,4-bound phenylene rings and specifically does not contain phenylene rings;
where the amino compound having at least two primary amino groups is not 1,3-diamino-2-hydroxy-propane or 1,3-diamino-2-hydroxy-2-methyl-propane; and
where the polymer comprises at least 8, preferably at least 10 imidazolium rings;
and at least one carrier and/or at least one auxiliary agent.

Especially, the main chain of the at least one imidazolium compound apart from the nitrogen atoms of the imidazolium groups does not contain any quaternary nitrogen atoms that bear 4 residues that are different from hydrogen.

Especially, the main chain of the at least one imidazolium compound does not contain quaternary ammonium groups of the formula —$(N^+R^AR^B)$—, wherein $R^A$ and $R^B$ may have the same or different meanings, selected from alkyl, monohydroxyalkyl and polyhydroxyalkyl.

In particular, the biocide composition according to the invention is:
  a plant protection composition; especially a fungicidal composition, or
  a personal care composition, or
  a home care composition, or
  a composition used for industrial or institutional or hospital disinfection,
  a material protection composition, or
  a pharmaceutical composition.

Special embodiments of the personal care composition according to the invention are:
  a cosmetic composition, or
  a hygiene composition.

In a further aspect, the invention provides an antimicrobial polymer composition or coating composition, wherein the polymer composition or the coating comprises an effective antimicrobial amount of at least one polymeric, ionic compound comprising imidazolium groups, as defined above and in the following.

The imidazolium compounds according to the invention show a rapid effect and a broad range of applications against various microorganisms. Thus, in a first variant, the imidazolium compound can be used as disinfectants and general biocidal products, e.g. as defined in main group 1 of the EU Biocidal Products Directive (Directive 98/8/EC). The imidazolium compounds according to the invention can be used advantageously as or in:
  Human hygiene biocidal products
  Private area and public health area disinfectants and other biocidal products
  Veterinary hygiene biocidal products
  Food and feed area disinfectants
  Drinking water disinfectants The imidazolium compounds according to the invention also show a microbiostatic effect over a long period of time effect against various microorganisms. Thus, in a second variant, the imidazolium compound can be used as preservatives, e.g. as defined in main group 2 of the EU Biocidal Products Directive (Directive 98/8/EC). The imidazolium compounds according to the invention can be used advantageously as or in:
  In-can preservatives
  Film preservatives
  Wood preservatives
  Fibre, leather, rubber and polymerised materials preservatives
  Masonry preservatives
  Preservatives for liquid-cooling and processing systems
  Slimicides
  Metalworking-fluid preservatives In a further aspect, the invention provides a method for combating harmful organisms or for protecting human beings, animals, materials or processes from the effects of these harmful organisms, wherein the habitat of the harmful organism or the human being, animal or material to be protected is brought into contact with a biocide composition or the biocide composition is employed in said process, wherein the biocide composition comprises at least one polymeric, ionic compound comprising imidazolium groups, as defined above and in the following.

In a further aspect, the invention provides a method for combating harmful fungi, which method comprises treating the fungi or materials, plants, parts thereof, the locus where the plants grow or are to grow or plants' propagation material to be protected from fungal attack with an effective amount of at least one polymeric, ionic compound comprising imidazolium groups (imidazolium compound), obtainable by reacting
a) at least one α-dicarbonyl compound,
b) at least one aldehyde,
c) at least one amino compound having at least two primary amino groups,
d) optionally an amino compound having only one primary amino group and
e) at least one protic acid,
and optionally subjecting the reaction product to an anion exchange,
where in the components a) and b) the aldehyde carbonyl groups may also be present as hemiacetal or acetal and the ketone carbonyl groups may also be present as hemiketal or ketal;
or with a composition comprising said polymeric, ionic compound.

Preferably, the amino compound c) having at least two primary amino groups is not 1,3-diamino-2-hydroxy-propane or 1,3-diamino-2-hydroxy-2-methyl-propane.

Alternatively or additionally, the polymer comprises preferably at least 8, more preferably at least 10 imidazolium rings More preferably, the ionic compound comprising imidazolium groups is as defined above and in the following.

In a further aspect, the invention provides the use of at least one imidazolium compound, as defined above and in the following, as biocide.

In a further aspect, the invention provides the use of at least one polymeric, ionic compound comprising imidazolium groups (imidazolium compound), obtainable by reacting
a) at least one α-dicarbonyl compound,
b) at least one aldehyde,
c) at least one amino compound having at least two primary amino groups,
d) optionally an amino compound having only one primary amino group and
e) at least one protic acid,
and optionally subjecting the reaction product to an anion exchange,
where in the components a) and b) the aldehyde carbonyl groups may also be present as hemiacetal or acetal and the ketone carbonyl groups may also be present as hemiketal or ketal;
for combating harmful fungi.

Preferably, the amino compound c) having at least two primary amino groups is not 1,3-diamino-2-hydroxy-propane or 1,3-diamino-2-hydroxy-2-methyl-propane.

Alternatively or additionally, the polymer comprises preferably at least 8, more preferably at least 10 imidazolium rings More preferably, the ionic compound comprising imidazolium groups is as defined above and in the following.

In a further aspect, the invention provides a composition, comprising at least one imidazolium compound, as defined above and in the following, wherein the imidazolium compound performs a function in the final product different from the function as biocide. The imidazolium compound may perform this function as an alternative to or in addition to the function as biocide.

A preferred embodiment of a composition, wherein the imidazolium compound performs a function in the final product different from the function as biocide, is a personal care composition, comprising
A) at least one polymeric, ionic compound comprising imidazolium groups (imidazolium compound), obtainable by reacting
   a) at least one α-dicarbonyl compound,
   b) at least one aldehyde,
   c) at least one amino compound having at least two primary amino groups,
   d) optionally an amino compound having only one primary amino group and
   e) at least one protic acid,
   and optionally subjecting the reaction product to an anion exchange,
   where the main chain of the at least one compound comprising imidazolium groups does not contain benzene rings, and
   where in the components a) and b) the aldehyde carbonyl groups may also be present as hemiacetal or acetal and the ketone carbonyl groups may also be present as hemiketal or ketal,
C) optionally at least one cosmetically acceptable active ingredient, and
D) optionally at least one cosmetically acceptable auxiliary.

A first special embodiment is a cosmetic composition, comprising in a cosmetically acceptable medium
   at least one imidazolium compound (=component A), as defined above and in the following,
   at least one surfactant and
   at least one cosmetically acceptable active ingredient that is beneficial to keratin materials.

The combination of at least one imidazolium compound according to the invention, at least one surfactant and at least one cosmetically acceptable active ingredient that is beneficial to keratin materials may lead to an increase of the deposition of the beneficial agent on keratin materials and thereby to an increase in the efficacy of said beneficial agents or to reduce the amount of said agent used.

A second special embodiment is a cosmetic composition, comprising in a cosmetically acceptable medium
   at least one imidazolium compound (=component A), as defined above and in the following, and
   at least one associative polymer.

Cosmetic compositions, in particular hair compositions, such as a shampoo or a conditioner, are most commonly in the form of a liquid having different viscosities. Products of which the texture is sufficiently thick to remain on the hair, without running, for a certain period of time, are desirable. This thickener, or even gel, texture, should not impair the qualities of the product when used. The use of conventional thickener polymers having usually very high molar masses creates problems, such as a relatively unpleasant texture and poor spreadability of the gels obtained. It was now surprisingly found that a cosmetic composition comprising at least one imidazolium compound according to the invention and at least one associative polymer remedies these drawbacks. The compositions according to the present invention give hair more mass, more body, and more sheen compared with compositions comprising an associative polymer in the absence of at least one imidazolium compound.

A third special embodiment is an antidandruff composition, comprising in a cosmetically acceptable medium at least one imidazolium compound (=component A), as defined above and in the following, and optionally at least one antidandruff agent different from the imidazolium compound.

Antidandruff products, which have been proposed in order to combat the formation of dandruff, which is generally accompanied by a microbial and/or fungal proliferation, are either products which inhibit microbial proliferation, or keratolytic products. However, hair treated with antidandruff agents has a coarse, charged feel. In addition, the use of cationic polymers from the prior art for this purpose can present various drawbacks. On account of their high affinity for the hair, some of these polymers can become deposited in large amount during repeated use, and give undesirable effects, such as an unpleasant, charged feel, stiffness of the hair and an inter-fibre adhesion which affects styling. It has now been surprisingly found that the imidazolium compounds of the invention used alone or in combination with conventional antidandruff agents can allow these drawbacks to be overcome or lessened.

A fourth special embodiment is a composition for the treatment of acne and cutaneous disorders linked to hyperseborrhoea, comprising in a cosmetically acceptable medium at least one imidazolium compound (=component A), as defined above and in the following.

A fifth special embodiment is a hair dye composition, comprising in a cosmetically acceptable medium at least one imidazolium compound (=component A), as defined above and in the following, and at least one dye, preferably at least one cationic dye.

A sixth special embodiment is a cosmetic composition for treating a keratinous substrate, comprising in a cosmetically acceptable medium at least one imidazolium compound (=component A), as defined above and in the following, and at least one fatty quaternary amine.

A seventh special embodiment is a cosmetic composition for treating a keratinous substrate, comprising in a cosmetically acceptable medium at least one imidazolium compound (=component A), as defined above and in the following, and at least one alkoxysilane with solubilizing functional groups.

In a further aspect, the invention provides the use of at least one imidazolium compound, as defined above and in the following, as auxiliary in pharmacy, preferably as or in (a) coating(s) for solid drug forms, as surface-active compound, as or in (an) adhesive(s) and as or in (a) coating(s) for the textile, paper, printing and leather industry.

DESCRIPTION OF THE INVENTION

In the context of the invention, the expression "harmful organism" comprises organisms which have a detrimental effect on humans, their activities or the products they use or produce, or on animals or the environment. This includes pathogenic agents. The term "harmful organism" also comprises organisms which have an unwanted presence.

In the context of the invention, the expression "unsubstituted or substituted alkyl, alkoxy, alkylthio, cycloalkyl, cycloalkoxy, cycloalkylthio, aryl, aryloxy, arylthio", represents unsubstituted or substituted alkyl, unsubstituted or substituted alkoxy, unsubstituted or substituted alkylthio, unsubstituted or substituted cycloalkyl, unsubstituted or substituted cycloalkoxy, unsubstituted or substituted cycloalkylthio, unsubstituted or substituted aryl, unsubstituted or substituted aryloxy, unsubstituted or substituted arylthio.

In the context of the present invention, the expression "alkyl" comprises straight-chain or branched alkyl groups. Alkyl is preferably $C_1$-$C_{30}$-alkyl, more preferably $C_1$-$C_{20}$-alkyl even more preferably $C_1$-$C_{12}$-alkyl and in particular $C_1$-$C_6$-alkyl. Examples of alkyl groups are especially methyl, ethyl, n-propyl, isopropyl, n-butyl, isobutyl, sec-butyl, tert-butyl, n-pentyl, neo-pentyl, n-hexyl, n-heptyl, n-octyl, n-nonyl, n-decyl, n-undecyl, n-dodecyl, n-tridecyl, n-tetradecyl, n-hexadecyl, n-octadecyl and n-eicosyl.

Examples for $C_1$-$C_6$-alkyl are methyl, ethyl, n-propyl, isopropyl, n-butyl, isobutyl, sec-butyl, tert-butyl, n-pentyl, neo-pentyl, n-hexyl, and position isomers thereof.

Examples for $C_1$-$C_{12}$-alkyl are, apart those mentioned above for $C_1$-$C_6$-alkyl, n-heptyl, n-octyl, 2-ethylhexyl, n-nonyl, n-decyl, 2-propylheptyl, n-undecyl, n-dodecyl and position isomers thereof.

Examples for $C_1$-$C_{20}$-alkyl are, apart those mentioned above for $C_1$-$C_{12}$-alkyl, n-tridecyl, n-tetradecyl, n-hexadecyl, n-heptadecyl, n-octadecyl, n-nonadecyl, n-eicosyl and position isomers thereof.

Examples for $C_1$-$C_{30}$-alkyl are, apart those mentioned above for $C_1$-$C_{20}$-alkyl, n-henicosyl, n-docosy, n-tricosyl, n-tetracosy, n-pentacosyl, n-hexacosyl, n-octacosy, n-nonacosyl, n-triacontyl and position isomers thereof.

The expression alkyl also comprises alkyl radicals whose carbon chains may be interrupted by one or more nonadjacent groups which are selected from —O—, —S—, —NR$^b$—, —C(=O)—, —S(=O)— and/or —S(=O)$_2$—. R$^b$ is preferably hydrogen, alkyl, cycloalkyl aryl or a group $+$—CH$_2$CH$_2$—O$+_y$—R$^c$, wherein y is 1, 2, 3, 4, 5 or 6 and R$^c$ is hydrogen or $C_1$-$C_4$-alkyl. Preferably however, the term alkyl does not comprise alkyl radicals whose carbon chains may be interrupted by one or more nonadjacent groups which are selected from —O—, —S—, —NR$^b$—, —C(=O)—, —S(=O)— and/or —S(=O)$_2$— unless explicitly specified.

Substituted alkyl groups may, depending on the length of the alkyl chain, have one or more (e.g. 1, 2, 3, 4, 5 or more than 5) substituents. These are preferably each independently selected from cycloalkyl, aryl, fluorine, chlorine, bromine, hydroxyl, mercapto, cyano, nitro, nitroso, formyl, acyl, COOH, carboxylate, alkylcarbonyloxy, carbamoyl, SO$_3$H, sulfonate, sulfamino, sulfamide, amidino, NE$^1$E$^2$, where E$^1$ and E$^2$ are each independently hydrogen, alkyl, cycloalkyl or aryl. Cycloalkyl and aryl substituents of the alkyl groups may in turn be unsubstituted or substituted; suitable substituents are the substituents mentioned below for these groups.

The above remarks regarding alkyl also apply to the alkyl moiety in alkoxy (an alkyl radical bound via an oxygen atom to the remainder of the molecule) and alkylthio (=alkylsulfanyl; an alkyl radical bound via a sulfur atom to the remainder of the molecule).

Examples for $C_1$-$C_6$-alkoxy are methoxy, ethoxy, n-propoxy, isopropoxy, n-butoxy, isobutoxy, sec-butoxy, tert-butoxy, n-pentoxy, neo-pentoxy, n-hexoxy, and position isomers thereof.

Examples for $C_1$-$C_{20}$-alkoxy are, apart those mentioned above for $C_1$-$C_6$-alkoxy, n-heptoxy, n-octyloxy, n-nonyloxy, n-decyloxy, n-undecyloxy, n-dodecyloxy, n-tridecyloxy, n-tetradecyloxy, n-pentadecyloxy, n-hexadecyloxy, n-heptadecyloxy, n-octadecyloxy, n-nonadecyloxy, n-docosyloxy and position isomers thereof.

Examples for $C_1$-$C_6$-alkylthio are methylthio, ethylthio, n-propylthio, isopropylthio, n-butylthio, isobutylthio, sec-butylthio, tert-butylthio, n-pentylthio, neo-pentylthio, n-hexylthio, and position isomers thereof.

Examples for $C_1$-$C_{20}$-alkylthio are, apart those mentioned above for $C_1$-$C_6$-alkyl, n-heptylthio, n-octylthio, 2-ethylhexylthio, n-nonylthio, n-decylthio, 2-propylheptylthio, n-undecylthio, n-dodecylthio, n-tridecylthio, n-tetradecylthio, n-hexadecylthio, n-heptadecylthio, n-octadecylthio, n-nonadecylthio, n-eicosylthio and position isomers thereof.

In the context of the present invention, the term "cycloalkyl" denotes a mono-, bi- or tricyclic hydrocarbon radical having usually from 3 to 20 ("$C_3$-$C_{20}$-cycloalkyl"), preferably 3 to 12 ("$C_3$-$C_{12}$-cycloalkyl"), more preferably 3 to 10 ("$C_3$-$C_{10}$-cycloalkyl"), in particular 3 to 8 ("$C_3$-$C_8$-cycloalkyl"), e.g. 5 to 8 ("$C_5$-$C_8$-cycloalkyl"), carbon atoms such as cyclopropyl, cyclobutyl, cyclopentyl, cyclohexyl, cycloheptyl, cyclooctyl, cyclododecyl, cyclopentadecyl, norbornyl, bicyclo[2.2.2]octyl or adamantyl.

Preferably, the term cycloalkyl denotes a monocyclic hydrocarbon radical.

Examples for $C_3$-$C_8$-cycloalkyl are cyclopropyl, cyclobutyl, cyclopentyl, cyclohexyl, cycloheptyl and cyclooctyl.

Substituted cycloalkyl groups may, depending on the ring size, have one or more (e.g. 1, 2, 3, 4, 5 or more than 5) substituents. These are preferably each independently selected from alkyl, alkoxy, alkylthio, cycloalkyl, aryl, fluorine, chlorine, bromine, hydroxyl, mercapto, cyano, nitro, nitroso, formyl, acyl, COOH, carboxylate, alkylcarbonyloxy, carbamoyl, $SO_3H$, sulfonate, sulfamino, sulfamide, amidino, $NE^3E^4$, where $E^3$ and $E^4$ are each independently hydrogen, alkyl, cycloalkyl or aryl. In the case of substitution, the cycloalkyl groups preferably bear one or more, for example one, two, three, four or five, $C_1$-$C_6$-alkyl groups.

The above remarks regarding cycloalkyl also apply to the cycloalkyl moiety in cycloalkoxy (a cycloalkyl radical bound via an oxygen atom to the remainder of the molecule) and cycloalkylthio (=cycloalkylsulfanyl; a cycloalkyl radical bound via a sulfur atom to the remainder of the molecule).

Examples for $C_3$-$C_8$-cycloalkoxy are cyclopropoxy, cyclobutoxy, cyclopentoxy, cyclohexoxy, cycloheptoxy and cyclooctoxy.

Examples for $C_3$-$C_8$-cycloalkylthio are cyclopropylthio, cyclobutylthio, cyclopentylthio, cyclohexylthio, cycloheptylthio and cyclooctylthio.

In the context of the present invention, the term "aryl" refers to mono- or polycyclic aromatic hydrocarbon radicals. Aryl usually is an aromatic radical having 6 to 24 carbon atoms, preferably 6 to 20 carbon atoms, especially 6 to 14 carbon atoms as ring members. Aryl is preferably phenyl, naphthyl, indenyl, fluorenyl, anthracenyl, phenanthrenyl, naphthacenyl, chrysenyl, pyrenyl, coronenyl, perylenyl, etc., and more preferably phenyl or naphthyl. Specifically, aryl is phenyl.

Substituted aryls may, depending on the number and size of their ring systems, have one or more (e.g. 1, 2, 3, 4, 5 or more than 5) substituents. These are preferably each independently selected from alkyl, alkoxy, alkylthio, cycloalkyl, aryl, fluorine, chlorine, bromine, hydroxyl, mercapto, cyano, nitro, nitroso, formyl, acyl, COOH, carboxylate, alkylcarbonyloxy, carbamoyl, $SO_3H$, sulfonate, sulfamino, sulfamide, amidino, $NE^5E^6$, where $E^5$ and $E^6$ are each independently hydrogen, alkyl, cycloalkyl, heterocycloalkyl, aryl or hetaryl. The alkyl, alkoxy, alkylthio, cycloalkyl and aryl substituents on the aryl may in turn be unsubstituted or substituted. Reference is made to the substituents mentioned above for these groups. The substituents on the aryl are preferably selected from alkyl and alkoxy. Substituted aryl is more preferably substituted phenyl which generally bears 1, 2, 3, 4 or 5, preferably 1, 2 or 3, substituents.

Substituted aryl is preferably aryl substituted by at least one alkyl group ("alkaryl", also referred to hereinafter as alkylaryl). Alkaryl groups may, depending on the size of the aromatic ring system, have one or more (e.g. 1, 2, 3, 4, 5, 6, 7, 8, 9 or more than 9) alkyl substituents. The alkyl substituents may be unsubstituted or substituted. In this regard, reference is made to the above statements regarding unsubstituted and substituted alkyl. In a preferred embodiment, the alkaryl groups have exclusively unsubstituted alkyl substituents. Alkaryl is preferably phenyl which bears 1, 2, 3, 4 or 5, preferably 1, 2 or 3, more preferably 1 or 2, alkyl substituents.

Aryl which bears one or more radicals is, for example, 2-, 3- and 4-methylphenyl, 2,4-, 2,5-, 3,5- and 2,6-dimethylphenyl, 2,4,6-trimethylphenyl, 2-, 3- and 4-ethylphenyl, 2,4-, 2,5-, 3,5- and 2,6-diethylphenyl, 2,4,6-triethylphenyl, 2-, 3- and 4-propylphenyl, 2,4-, 2,5-, 3,5- and 2,6-dipropylphenyl, 2,4,6-tripropylphenyl, 2-, 3- and 4-isopropylphenyl, 2,4-, 2,5-, 3,5- and 2,6-diisopropylphenyl, 2,4,6-triisopropylphenyl, 2-, 3- and 4-butylphenyl, 2,4-, 2,5-, 3,5- and 2,6-dibutylphenyl, 2,4,6-tributylphenyl, 2-, 3- and 4-isobutylphenyl, 2,4-, 2,5-, 3,5- and 2,6-diisobutylphenyl, 2,4,6-triisobutylphenyl, 2-, 3- and 4-sec-butylphenyl, 2,4-, 2,5-, 3,5- and 2,6-di-sec-butylphenyl, 2,4,6-tri-sec-butylphenyl, 2-, 3- and 4-tert-butylphenyl, 2,4-, 2,5-, 3,5- and 2,6-di-tert-butylphenyl and 2,4,6-tri-tert-butylphenyl; 2-, 3- and 4-methoxyphenyl, 2,4-, 2,5-, 3,5- and 2,6-dimethoxyphenyl, 2,4,6-trimethoxyphenyl, 2-, 3- and 4-ethoxyphenyl, 2,4-, 2,5-, 3,5- and 2,6-diethoxyphenyl, 2,4,6-triethoxyphenyl, 2-, 3- and 4-propoxyphenyl, 2,4-, 2,5-, 3,5- and 2,6-dipropoxyphenyl, 2-, 3- and 4-isopropoxyphenyl, 2,4-, 2,5-, 3,5- and 2,6-diisopropoxyphenyl and 2-, 3- and 4-butoxyphenyl.

The above remarks regarding aryl also apply to the aryl moiety in aryloxy (an aryl radical bound via an oxygen atom to the remainder of the molecule) and arylthio (=arylsulfanyl; an aryl radical bound via a sulfur atom to the remainder of the molecule).

The term alkylene refers to a linear or branched diradical of an alkane (or, in other words, a divalent alkyl radical).

$C_2$-$C_3$-Alkylene is a linear or branched divalent alkyl radical having 2 or 3 carbon atoms. Examples are 1,1-ethylene [$CH(CH_3)$], 1,2-ethylene ($CH_2CH_2$), 1,1-propylene [$CH(CH_2CH_3)$], 2,2-propylene [—$C(CH_3)_2$—], 1,2-propylene [$CH_2CH(CH_3)$] or 1,3-propylene ($CH_2CH_2CH_2$).

$C_1$-$C_3$-Alkylene is a linear or branched divalent alkyl radical having 1, 2 or 3 carbon atoms. Examples are, apart those mentioned above for $C_2$-$C_3$-alkylene, also methylene ($CH_2$).

$C_2$-$C_6$-Alkylene is a linear or branched divalent alkyl radical having 2, 3, 4, 5 or 6 carbon atoms. Examples are, apart those mentioned above for $C_2$-$C_3$-alkylene, n-butylene [$(CH_2)_4$], [$(CH_2)_3CH(CH_3)$], ($CH_2CH(CH_3)CH_2$), [$CH(CH_2CH_2CH_3)$], [$CH_2CH(CH_2CH_3)$], [—$C(CH_3)_2CH_2$—], n-pentylene [$(CH_2)_5$], n-hexylene [hexamethylene; $(CH_2)_6$] and position isomers thereof.

$C_1$-$C_6$-Alkylene is a linear or branched divalent alkyl radical having 1, 2, 3, 4, 5 or 6 carbon atoms. Examples are, apart from the examples mentioned above for $C_2$-$C_6$-alkylene, also methylene ($CH_2$).

$C_1$-$C_{30}$-Alkylene is a linear or branched divalent alkyl radical having 1 to 30 carbon atoms. Examples for $C_1$-$C_{30}$-alkylene are, apart from the examples mentioned above for $C_1$-$C_6$-alkylene, diradicals ($CH_2$)$_x$, wherein x is an integer from 7 to 30, such as heptamethylene, octamethylene, nonamethylene, decamethylene and the like, and position isomers thereof.

$C_4$-$C_{12}$-Alkylene is a linear or branched divalent alkyl radical having 4 to 12 carbon atoms. Examples for $C_4$-$C_{12}$-alkylene are n-butylene [$(CH_2)_4$], [$(CH_2)_3CH(CH_3)$], ($CH_2CH(CH_3)CH_2$), [$CH(CH_2CH_2CH_3)$], [$CH_2CH(CH_2CH_3)$], [—$C(CH_3)_2CH_2$—], n-pentylene [$(CH_2)_5$], n-hexylene [hexamethylene; $(CH_2)_6$], heptamethylene, octamethylene, nonamethylene, decamethylene, undecamethylene, dodecamethylene, and position isomers thereof.

$C_4$-$C_{20}$-Alkylene is a linear or branched divalent alkyl radical having 4 to 20 carbon atoms. Examples for $C_4$-$C_{20}$-alkylene are, apart from the examples mentioned above for $C_4$-$C_{12}$-alkylene, diradicals $(CH_2)_x$, wherein x is an integer from 13 to 20, and position isomers thereof.

$C_3$-$C_{20}$-Alkylene is a linear or branched divalent alkyl radical having 3 to 20 carbon atoms. Examples for $C_3$-$C_{20}$-alkylene are, apart from the examples mentioned above for $C_4$-$C_{20}$-alkylene, 1,1-propylene [$CH(CH_2CH_3)$], 2,2-propylene [—$C(CH_3)_2$—], 1,2-propylene [$CH_2CH(CH_3)$] or 1,3-propylene ($CH_2CH_2CH_2$).

Alkenylene is a linear or branched aliphatic mono- or poly-, e.g. mono- or di-, olefinically unsaturated divalent radical having, for example, 2 to 20 or 2 to 10 or 4 to 8 carbon atoms. If the radical comprises more than one carbon-carbon double bond, these are preferably not vicinal, i.e. not allenic.

Alkynylene is a linear or branched aliphatic divalent radical having, for example, 2 to 20 or 2 to 10 or 4 to 8 carbon atoms which comprises one or more, e.g. 1 or 2, carbon-carbon triple bonds.

$C_5$-$C_8$-Cycloalkylene is a divalent monocyclic, saturated hydrocarbon group having 5 to 8 carbon ring members. Examples are cyclopentane-1,2-diyl, cyclopentane-1,3-diyl, cyclohexane-1,2-diyl, cyclohexane-1,3-diyl, cyclohexane-1,4-diyl, cycloheptane-1,2-diyl, cycloheptane-1,3-diyl, cycloheptane-1,4-diyl, cyclooctane-1,2-diyl, cyclooctane-1,3-diyl, cyclooctane-1,4-diyl and cyclooctane-1,5-diyl.

Carboxylate and sulfonate respectively represent a derivative of a carboxylic acid function and a sulfonic acid function, especially a metal carboxylate or sulfonate, a carboxylic ester or sulfonic ester function or a carboxamide or sulfonamide function.

In context of the radical A (see below) being an alkylene group which may be substituted by a carboxylate group, this term is limited to a carboxylate anion (COO⁻).

The expression "halogen" denotes in each case fluorine, bromine, chlorine or iodine, particularly chlorine, bromide or iodine.

Imidazolium Compound

The following general definition of the imidazolium compounds employed according to the invention applies to all concrete compositions comprising at least one imidazolium compound mentioned in this application. The following general definition of the imidazolium compounds also applies to all concrete uses of those compounds mentioned in this application. Possible differences (if any) are mentioned for each individual composition or use.

Suitable imidazolium compounds for the biocide compositions according to the invention and methods for their production are described in WO 2010/072571 which is incorporated herein by reference. Accordingly, the imidazolium compounds can be obtained by a polycondensation reaction of at least one α-dicarbonyl compound, at least one aldehyde, at least one amino compound having at least two primary amino groups and at least one protic acid as essential starting materials. In a polycondensation, polymerization occurs with elimination of a low molecular weight compound, such as water or alcohol. In the present case, water is eliminated. When the carbonyl groups of the α-dicarbonyl compound are present completely or partly as ketal and/or the aldehyde group of the aldehyde is present as acetal or hemiacetal, an alcohol is correspondingly eliminated instead of water.

a) α-dicarbonyl compound

The α-dicarbonyl compound is preferably selected from compounds of the formula (I)

$$R^1\text{—CO—CO—}R^2 \quad (I)$$

wherein $R^1$ and $R^2$ are independently selected from hydrogen and in each case unsubstituted or substituted alkyl, alkoxy, alkylthio, cycloalkyl, cycloalkoxy, cycloalkylthio, aryl, aryloxy, arylthio. Preferably, $R^1$ and $R^2$ are independently selected from hydrogen and in each case unsubstituted or substituted alkyl, cycloalkyl and aryl and more preferably from hydrogen and in each case unsubstituted or substituted $C_1$-$C_{20}$-alkyl, $C_3$-$C_8$-cycloalkyl and aryl.

The α-dicarbonyl compound a) preferably comprises or consists of glyoxal. Thus, in particular $R^1$ and $R^2$ are hydrogen.

The aldehyde or keto group of the compound a) can also be present as hemiacetal, acetal, hemiketal or ketal, preferably of a lower alcohol, in particular a $C_1$-$C_{10}$-alkanol. In this case, the alcohol is eliminated in the condensation reaction forming the imidazolium compound.

Preferably, the compound a) is not employed in form of a hemiacetal, acetal, hemiketal or ketal.

b) Aldehyde

The aldehyde b) is preferably selected from compounds of the formula (II)

$$R^3\text{—CHO} \quad (II)$$

wherein $R^3$ is selected from hydrogen, alkyl, cycloalkyl and aryl.

Preferably, $R^3$ is selected from hydrogen, $C_1$-$C_{20}$-alkyl, $C_3$-$C_8$-cycloalkyl, optionally substituted aryl and a radical of the formula —$CH_2$—$[O$—$CH_2CH_2$—$]_x$—$OR^a$, wherein x is 1, 2, 3, 4, 5 or 6 and $R^a$ is hydrogen or $C_1$-$C_4$-alkyl, and is more preferably selected from hydrogen, $C_1$-$C_{20}$-alkyl, a group —$CH_2$—$[O$—$CH_2CH_2$—$]_x$—$OR^a$, wherein x is 1, 2, 3, 4, 5 or 6 and $R^a$ is hydrogen or $C_1$-$C_4$-alkyl and phenyl which may be substituted by 1, 2, 3, 4 or 5 radicals selected from $C_1$-$C_{20}$-alkyl, $C_1$-$C_6$-haloalkyl, $C_1$-$C_{20}$-alkoxy, $C_1$-$C_6$-haloalkoxy and NR'R", where R' and R'R" are, independently of each other, selected from hydrogen and $C_1$-$C_6$-alkyl.

Suitable aldehydes are e.g. formaldehyde, acetaldehyde, propionaldehyde, butanal, pentanal, hexanal, heptanal, octanal, nonanal, decanal, undecanal, dodecanal, tridecanal, tetradecanal and the higher homologs with up to 20 carbon atoms, benzaldehyde, substituted benzaldehydes, such as 2-, 3- or 4-methylbenzaldehyde, 2-, 3- or 4-trifluoromethylbenzaldehyde or 2-, 3- or 4-methoxybenzaldehyde, and aldehydes of formula $CH(=O)$—$CH_2$—$[O$—$CH_2CH_2$—$]_x$—$OR^a$, wherein x is 1, 2, 3, 4, 5 or 6 and $R^a$ is hydrogen or $C_1$-$C_4$-alkyl, derived from a polyethylene glycol or polythyleneglycol monoether of formula $HOCH_2CH_2$—$[O$—$CH_2CH_2$—$]_x$—$OR^a$, wherein x is 1, 2, 3, 4, 5 or 6 and $R^a$ is hydrogen or $C_1$-$C_4$-alkyl, in which one $CH_2OH$ group in oxidized to a CHO group.

The aldehyde group of the aldehyde b) can also be present as hemiacetal or acetal, preferably as hemiacetal or acetal of a lower alcohol, in particular a $C_1$-$C_{10}$-alkanol. In this case, the alcohol is eliminated in the condensation reaction forming the imidazolium compound.

The aldehyde group is preferably not present as hemiacetal or acetal.

Preferably, component b) comprises or consists of a formaldehyde source. Thus, in particular $R^3$ is hydrogen. Suitable formaldehyde sources are formaldehyde, formaldehyde oligomers (e.g. trioxane) and polymers of formaldehyde (e.g. paraformaldehyde). More preferably, component b) comprises or consists of formaldehyde. In a suitable embodiment, the formaldehyde is employed as an aqueous solution (formalin solution).

Alternatively, the aldehyde is preferably selected from benzaldehyde and an aldehyde of formula $R^3$—CHO, where $R^3$ is $C_1$-$C_{20}$-alkyl, more preferably from acetaldehyde, propionaldehyde, butanal, pentanal, hexanal, heptanal, octanal, nonanal, decanal, undecanal, dodecanal, tridecanal, tetradecanal and the higher homologs with up to 20 carbon atoms, and benzaldehyde.

Specifically, the aldehyde is selected from formaldehyde (or a formaldehyde source), dodecanal and benzaldehyde and is very specifically formaldehyde (or a formaldehyde source).

c) Amino Compound Having at Least Two Primary Amino Groups

The amino compound is preferably selected from compounds of the formula (III)

$$A(NH_2)_m \qquad (III)$$

wherein
m is an integer greater than or equal to 2, and
A is an m-valent organic radical.

In the formula (III), m indicates the number of primary amino groups bound to the group A. m can assume very large values, e.g. m can be an integer from 2 to 10 000, in particular from 2 to 5000. Very high values of m are present, e.g. if the compound c) of the formula (III) comprises a nitrogen-comprising polymer.

If only amino compounds c) of the formula (III) are employed, wherein m is 2 (diamines), the obtained imidazolium compounds are linear.

If at least one amino compound c) of the formula (III) is employed, wherein m is greater than 2, the obtained imidazolium compounds are branched.

In a preferred embodiment, m is an integer from 2 to 6, in particular from 2 to 4. More preferably, m is 2 (diamine) or m is 3 (triamine). In particular, m is 2.

In alternative embodiment, component c) comprises at least one amino compound having two primary amino groups and at least one amino compound having three primary amino groups. In this embodiment, m is a real number in a range of greater than 2 and less than 3.

The group A can be, in particular, a hydrocarbon group, which can be substituted or interrupted by functional groups comprising heteroatoms.

In a preferred embodiment, component c) is selected from amines of the formula 1

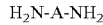

$$H_2N\text{-}A\text{-}NH_2 \qquad (1)$$

wherein
A is a divalent aliphatic, alicyclic, aliphatic-alicyclic, aromatic or araliphatic radical, where the aliphatic moieties in the aforementioned aliphatic, aliphatic-alicyclic or araliphatic radicals may be interrupted by one or more nonadjacent groups which are selected from —O—, —S— and —N($R^b$)—, where $R^b$ is selected from hydrogen, $C_1$—$C_{20}$-alkyl and a group —[$CH_2CH_2$—O—]$_y$—$R^c$, wherein y is 1, 2, 3, 4, 5 or 6 and $R^c$ is hydrogen or $C_1$-$C_4$-alkyl; where alicyclic or aromatic moieties in the aforementioned alicyclic, aliphatic-alicyclic, aromatic or araliphatic radicals may be substituted by 1, 2, 3 or 4 radicals selected from $C_1$-$C_{20}$-alkyl, $C_1$-$C_{20}$-alkoxy, a radical of the formula —O—[$CH_2CH_2O$]$_z$—$R^d$, where $R^d$ is hydrogen or $C_1$-$C_4$-alkyl and z is 1, 2, 3, 4, 5 or 6; carboxyl and carboxylate, and where the aliphatic moieties in the aforementioned aliphatic, aliphatic-alicyclic or araliphatic radicals may be substituted by 1, 2, 3 or 4 radicals selected from $C_1$-$C_{20}$-alkoxy, a radical of the formula —O—[$CH_2CH_2O$]$_z$—$R^d$, where $R^d$ is hydrogen or $C_1$-$C_4$-alkyl and z is 1, 2, 3, 4, 5 or 6, carboxyl and carboxylate; with the proviso that the aromatic or araliphatic radicals do not contain 1,4-bound phenylene rings;

amines of the formula 2

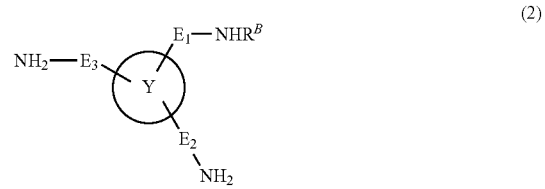

in which
Y is $CR^C$, N, $C_2$-$C_6$-alkyl or $C_3$-$C_6$-cycloalkyl;
$E_1$, $E_2$ and $E_3$, independently of each other, are a single bond, $C_1$-$C_{10}$-alkylene, —$NR^D$—$C_2$-$C_{10}$-alkylene or —O—$C_1$-$C_{10}$-alkylene, with the proviso that $E_1$, $E_2$ and $E_3$ are not a single bond and are not —$NR^D$—$C_2$-$C_{10}$-alkylene when Y is N;
$R^C$ is H, $C_1$-$C_4$-alkyl, $C_2$-$C_4$-hydroxyalkyl or $C_1$-$C_4$-alkoxy and is preferably H, $C_1$-$C_4$-alkyl or $C_1$-$C_4$-alkoxy; and
$R^B$ and $R^D$, independently of each other, are H, $C_1$-$C_4$-alkyl, $C_2$-$C_4$-hydroxyalkyl or $C_1$-$C_4$-alkoxy and are preferably H, $C_1$-$C_4$-alkyl or $C_1$-$C_4$-alkoxy; and
mixtures thereof.

Divalent aliphatic radicals are those which comprise no cycloaliphatic, aromatic or heterocyclic constituents. Examples are alkylene, alkenylene and alkynylene radicals.

Divalent alicyclic radicals can comprise one or more, e.g. one or two, alicyclic radicals; however, they comprise no aromatic or heterocyclic constituents. The alicyclic radicals can be substituted by aliphatic radicals, but bonding sites for the $NH_2$ groups are located on the alicyclic radical.

Divalent aliphatic-alicyclic radicals comprise not only at least one divalent aliphatic radical but also at least one divalent alicyclic radical, it being possible for the two bonding sites for the $NH_2$ groups to both either be located on the alicyclic radical(s) or both on the aliphatic radical(s) or one on an aliphatic radical and the other on an alicyclic radical.

Divalent aromatic radicals can comprise one or more, e.g. one or two, aromatic radicals; however, they comprise no alicyclic or heterocyclic constituents. The aromatic radicals can be substituted by aliphatic radicals, but both bonding sites for the $NH_2$ groups are located on the aromatic radical(s).

Divalent araliphatic radicals comprise not only at least one divalent aliphatic radical but also at least one divalent aromatic radical, it being possible for the two bonding sites for the NH$_2$ groups to be located either both on the aromatic radical(s) or both on the aliphatic radical(s) or one on an aliphatic radical and the other on an aromatic radical.

Preferably, the divalent aliphatic radicals A are selected from linear and branched C$_1$-C$_{30}$-alkylene which may be interrupted by one or more nonadjacent groups which are selected from —O—, —S— and —N(R$^b$)—, where R$^b$ is selected from hydrogen, C$_1$-C$_{20}$-alkyl and a group $\{CH_2CH_2-O\}_y R^c$, wherein y is 1, 2, 3, 4, 5 or 6 and R$^c$ is hydrogen or C$_1$-C$_4$-alkyl; and/or may be substituted by 1, 2, 3 or 4 radicals selected from C$_1$-C$_{20}$-alkoxy, a radical of the formula —O$\{$CH$_2$CH$_2$O$\}_z$—R$^d$, where R$^d$ is hydrogen or C$_1$-C$_4$-alkyl and z is 1, 2, 3, 4, 5 or 6, carboxyl and carboxylate.

More preferably, the divalent aliphatic radical A is linear or branched C$_2$-C$_{20}$-alkylene, even more preferably linear or branched C$_3$-C$_{20}$-alkylene, particularly preferably linear or branched C$_4$-C$_{20}$-alkylene and in particular linear or branched C$_4$-C$_{12}$-alkylene; specifically a linear C$_4$-C$_{12}$-alkylene. The alkylene chain may carry a carboxyl or carboxylate group. Preferably, the alkylene biradical is linear. Examples of suitable amines in which the radical A has this meaning (C$_2$-C$_{20}$-alkylene) are 1,2-ethylenediamine, 1,2- and 1,3-propylenediamine, 2,2-dimethyl-1,3-propanediamine, 1,4-butylenediamine, 1,5-pentylenediamine, hexamethylenediamine, heptamethylenediamine, octamethylenediamine, nonamethylenediamine, decamethylenediamine, undecamethylenediamine, dodecamethylenediamine, tridecamethylenediamine, tetradecamethylenediamine, pentadecamethylenediamine, hexadecamethylenediamine, heptadecamethylenediamine, octadecamethylenediamine, nonadecamethylenediamine, eicosamethylenediamine, 2-butyl-2-ethyl-1,5-pentamethylenediamine, 2,2,4- or 2,4,4-trimethyl-1,6-hexamethylenediamine, 1,5-diamino-2-methylpentane, 1,4-diamino-4-methylpentane and the like. Among these, preference is given to 1,4-butylene diamine, 1,5-pentylene diamine, 1,6-hexylene diamine, 1,8-octylene diamine, 1,12-dodecylenediamine and mixtures thereof. Also preferred are the carboxyl- or carboxylate-substituted alkylene diamines of formulae NH$_2$—CH(COOH) CH$_2$CH$_2$CH$_2$—NH$_2$ and NH$_2$—CH(COO$^-$)CH$_2$CH$_2$CH$_2$—NH$_2$.

In an alternatively more preferred embodiment, the divalent aliphatic radical A is a group $\{B-X\}_k-B-$ in which each X independently is —O—, —S— or —N(R$^b$)—, where R$^b$ is selected from hydrogen, C$_1$-C$_{20}$-alkyl and a group $\{CH_2CH_2-O\}_y-R^c$, wherein y is 1, 2, 3, 4, 5 or 6 and R$^c$ is hydrogen or C$_1$-C$_4$-alkyl, preferably O, each B independently is C$_2$-C$_6$-alkylene, preferably C$_2$-C$_3$-alkylene; and k is an integer from 1 to 100, preferably 1 to 10 and more preferably 2 to 4. Examples of suitable amines in which the radical A has this meaning are amine-terminated polyoxyalkylene polyols, for example Jeff-Amines, such as 1,8-diamino-3,6-dioxaoctan, 1,13-diamino-4,7,10-trioxamidecan, 4,9-dioxadodecane-1,12-diamine and 4,7,10-trioxamidecane-1,13-diamine, or else more regular amine-terminated polyoxyalkylenediols (amine-terminated polyalkylene glycols; amine-terminated polyalkylene oxides), such as amine-terminated polyethylene glycols, amine-terminated polypropylene glycols or amine-terminated polybutylene glycols. The three last-mentioned amines (amine-terminated polyalkylene glycols) preferably have a molecular weight of from 100 to 3000 g/mol. Among these, preference is given to amines NH$_2$—[CH$_2$CH$_2$O]$_x$—CH$_2$CH$_2$—NH$_2$ with x being 2 or 3, preferably 2, and NH$_2$—CH$_2$CH$_2$CH$_2$—[CH$_2$CH$_2$O]$_x$—CH$_2$CH$_2$CH$_2$—NH$_2$ with x being 2 or 3, preferably 2.

Preferably, the divalent alicyclic radicals A are selected from C$_5$-C$_8$-cycloalkylene which may carry 1, 2, 3 or 4 C$_1$-C$_4$-alkyl radicals. Examples of suitable amines in which the radical A has this meaning are cyclopentylenediamine, such as 1,2-diaminocyclopentane or 1,3-diaminocyclopentane, cyclohexylenediamine, such as 1,2-diaminocyclohexane, 1,3-diaminocyclohexane or 1,4-diaminocyclohexane, 1-methyl-2,4-diaminocyclohexane, 1-methyl-2,6-diaminocyclohexane, cycloheptylenediamine, such as 1,2-diaminocycloheptane, 1,3-diaminocycloheptane or 1,4-diaminocycloheptane, and cyclooctylenediamine, such as 1,2-diaminocyclooctane, 1,3-diaminocyclooctane, 1,4-diaminocyclooctane or 1,5-diaminocyclooctane. The amino groups (NH$_2$ groups) may be in the cis or trans position relative to one another.

Preferably, the divalent aliphatic-alicyclic radicals A are selected from C$_1$-C$_4$-alkylene-C$_5$-C$_8$-cycloalkylene, C$_5$-C$_8$-cycloalkylene-C$_1$-C$_4$alkylene-C$_5$-C$_8$-cycloalkylene and C$_1$-C$_4$-alkylene-C$_5$-C$_8$-cycloalkylene-C$_1$-C$_4$-alkylene, where the cycloalkylene radicals may carry 1, 2, 3 or 4 C$_1$-C$_4$-alkyl radicals. Examples of suitable amines in which the radical A has this meaning are diaminodicyclohexylmethane, such as bis(4-aminocyclohexyl)methane or bis(3-aminocyclohexyl)methane; isophoronediamine, bis(aminomethyl)cyclohexane, such as 1,1-bis(aminomethyl)cyclohexane, 1,2-bis(aminomethyl)cyclohexane, 1,3-bis(aminomethyl)cyclohexane or 1,4-bis(aminomethyl)cyclohexane, 2-aminopropylcyclohexylamine, 3(4)-aminomethyl-1-methylcyclohexylamine, 2-(2-aminopropyl)-cyclohexylamine and the like. The groups bonded to the alicyclic radical can in each case assume any desired position (cis/trans) relative to one another.

Preferably, the divalent aromatic radicals A are selected from 1,2-phenylene, 1,3-phenylene, naphthylene and biphenylene, with the phenylene radicals possibly carrying 1, 2, 3 or 4 radicals selected from C$_1$-C$_{20}$-alkyl, C$_1$-C$_{20}$-alkoxy and a radical of the formula —O$\{$CH$_2$CH$_2$O$\}_z$—R$^d$, where R$^d$ is hydrogen or C$_1$-C$_4$-alkyl and z is 1, 2, 3, 4, 5 or 6. Examples of suitable amines in which the radical A has this meaning are o-phenylenediamine, m-phenylenediamine, tolylenediamine, such as o-, m- and p-tolylenediamine, xylylenediamine, and naphthylenediamine, such as 1,2-, 1,3-, 1,4-, 1,5-, 1,8-, 2,3-, 2,6- and 2,7-naphthylene.

Preferably, the divalent araliphatic radicals A are selected from phenylene-C$_1$-C$_4$-alkylene, phenylene-C$_1$-C$_4$-alkylene-phenylene and C$_1$-C$_4$-alkylene-phenylene-C$_1$-C$_4$-alkylene, with the phenylene radicals possibly carrying 1, 2, 3 or 4 radicals selected from C$_1$-C$_{20}$-alkyl, C$_1$-C$_{20}$-alkoxy and a radical of the formula —O$\{$CH$_2$CH$_2$O$\}_z$—R$^d$, where R$^d$ is hydrogen or C$_1$-C$_4$-alkyl and z is 1, 2, 3, 4, 5 or 6. Examples of suitable amines in which the radical A has this meaning are diaminodiphenylmethane, such as 2,2'-, 3,3'- and 4,4'-diaminodiphenylmethane, 3-aminomethyl-benzylamine and the like.

Examples for amines 2 are compounds of the formula (2.A)

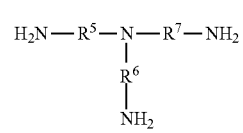

(2.A)

wherein R$^5$, R$^6$ and R$^7$ are each, independently of one another, a C$_1$-C$_{10}$ alkylene group, particularly preferably a $C_2$-$C_6$-alkylene group; such as N,N-bis(3-aminopropyl)ethylenediamine, N,N-bis(3-aminopropyl)propane-1,3-diamine, N,N-bis(3-aminopropyl)butane-1,4-diamine, tris(2-aminoethyl)amine, tris(2-aminopropyl)amine, tris(3-aminopropyl)amine, tris(2-aminobutyl)amine, tris(3-aminobutyl)amine, tris(4-aminobutyl)amine, tris(5-aminopentyl)amine and tris(6-aminohexyl)amine. In a preferred embodiment, $R^5$, $R^6$ and $R^7$ have the same meaning. A preferred compound (2.A) is tris(2-aminoethyl)amine ($R^5$=$R^6$=$R^7$=ethylene).

Further examples of amines 2 are trisaminohexane, trisaminononane, 4-aminomethyl-1,8-octamethylenediamine and the like.

Further examples of amines 2 are the compounds of following structures (2.B) or (2.C):

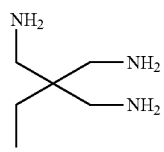

(2.B)

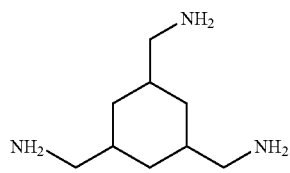

(2.C)

Further examples of amines 2 are amines of the formula 2, wherein Y is $CR^C$, where $R^C$ is H or $C_1$-$C_4$-alkyl, and $E_1$, $E_2$ and $E_3$, independently of each other, are —O—$C_1$-$C_6$-alkylene, preferably —O—$CH_2CH_2CH(CH_3)$—. Among these, preference is given to a compound wherein Y is $CR^C$, where $R^C$ is ethyl, and $E_1$, $E_2$ and $E_3$ are —O—$CH_2CH_2CH(CH_3)$—.

Among the above compounds 2, preference is given to the amine of the formula 2, wherein Y is $CR^C$, where $R^C$ is ethyl, and $E_1$, $E_2$ and $E_3$ are —O—$CH_2CH_2CH(CH_3)$—.

In particular, the amine c) is selected from:
compounds of the formula $H_2N$—$(CH_2)_m$—$NH_2$, wherein m is an integer of 3 to 20, preferably 4 to 20, more preferably 4 to 12, where a $CH_2$ group may be substituted by a carboxyl or carboxylate group, such as 1,3-propylenediamine, 1,4-butylenediamine, 1,5-pentylenediamine, hexamethylenediamine, heptamethylenediamine, octamethylenediamine, nonamethylenediamine, decamethylenediamine, undecamethylenediamine, dodecamethylenediamine, tridecamethylenediamine, tetradecamethylenediamine, pentadecamethylenediamine, hexadecamethylenediamine, heptadecamethylenediamine, octadecamethylenediamine, nonadecamethylenediamine, eicosamethylenediamine, the carboxyl- or carboxylate-substituted alkylene diamines of formulae $NH_2$—$CH(COOH)CH_2CH_2CH_2$—$NH_2$ or $NH_2$—$CH(COO^-)CH_2CH_2CH_2$—$NH_2$; especially 1,4-butylene diamine, 1,5-pentylene diamine, 1,6-hexylene diamine, 1,8-octylene diamine, 1,12-dodecylenediamine and the carboxyl- or carboxylate-substituted alkylene diamines of formulae $NH_2$—$CH(COOH)CH_2CH_2CH_2CH_2$—$NH_2$ or $NH_2$—$CH(COO^-)CH_2CH_2CH_2CH_2$—$NH_2$;
compounds of the formula $NH_2$—$[$—B—X—$]_k$—B—$NH_2$; in which each X independently is —O—, —S— or —N($R^b$)—, where $R^b$ is selected from hydrogen, $C_1$-$C_{20}$-alkyl and a group —$[$—$CH_2CH_2$—O—$]_y$—$R^c$, wherein y is 1, 2, 3, 4, 5 or 6 and $R^c$ is hydrogen or $C_1$-$C_4$-alkyl, preferably O; each B independently is $C_2$-$C_6$-alkylene, preferably $C_2$-$C_3$-alkylene; and k is an integer from 1 to 100, preferably 1 to 10, more preferably 2 to 4, such as 1,8-diamino-3,6-dioxaoctan, 1,13-diamino-4,7,10-trioxamidecan, 4,9-dioxadodecane-1,12-diamine and 4,7,10-trioxamidecane-1,13-diamine, or else more regular amine-terminated polyoxyalkylenediols (amine-terminated polyalkylene glycols; amine-terminated polyalkylene oxides), such as amine-terminated polyethylene glycols, amine-terminated polypropylene glycols or amine-terminated polybutylene glycols; especially $NH_2$—$[CH_2CH_2O]_x$—$CH_2CH_2$—$NH_2$ with x being 2 or 3, preferably 2, and $NH_2$—$CH_2CH_2CH_2$—$[CH_2CH_2O]_x$—$CH_2CH_2CH_2$—$NH_2$ with x being 2 or 3, preferably 2;

bis(4-aminocyclohexyl)methane, bis(3-aminocyclohexyl)methane, isophoronediamine, 1,1-bis(aminomethyl)cyclohexane, 1,2-bis(aminomethyl)cyclohexane, 1,3-bis(aminomethyl)cyclohexane, 1,4-bis(aminomethyl)cyclohexane, 2-aminopropylcyclohexylamine, 3(4)-aminomethyl-1-methylcyclohexylamine, 2-(2-aminopropyl)-cyclohexylamine; especially bis(4-aminocyclohexyl)methane, bis(3-aminocyclohexyl)methane, isophoronediamine;

3-aminomethyl-benzylamine;
amines of the formula 2, wherein Y is $CR^C$, where $R^C$ is H or $C_1$-$C_4$-alkyl, and $E_1$, $E_2$ and $E_3$, independently of each other, are —O—$C_1$-$C_6$-alkylene, preferably —O—$CH_2CH_2CH(CH_3)$—; especially the amine of the formula 2, wherein Y is $CR^C$, where $R^C$ is ethyl, and $E_1$, $E_2$ and $E_3$ are —O—$CH_2CH_2CH(CH_3)$—; and mixtures thereof.

It is of course also possible to use in the biocide compositions of the invention imidazolium compounds that are obtained from a mixture of two or more than two different amino compounds c). If an amine of formula 2 is used, it is even preferred to use it in combination with a diamine $A(NH_2)_m$ with m being 2. In a preferred embodiment, the mixture of amino compounds c) comprises at least two amino compounds having different numbers of primary amino groups. The use of diamines (m=2) in admixture with amino compounds having more than two primary amino groups (m>2), e.g. triamines, enables the desired degree of crosslinking or degree of branching to be set via the proportion of amines with m=2 to amines m>2.

Preferred mixtures of amino compounds c) are the following:
tris(2-aminoethyl)amine and ethylene diamine
tris(2-aminoethyl)amine and 1,3-propylene diamine
tris(2-aminoethyl)amine and 1,4-butylenediamine
tris(2-aminoethyl)amine and 1,5-pentylene diamine
tris(2-aminoethyl)amine and 1,6-hexylene diamine
the amine of the formula 2, wherein Y is $CR^C$, where $R^C$ is ethyl, and $E_1$, $E_2$ and $E_3$ are —O—$CH_2CH_2CH(CH_3)$— and 1,4-butylenediamine.

In a preferred embodiment, the amino compound c) has a molecular weight of less than 10 000 g/mol, particularly preferably less than 5000 g/mol, very particularly preferably less than 1000 g/mol, in particular less than 500 g/mol.

Possible diamines and triamines are, in particular, compounds having a molecular weight of from 60 to 500 g/mol or from 60 to 250 g/mol.

In a further preferred embodiment, component c) is selected from nitrogen-comprising polymers. Preferably, component c) is selected from polyvinylamine polymers.

Suitable polyvinylamine polymers are obtainable by free radical polymerization of ethylenically unsaturated monomers having a nitrogen containing group that can be transferred into a primary amino group. In particular, such monomers are selected from vinylcarboxamides which comprise amido groups that are capable of hydrolysis under formation of primary amino groups.

Suitable polyvinylamine polymers c) are described inter alia in U.S. Pat. No. 4,421,602, U.S. Pat. No. 5,334,287, EP-A 216 387, U.S. Pat. No. 5,981,689, WO 00/63295, U.S. Pat. No. 6,121,409 and U.S. Pat. No. 6,132,558. The teaching of those documents is incorporated herein by reference. They are prepared in general by hydrolysis of polymers comprising N-vinylcarboxamide units. These polymers contain in polymerized form monomers selected from e.g. N-vinylformamide, N-vinyl-N-methylformamide, N-vinylacetamide, N-vinyl-N-methyl-acetamide, N-vinyl-N-ethyl-acetamide, N-vinylpropionamide and mixtures thereof. It is possible to use comonomers from different monomer classes. Preferred polyvinylamines polymers c) are homopolymers of N-vinylformamide.

The homo- and copolymers which comprise N-vinylcarboxamide units incorporated in the form of polymerized units can be partly or completely hydrolyzed by known methods. The degree of hydrolysis is generally in a range from 1 to 100 mol %, preferably from 10 to 99 mol %, particularly preferably from 20 to 95 mol % and especially preferably from 30 to 90 mol %. The degree of hydrolysis corresponds to the content of primary vinylamine groups in the polymers, in mol %. The hydrolysis of the polymers described above is effected by known processes, by the action of acids (e.g. mineral acids, such as sulfuric acid, hydrochloric acid or phosphoric acid, carboxylic acids, such as formic acid or acetic acid, or sulfonic acids or phosphonic acids), bases or enzymes, as described, for example, in DE-A 31 28 478 and U.S. Pat. No. 6,132,558. With the use of acids as hydrolysis agents, the vinylamine units of the polymers are present as an ammonium salt, while the free amino groups form in the hydrolysis with bases.

Suitable polyvinylamine polymers c) preferably have a number average molecular weight in a range of from 220 to 1 000 000, preferably from 440 to 100 000 and in particular 750 to 50 000.

Suitable poly(alkyleneimines) polymers c) include the homopolymers of ethyleneimine (aziridine) or its higher homologues, the copolymers of ethyleneimine or its higher homologues with further monomers, and also the graft polymers, e.g. of polyamidoamines or polyvinylamines, with ethyleneimine or its higher homologues. The poly (alkyleneimines) can be crosslinked or uncrosslinked. They can be modified, e.g. by reaction with alkylene oxides, dialkyl or alkylene carbonates or $C_1$- to $C_4$-carboxylic acids or derivatives of $C_1$- to $C_4$-carboxylic acids.

Suitable poly(alkyleneimines) are obtainable by customary processes known to the person skilled in the art and are commercially available. Suitable poly(alkyleneimine)s are all polymers which are obtainable by cationically initiated polymerization of alkyleneimines and/or N-substituted alkyleneimines. Preferred poly(alkyleneimines) are polyethyleneimines. They are obtainable by cationically initiated polymerization of ethyleneimine (aziridine) and/or N-substituted aziridines.

Poly(alkyleneimines) useful as component c) also include the polymers of higher homologues of ethyleneimine, such as propyleneimine (2-methylaziridine), 1- or 2-butyleneimine (2-ethylaziridine or 2,3-dimethylaziridine). The poly(alkyleneimines) are preferably homopolymers of ethyleneimine.

Catalysts which can be used for the cationic polymerization of alkyleneimines are, for example, Brønsted acids, such as sulfuric acid, phosphoric acid, p-toluenesulfonic acid, or carboxylic acids, such as formic acid, acetic acid or propionic acid, or Lewis acids, such as halides, for example zinc chloride or alkyl halides, such as methyl chloride, ethyl chloride, benzyl chloride or ethylene chloride. Suitable polyethyleneimines can also be obtained by reaction of ethylene chloride with ammonia and amines. Polymers of this type are commercial products.

Useful poly(alkyleneimines) c) also include alkyleneimine polymers obtainable by grafting polyvinylamines with at least one alkyleneimine. Preferred are the graft polymers of ethyleneimine. Suitable polyvinylamines and poly(amidoamines) are mentioned before and in the following.

Suitable poly(alkyleneimines) c) preferably have a number average molecular weight in the range of from 150 to 1 000 000, more preferably 250 to 10 000.

Further suitable nitrogen containing polymer c) are poly (amidoamines). Poly(amidoamines) in the sense of the invention comprise nitrogen atoms in the form of amide groups and nitrogen atoms in the form of amine groups. Poly(amidoamines) are obtainable, for example, by condensing polycarboxylic acids with polyamines.

Suitable polycarboxylic acids for the preparation of poly (amidoamines) are e.g. aliphatic and alicyclic acids. Those aliphatic and alicyclic acids may have e.g. 2 to 30 carbon atoms. Preferred are dicarboxylic acids, for example, oxalic acid, malonic acid, succinic acid, maleic acid, adipic acid, glutaric acid, suberic acid, sebacic acid, heptanedioic acid, octanedioic acid, nonanedioic acid, undecane-α,ω-dicarboxylic acid, dodecane-α,ω-dicarboxylic acid, cis- and trans-cyclohexane-1,2-dicarboxylic acid, cis and trans cyclohexane-1,3-dicarboxylic acid, cis and trans cyclohexane-1,4-dicarboxylic acid, cis and trans cyclopentane-1,2-dicarboxylic acid, cis and trans cyclopentane-1,3-dicarboxylic acid.

In particular, the poly(amidoamines) c) do not contain aromatic dicarboxylic acids, e.g. phthalic acid, isophthalic acid or terephthalic acid.

Suitable tricarboxylic acids or polycarboxylic acids for the preparation of poly(amidoamines) c) are e.g. 1,2,3-propanetricarboxylic acid or 1,3,5-cyclohexanetricarboxylic acid.

The carboxylic acids can also be employed for the preparation of poly(amidoamines) in the form of derivatives. Such derivatives are preferably anhydrides, acyl chlorides and esters. In the polycarboxylic acids all or only a part of the acid groups may be derivatised. Preferred esters are esters of $C_1$-$C_8$-alcanols, especially the methyl ester or ethyl ester.

Suitable polyamines for the preparation of poly(amidoamines) contain at least two primary or secondary nitrogen atoms capable of forming amide groups. The total number of basic nitrogen atoms in the polyamines is preferably in the range of from 3 to 100, more preferably 3 to 25, e.g. 4 to 10. In the preparation of the poly(amidoamines), it is possible to use mixtures of two or more polycarboxylic acids as well as mixtures of two or more polyamines. Examples of suitable polyamines are diethylenetriamine, triethylenetetramine, tetraethylene pentamine, dipropylene triamine, tripropylene tetramine, dihexamethylene triamine, aminopropylethylenediamine and bisaminopropylethylenediamine. Suitable polyamines are also polyalkylenepolyamines. The polyamines can be present in a mixture with diamines. Useful diamines include for example 1,2-diaminoethane, 1,3-diaminopropane, 1,4-diaminobutane, 1,5-diaminopentane, 1,6-diaminohexane, 1,8-diaminooctane, isophoronediamine, 4,4'-diaminodiphenyl-methane, 1,4-bis(3-aminopropyl)piperazine, 4,9-dioxadodecane-1,12-diamine, 4,7,10-trioxamidecane-1,13-diamine or α,ω-diamino compounds of polyalkylene oxides.

Lactones or lactams of carboxylic acids having 4 to 8 carbon atoms may also be used in the condensation for the preparation of poly(amidoamines).

Suitable poly(amidoamines) have at least two terminal amino groups (—NH, —NH$_2$) or both.

Suitable as poly(amidoamines) are also poly(amidoamines) grafted with at least one alkyleneimine, e.g. grafted with ethyleneimine. Grafted poly(amidoamines) are obtainable from the above-described poly(amidoamines) by reaction with at least one alkyleneimine in the presence of Brønsted acids or Lewis acids, such as sulfuric acid or boron trifluoride etherates. The reaction temperature is preferably in the range of from 80 to 100° C. Compounds of this type are described, for example, in U.S. Pat. No. 4,144,123 and DE-B-24 34 816. The teaching of these documents is incorporated by reference. Suitable poly(amidoamines) grafted with ethyleneimine have, for example, an average molecular weight of from 3000 to 1 000 000 daltons. The graft polymers generally contain from 10 to 90% by weight of polyamidoamines as a grafting base and from 90 to 10% by weight of alkyleneimine as a graft.

Suitable poly(amidoamines) c) preferably have a number average molecular weight in the range of from 150 to 1 000 000, more preferably 250 to 10 000.

d) Other Starting Materials

In the process of the invention, it is possible to use further compounds, e.g. in order to introduce specific end groups into the polymer or bring about additional crosslinking by means of further functional groups, to set defined properties or to make further reactions on the resulting polymer (polymer-analogous reactions) at a later point in time possible.

Thus, if desired, it is possible to make concomitant use of, for example, compounds having only one primary amino group (=component d)) in order to influence the molecular weight of the polymeric imidazolium compounds. The compound having only one primary amino group leads to chain termination and then forms the end group of the polymer chain concerned. The higher the proportion of compounds having only one primary amino group, the lower the molecular weight. Based on 100 mol of amino compounds having at least two primary amino groups, it is possible, in a preferred embodiment, to use, for example, from 0 to 10 mol of compounds having only one primary group.

e) Protic Acid

The anions of the imidazolium compound are derived from the anions of the protic acid(s) employed as component e). It is also possible to subject the imidazolium compound to an anion exchange. This allows the preparation of imidazolium compounds with anions for which no corresponding stable protic acid exists. The anion exchange can be effected by known methods, e.g. transprotonation, reaction with a metal salt, ion exchange chromatography, electrolytically or by means of a combination of these measures.

The imidazolium compound employed according to the invention comprises anions that act as counterions to the imidazolium cations. The anions are selected from anions of the formula $Y^{n-}$, wherein n is the valency of the anion. The corresponding protic acid can be represented by the formula $Y^{n-}(H^+)_n$.

In a first embodiment, the anions of the formula $Y^{n-}$ are selected from anions of inorganic acids and low molecular weight organic acid. In this embodiment, m is preferably an integer from 1 to 6, more preferably an integer from 1 to 4, in particularly 1 or 2. In a special embodiment, n is 1.

In a second embodiment, the anions of the formula $Y^{n-}$ are selected from anions of polymeric protic acids, e.g. polyacrylic acid. In this embodiment, n can assume very high values. Suitable polymeric protic acids comprise at least one ethylenically unsaturated organic acid in polymerized form. Preferred ethylenically unsaturated organic acid are selected from acrylic acid, methacrylic acid, maleic acid, fumaric acid, itaconic acid, etc. and mixtures thereof. Especially preferred are the homo- and copolymers of acrylic acid and/or methacrylic acid. Suitable polymeric protic acids are also the copolymers of at least one ethylenically unsaturated organic acid, preferably selected from acrylic acid methacrylic acid, maleic acid, fumaric acid, itaconic acid with at least one copolymerizable comonomer, e.g. selected from (meth)acrylates, vinyl esters or aromatic monomers such as styrene and mixtures thereof.

The anions of the imidazolium compound (=anions of the formula $Y^{n-}$) and the anions of the corresponding protic acid (=$Y^{n-}$ $(H^+)_n$) are preferably selected from:

the group of halides and halogen-comprising anions of the general formulae:
$F^-$, $Cl^-$, $Br^-$, $I^-$, $BF_4^-$, $PF_6^-$, $AlCl_4^-$, $Al_2Cl_7^-$, $Al_3Cl_{10}^-$, $AlBr_4^-$, $FeCl_4^-$, $BCl_4^-$, $SbF_6^-$, $AsF_6$, —$ZnCl_3^-$, $SnCl_3^-$, $CuCl_2^-$;

the group of pseudohalides and other nitrogen-containing anions of the formulae:
$CN^-$, $SCN^-$, $OCN^-$, $NO_2^-$, $NO_3^-$, $N(CN)^-$;

the group of sulfates, sulfites and sulfonates of the general formulae:
$SO_4^{2-}$, $HSO_4^-$, $SO_3^{2-}$, $HSO_3^-$, $R^aOSO_3^-$, $R^aSO_3^-$;

the group of phosphates of the general formulae:
$PO_4^{3-}$, $HPO_4^{2-}$, $H_2PO_4^-$, $R^aPO_4^{2-}$, $HR^aPO_4^-$, $R^aR^bPO_4^-$;

the group of phosphonates and phosphinates of the general formulae:
$R^aHPO_3^-$, $R^aR^bPO_2^-$, $R^aR^bPO_3^-$;

the group of phosphites of the general formulae:
$PO_3^{3-}$, $HPO_3^{2-}$, $H_2PO_3^-$, $R^aPO_3^{2-}$, $R^aHPO_3^-$, $R^aR^bPO_3^-$;

the group of phosphonites and phosphinites of the general formulae:
$R^aR^bPO_2^-$, $R^aHPO_2^-$, $R^aR^bPO^-$, $R^aHPO^-$;

the group of carboxylates and polybasic carboxylic acids of the formulae:
$R^aCOO^-$; $R^e(COO^-)_f$;

the group of borates of the general formulae:
$BO_3^{3-}$, $HBO_3^{2-}$, $H_2BO_3^-$, $R^aR^bBO_3^-$, $R^aHBO_3^-$, $R^aBO_3^{2-}$, $B(OR^a)(OR^b)(OR^c)(OR^d)^-$, $B(HSO_4)^-$, $B(R^aSO_4)^-$;

the group of boronates of the general formulae:
$R^aBO_2^{2-}$, $R^aR^bBO^-$;

the group of halogenated hydrocarbons of the general formulae:
$CF_3SO_3^-$, $(CF_3SO_3)_2N^-$, $CF_3CO_2^-$, $CCl_3CO_2^-$;

the group of carbonates and carbonic esters of the general formulae:
$HCO_3^-$, $CO_3^{2-}$, $R^aCO_3^-$;

the group of silicates and silicic esters of the general formulae:
$SiO_4^{4-}$, $HSiO_4^{3-}$, $H_2SiO_4^{2-}$, $H_3SiO_4^-$, $R^aSiO_4^{3-}$, $R^aR^bSiO_4^{2-}$, $R^aR^bR^cSiO_4^-$, $HR^aSiO_4^{2-}$, $H_2R^aSiO_4^-$, $HR^aR^bSiO_4^-$;

the group of alkylsilane and arylsilane salts of the general formulae:
$R^aSiO_3^{3-}$, $R^aR^bSiO_2^{2-}$, $R^aR^bR^cSiO^-$, $R^aR^bR^cSiO_3^-$, $R^aR^bR^cSiO_2^-$, $R^aR^bSiO_3^{2-}$;
the group of carboximides, bis(sulfonyl)imides and sulfonylimides of the general formulae:

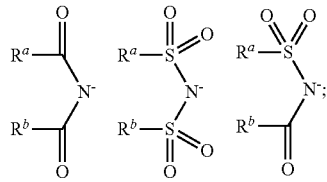

the group of methides of the general formula:

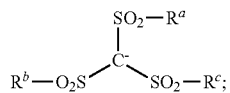

the group of alkoxides and aryloxides of the general formula:
$R^aO^-$;
the group of halometalates of the general formula:
$[M_rHal_t]^{s-}$,
where M is a metal and Hal is fluorine, chlorine, bromine or iodine, r and t are positive integers and indicate the stoichiometry of the complex and s is a positive integer and indicates the charge on the complex;
the group of sulfides, hydrogensulfides, polysulfides, hydrogenpolysulfidesn and thiolates of the general formulae:
$S^{2-}$, $HS^-$, $[S_v]^{2-}$, $[HS_v]^-$, $[R^aS]^-$,
where v is a positive integer from 2 to 10;
the group of complex metal ions such as $Fe(CN)_6^{3-}$, $Fe(CN)_6^{4-}$, $MnO_4^-$, $Fe(CO)_4$.

In the above formulae, $R^a$, $R^b$, $R^b$ and $R^d$ are each, independently of one another, nonacidic hydrogen, $C_1$-$C_{30}$-alkyl and aryl-, heteroaryl-, cycloalkyl-, halogen-, hydroxy-, amino-, carboxy-, formyl-, —O—, —CO—, —CO—O— or —CO—N<substituted derivatives thereof, for example methyl, ethyl, 1-propyl, 2-propyl, 1-butyl, 2-butyl, 2-methyl-1-propyl (isobutyl), 2-methyl-2-propyl (tert-butyl), 1-pentyl, 2-pentyl, 3-pentyl, 2-methyl-1-butyl, 3-methyl-1-butyl, 2-methyl-2-butyl, 3-methyl-2-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2-methyl-3-pentyl, 3-methyl-3-pentyl, 2,2-dimethyl-1-butyl, 2,3-dimethyl-1-butyl, 3,3-dimethyl-1-butyl, 2-ethyl-1-butyl, 2,3-dimethyl-2-butyl, 3,3-dimethyl-2-butyl, heptyl, octyl, nonyl, decyl, undecyl, dodecyl, tridecyl, tetradecyl, pentadecyl, hexadecyl, heptadecyl, octadecyl, nonadecyl, icosyl, henicosyl, docosyl, tricosyl, tetracosyl, pentacosyl, hexacosyl, heptacosyl, octacosyl, nonacosyl, triacontyl, phenylmethyl(benzyl), diphenylmethyl, triphenylmethyl, 2-phenylethyl, 3-phenylpropyl, cyclopentylmethyl, 2-cyclopentylethyl, 3-cyclopentyl-propyl, cyclohexylmethyl, 2-cyclohexylethyl, 3-cyclohexylpropyl, methoxy, ethoxy, formyl, acetyl or $C_qF_{2(q-a)+(1-b)}H_{2a+b}$ where q≤30, 0≤a≤q and b=0 or 1 (for example $CF_3$, $C_2F_5$, $CH_2CH_2$—$C_{(q-2)}F_{2(q-2)+1}$, $C_6F_{13}$, $C_8F_{17}$, $C_{10}F_{21}$, $C_{12}F_{25}$);
$C_3$-$C_{12}$-cycloalkyl and aryl-, heteroaryl-, cycloalkyl-, halogen-, hydroxy-, amino-, carboxy-, formyl-, —O—, —CO— or —CO—O-substituted derivatives thereof, for example cyclopentyl, 2-methyl-1-cyclopentyl, 3-methyl-1-cyclopentyl, cyclohexyl, 2-methyl-1-cyclohexyl, 3-methyl-1-cyclohexyl, 4-methyl-1-cyclohexyl or $C_qF_{2(q-a)-(1-b)}H_{2a-b}$, where q≤30, 0≤a≤q and b=0 or 1;
$C_2$-$C_{30}$-alkenyl and aryl-, heteroaryl-, cycloalkyl-, halogen-, hydroxy-, amino-, carboxy-, formyl-, —O—, —CO— or —CO—O-substituted derivatives thereof, for example 2-propenyl, 3-butenyl, cis-2-butenyl, trans-2-butenyl or $C_qF_{2(q-a)-(1-b)}H_{2a-b}$ where q≤30, 0≤a≤q and b=0 or 1;
$C_3$-$C_{12}$-cycloalkenyl and aryl-, heteroaryl-, cycloalkyl-, halogen-, hydroxy-, amino-, carboxy-, formyl-, —O—, —CO— or —CO—O-substituted derivatives thereof, for example 3-cyclopentenyl, 2-cyclohexenyl, 3-cyclohexenyl, 2,5-cyclohexadienyl or $C_qF_{2(q-a)-3(1-b)}H_{2a-3b}$ where q≤30, 0≤a≤q and b=0 or 1;
aryl or heteroaryl having from 2 to 30 carbon atoms and alkyl-, aryl-, heteroaryl-, cycloalkyl-, halogen-, hydroxy-, amino-, carboxy-, formyl-, —O—, —CO— or —CO—O-substituted derivatives thereof, for example phenyl, 2-methylphenyl (2-tolyl), 3-methyl-henyl (3-tolyl), 4-methylphenyl, 2-ethylphenyl, 3-ethylphenyl, 4-ethylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 4-phenylphenyl, 1-naphthyl, 2-naphthyl, 1-pyrrolyl, 2-pyrrolyl, 3-pyrrolyl, 2-pyridinyl, 3-pyridinyl, 4-pyridinyl or $C_6F_{(5-a)}H_a$, where 0≤a≤5; or
two radicals form an unsaturated, saturated or aromatic ring which may optionally be substituted by functional groups, aryl, alkyl, aryloxy, alkyloxy, halogen, heteroatoms and/or heterocycles and may optionally be interrupted by one or more oxygen and/or sulfur atoms and/or one or more substituted or unsubstituted imino groups.

Particular preference is given to $R^a$, $R^b$, $R^c$ and $R^d$ each being, independently of one another, hydrogen and particularly preferably a $C_1$-$C_{10}$-alkyl group, preferably a $C_1$-$C_4$-alkyl group.

$R^e$ (see above formula for the polybasic carboxylic acid) is an organic radical to which a plurality of carboxylic acid groups are bound. Correspondingly, f is an integer of at least 2. Preferably, f is an integer of 2 to 100 000, more preferably, 2 to 10 000. Such polybasic carboxylic acids can be, for example, maleic acid or itaconic acid, phthalic acid, isophthalic acid or terephthalic acid; other possibilities are polymeric compounds which can be obtained, for example, by free-radical polymerization of ethylenically unsaturated compounds using, possibly among others, monomers having one or two carboxylic acid groups, e.g. (meth)acrylic acid.

Particular preference is given to carboxylic acids, i.e. protic acids of the above carboxylates of the general formulae:

$R^aCOO^-$ and $R^e(\text{—}COO^-)_f$

As such carboxylic acids or carboxylates, particular mention may be made of organic compounds which have from 1 to 20 carbon atoms and comprise one or two carboxylate groups, preferably one carboxylate group.

The carboxylic acids or carboxylates can be aliphatic or aromatic compounds. Here, aromatic compounds are compounds comprising aromatic groups. Particular preference is given to aliphatic or aromatic compounds which, apart from the oxygen atoms of the carboxylate group, comprise no further heteroatoms or at most comprise one or two hydroxyl groups, carbonyl groups or ether groups. Very particular preference is given to aliphatic or aromatic compounds which comprise no further heteroatoms in addition to the oxygen atoms of the carboxylate group.

As compounds having two carboxylate groups, mention may be made of, for example, the anions of phthalic acid, of isophthalic acid, of $C_2$-$C_6$-dicarboxylic acids, e.g. oxalic acid, malonic acid, succinic acid, glutaric acid, adipic acid.

As compounds having one carboxylate group, mention may be made of the anions of aliphatic, aromatic, saturated or unsaturated $C_1$-$C_{20}$-carboxylic acids, in particular alkanecarboxylic acids, alkenecarboxylic acids, phenylacetic acid. Suitable alkanecarboxylic acids, alkenecarboxylic acids and alkadienecarboxylic acids are also known as fatty acids.

As anions $Y^-$, mention may be made of, in particular, the anions of $C_1$-$C_{20}$-alkanecarboxylic acids, which may optionally be substituted by one or two hydroxy groups, preferably one hydroxy group.

Further preferred protic acids or preferred anions of protic acids are, apart from carboxylic acids (carboxylates), also sulfonic acid, phosphoric acid or phosphonic acid, with the acid groups of the sulfonic acid, phosphoric acid or phosphonic acid being able to be partially esterified.

As phosphoric acid and esters thereof, mention may be made of, in particular, compounds of the formula VII

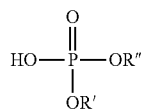

where R' and R" are each, independently of one another, hydrogen or a $C_1$-$C_{10}$-, preferably $C_1$-$C_4$-alkyl group.

As phosphonic acid and esters thereof, mention may be made of, in particular, compounds of the formula VIII

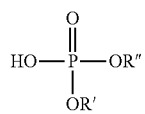

where R' and R" are each, independently of one another, hydrogen or a $C_1$-$C_{10}$-, preferably $C_1$-$C_4$-alkyl group.

Preferably, the at least one protic acid e) is not a hydrohalic acid, especially if the composition is a cosmetic or a personal care composition. Accordingly, the imidazolium compound employed in the biocide composition according to the invention does essentially not comprise anions of a hydrohalic acid ($F^-$, $Cl^-$, $Br^-$ and $I^-$). In the context of the invention, an imidazolium compound which does essentially not comprise anions of a hydrohalic acid denotes an imidazolium compound that comprises at the most 1 mole %, preferably at the most 0.1 mole %, more preferably at the most 0.01 mole, in particular at the most 0.001 mole %, based on the total anion content anions of a hydrohalic acid.

Preferably, the anions are selected from:
the group of carboxylates and polybasic carboxylic acids
the group of sulfates, sulfites and sulfonates,
the group of phosphates, and
the group of halogenated hydrocarbons.

In particular, the anions are selected from formate, acetate, propionate, butyrate, pentanoate, hexanoate, heptanoate, octanoate, glycolate (hydroxyacetate), adipate, succinate, phthalate, terephthalate, methoxyacetate, ($C_1$-$C_4$-alkoxy)($CH_2CH_2O$)$_x$$CH_2COO^-$ with x being 1-4, benzoate, hydrogenphosphate, sulfate, hydrogensulfate and methanesulfonate.

In case that the composition is a plant protection composition, especially a fungicidal composition, the anions of the at least one protic acid e) and/or the anions of the imidazolium compound can additionally be selected from chloride, bromide and iodide.

In a preferred embodiment, the biocide composition according to the invention comprises an imidazolium compound which consists essentially of repeat units of the general formula (IV), as defined in the following. Irrespective of the method of their preparation, imidazolium compound which consists essentially of repeat units of the general formula (IV), are particularly advantageous as biocides. Therefore, in a further aspect the invention provides a biocide composition, comprising at least one polymeric, ionic compound comprising imidazolium groups (imidazolium compound), which consists essentially of repeat units of the general formula (IV)

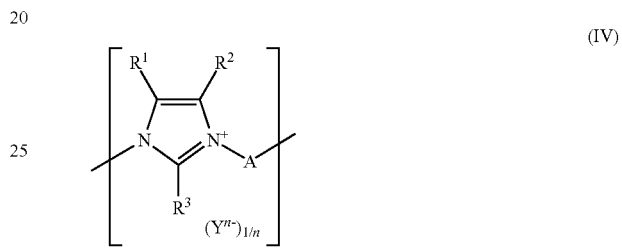

wherein
$R^1$ and $R^2$ are independently selected from hydrogen and in each case unsubstituted or substituted alkyl (preferably $C_1$-$C_{20}$-alkyl), alkoxy (preferably $C_1$-$C_{20}$-alkoxy), alkylthio (preferably $C_1$-$C_{20}$-alkylthio), cycloalkyl (preferably $C_3$-$C_8$-cycloalkyl), cycloalkoxy (preferably $C_3$-$C_8$-cycloalkoxy), cycloalkylthio (preferably $C_3$-$C_8$-cycloalkylthio), aryl, aryloxy, arylthio,
$R^3$ is selected from hydrogen, alkyl (preferably $C_1$-$C_{20}$-alkyl), cycloalkyl (preferably $C_3$-$C_8$-cycloalkyl), optionally substituted aryl and a group —$CH_2$—$[O$—$CH_2CH_2]_x$—$OR^a$, wherein x is 1, 2, 3, 4, 5 or 6 and $R^a$ is hydrogen or $C_1$-$C_4$-alkyl,
each A is independently has one of the general or preferred meanings given above and does not contain 1,4-bound phenylene units and is not 2-hydroxy-propane-1,3-diyl or 2-hydroxy-2-methyl-propane-1,3-diyl; and is preferably selected from a $C_1$-$C_{30}$-alkylene group which may be interrupted by one or more nonadjacent groups which are selected from —O—, —S— and —N($R^b$)—, where $R^b$ is selected from hydrogen, $C_1$-$C_{20}$-alkyl and a group $[CH_2CH_2$—$O]_y$—$R^b$ wherein y is 1, 2, 3, 4, 5 or 6 and $R^c$ is hydrogen or $C_1$-$C_4$-alkyl, preferably O; and is more preferably selected from a group —$(CH_2)_m$— wherein m is an integer of 3 to 20, preferably 4 to 20, more preferably 4 to 12, where one $CH_2$ group may be substituted by a carboxyl or carboxylate group, especially 1,4-butylene, 1,5-pentylene, 1,6-hexylene, 1,8-octylene and 1,12-dodecylene; a group $[B$—$X]_k$—$B$— in which each X independently is —O—, —S— or —N($R^b$)—, where $R^b$ is selected from hydrogen, $C_1$-$C_{20}$-alkyl and a group $[CH_2CH_2$—$O]_y$—$R^b$, wherein y is 1, 2, 3, 4, 5 or 6 and $R^b$ is hydrogen or $C_1$-$C_4$-alkyl, preferably O, each B independently is $C_2$-$C_6$-alkylene, preferably $C_2$-$C_3$-alkylene; and k is an integer from 1 to 100, preferably 1 to 10 and more preferably 2 to 4, especially —$[CH_2CH_2O]_x$—$CH_2CH_2$— with x being 2 or 3, preferably 2, and —CH$_2$CH$_2$CH$_2$—[CH$_2$CH$_2$O]$_x$—CH$_2$CH$_2$CH$_2$— with x being 2 or 3, preferably 2; and a group of one of the following formulae

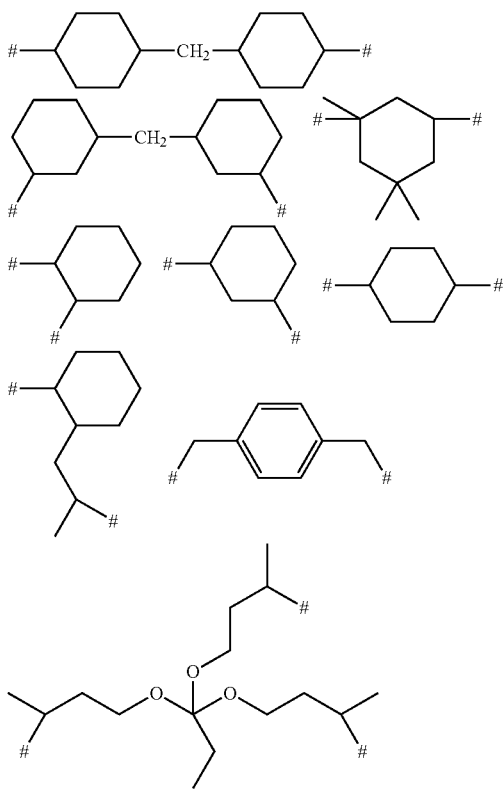

where # is the attachment point to the imidazolium ring; and

Y$^{n-}$ is an n-valent anion.

The polymeric, ionic compound preferably contains at least 8 repeating units IV, e.g. 8 to 500, preferably 8 to 300, more preferably 8 to 200, even more preferably 8 to 150 and in particular 10 to 150 repeating units IV.

In the imidazolium compounds the repeat units of the formula (IV) may have the same or different meanings. Thus, it is e.g. possible to employ a mixture of different amino compounds c) for the preparation of imidazolium compounds to obtain repeat units with different groups A. It is also possible that the imidazolium compounds comprise different anions Y$^{n-}$.

In the context of the invention, an imidazolium compound which consists essentially of repeat units of the general formula (IV) denotes an imidazolium compound that comprises least 60% by weight, preferably at least 70% by weight, more preferably at least 80% by weight, in particularly at least 90% by weight, especially at least 95% by weight, of structural units of the formula IV.

With regard to suitable and preferred meanings of R$^1$, R$^2$, R$^3$, A and Y$^{n-}$ reference is made to the afore-mentioned definitions of those groups.

In the structural units of the formula IV preferably R$^1$ and R$^2$ are hydrogen.

In the structural units of the formula IV specifically R$^3$ is hydrogen, C$_1$-C$_{20}$-alkyl or phenyl and more specifically hydrogen.

In a specific embodiment, in the structural units of the formula IV preferably A is selected from 1,4-butylene, 1,5-pentylene, 1,6-hexylene, 1,8-octylene, 1,12-dodecylene, 3,6-dioxa-1,8-octylene, 4,7,10-trioxa-1,13-tridecylene, a group —[B—X—]$_k$—B— in which each X independently is —O—, —S— or —N(R$^b$)—, where R$^b$ is selected from hydrogen, C$_1$-C$_{20}$-alkyl and a group —[CH$_2$CH$_2$—O—]$_y$—R$^c$ wherein y is 1, 2, 3, 4, 5 or 6 and R$^c$ is hydrogen or C$_1$-C$_4$-alkyl; preferably O, each B independently is C$_2$-C$_6$-alkylene, preferably C$_2$-C$_3$-alkylene; and k is an integer from 1 to 100, preferably 1 to 10 and more preferably 2 to 4; and a group of one of the following formulae

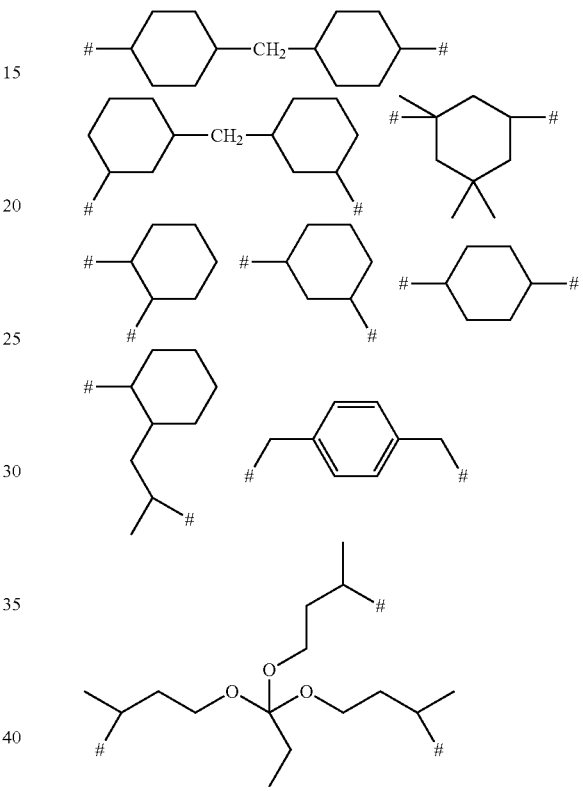

and mixtures thereof.

In a further preferred embodiment, the imidazolium compound comprises repeat units of the formula (IV), wherein A is derived from a mixture of amino compounds by formal elimination of the primary amino groups, comprising at least one amine with two primary amino groups and at least amine with more than two, in particular three, primary amino groups.

In the structural units of the formula IV preferably the anions Y$^{n-}$ are selected from formate, acetate, propionate, butyrate, pentanoate, hexanoate, heptanoate, octanoate, glycolate (hydroxyacetate), adipate, succinate, phthalate, terephthalate, (C$_1$-C$_4$-alcoxy)(CH$_2$CH$_2$O)$_x$CH$_2$COO$^-$ with x being 1-4, benzoate, sulfate, hydrogensulfate, methanesulfonate.

The polymeric ionic compound comprosing imidazolium groups preferably has a weight average molecular weight M$_w$ (determined according to the methods described in the examples) of from 300 bis 500000, more preferably of from 500 to 300000, even more preferably of from 1000 to 200000, in particular 2000 to 200000 and specifically 4000 to 200000. The dispersity PDI (M$_w$/M$_n$; M$_n$=number-average molecular weight) is preferably in the range from 1.1 to 20, more preferably from 1.5 to 15.

The biocide composition according to the invention can be employed against a wide variety of harmful organisms, in particular microorganisms, especially bacteria, fungi (including inter alia yeasts, slime molds (myxomycetes) and water molds (oomycetes) and the spores of the fungi), algae, viruses and mycoplasma. Examples of gram-positive bacteria are Micrococcaceae, Streptococcaceae, Bacilli, Lactobacillaceae, Actinomycetales, especially *Mycobacterium, Dermatophilus, Nocardiaceae, Streptomyces* and *Corynebacterium*. Examples of gram-negative microorganisms are Spirochaetales (e.g. Spirochaetaceae and Leptospiraceae), Pseudomonadaceae, Legionellaceae, Neisseriaceae, Enterobacteriaceae, Vibrionaceae, Pasteurellaceae, Bacteroidaceae, Veillonellaceae, Rickettsiaceae, Bartonellaceae and Chlamydiaceae, as well as Brucellaceae.

Examples of yeasts include the families Cryptococcaceae and Sporobolomycetaceae, in which are found human pathogenic kinds of *Candida, Trichospores* as well as *Cryptococcus neoformans*. Examples of these are *Candida albicans* and *Saccharomyces cerevisiae*.

An example of a mold within the family zygomycetes is Mucorales; examples of the family Hypomycetes are *Aspergillus* and *Penicillium* and an example of the family Bodariales is *Neurospora*. The representatives of molds most mentioned are, for example, *Alternaria alternata, Aspergillus niger* and *Penicillium funiculosum*.

Examples of algae include *Scenedesmus obliquus, Euglena gracillis, Chlorella pyrenoidosa, Chlamydomonas pulsatilla, Chlorella salina, Phaeodactylum tricornutum, Chlorella sp, Pleurococcus sp, Nostoc muscorum, Oscillatoria tenuis, Stichococcus bacillaris* and *Trentepohlia aurea*.

*Mycoplasma* denotes a special genus of bacteria that lack a cell wall. Examples are *M. pneumoniae* and *M. genitalium*.

In a special embodiment, the biocide composition according to the invention is employed against *Staphylococcus aureus* and *Pseudomonas aeruginosa*.

The ionic compounds comprising imidazolium groups (=imidazolium compounds) are in the following also denoted as component A).

The content of the imidazolium compounds in the biocide compositions of the invention can be varied over wide ranges. Preferably, the biocide composition comprises the at least one imidazolium compound in an amount of from 0.01 to 100 wt-%, more preferably 0.1 to 99.9 wt-%, in particular 0.5 to 95 wt-%, based on the total weight of the composition. Especially, the biocide composition comprises the at least one imidazolium compound in an amount of from 0.01 to 10 wt-%, more especially 0.05 to 5 wt-%, in particular 0.1 to 1 wt-%, based on the total weight of the composition.

In addition to at least one imidazolium compound (component A), the biocide compositions of the invention may comprise at least one further microbicidal compound different from the compounds of component (A) (=component B).

Suitable further microbicidal compounds (B) are selected from
  alcohols, including halogenated alcohols,
  isothiazolones,
  activated halogen compounds,
  formaldehyde release compounds,
  phenolic compounds,
  aldehydes,
  acids and esters,
  biphenyls,
  urea derivatives,
  O-acetals, O-formals,
  N-acetals, N-formals,
  benzamidines,
  phthalimides,
  pyridine derivatives,
  quaternary ammonium and phosphonium compounds,
  amines,
  amphoteric compounds,
  dithiocarbamates,
  compounds containing active oxygen such as peroxide,
    inorganic salts such as metal oxides, metal chlorides, metal sulfates, etc.,
  organic metal salts, such as Zn-pyrithion, Ag-lactate, etc.,
  mixtures thereof.

Examples of alcohol compounds which may serve as the microbiocidally effective component (B) are 2-bromo-2-nitropropane-1,3-diol and 2-(hydroxymethyl)-2-nitro-1,3-propanediol. Examples of isothiazolone compounds are 5-chloro-2-methyl-2H-isothiazol-3-one (CIT), 2-methyl-2H-isothiazol-3-one (MIT), 1,2-benzisothiazol-3(2H)-one, 2-n-octyl-2H-isothiazol-3-one, 4,5-dichloro-2-octyl-2H-isothiazol-3-one and 2-butyl-benzo-[d]isothiazol-3-one and mixtures thereof with one another, including a mixture of CIT with MIT or mixtures of CIT or MIT with any of 1,2-benzoisothiazol-3(2H)-one, 2-octyl-2H-isothiazol-3-one, 4,5-dichloro-2-octyl-2H-isothiazol-3-one and 2-butyl-benzo[d]isothiazol-3-one. Examples of other compounds are dibromodicyanobutane, [beta]-bromo-[beta]-nitrostyrene, 7a-ethyldihydro-1H,3H,5H-oxazolo[3,4-c]oxazole, tetrahydro-1,3,4,6-tetrakis(hydroxymethyl)-imidazo[4,5-d]-imidazole-2,5(1H,3H)-dione, 1,3-dimethyl-5,5-dimethylhydantoin, diazolidinyl ureas and imidazolidinyl ureas, N'-(3,4-dichlorophenyl)-N,N-dimethyl urea, 3,3'-methylenebis(5-methyl-oxazolidine), 2-sodiumsulfidopyridine-N-oxide and its metal salts, dibromonitritopropionamide, tetrakishydroxymethylphosphonium salts, ortho-phenylphenol and salts of ortho-phenylphenol, 1-(3-chloroallyl)-3,5,7-triaza-1-azodiadamantane salts, (5-chloro-2,4-dichlorophenoxy) phenol, 3,4,4'-trichlorocarbanilide (triclocarban), o-benzo-p-chlorophenol, p-hydroxybenzoates, 2-(thiocyanomethylthio) benzothiazole, 3,5-dimethyl-1,3,5-thiadiazinane-2-thione, 2,4-dichlorobenzyl alcohol, chlorothalonil, methylenebis(thiocyanate), peracetic acid, 4,4-dimethyl-oxazolidine, phenoxyethanol, phenoxypropanol, 2,6-dimethyl-m-dioxan-4-ol-acetate, glutaraldehyde, glyoxal, ortho-phthalaldehyde, 4-(2-nitrobutyl)-morpholine, triazines such as 1,3,5-tris-(2-hydroxyethyl)-1,3,5-hexahydrotriazine, quaternary ammonium compounds such as benzalkoniumchloride, polyhexamethylenebiguanide salts, poly(oxyethylene(dimethylimino)ethylene(dimethylimino)-ethylene dichloride, chlorhexidine gluconate, chloroisocyanurates, halogenated hydantoins such as 1-bromo-3-chloro-5,5-dimethylhydantoin and polamines such as polyvinylamine- and polyethylene imine derivatives. Further examples include IPBC, terbutryn, ziram, zineb, dichlofluanid, trichlofuanid, folpet, metal dihexa-2,4-dienoate, tebuconazole, 3-benzo[b]thien-2-yl-5,6-dihydro-1,4,2-oxathiazine, 4-oxide, pyrithiones, thiram, cybutryne, MBT, carbendazim, diuron, chlorotoluron, fluorometuron, thiabendazole, metazachlor, CuSCN, or dicopper oxide.

Preferred components (B) are 2-bromo-2-nitropropane-1,3-diol, 2-methyl-2H-isothiazol-3-one, 1,2-benzisothiazol-3(2H)-one, 2-n-octyl-2H-isothiazol-3-one, a mixture of 5-chloro-2-methyl-2H-isothiazol-3-one with 2-methyl-2H-isothiazol-3-one, dibromodicyanobutane, tetrahydro-1,3,4,6-tetrakis(hydroxymethyl)-imidazo[4,5-d]-imidazole-2,5(1H,3H)-dione, 3,3'-methylenebis(5-methyl-oxazolidine), 1,3-dimethyl-5,5-dimethylhydantoin, tetrakishydroxymethylphosphonium salts, ortho-phenylphenol and salts of ortho-phenylphenol, 1-(3-chloroallyl)-3,5,7-triaza-1-azodiadamantane salts, (5-chloro-2,4-dichlorophenoxy)phenol, 3,4,4'-trichlorocarbanilide (triclocarban), p-hydroxybenzoates, 2-(thiocyanomethylthio) benzothiazole, 3,5-dimethyl-1,3,5-thiadiazinane-2-thione), iodo-2-propynylbutylcarbamate, 2-sodiumsulfidopyridine-N-oxide and its metal salts, 2,4-dichlorobenzyl alcohol, chlorothalonil, methylenebis(thiocyanate), phenoxyethanol, phenoxypropanol, triazines such as 1,3,5-tris-(2-hydroxyethyl)-1,3,5-hexahydrotriazine, quaternary ammonium compounds such as benzalkoniumchloride, polyhexamethylene biguanide salts, poly(oxyethylene (dimethylmino)ethylene (dimethylimino)ethylene dichloride, chlorhexidine gluconate, chloroisocyanurates and polyvinylamines, especially the polyamines disclosed in WO-A-97/32477.

If the biocide composition according to the invention comprises components (A) and (B), the amounts of the components (A) and (B) in the composition are preferably 1 to 99 wt % of (A) and 99 to 1 wt % of (B), more preferably 10 to 90 wt % of (A) and 90 to 10 wt % of (B), especially 20 to 80 wt % of (A) and 80 to 20 wt % of (B). Preferably, the biocide composition comprises the sum of compounds (A) and (B) in an amount of from 0.01 to 100 wt %, more preferably 0.1 to 99.9 wt %, in particular 0.5 to 95 wt %, based on the total weight of the composition. Especially, the biocide composition comprises the sum of compounds (A) and (B) in an amount of from 0.01 to 10 wt %, more especially 0.05 to 5 wt-%, in particular 0.1 to 1 wt-%, based on the total weight of the composition.

The biocide composition according to the invention, comprising a component (A), optionally (B) and optionally further components can be made up into the usual formulations and preparations that are suitable for the desired purpose. The biocide composition according to the invention can be provided and/or applied as a solid or as a liquid. This encompasses compositions in form of aerosols. The biocide composition according to the invention can be formulated e.g. as powder, granulate, pellets, pills, agglomerates, solutions, emulsions, suspensions, dispersions, pastes, in combination with carrier materials, etc.

The biocide compositions according to the invention can be formulated free from solvent or with a suitable solvent. Generally, the imidazolium compounds used according to the invention are soluble in most protic solvents, swellable in most aprotic polar solvents and insoluble in most non-polar solvents. Suitable solvents for the biocide compositions according to the invention are selected from among water, alcohols, such as methanol, ethanol, n-propanol, isopropanol, n-butanol, tert-butanol, diols and polyols, such as ethanediol and propanediol, amino alcohols, such as ethanolamine, diethanolamine and triethanolamine, ethers, e.g. tetrahydrofuran, diethyl ether, methyl tert-butyl ether and diethylene glycol monomethyl ether, ketones, such as acetone and methyl ethyl ketone, esters, e.g. ethyl acetate, formamide, dimethylformamide (DMF), dimethylacetamide, dimethyl sulfoxide (DMSO), acetonitrile, aromatic solvents, e.g. benzene, toluene, ethylbenzene or xylenes, halogenated solvents, e.g. dichloromethane, chloroform, carbon tetrachloride, dichloroethane or chlorobenzene, aliphatic solvents, e.g. pentane, hexane, heptane, octane, ligroin, petroleum ether, cyclohexane and decalin, and mixtures thereof.

The solvent is preferably selected from among water, water-miscible organic solvents and mixtures thereof. The solvent is particularly preferably selected from among water, methanol, ethanol, n-propanol, isopropanol, n-butanol, tert-butanol and mixtures thereof.

A multitude of different active substances and additives can be formulated in the biocide compositions according to the invention.

Fungicidal Composition

In another aspect, the invention relates to a fungicidal composition at least one polymeric, ionic compound comprising imidazolium groups (imidazolium compound), obtainable by reacting
a) at least one α-dicarbonyl compound,
b) at least one aldehyde,
c) at least one amino compound having at least two primary amino groups,
d) optionally an amino compound having only one primary amino group and
e) at least one protic acid,
and optionally subjecting the reaction product to an anion exchange,
where in the components a) and b) the aldehyde carbonyl groups may also be present as hemiacetal or acetal and the ketone carbonyl groups may also be present as hemiketal or ketal.

Preferably, the amino compound having at least two primary amino groups is not 1,3-diamino-2-hydroxy-propane or 1,3-diamino-2-hydroxy-2-methyl-propane; and/or the polymer comprises at least 8, preferably at least 10 imidazolium rings; and/or the main chain of the at least one compound comprising imidazolium groups does not contain 1,4-bound phenylene rings and/or the main chain of the at least one imidazolium compound apart from the nitrogen atoms of the imidazolium groups does not contain any quaternary nitrogen atoms that bear 4 residues that are different from hydrogen.

In one preferred embodiment, the amino compound having at least two primary amino groups is not 1,3-diamino-2-hydroxy-propane or 1,3-diamino-2-hydroxy-2-methyl-propane.

In another embodiment, the polymer comprises at least 8, preferably at least 10 imidazolium rings.

In another embodiment, the main chain of the at least one compound comprising imidazolium groups does not contain 1,4-bound phenylene rings In another embodiment, the main chain of the at least one imidazolium compound apart from the nitrogen atoms of the imidazolium groups does not contain any quaternary nitrogen atoms that bear 4 residues that are different from hydrogen.

In one preferred embodiment, the amino compound having at least two primary amino groups is not 1,3-diamino-2-hydroxy-propane or 1,3-diamino-2-hydroxy-2-methyl-propane and the polymer comprises at least 8, preferably at least 10 imidazolium rings.

In particular, the polymer has one of the general or preferred meanings given above in context with the biocidal composition, and the fungicidal composition has one of the general or preferred meanings given above for the biocidal composition; i.e. the above-described biocidal composition is preferably a fungicidal composition.

In a particular embodiment, the composition contains at least one further agrochemically active compound V, e.g. at least one herbicide, insecticide, growth regulator, fungicide (different of course from the imidazolium compound) or fertilizer.

The fungicidal composition containing the polymeric, ionic compound containing imidazolium rings and at least one further agrochemically active compound V may be a physical mixture of these components. Accordingly, the invention also provides a mixture comprising these components. However, the composition may also be any combination of these components, it not being required for the polymeric, ionic compound and compound V to be present together in the same formulation.

An example of a composition according to the invention or to be used according to the invention in which the at least one polymeric, ionic compound and the at least one compound V are not present together in the same formulation is a combipack. In a combipack, two or more components of a combipack are packaged separately, i.e., not jointly preformulated. As such, combipacks include one or more separate containers such as vials, cans, bottles, pouches, bags or canisters, each container containing a separate component for an agrochemical composition. One example is a two-component combipack. Accordingly the present invention also relates to a two-component combipack, comprising a first component which in turn comprises at least one compound polymeric, ionic compound, a liquid or solid carrier and, if appropriate, at least one surfactant and/or at least one customary auxiliary, and a second component which in turn comprises at least one compound V, a liquid or solid carrier and, if appropriate, at least one surfactant and/or at least one customary auxiliary. More details, e.g. as to suitable liquid and solid carriers, surfactants and customary auxiliaries are described below.

Practical agricultural experience has shown that the repeated and exclusive application of an individual active compound in the control of harmful fungi leads in many cases to a rapid selection of those fungus strains which have developed natural or adapted resistance against the active compound in question. Effective control of these fungi with the active compound in question is then no longer possible. To reduce the risk of the selection of resistant fungus strains, mixtures of different active compounds are nowadays conventionally employed for controlling harmful fungi. By combining active compounds having different mechanisms of action, it is possible to ensure successful control over a relatively long period of time.

Using the polymeric, ionic compound comprising imidazolium groups in combination with at least one agrochemically active compound V results in many cases in an expansion of the fungicidal spectrum of activity being obtained or in a prevention of fungicide resistance development. Furthermore, in many cases, synergistic effects are obtained.

The following list of active compounds V, in conjunction with which the polymeric, ionic compounds according to the invention comprising imidazolium groups can be used, is intended to illustrate the possible combinations but does not limit them:

A) Respiration Inhibitors
  Inhibitors of complex III at $Q_o$ site (e.g. strobilurins): azoxystrobin, coumethoxystrobin, coumoxystrobin, dimoxystrobin, enestroburin, fenaminstrobin, fenoxystrobin/flufenoxystrobin, fluoxastrobin, kresoxim-methyl, metominostrobin, orysastrobin, picoxystrobin, pyraclostrobin, pyrametostrobin, pyraoxystrobin, trifloxystrobin, 2-[2-(2,5-dimethylphenoxymethyl)-phenyl]-3-methoxy-acrylic acid methyl ester and 2 (2-(3-(2,6-dichlorophenyl)-1-methyl-allylideneaminooxymethyl)-phenyl)-2-methoxyimino-N methyl-acetamide, pyribencarb, triclopyricarb/chlorodincarb, famoxadone, fenamidone;
  inhibitors of complex III at $Q_i$ site: cyazofamid, amisulbrom, [(3S,6S,7R,8R)-8-benzyl-3-[(3-acetoxy-4 methoxy-pyridine-2-carbonyl)amino]-6-methyl-4,9-dioxo-1,5-dioxonan-7-yl] 2 methylpropanoate, [(3S,6S,7R,8R)-8-benzyl-3-[[3-(acetoxymethoxy)-4-methoxy-pyridine-2 carbonyl]amino]-6-methyl-4,9-dioxo-1,5-dioxonan-7-yl]2 methylpropanoate, [(3S,6S,7R,8R)-8-benzyl-3-[(3-isobutoxycarbonyloxy-4-methoxy-pyridine-2 carbonyl)amino]-6-methyl-4,9-dioxo-1,5-dioxonan-7-yl]2-methylpropanoate, [(3S,6S,7R,8R)-8-benzyl-3-[[3-(1,3-benzodioxol-5-ylmethoxy)-4-methoxy-pyridine-2-carbonyl]amino]-6-methyl-4,9-dioxo-1,5-dioxonan-7-yl]2-methylpropanoate; (3S,6S,7R,8R)-3-[[(3-hydroxy-4-methoxy-2-pyridinyl)carbonyl]amino]-6 methyl-4,9-dioxo-8-(phenylmethyl)-1,5-dioxonan-7-yl 2-methylpropanoate
  inhibitors of complex II (e.g. carboxamides): benodanil, bixafen, boscalid, carboxin, fenfuram, fluopyram, flutolanil, fluxapyroxad, furametpyr, isopyrazam, mepronil, oxycarboxin, penflufen, penthiopyrad, sedaxane, tecloftalam, thifluzamide, N-(4'-trifluoromethylthiobiphenyl-2-yl)-3-difluoromethyl-1-methyl-1H pyrazole-4-carboxamide, N-(2-(1,3,3-trimethyl-butyl)-phenyl)-1,3-dimethyl-5 fluoro-1H-pyrazole-4 carboxamide, N-[9-(dichloromethylene)-1,2,3,4-tetrahydro-1,4-methanonaphthalen-5-yl]-3-(difluoromethyl)-1-methyl-1H-pyrazole-4-carboxamide, 3 (difluoromethyl)-1-methyl-N-(1,1,3-trimethylindan-4-yl)pyrazole-4-carboxamide, 3 (trifluoromethyl)-1-methyl-N-(1,1,3-trimethylindan-4-yl)pyrazole-4-carboxamide, 1,3-dimethyl-N-(1,1,3-trimethylindan-4-yl)pyrazole-4-carboxamide, 3-(trifluoromethyl)-1,5-dimethyl-N-(1,1,3-trimethylindan-4-yl)pyrazole-4-carboxamide, 3-(difluoromethyl)-1,5-dimethyl-N-(1,1,3-trimethylindan-4-yl)pyrazole-4-carboxamide, 1,3,5-trimethyl-N-(1,1,3-trimethylindan-4-yl)pyrazole-4-carboxamide;
  other respiration inhibitors (e.g. complex I, uncouplers): diflumetorim, (5,8-difluoroquinazolin-4-yl)-{2-[2-fluoro-4-(4-trifluoromethylpyridin-2-yloxy)-phenyl]-ethyl}-amine; nitrophenyl derivates: binapacryl, dinobuton, dinocap, fluazinam; ferimzone; organometal compounds: fentin salts, such as fentin-acetate, fentin chloride or fentin hydroxide; ametoctradin; and silthiofam;

B) Sterol Biosynthesis Inhibitors (SBI Fungicides)
  C14 demethylase inhibitors (DMI fungicides): triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole, 1-[rel-(2S;3R)-3-(2-chlorophenyl)-2-(2,4-difluorophenyl)-oxiranylmethyl]-5 thiocyanato-1H-[1,2,4]triazole, 2-[rel-(2S;3R)-3-(2-chlorophenyl)-2-(2,4-difluorophenyl)-oxiranylmethyl]-2H [1,2,4] triazole-3-thiol; imidazoles: imazalil, pefurazoate, prochloraz, triflumizol; pyrimidines, pyridines and piperazines: fenarimol, nuarimol, pyrifenox, triforine;
  Delta14-reductase inhibitors: aldimorph, dodemorph, dodemorph-acetate, fenpropimorph, tridemorph, fenpropidin, piperalin, spiroxamine;
  Inhibitors of 3-keto reductase: fenhexamid;

C) Nucleic Acid Synthesis Inhibitors
  phenylamides or acyl amino acid fungicides: benalaxyl, benalaxyl-M, kiralaxyl, metalaxyl, metalaxyl-M (mefenoxam), ofurace, oxadixyl;

others: hymexazole, octhilinone, oxolinic acid, bupirimate, 5-fluorocytosine, 5-fluoro-2-(p-tolylmethoxy) pyrimidin-4-amine, 5-fluoro-2-(4-fluorophenylmethoxy)pyrimidin-4 amine;

D) Inhibitors of Cell Division and Cytoskeleton tubulin inhibitors, such as benzimidazoles, thiophanates: benomyl, carbendazim, fuberidazole, thiabendazole, thiophanate-methyl; triazolopyrimidines: 5-chloro-7 (4 methyl piperidin-1-yl)-6-(2,4,6-trifluorophenyl)-[1,2,4]tri azolo[1,5a]pyrimidine other cell division inhibitors: diethofencarb, ethaboxam, pencycuron, fluopicolide, zoxamide, metrafenone, pyriofenone;

E) Inhibitors of Amino Acid and Protein Synthesis methionine synthesis inhibitors (anilino-pyrimidines): cyprodinil, mepanipyrim, pyrimethanil;

protein synthesis inhibitors: blasticidin-S, kasugamycin, kasugamycin hydrochloride-hydrate, mildiomycin, streptomycin, oxytetracyclin, polyoxine, validamycin A;

F) Signal Transduction Inhibitors

MAP/histidine kinase inhibitors: fluoroimid, iprodione, procymidone, vinclozolin, fenpiclonil, fludioxonil;

G protein inhibitors: quinoxyfen;

G) Lipid and Membrane Synthesis Inhibitors

Phospholipid biosynthesis inhibitors: edifenphos, iprobenfos, pyrazophos, isoprothiolane;

lipid peroxidation: dicloran, quintozene, tecnazene, tolclofos-methyl, biphenyl, chloroneb, etridiazole;

phospholipid biosynthesis and cell wall deposition: dimethomorph, flumorph, mandipropamid, pyrimorph, benthiavalicarb, iprovalicarb, valifenalate and N-(1-(1-(4-cyano-phenylethanesulfonyl)-but-2-yl) carbamic acid-(4-fluorophenyl) ester;

compounds affecting cell membrane permeability and fatty acides: propamocarb, propamo carb-hydrochlorid fatty acid amide hydrolase inhibitors: 1-[4-[4-[5-(2,6-difluorophenyl)-4,5-dihydro-3 isoxazolyl]-2-thiazolyl]-1-piperidinyl]-2-[5-methyl-3-(trifluoromethyl)-1H-pyrazol-1-yl]ethanone H) Inhibitors with Multi Site Action inorganic active substances: Bordeaux mixture, copper acetate, copper hydroxide, copper oxychloride, basic copper sulfate, sulfur;

thio- and dithiocarbamates: ferbam, mancozeb, maneb, metam, metiram, propineb, thiram, zineb, ziram;

organochlorine compounds (e.g. phthalimides, sulfamides, chloronitriles): anilazine, chlorothalonil, captafol, captan, folpet, dichlofluanid, dichlorophen, flusulfamide, hexachlorobenzene, pentachlorphenole and its salts, phthalide, tolylfluanid, N-(4-chloro-2-nitro-phenyl)-N-ethyl-4-methyl-benzenesulfonamide;

guanidines and others: guanidine, dodine, dodine free base, guazatine, guazatine-acetate, iminoctadine, iminoctadine-triacetate, iminoctadine-tris(albesilate), dithianon, 2,6-dimethyl-1H,5H-[1,4]dithiino[2,3-c:5,6-c']dipyrrole-1,3,5,7(2H,6H)-tetraone;

I) Cell Wall Synthesis Inhibitors inhibitors of glucan synthesis: validamycin, polyoxin B;

melanin synthesis inhibitors: pyroquilon, tricyclazole, carpropamid, dicyclomet, fenoxanil;

J) Plant Defence Inducers acibenzolar-S-methyl, probenazole, isotianil, tiadinil, prohexadione-calcium; phosphonates: fosetyl, fosetyl-aluminum, phosphorous acid and its salts;

K) Unknown Mode of Action bronopol, chinomethionat, cyflufenamid, cymoxanil, dazomet, debacarb, diclo mezine, difenzoquat, difenzoquat-methylsulfate, diphenylamin, fenpyrazamine, flumetover, flusulfamide, flutianil, methasulfocarb, nitrapyrin, nitrothal-isopropyl, oxin-copper, proquinazid, tebufloquin, tecloftalam, triazoxide, 2-butoxy-6-iodo-3 propylchromen-4-one, N-(cyclo propyl-methoxyimino-(6-difluoro-methoxy-2,3 di fluorophenyl)-methyl)-2-phenyl acetamide, N'-(4-(4-chloro-3-trifluoromethyl-phen oxy)-2,5-dimethyl-phenyl)-N-ethyl-N methyl formamidine, N' (4-(4-fluoro-3-trifluoro methyl-phenoxy)-2,5-dimethyl-phenyl)-N-ethyl-N-methyl formamidine, N'-(2-methyl-5-trifluoromethyl-4-(3-trimethyl silanyl-prop oxy)-phenyl)-N-ethyl-N-methyl forma midine, N'-(5-difluoromethyl-2 methyl-4-(3-tri methylsilanyl-propoxy)-phenyl)-N-ethyl-N-methyl formamidine, 2-{1-[2-(5-methyl-3-trifluoromethyl-pyrazole-1-yl)-acetyl]-piperidin-4-yl}-thiazole-4 carboxylic acid methyl-(1,2,3,4-tetrahydro-naphthalen-1-yl)-amide, 2-{1-[2-(5-meth yl-3-trifluoromethyl-pyrazole-1-yl)-acetyl]-piperidin-4-yl}-thiazole-4-carboxylic acid methyl-(R)-1,2,3,4-tetrahydro-naphthalen-1-yl-amide, 1-[4-[4-[5-(2,6-difluorophenyl)-4,5-dihydro-3-isoxazolyl]-2-thiazolyl]-1-piperidinyl] 2-[5-methyl-3-(trifluoromethyl)-1H-pyrazol-1-yl]ethanone, methoxy-acetic acid 6-tert-butyl-8-fluoro-2,3-dimethyl-quinolin-4-yl ester, N-Methyl-2-{1-[(5-methyl-3-tri fluoro methyl-1H-pyr azol-1-yl)-acetyl]-piperi din-4-yl}-N-[(1,2,3,4-tetrahydro naphthalen-1-yl]-4-thi azolecarboxamide, 3-[5-(4-methylphenyl)-2,3-dimethyl-isoxazolidin-3 yl]-pyridine, 3-[5-(4-chloro-phenyl)-2,3-dimethyl-isoxazolidin-3-yl]-pyridine (pyrisoxazole), N-(6-methoxy-pyridin-3-yl) cyclopropane carboxylicacid amide, 5-chloro-1 (4,6-dimethoxy-pyrimidin-2-yl)-2-methyl-1H-ben zoimidazole, 2-(4-chloro-phenyl)-N-[4-(3,4-dimeth oxy-phenyl)-isoxazol-5-yl]-2-prop-2-ynyloxy-acetamide;

L) Antifungal biocontrol agents, plant bioactivators: *Ampelomyces quisqualis* (e.g. AQ 10® from Intrachem Bio GmbH & Co. KG, Germany), *Aspergillus flavus* (e.g. AFLAGUARD® from Syngenta, CH), *Aureobasidium pullulans* (e.g. BOTECTOR® from bio-ferm GmbH, Germany), *Bacillus pumilus* (e.g. NRRL Accession No. B 30087 in SONATA® and BALLAD® Plus from AgraQuest Inc., USA), *Bacillus subtilis* (e.g. isolate NRRL-Nr. B-21661 in RHAPSODY®, SERENADE® MAX and SERENADE® ASO from AgraQuest Inc., USA), *Bacillus subtilis* var. amylolique faciens FZB24 (e.g. TAEGRO® from Novozyme Biologicals, Inc., USA), *Candida oleophila* 1-82 (e.g. ASPIRE® from Ecogen Inc., USA), *Candida saitoana* (e.g. BIOCURE® (in mixture with lysozyme) and BIOCOAT® from Micro Flo Company, USA (BASF SE) and Arysta), Chitosan (e.g. ARMOURZEN from BotriZen Ltd., NZ), *Clonostachys rosea* f. *catenulata*, also named *Gliocladium catenulatum* (e.g. isolate J1446: PRESTOP® from Verdera, Finland), *Coniothyrium minitans* (e.g. CONTANS® from Prophyta, Germany), *Cryphonectria parasitica* (e.g. *Endothia parasitica* from CNICM, France), *Cryptococcus albidus* (e.g. YIELD PLUS® from Anchor Bio-Technologies, South Africa), *Fusarium oxysporum* (e.g. BIOFOX® from S.I.A.P.A., Italy, FUSACLEAN® from Natural Plant Protection, France), *Metschnikowia fructicola* (e.g. SHEMER® from Agrogreen, Israel), *Microdochium* dimerum (e.g. ANTIBOT® from Agrauxine, France), *Phlebiopsis gigantea* (e.g. ROTSOP® from Verdera, Finland), *Pseudozyma flocculosa* (e.g. SPORODEX® from Plant Products Co. Ltd., Canada), *Pythium oligandrum* DV74 (e.g. POLYVERSUM® from Remeslo SSRO, Biopreparaty, Czech Rep.), *Reynoutria sachlinensis* (e.g. REGALIA® from Marrone BioInnovations, USA), *Talaromyces flavus* V117b (e.g. PROTUS® from Prophyta, Germany), *Trichoderma asperellum* SKT-1 (e.g. ECO-HOPE® from Kumiai Chemical Industry Co., Ltd., Japan), *T. atroviride* LC52 (e.g. SENTINEL® from Agrimm Technologies Ltd, NZ), *T. harzianum* T-22 (e.g. PLANTSHIELD® der Firma BioWorks Inc., USA), *T. harzianum* TH 35 (e.g. ROOT PRO® from Mycontrol Ltd., Israel), *T. harzianum* T-39 (e.g. TRICHODEX® and TRICHODERMA 2000® from Mycontrol Ltd., Israel and Makhteshim Ltd., Israel), *T. harzianum* and *T. viride* (e.g. TRICHOPEL from Agrimm Technologies Ltd, NZ), *T. harzianum* ICC012 and *T. viride* ICC080 (e.g. REMEDIER® WP from Isagro Ricerca, Italy), *T. polysporum* and *T. harzianum* (e.g. BINAB® from BINAB Bio-Innovation AB, Sweden), *T. stromaticum* (e.g. TRICO-VAB® from C.E.P.L.A.C., Brazil), *T. virens* GL-21 (e.g. SOILGARD® from Certis LLC, USA), *T. viride* (e.g. TRIECO® from Ecosense Labs. (India) Pvt. Ltd., Indien, BIO-CURE® F from T. Stanes & Co. Ltd., Indien), *T. viride* TV1 (e.g. *T. viride* TV1 from Agribiotec srl, Italy), *Ulocladium oudemansii* HRU3 (e.g. BOTRY-ZEN® from Botry-Zen Ltd, NZ);

M) Growth Regulators abscisic acid, amidochlor, ancymidol, 6-benzylaminopurine, brassinolide, butralin, chlormequat (chlormequat chloride), choline chloride, cyclanilide, daminozide, dike¬gulac, dimethipin, 2,6-dimethylpuridine, ethephon, flumetralin, flurprimidol, fluthi¬acet, forchlorfenuron, gibberellic acid, inabenfide, indole-3-acetic acid, maleic hydrazide, mefluidide, mepiquat (mepiquat chloride), naphthaleneacetic acid, N 6 benzyladenine, paclobutrazol, prohexadione (prohexadione-calcium), prohydrojasmon, thidiazuron, triapenthenol, tributyl phosphorotrithioate, 2,3,5 triiodobenzoic acid, trinexapac-ethyl and uniconazole;

N) Herbicides acetamides: acetochlor, alachlor, butachlor, dimethachlor, dimethenamid, flufenacet, mefenacet, metolachlor, metazachlor, napropamide, naproanilide, pethoxamid, pretilachlor, propachlor, thenylchlor;

amino acid derivatives: bilanafos, glyphosate, glufosinate, sulfosate;

aryloxyphenoxypropionates: clodinafop, cyhalofop-butyl, fenoxaprop, fluazifop, haloxyfop, metamifop, propaquizafop, quizalofop, quizalofop-P-tefuryl;

Bipyridyls: diquat, paraquat;

(thio)carbamates: asulam, butylate, carbetamide, desmedipham, dimepiperate, eptam (EPTC), esprocarb, molinate, orbencarb, phenmedipham, prosulfocarb, pyributicarb, thiobencarb, triallate;

cyclohexanediones: butroxydim, clethodim, cycloxydim, profoxydim, sethoxydim, tepraloxydim, tralkoxydim;

dinitroanilines: benfluralin, ethalfluralin, oryzalin, pendimethalin, prodiamine, trifluralin;

diphenyl ethers: acifluorfen, aclonifen, bifenox, diclofop, ethoxyfen, fomesafen, lactofen, oxyfluorfen;

hydroxybenzonitriles: bomoxynil, dichlobenil, ioxynil;

imidazolinones: imazamethabenz, imazamox, imazapic, imazapyr, imazaquin, imazethapyr;

phenoxy acetic acids: clomeprop, 2,4-dichlorophenoxyacetic acid (2,4-D), 2,4-DB, dichlorprop, MCPA, MCPA-thioethyl, MCPB, Mecoprop;

pyrazines: chloridazon, flufenpyr-ethyl, fluthiacet, norflurazon, pyridate;

pyridines: aminopyralid, clopyralid, diflufenican, dithiopyr, fluridone, fluoroxypyr, picloram, picolinafen, thiazopyr;

sulfonyl ureas: amidosulfuron, azimsulfuron, bensulfuron, chlorimuron-ethyl, chlorsulfuron, cinosulfuron, cyclosulfamuron, ethoxysulfuron, flazasulfuron, flucetosulfuron, flupyrsulfuron, foramsulfuron, halosulfuron, imazosulfuron, iodosulfuron, mesosulfuron, metazosulfuron, metsulfuron-methyl, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, 1 ((2-chloro-6-propyl-imidazo[1,2-b]pyridazin-3-yl)sulfonyl)-3-(4,6-dimethoxy-pyrimidin-2-yl)urea;

triazines: ametryn, atrazine, cyanazine, dimethametryn, ethiozin, hexazinone, metamitron, metribuzin, prometryn, simazine, terbuthylazine, terbutryn, triaziflam;

ureas: chlorotoluron, daimuron, diuron, fluometuron, isoproturon, linuron, metha¬benzthiazuron, tebuthiuron;

other acetolactate synthase inhibitors: bispyribac-sodium, cloransulam-methyl, diclosulam, florasulam, flucarbazone, flumetsulam, metosulam, ortho-sulfamuron, penoxsulam, propoxycarbazone, pyribambenz-propyl, pyribenzoxim, pyriftalid, pyriminobac-methyl, pyrimisulfan, pyrithiobac, pyroxasulfone, pyroxsulam;

others: amicarbazone, aminotriazole, anilofos, beflubutamid, benazolin, bencarbazone, benfluresate, benzofenap, bentazone, benzobicyclon, bicyclopyrone, bromacil, bromobutide, butafenacil, butamifos, cafenstrole, carfentrazone, cinidon-ethyl, chlorthal, cinmethylin, clomazone, cumyluron, cyprosulfamide, dicamba, difenzoquat, diflufenzopyr, *Drechslera monoceras*, endothal, ethofumesate, etobenzanid, fenoxasulfone, fentrazamide, flumiclorac-pentyl, flumioxazin, flupoxam, fluorochloridone, flurtamone, indanofan, isoxaben, isoxaflutole, lenacil, propanil, propyzamide, quinclorac, quinmerac, mesotrione, methyl arsonic acid, naptalam, oxadiargyl, oxadiazon, oxaziclomefone, pentoxazone, pinoxaden, pyraclonil, pyraflufen-ethyl, pyrasulfotole, pyrazoxyfen, pyrazolynate, quinoclamine, saflufenacil, sulcotrione, sulfentrazone, terbacil, tefuryltrione, tembotrione, thiencarbazone, topramezone, (3-[2-chloro-4-fluoro-5-(3-methyl-2,6-dioxo-4-trifluoromethyl-3,6-dihydro-2H-pyrimidin-1-yl)-phenoxy]-pyridin-2-yloxy)-acetic acid ethyl ester, 6-amino-5-chloro-2-cyclopropyl-pyrimidine-4-carboxylic acid methyl ester, 6-chloro-3-(2-cyclopropyl-6-methyl-phenoxy)-pyridazin-4-ol, 4-amino-3-chloro-6-(4-chloro-phenyl)-5-fluoro-pyridine-2-carboxylic acid, 4-amino-3-chloro-6-(4-chloro-2-fluoro-3-methoxy-phenyl)-pyridine-2-carboxylic acid methyl ester, and 4-amino-3-chloro-6-(4-chloro-3-dimethylamino-2-fluoro-phenyl)-pyridine-2-carboxylic acid methyl ester.

O) Insecticides organo(thio)phosphates: acephate, azamethiphos, azinphos-methyl, chlorpyrifos, chlorpyrifos-methyl, chlorfenvinphos, diazinon, dichlorvos, dicrotophos, dimethoate, disulfoton, ethion, fenitrothion, fenthion, isoxathion, malathion, methamidophos, methidathion, methyl-parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, tetrachlorvinphos, terbufos, triazophos, trichlorfon;

carbamates: alanycarb, aldicarb, bendiocarb, benfuracarb, carbaryl, carbofuran, carbosulfan, fenoxycarb, furathiocarb, methiocarb, methomyl, oxamyl, pirimicarb, propoxur, thiodicarb, triazamate;

pyrethroids: allethrin, bifenthrin, cyfluthrin, cyhalothrin, cyphenothrin, cypermethrin, alpha-cypermethrin, beta-cypermethrin, zeta-cypermethrin, deltamethrin, esfen¬ valerate, etofenprox, fenpropathrin, fenvalerate, imiprothrin, lambda-cyhalothrin, permethrin, prallethrin, pyrethrin I and II, resmethrin, silafluofen, taufluvalinate, tefluthrin, tetramethrin, tralomethrin, transfluthrin, profluthrin, dimefluthrin;

insect growth regulators: a) chitin synthesis inhibitors: benzoylureas: chlorfluazuron, cyramazin, diflubenzuron, flucycloxuron, flufenoxuron, hexaflumuron, lufenuron, novaluron, teflubenzuron, triflumuron; buprofezin, diofenolan, hexythiazox, etox¬azole, clofentazine; b) ecdysone antagonists: halofenozide, methoxyfenozide, tebufenozide, azadirachtin; c) juvenoids: pyriproxyfen, methoprene, fenoxycarb; d) lipid biosynthesis inhibitors: spirodiclofen, spiromesifen, spirotetramat;

nicotinic receptor agonists/antagonists compounds: clothianidin, dinotefuran, flupyradifurone, imidacloprid, thiamethoxam, nitenpyram, acetamiprid, thiacloprid, 1 2-chloro-thiazol-5-ylmethyl)-2-nitrimino-3,5-dimethyl-[1,3,5]triazinane;

GABA antagonist compounds: endosulfan, ethiprole, fipronil, vaniliprole, pyrafluprole, pyriprole, 5-amino-1-(2,6-dichloro-4-methyl-phenyl)-4-sulfinamoyl-1H pyrazole-3-carbothioic acid amide;

macrocyclic lactone insecticides: abamectin, emamectin, milbemectin, lepimectin, spinosad, spinetoram;

mitochondrial electron transport inhibitor (METI) I acaricides: fenazaquin, pyridaben, tebufenpyrad, tolfenpyrad, flufenerim;

METI II and III compounds: acequinocyl, fluacyprim, hydramethylnon;

Uncouplers: chlorfenapyr;

oxidative phosphorylation inhibitors: cyhexatin, diafenthiuron, fenbutatin oxide, propargite;

moulting disruptor compounds: cryomazine;

mixed function oxidase inhibitors: piperonyl butoxide;

sodium channel blockers: indoxacarb, metaflumizone;

others: benclothiaz, bifenazate, cartap, flonicamid, pyridalyl, pymetrozine, sulfur, thiocyclam, flubendiamide, chlorantraniliprole, cyazypyr (HGW86), cyenopyrafen, flupyrazofos, cyflumetofen, amidoflumet, imicyafos, bistrifluoron, and pyrifluquinazon.

The compounds V, their preparation and their biological activity e.g. against harmful fungi, pests or weed is known (cf.:http://www.alanwood.net/pesticides/); these substances are commercially available and known, for example, from the references below:

benalaxyl, methyl N-(phenylacetyl)-N-(2,6-xylyl)-DL-alaninate (DE 29 03 612); metalaxyl, methyl N-(methoxy-acetyl)-N-(2,6-xylyl)-DL-alaninate (GB 15 00 581); ofurace, (RS)-α-(2-chloro-N-2,6-xylylacetamido)-γ-butyrolactone [CAS RN 58810-48-3]; oxadixyl; N-(2,6-dimethylphenyl)-2-methoxy-N-(2-oxo-3-oxazolidinyl) acetamide (GB 20 58 059); aldimorph, "4-alkyl-2,5(or 2,6)-dimethylmorpholine", comprising 65-75% of 2,6-dimethylmorpholine and 25-35% of 2,5-dimethylmorpholine, comprising more than 85% of 4-dodecyl-2,5(or 2,6)-dimethylmorpholine, where "alkyl" also includes octyl, decyl, tetradecyl and hexadecyl, with a cis/trans ratio of 1:1 [CAS RN 91315-15-0]; dodine, 1-dodecylguanidinium acetate (Plant Dis. Rep., Vol. 41, p. 1029 (1957)); dodemorph, 4-cyclododecyl-2,6-dimethylmorpholine (DE 1198125); fenpropimorph, (RS)-cis-4-[3-(4-tert-butylphenyl)-2-methylpropyl]-2,6-dimethylmorpholine (DE 27 52 096); fenpropidin, (RS)-1-[3-(4-tert-butylphenyl)-2-methylpropyl]piperidine (DE 27 52 096); guazatine, mixture of the reaction products from the amidation of technical grade iminodi(octa-methylene)diamine, comprising various guanidines and polyamines [CAS RN 108173-90-6]; iminoctadine, 1,1'-iminodi(octamethylene)diguanidine (Congr. Plant Pathol. 1, p. 27 (1968); spiroxamine, (8-tert-butyl-1,4-dioxaspiro[4.5]dec-2-yl)diethylamine (EP-A 281 842); tridemorph, 2,6-dimethyl-4-tridecylmorpholine (DE 11 64 152); pyrimethanil, 4,6-dimethylpyrimidin-2-ylphenylamine (DD-A 151 404); mepanipyrim, (4-methyl-6-prop-1-ynylpyrimidin-2-yl)phenylamine (EP-A 224 339); cyprodinil, (4-cyclopropyl-6-methylpyrimidin-2-yl)phenylamine (EP-A 310 550); cycloheximid, 4-{(2R)-2-[(1S,3S,5S)-3,5-dimethyl-2-oxocyclohexyl]-2-hydroxyethyl}piperidine-2,6-dione [CAS RN 66-81-9]; griseofulvin, 7-chloro-2',4,6-trimethoxy-6'-methylspiro[benzo-furan-2(3H), 1'-cyclohex-2'-ene]-3,4'-dione [CAS RN 126-07-8]; kasugamycin, 3-O—[2-amino-4-[(carboxylminomethyl)amino]-2,3,4,6-tetradeoxy-α-D-arabino-hexopyranosyl]-D-chiro-inositol [CAS RN 6980-18-3]; natamycin, (8E,14E,16E,18E,20E)-(1R,3S,5R, 7R,12R,22R,24S,25R,26S)-22-(3-amino-3,6-dideoxyl-β-D-mannopyranosyloxy)-1,3,26-trihydroxy-12-methyl-10-oxo-6,11,28-trioxatricyclo[22.3.1.05,7]octacosa-8,14,16,18,20-pentaene-25-carboxylic acid [CAS RN 7681-93-8]; polyoxin, 5-(2-amino-5-O-carbamoyl-2-deoxy-L-xylonamido)-1-(5-carboxy-1,2,3,4-tetrahydro-2,4-dioxopyrimidin-1-yl)-1,5-dideoxyl-β-D-allofuranuronic acid [CAS RN 22976-86-9]; streptomycin, 1,1'-{1-L-(1,3,5/2,4,6)-4-[5-deoxy-2-O-(2-deoxy-2-methylamino-α-L-glucopyranosyl)-3-C-formyl-α-L-lyxofuranosyloxy]-2,5,6-trihydroxycyclohex-1,3-ylene}diguanidine (J. Am. Chem. Soc. 69, p. 1234 (1947)); bitertanol, β-([1,1'-biphenyl]-4-yloxy)-α-(1,1-dimethylethyl)-1H-1,2,4-triazole-1-ethanol (DE 23 24 020); bromuconazole, 1-[[4-bromo-2-(2,4-dichlorophenyl)tetrahydro-2-furanyl]methyl]-1H-1,2,4-triazole (Proc. Br. Crop. Prot. Conf. 1990-Pests Dis. Vol. 1, p. 459); cyproconazole, 2-(4-chlorophenyl)-3-cyclopropyl-1-[1,2,4]triazol-1-ylbutan-2-ol (U.S. Pat. No. 4,664,696); difenoconazole, 1-{2-[2-chloro-4-(4-chlorophenoxy)phenyl]-4-methyl-[1,3]dioxolan-2-ylmethyl}-1H-[1,2,4]triazole (GB-A 2 098 607); diniconazole, (βE)-β-[(2,4-dichlorophenyl)methylene]-α-(1,1-dimethylethyl)-1H-1,2,4-triazole-1-ethanol (Noyaku Kagaku, 1983, Vol. 8, p. 575); enilconazole (imazalil), 1-[2-(2,4-dichlorphenyl)-2-(2-propenyloxy)ethyl]-1H-imidazole (Fruits 28, p. 545, 1973); epoxiconazole, (2RS,3SR)-1-[3-(2-chlorophenyl)-2,3-epoxy-2-(4-fluorophenyl)propyl]-1H-1,2,4-triazole (EP-A 196 038); fenbuconazole, α-[2-(4-chloro-phenyl)ethyl]-α-phenyl-1H-1,2,4-triazole-1-propanenitrile (Proc. Br. Crop Prot. Conf. 1988—Pests Dis. Vol. 1, p. 33); fluquinconazole, 3-(2,4-dichlorophenyl)-6-fluoro-2-[1,2,4]-triazol-1-yl-3H-quinazolin-4-one (Proc. Br. Crop Prot. Conf.-Pests Dis., 5-3, 411 (1992)); flusilazole, 1-{[bis-(4-fluorophenyl)methylsilanyl]methyl}-1H-[1,2,4] triazole (Proc. Br. Crop Prot. Conf.-Pests Dis., 1, 413 (1984)); flutriafol, α-(2-fluorophenyl)-α-(4-fluorophenyl)-1H-1,2,4-triazole-1-ethanol (EP 15 756); hexaconazole, 2-(2,4-dichlorophenyl)-1-[1,2,4]triazol-1-ylhexan-2-ol (CAS RN 79983-71-4); ipconazole, 2-[(4-chlorophenyl)methyl]-5-(1-methylethyl)-1-(1H-1,2,4-triazol-1-ylmethyl)cyclopentanol (EP 267 778), metconazole, 5-(4-chlorobenzyl)-2,2-dimethyl-1-[1,2,4]triazol-1-ylmethyl-cyclopentanol (GB 857 383); myclobutanil, 2-(4-chlorophenyl)-2-[1,2,4]triazol-1-yl-methylpentanenitrile (CAS RN 88671-89-0); penconazole, 1-[2-(2,4-dichlorophenyl)-pentyl]-1H-[1,2,4]triazole (Pesticide Manual, 12th Ed. (2000), S.712); propiconazole, 1-[[2-(2,4-dichlorophenyl)-4-propyl-1,3-dioxolan-2-yl]methyl]-1H-1,2,4-triazole (BE 835 579); prochloraz, N-(propyl-[2-(2,4,6-trichlorophenoxy)ethyl])imidazole-1-carboxamide (U.S. Pat. No. 3,991,071); prothioconazole, 2-[2-(1-chlorocyclopropyl)-3-(2-chlorophenyl)-2-hydroxypropyl]-2,4-dihydro-[1,2,4]triazole-3-thione (WO 96/16048); simeconazole, α-(4-fluorophenyl)-α-[(trimethylsilyl)methyl]-1H-1,2,4-triazole-1-ethanol [CAS RN 149508-90-7]; tebuconazole, 1-(4-chlorophenyl)-4,4-dimethyl-3-[1,2,4]triazol-1-ylmethylpentan-3-ol (EP-A 40 345); tetraconazole, 1-[2-(2,4-dichlorophenyl)-3-(1,1,2,2-tetrafluoroethoxy)propyl]-1H-1,2,4-triazole (EP 234 242); triadimefon, 1-(4-chlorophenoxy)-3,3-dimethyl-1-(1H-1,2,4-triazol-1-yl)-2-butanone (BE 793 867); triadimenol, β-(4-chlorophenoxy)-α-(1,1-dimethylethyl)-1H-1,2,4-triazole-1-ethanol (DE 23 24 010); triflumizol, (4-chloro-2-trifluoromethylphenyl)-(2-propoxy-1-[1,2,4]triazol-1-ylethyliden)-amine (JP-A 79/119 462); triticonazole, (5E)-5-[(4-chlorophenyl)methylene]-2,2-dimethyl-1-(1H-1,2,4-triazol-1-ylmethyl)cyclopentanol (FR 26 41 277); iprodione, N-isopropyl-3-(3,5-dichlorophenyl)-2,4-dioxoimidazolidine-1-carboxamide (GB 13 12 536); myclozolin, (RS)-3-(3,5-dichlorophenyl)-5-methoxymethyl-5-methyl-1,3-oxazolidine-2,4-dione [CAS RN 54864-61-8]; procymidone, N-(3,5-dichlorophenyl)-1,2-dimethyl-cyclopropane-1,2-dicarboximide (U.S. Pat. No. 3,903,090); vinclozolin, 3-(3,5-dichlorophenyl)-5-methyl-5-vinyloxazolidine-2,4-dione (DE-A 22 07 576); ferbam, iron(3+) dimethyldithiocarbamate (U.S. Pat. No. 1,972,961); nabam, disodium ethylenebis-(dithiocarbamate) (U.S. Pat. No. 2,317,765); maneb, manganese ethylenebis(dithiocarbamate) (U.S. Pat. No. 2,504,404); mancozeb, manganese ethylenebis(dithiocarbamate) polymer complex zinc salt (GB 996 264); metam, methyldithiocarbaminic acid (U.S. Pat. No. 2,791,605); metiram, zinc ammoniate ethylenebis(dithiocarbamate) (U.S. Pat. No. 3,248,400); propineb, zinc propylenebis-(dithiocarbamate) polymer (BE 611 960); polycarbamate, bis(dimethylcarbamo-dithioato-S,S')[μ-[[1,2-ethanediylbis[carbamodithioato-S,S']](2-)]]di[zinc] [CAS RN 64440-88-6]; thiram, bis(dimethylthiocarbamoyl) disulfide (DE 642 532); ziram, dimethyldithiocarbamate [CAS RN 137-30-4]; zineb, zinc ethylenebis(dithiocarbamate) (U.S. Pat. No. 2,457,674); anilazine, 4,6-dichloro-N-(2-chlorophenyl)-1,3,5-triazine-2-amine (U.S. Pat. No. 2,720,480); benomyl, N-butyl-2-acetylaminobenzoimidazole-1-carboxamide (U.S. Pat. No. 3,631,176); boscalid, 2-chloro-N-(4'-chlorobiphenyl-2-yl)nicotinamide (EP-A 545 099); carbendazim, methyl (1H-benzoimidazol-2-yl)carbamate (U.S. Pat. No. 3,657,443); carboxin, 5,6-dihydro-2-methyl-N-phenyl-1,4-oxathiin-3-carboxamide (U.S. Pat. No. 3,249,499); oxycarboxin, 5,6-dihydro-2-methyl-1,4-oxathiin-3-carboxanilide 4,4-dioxide (U.S. Pat. No. 3,399,214); cyazofamid, 4-chloro-2-cyano-N,N-dimethyl-5-(4-methylphenyl)-1H-imidazole-1-sulfonamide (CAS RN 120116-88-3]; dazomet, 3,5-dimethyl-1,3,5-thiadiazinane-2-thione (Bull. Soc. Chim. Fr. 15, p. 891 (1897)); dithianon, 5,10-dioxo-5,10-dihydronaphtho[2,3-b][1,4]dithiin-2,3-dicarbonitrile (GB 857 383); famoxadone, (RS)-3-anilino-5-methyl-5-(4-phenoxyphenyl)-1,3-oxazolidine-2,4-dione [CAS RN 131807-57-3]; fenamidone, (S)-1-anilino-4-methyl-2-methylthio-4-phenylimidazolin-5-one [CAS RN 161326-34-7]; fenarimol, α-(2-chlorophenyl)-α-(4-chlorophenyl)-5-pyrimidinemethanol (GB 12 18 623); fuberidazole, 2-(2-furanyl)-1H-benzimidazole (DE 12 09 799); flutolanil, α,α,α-trifluoro-3'-isopropoxy-o-toluanilide (JP 1104514); furametpyr, 5-chloro-N-(1,3-dihydro-1,1,3-trimethyl-4-isobenzofuranyl)-1,3-dimethyl-1H-pyrazole-4-carboxamide [CAS RN 123572-88-3]; isoprothiolane, diisopropyl 1,3-dithiolan-2-ylidenemalonate (Proc. Insectic. Fungic. Conf. 8. Vol. 2, p. 715 (1975)); mepronil, 3'-isopropoxy-o-toluanilide (U.S. Pat. No. 3,937,840); nuarimol, α-(2-chlorophenyl)-α-(4-fluorophenyl)-5-pyrimidinemethanol (GB 12 18 623); fluopicolide (picobenzamid), 2,6-dichloro-N-(3-chloro-5-trifluoromethylpyridin-2-ylmethyl)benzamide (WO 99/42447); probenazole, 3-allyloxy-1,2-benzothiazole 1,1-dioxide (Agric. Biol. Chem. 37, p. 737 (1973)); proquinazid, 6-iodo-2-propoxy-3-propylquinazolin-4(3H)-one (WO 97/48684); pyrifenox, 2',4'-dichloro-2-(3-pyridyl)acetophenone (EZ)-O-methyloxime (EP 49 854); pyroquilon, 1,2,5,6-tetrahydropyrrolo[3,2,1-ij]quinolin-4-one (GB 139 43 373) quinoxyfen, 5,7-dichloro-4-(4-fluorophenoxy)quinoline (U.S. Pat. No. 5,240,940); silthiofam, N-allyl-4,5-dimethyl-2-(trimethylsilyl)thiophene-3-carboxamide [CAS RN 175217-20-6]; thiabendazole, 2-(1,3-thiazol-4-yl)benzimidazole (U.S. Pat. No. 3,017,415); thifluzamide, 2',6'-dibromo-2-methyl-4'-trifluormethoxy-4-trifluormethyl-1,3-thiazole-5-carboxanilide [CAS RN 130000-40-7]; thiophanate-methyl, 1,2-phenylenebis(iminocarbonothioyl)bis(dimethylcarbamate) (DE-A 19 30 540); tiadinil, 3'-chloro-4,4'-dimethyl-1,2,3-thiadiazole-5-carboxanilide [CAS RN 223580-51-6]; tricyclazole, 5-methyl-1,2,4-triazolo[3,4-b][1,3]benzothiazole [CAS RN 41814-78-2]; triforine, N,N'-{piperazine-1,4-diylbis[(trichlormethyl)methylene]}diformamide (DE 19 01 421); Bordeaux mixture, mixture of $CuSO_4 \times 3Cu(OH)_2 \times 3CaSO_4$ [CAS RN 8011-63-0]; copper acetate, $Cu(OCOCH_3)_2$ [CAS RN 8011-63-0]; copper oxychloride, $Cu_2Cl(OH)_3$ [CAS RN 1332-40-7]; basic copper sulfate, $CuSO_4$ [CAS RN 1344-73-6]; binapacryl, (RS)-2-sec-butyl-4,6-dinitrophenyl 3-methylcrotonate [CAS RN 485-31-4]; dinocap, mixture of 2,6-dinitro-4-octylphenylcrotonate and 2,4-dinitro-6-octylphenylcrotonate, where "octyl" is a mixture of 1-methylheptyl, 1-ethylhexyl and 1-propylpentyl (U.S. Pat. No. 2,526,660); dinobuton, (RS)-2-sec-butyl-4,6-dinitrophenyl isopropyl carbonate [CAS RN 973-21-7]; nitrothal-isopropyl, diisopropyl 5-nitroisophthalate (Proc. Br. Insectic. Fungic. Conf. 7., Vol. 2, p. 673 (1973)); fenpiclonil, 4-(2,3-dichloro-phenyl)-1H-pyrrole-3-carbonitrile (Proc. 1988 Br. Crop Prot. Conf.—Pests Dis., Vol. 1, p. 65); fludioxonil, 4-(2,2-difluorobenzo[1,3]dioxol-4-yl)-1H-pyrrole-3-carbonitrile (The Pesticide Manual, publ. The British Crop Protection Council, 10th ed. (1995), p. 482); acibenzolar-5-methyl, methyl 1,2,3-benzothiadiazol-7-carbothioate [CAS RN 135158-54-2]; flubenthiavalicarb (benthiavalicarb), isopropyl {(S)-1-[(1R)-1-(6-fluorobenzo-thiazol-2-yl)-ethylcarbamoyl]-2-methylpropyl}carbamate (JP-A 09/323,984); carpropamid, 2,2-dichloro-N-[1-(4-chlorophenyl)ethyl]-1-ethyl-3-methylcyclopropanecarbox-amide [CAS RN 104030-54-8]; chlorothalonil, 2,4,5,6-tetrachloroisophthalonitrile (U.S. Pat. No. 3,290,353); cyflufenamid, (Z)—N-[α-(cyclopropylmethoxyimino)-2,3-difluoro-6-(trifluoromethyl)benzyl]-2-phenylacetamide (WO 96/19442); cymoxanil, 1-(2-cyano-2-methoxy-iminoacetyl)-3-ethylurea (U.S. Pat. No. 3,957,847); diclomezine, 6-(3,5-dichlorophenyl-p-tolyl)-pyridazin-3(2H)-one (U.S. Pat. No. 4,052,395) diclocymet, (RS)-2-cyano-N—[(R)-1-(2,4-dichloro-phenyl)

ethyl]-3,3-dimethylbutyramide [CAS RN 139920-32-4]; diethofencarb, isopropyl 3,4-diethoxycarbanilate (EP 78 663); edifenphos, O-ethyl S,S-diphenyl phosphoro-dithioate (DE 14 93 736) ethaboxam, N-(cyano-2-thienylmethyl)-4-ethyl-2-(ethylamino)-5-thiazolecarboxamide (EP-A 639 574); fenhexamid, N-(2,3-dichloro-4-hydroxyphenyl)-1-methylcyclohexanecarboxamide (Proc. Br. Crop Prot. Conf.—Pests Dis., 1998, Vol. 2, p. 327); fentin acetate, triphenyltin (U.S. Pat. No. 3,499,086); fenoxanil, N-(1-cyano-1,2-di-methylpropyl)-2-(2,4-dichlorophenoxy)propanamide (EP 262 393); ferimzone, mepanipyrim, (Z)-2'-methylacetophenone-4,6-dimethylpyrimidin-2-ylhydrazone [CAS RN 89269-64-7]; fluazinam, 3-chloro-N-[3-chloro-2,6-dinitro-4-(trifluoromethyl)phenyl]-5-(trifluoromethyl)-2-pyridinamine (The Pesticide Manual, publ. The British Crop Protection Council, 10th ed. (1995), p. 474); fosetyl, fosetyl-aluminum, ethylphosphonate (FR 22 54 276); iprovalicarb, isopropyl [(1S)-2-methyl-1-(1-p-tolylethylcarbamoyl)propyl]-carbamate (EP-A 472 996); hexachlorbenzene (C. R. Seances Acad. Agric. Fr. 31, p. 24, 1945); metrafenon, 3'-bromo-2,3,4,6'-tetramethoxy-2',6-dimethylbenzophenone (U.S. Pat. No. 5,945,567); pencycuron, 1-(4-chlorobenzyl)-1-cyclopentyl-3-phenylurea (DE 27 32 257); penthiopyrad, (RS)—N-[2-(1,3-dimethylbutyl)-3-thienyl]-1-methyl-3-(trifluoromethyl)-1H-pyrazole-4-carboxamide (JP 10130268); propamocarb, propyl 3-(dimethyl-amino)propylcarbamate (DE 15 67 169); phthalide (DE 16 43 347); toloclofos-methyl, O-2,6-dichloro-p-tolyl O,O-dimethyl phosphorothioate (GB 14 67 561); quintozene, pentachlornitrobenzene (DE 682 048); zoxamide, (RS)-3,5-dichloro-N-(3-chloro-1-ethyl-1-methyl-2-oxopropyl)-p-toluamide [CAS RN 156052-68-5]; azoxystrobin, methyl 2-{2-[6-(2-cyano-1-vinylpenta-1,3-dienyloxy)pyrimidin-4-yloxy]phenyl}-3-methoxyacrylate (EP 382 375), dimoxystrobin, (E)-2-(methoxyimino)-N-methyl-2-[α-(2,5-xylyl-oxy)-o-tolyl] acetamide (EP 477 631); enestroburin, methyl 2-{2-[3-(4-chlorophenyl)-1-methylallylideneaminooxymethyl]phenyl}-3-methoxyacrylate (EP 936 213); fluoxastrobin, (E)-{2-[6-(2-chlorophenoxy)-5-fluoropyrimidin-4-yloxy]phenyl}(5,6-dihydro-1,4,2-dioxazin-3-yl)methanone O-methyloxime (WO 97/27189); kresoxim-methyl, methyl (E)-methoxyimino[α-(o-tolyloxy)-o-tolyl]acetate (EP 253 213); metominostrobin, (E)-2-(methoxyimino)-N-methyl-2-(2-phenoxyphenyl)acetamide (EP 398 692); orysastrobin, (2E)-2-(methoxyimino)-2-{2-[(3E,5E,6E)-5-(methoxy-imino)-4,6-dimethyl-2,8-dioxa-3,7-diazanona-3,6-dien-1-yl]phenyl}-N-methylacetamide (WO 97/15552); picoxystrobin, methyl 3-methoxy-2-[2-(6-trifluoromethylpyridin-2-yloxy-methyl)phenyl]acrylate (EP 278 595); pyraclostrobin, methyl N-{2-[1-(4-chlorophenyl)-1H-pyrazol-3-yloxymethyl]phenyl}(N-methoxy)carbamate (WO 96/01256); trifloxystrobin, methyl (E)-methoxyimino-{(E)-α-[1-(α,α,α-trifluoro-m-tolyl)ethylidene-aminooxy]o-tolyl}acetate (EP 460 575); captafol, N-(1,1,2,2-tetrachloroethylthio)cyclohex-4-ene-1,2-dicarboximide (Phytopathology, Vol. 52, p. 754 (1962)); captan, N-(trichloromethylthio)cyclohex-4-ene-1,2-dicarboximide (U.S. Pat. No. 2,553,770); dichlofluanid, N-di-chlorofluoromethylthio-N',N'-dimethyl-N-phenylsulfamide (DE 11 93 498); folpet, N-(trichloromethylthio)phthalimide (U.S. Pat. No. 2,553,770); tolylfluanid, N-dlchlorofluoromethyl-thio-N',N'-dimethyl-N-p-tolylsulfamide (DE 11 93 498); dimethomorph, 3-(4-chloro-phenyl)-3-(3,4-dimethoxyphenyl)-1-morpholin-4-yl-propenone (EP 120 321); flumetover, 2-(3,4-dimethoxyphenyl)-N-ethyl-α,α,α-trifluoro-N-methyl-p-toluamide [AGROW no. 243, 22 (1995)]; flumorph, 3-(4-fluorophenyl)-3-(3,4-dimethoxyphenyl)-1-morpholin-4-ylpropenone (EP 860 438); 5-Amino-2-isopropyl-3-oxo-4-o-tolyl-2,3-dihydro-pyrazole-1-carbothioic acid S-allyl ester (CN1939128).

The compounds described by IUPAC nomenclature, their preparation and their fungicidal activity are also known (cf. Can. J. Plant Sci. 48(6), 587-94, 1968; EP-A 141 317; EP-A 152 031; EP-A 226 917; EP-A 243 970; EP-A 256 503; EP-A 428 941; EP-A 532 022; EP-A 1 028 125; EP-A 1 035 122; EP-A 1 201 648; EP-A 1 122 244, JP 2002316902; DE 19650197; DE 10021412; DE 102005009458; U.S. Pat. No. 3,296,272; U.S. Pat. No. 3,325,503; WO 98/46608; WO 99/14187; WO 99/24413; WO 99/27783; WO 00/29404; WO 00/46148; WO 00/65913; WO 01/54501; WO 01/56358; WO 02/22583; WO 02/40431; WO 03/10149; WO 03/11853; WO 03/14103; WO 03/16286; WO 03/53145; WO 03/61388; WO 03/66609; WO 03/74491; WO 04/49804; WO 04/83193; WO 05/120234; WO 05/123689; WO 05/123690; WO 05/63721; WO 05/87772; WO 05/87773; WO 06/15866; WO 06/87325; WO 06/87343; WO 07/82098; WO 07/90624, WO 11/028,657). N-methyl-2-{1-[(5-methyl-3-trifluoromethyl-1H-pyrazol-1-yl)-acetyl]-piperidin-4-yl}-N-[(1R)-1,2,3,4-tetrahydronaphthalen-1-yl]-4-thiazolecarboxamide has been described in WO 2007/014290.

It is preferred that the compositions comprise as compounds V fungicidal compounds that are independently of each other selected from the groups of fungicides A), B), C), D), E), F), G), H), I), J), K) and L).

Preference is given to mixtures comprising as compound V at least one active substance selected from group A) and particularly selected from azoxystrobin, dimoxystrobin, fluoxastrobin, kresoxim-methyl, orysastrobin, picoxystrobin, pyraclostrobin, trifloxystrobin; famoxadone, fenamidone; bixafen, boscalid, fluopyram, fluxapyroxad, isopyrazam, penflufen, penthiopyrad, sedaxane; ametoctradin, cyazofamid, fluazinam, fentin salts, such as fentin acetate. Preference is also given to mixtures comprising as compound V at least one active substance selected from group B) and particularly selected from cyproconazole, difenoconazole, epoxiconazole, fluquinconazole, flusilazole, flutriafol, metconazole, myclobutanil, penconazole, propiconazole, prothioconazole, triadimefon, triadimenol, tebuconazole, tetraconazole, triticonazole, prochloraz, fenarimol, triforine; dodemorph, fenpropimorph, tridemorph, fenpropidin, spiroxamine; fenhexamid.

Preference is also given to mixtures comprising as compound V at least one active substance selected from group C) and particularly selected from metalaxyl, (metalaxyl-M) mefenoxam, ofurace.

Preference is also given to mixtures comprising as compound V at least one active substance selected from group D) and particularly selected from benomyl, carbendazim, thiophanate-methyl, ethaboxam, fluopicolide, zoxamide, metrafenone, pyriofenone.

Preference is also given to mixtures comprising as compound V at least one active substance selected from group E) and particularly selected from cyprodinil, mepanipyrim, pyrimethanil.

Preference is also given to mixtures comprising as compound V at least one active substance selected from group F) and particularly selected from iprodione, fludioxonil, vinclozolin, quinoxyfen.

Preference is also given to mixtures comprising as compound V at least one active substance selected from group G) and particularly selected from dimethomorph, flumorph, iprovalicarb, benthiavalicarb, mandipropamid, propamocarb.

Preference is also given to mixtures comprising as compound V at least one active substance selected from group H) and particularly selected from copper acetate, copper hydroxide, copper oxychloride, copper sulfate, sulfur, mancozeb, metiram, propineb, thiram, captafol, folpet, chlorothalonil, dichlofluanid, dithianon.

Preference is also given to mixtures comprising as compound V at least one active substance selected from group I) and particularly selected from carpropamid and fenoxanil.

Preference is also given to mixtures comprising as compound V at least one active substance selected from group J) and particularly selected from acibenzolar-5-methyl, probenazole, tiadinil, fosetyl, fosetyl-aluminium, $H_3PO_3$ and salts thereof.

Preference is also given to mixtures comprise as compound V at least one active substance selected from group K) and particularly selected from cymoxanil, proquinazid and N-methyl-2-{1-[(5-methyl-3-trifluoromethyl-1H-pyrazol-1-yl)-acetyl]-30 piperidin-4-yl}-N-[(1R)-1,2,3,4-tetrahydronaphthalen-1-yl]-4-thiazolecarboxamide.

Preference is also given to mixtures comprising as compound V at least one active substance selected from group L) and particularly selected from *Bacillus subtilis* strain NRRL No. B-21661, *Bacillus pumilus* strain NRRL No. B-30087 and *Ulocladium oudemansii*.

More preference is given to following compounds V: pyraclostrobin, epoxiconazole, 2-[rel-(2S;3R)-3-(2-chlorophenyl)-2-(2,4-difluorophenyl)-oxiranyl methyl]-2H [1,2,4]triazole-3-thiol and fluxapyroxade.

Specific compositions contain following fungicides:

An imidazolium compound F15 or F19 (formulae see in the examples) and a compound V selected from pyraclostrobin, epoxiconazole, 2-[rel-(2S;3R)-3-(2-chlorophenyl)-2-(2,4-difluorophenyl)-oxiranyl methyl]-2H [1,2,4] triazole-3-thiol and fluxapyroxade.

More specific compositions contain following fungicides:

An imidazolium compound F15 and a compound V selected from pyraclostrobin, epoxiconazole, 2-[rel-(2S;3R)-3-(2-chlorophenyl)-2-(2,4-difluorophenyl)-oxiranyl methyl]-2H [1,2,4]triazole-3-thiol and fluxapyroxade; an imidazolium compound F19 and a compound V selected from epoxiconazole and 2-[rel-(2S;3R)-3-(2-chlorophenyl)-2-(2,4-difluorophenyl)-oxiranyl methyl]-2H [1,2,4]triazole-3-thiol.

The polymeric, ionic compound comprising imidazolium groups and the fungicidal compositions according to the invention containing it are suitable as fungicides. They are distinguished by an outstanding effectiveness against a broad spectrum of phytopathogenic fungi, including soil-borne fungi, which derive especially from the classes of the Plasmodiophoromycetes, Peronosporomycetes (syn. Oomycetes), Chytridiomycetes, Zygomycetes, Ascomycetes, Basidiomycetes and Deuteromycetes (syn. Fungi imperfecti). Some are systemically effective and they can be used in crop protection as foliar fungicides, fungicides for seed dressing and soil fungicides. Moreover, they are suitable for controlling harmful fungi, which inter alia occur in wood or roots of plants.

The polymeric, ionic compound comprising imidazolium groups and the fungicidal compositions according to the invention containing it are particularly important in the control of a multitude of phytopathogenic fungi on various cultivated plants, such as cereals, e.g. wheat, rye, barley, triticale, oats or rice; beet, e.g. sugar beet or fodder beet; fruits, such as pomes, stone fruits or soft fruits, e.g. apples, pears, plums, peaches, almonds, cherries, strawberries, raspberries, blackberries or gooseberries; leguminous plants, such as lentils, peas, alfalfa or soy beans; oil plants, such as rape, mustard, olives, sunflowers, coconut, cocoa beans, castor oil plants, oil palms, ground nuts or soybeans; cucurbits, such as squashes, cucumber or melons; fiber plants, such as cotton, flax, hemp or jute; citrus fruit, such as oranges, lemons, grapefruits or mandarins; vegetables, such as spinach, lettuce, asparagus, cabbages, carrots, onions, tomatoes, potatoes, cucurbits or paprika; lauraceous plants, such as avocados, cinnamon or camphor; energy and raw material plants, such as corn, soybean, rape, sugar cane or oil palm; corn; tobacco; nuts; coffee; tea; bananas; vines (table grapes and grape juice grape vines); hop; turf; natural rubber plants or ornamental and forestry plants, such as flowers, shrubs, broad-leaved trees or evergreens, e.g. conifers; and on the plant propagation material, such as seeds, and the crop material of these plants.

Preferably the polymeric, ionic compound comprising imidazolium groups and the fungicidal compositions according to the invention containing it are used for controlling a multitude of fungi on field crops, such as potatoes sugar beets, tobacco, wheat, rye, barley, oats, rice, corn, cotton, soybeans, rape, legumes, sunflowers, coffee or sugar cane; fruits; vines; ornamentals; or vegetables, such as cucumbers, tomatoes, beans or squashes.

The term "plant propagation material" is to be understood to denote all the generative parts of the plant such as seeds and vegetative plant material such as cuttings and tubers (e.g. potatoes), which can be used for the multiplication of the plant. This includes seeds, roots, fruits, tubers, bulbs, rhizomes, shoots, sprouts and other parts of plants, including seedlings and young plants, which are to be transplanted after germination or after emergence from soil. These young plants may also be protected before transplantation by a total or partial treatment by immersion or pouring. Preferably, treatment of plant propagation materials with the polymeric, ionic compound comprising imidazolium rings and compositions thereof, respectively, is used for controlling a multitude of fungi on cereals, such as wheat, rye, barley and oats; rice, corn, cotton and soybeans.

The term "cultivated plants" is to be understood as including plants which have been modified by breeding, mutagenesis or genetic engineering including but not limiting to agricultural biotech products on the market or in development (cf. http://www.bio.org/speeches/pubs/er/agri_products.asp). Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-transitional modification of protein(s), oligo- or polypeptides e.g. by glycosylation or polymer additions such as prenylated, acetylated or farnesylated moieties or PEG moieties.

Plants that have been modified by breeding, mutagenesis or genetic engineering, e.g. have been rendered tolerant to applications of specific classes of herbicides, such as hydroxyphenylpyruvate dioxygenase (HPPD) inhibitors; acetolactate synthase (ALS) inhibitors, such as sulfonyl ureas (see e.g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073) or imidazolinones (see e.g. U.S. Pat. No. 6,222,100, WO 01/82685, WO 00/026390, WO 97/41218, WO 98/002526, WO 98/02527, WO 04/106529, WO 05/20673, WO 03/014357, WO 03/13225, WO 03/14356, WO 04/16073); enolpyruvylshikimate-3-phosphate synthase (EPSPS) inhibitors, such as glyphosate (see e.g. WO 92/00377); glutamine synthetase (GS) inhibitors, such as glufosinate (see e.g. EP-A 242 236, EP-A 242 246) or oxynil herbicides (see e.g. U.S. Pat. No. 5,559,024) as a result of conventional methods of breeding or genetic engineering. Several cultivated plants have been rendered tolerant to herbicides by conventional methods of breeding (mutagenesis), e.g. Clearfield® summer rape (Canola, BASF SE, Germany) being tolerant to imidazolinones, e.g. imazamox. Genetic engineering methods have been used to render cultivated plants such as soybean, cotton, corn, beets and rape, tolerant to herbicides such as glyphosate and glufosinate, some of which are commercially available under the trade names RoundupReady® (glyphosate-tolerant, Monsanto, U.S.A.) and LibertyLink® (glufosinate-tolerant, Bayer CropScience, Germany).

Furthermore, plants are also covered that are by the use of recombinant DNA techniques capable to synthesize one or more insecticidal proteins, especially those known from the bacterial genus *Bacillus*, particularly from *Bacillus thuringiensis*, such as δ-endotoxins, e.g. CryIA(b), CryIA(c), CryIF, CryIF(a2), CryIIA(b), CryIIIA, CryIIIB(b1) or Cry9c; vegetative insecticidal proteins (VIP), e.g. VIP1, VIP2, VIP3 or VIP3A; insecticidal proteins of bacteria colonizing nematodes, e.g. Photorhabdus spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyltransferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, e.g. WO 02/015701). Further examples of such toxins or genetically modified plants capable of synthesizing such toxins are disclosed, e.g., in EP A 374 753, WO 93/007278, WO 95/34656, EP A 427 529, EP A 451 878, WO 03/18810 and WO 03/52073. The methods for producing such genetically modified plants are generally known to the person skilled in the art and are described, e.g. in the publications mentioned above. These insecticidal proteins contained in the genetically modified plants impart to the plants producing these proteins tolerance to harmful pests from all taxonomic groups of athropods, especially to beetles (Coeloptera), two-winged insects (Diptera), and moths (Lepidoptera) and to nematodes (Nematoda). Genetically modified plants capable to synthesize one or more insecticidal proteins are, e.g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme Phosphinothricin-N-Acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt11 (e.g. Agrisure® CB) and Bt176 from Syngenta Seeds SAS, France, (corn cultivars producing the Cry1Ab toxin and PAT enyzme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the Cry1F toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e.g. EP A 392 225), plant disease resistance genes (e.g. potato cultivars, which express resistance genes acting against *Phytophthora infestans* derived from the mexican wild potato *Solanum bulbocastanum*) or T4-lysozym (e.g. potato cultivars capable of synthesizing these proteins with increased resistance against bacteria such as *Erwinia amylvora*). The methods for producing such genetically modified plants are generally known to the person skilled in the art and are described, e.g. in the publications mentioned above.

Furthermore, plants are also covered that are by the use of recombinant DNA techniques capable to synthesize one or more proteins to increase the productivity (e.g. bio mass production, grain yield, starch content, oil content or protein content), tolerance to drought, salinity or other growth-limiting environmental factors or tolerance to pests and fungal, bacterial or viral pathogens of those plants. Furthermore, plants are also covered that contain by the use of recombinant DNA techniques a modified amount of substances of content or new substances of content, specifically to improve human or animal nutrition, e.g. oil crops that produce health-promoting long-chain omega-3 fatty acids or unsaturated omega-9 fatty acids (e.g. Nexera® rape, DOW Agro Sciences, Canada).

Furthermore, plants are also covered that contain by the use of recombinant DNA techniques a modified amount of substances of content or new substances of content, specifically to improve raw material production, e.g. potatoes that produce increased amounts of amylopectin (e.g. Amflora® potato, BASF SE, Germany).

The polymeric, ionic compound comprising imidazolium groups and the fungicidal compositions according to the invention containing it are particularly suitable for controlling the following plant diseases:

*Albugo* spp. (white rust) on ornamentals, vegetables (e.g. *A. candida*) and sunflowers (e.g. *A. tragopogonis*); *Alternaria* spp. (*Alternaria* leaf spot) on vegetables, rape (*A. brassicola* or *brassicae*), sugar beets (*A. tenuis*), fruits, rice, soybeans, potatoes (e.g. *A. solani* or *A. alternata*), tomatoes (e.g. *A. solani* or *A. alternata*) and wheat; *Aphanomyces* spp. on sugar beets and vegetables; *Ascochyta* spp. on cereals and vegetables, e.g. *A. tritici* (anthracnose) on wheat and *A. hordei* on barley; *Bipolaris* and *Drechslera* spp. (teleomorph: *Cochliobolus* spp.) on corn (e.g. *D. maydis*), cereals (e.g. *B. sorokiniana*: spot blotch), rice (e.g. *B. oryzae*) and turfs; Blumeria (formerly *Erysiphe*) graminis (powdery mildew) on cereals (e.g. on wheat or barley); *Botrytis cinerea* (teleomorph: *Botryotinia fuckeliana*: grey mold) on fruits and berries (e.g. strawberries), vegetables (e.g. lettuce, carrots, celery and cabbages), rape, flowers, vines, forestry plants and wheat; *Bremia lactucae* (downy mildew) on lettuce; Cerato¬cystis (syn. *Ophiostoma*) spp. (rot or wilt) on broad-leaved trees and evergreens, e.g. *C. ulmi* (Dutch elm disease) on elms; *Cercospora* spp. (*Cercospora* leaf spots) on corn, rice, sugar beets (e.g. *C. beticola*), sugar cane, vegetables, coffee, soybeans (e.g. *C. sojina* or *C. kikuchii*) and rice; *Cladosporium* spp. on tomatoes (e.g. *C. fulvum*: leaf mold) and cereals, e.g. *C. herbarum* (black ear) on wheat; *Claviceps purpurea* (ergot) on cereals; *Cochliobolus* (anamorph: *Helminthosporium* of *Bipolaris*) spp. (leaf spots) on corn (*C. carbonum*), cereals (e.g. *C. sativus*, anamorph: *B. sorokiniana*) and rice (e.g. *C. miyabeanus*, anamorph: *H. oryzae*); *Colletotrichum* (teleomorph: *Glomerella*) spp. (anthracnose) on cotton (e.g. *C. gossypii*), corn (e.g. *C. graminicola*), soft fruits, potatoes (e.g. *C. coccodes*: black dot), beans (e.g. *C. lindemuthianum*) and soybeans (e.g. *C. truncatum* or *C. gloeosporioides*); *Corticium* spp., e.g. *C. sasakii* (sheath blight) on rice; *Coryne¬spora cassiicola* (leaf spots) on soybeans and ornamentals; *Cycloconium* spp., e.g. *C. oleaginum* on olive trees; *Cylindrocarpon* spp. (e.g. fruit tree canker or young vine decline, teleomorph: *Nectria* or *Neonectria* spp.) on fruit trees, vines (e.g. *C. lirio¬dendri*, teleomorph: *Neonectria liriodendri*: Black Foot Disease) and ornamentals; *Dematophora* (teleomorph: *Rosellinia*) necatrix (root and stem rot) on soybeans; *Diaporthe* spp., e.g. *D. phaseolorum* (damping off) on soybeans; Drechs¬lera (syn. *Helminthosporium*, teleomorph: *Pyrenophora*) spp. on corn, cereals, such as barley (e.g. *D. teres*, net blotch) and wheat (e.g. *D. tritici-repentis*: tan spot), rice and turf; Esca (dieback, apoplexy) on vines, caused by *Formitiporia* (syn. *Phellinus*) *punctata*, *F. mediterranea*, *Phaeomoniella chlamydospora* (earlier *Phaeoacremonium chlamydo¬sporum*), *Phaeoacremonium aleophilum* and/or *Botryosphaeria obtusa*; *Elsinoe* spp. on pome fruits (*E. pyri*), soft fruits (*E. veneta*: anthracnose) and vines (*E. ampelina*: anthracnose); *Entyloma oryzae* (leaf smut) on rice; *Epicoccum* spp. (black mold) on wheat; *Erysiphe* spp. (powdery mildew) on sugar beets (*E. betae*), vegetables (e.g. *E. pisi*), such as cucurbits (e.g. *E. cichoracearum*), cabbages, rape (e.g. *E. crucife¬rarum*); *Eutypa lata* (*Eutypa* canker or dieback, anamorph: *Cytosporina lata*, syn. *Liber¬tella blepharis*) on fruit trees, vines and ornamental woods; *Exserohilum* (syn. Helmin¬thosporium) spp. on corn (e.g. *E. turcicum*); *Fusarium* (teleomorph: *Gibberella*) spp. (wilt, root or stem rot) on various plants, such as *F. graminearum* or *F. culmorum* (root rot, scab or head blight) on cereals (e.g. wheat or barley), *F. oxysporum* on tomatoes, *F. solani* on soybeans and *F. verticillioides* on corn; *Gaeumannomyces graminis* (take-all) on cereals (e.g. wheat or barley) and corn; *Gibberella* spp. on cereals (e.g. *G. zeae*) and rice (e.g. *G. fujikuroi*: Bakanae disease); *Glomerella cingulata* on vines, pome fruits and other plants and *G. gossypii* on cotton; Grain¬staining complex on rice; *Guignardia bidwellii* (black rot) on vines; *Gymnosporangium* spp. on rosaceous plants and junipers, e.g. *G. sabinae* (rust) on pears; Helmintho¬sporium spp. (syn. *Drechslera*, teleomorph: *Cochliobolus*) on corn, cereals and rice; *Hemileia* spp., e.g. *H. vastatrix* (coffee leaf rust) on coffee; *Isariopsis clavispora* (syn. *Cladosporium vitis*) on vines; *Macrophomina phaseolina* (syn. phaseoli) (root and stem rot) on soybeans and cotton; *Microdochium* (syn. *Fusarium*) *nivale* (pink snow mold) on cereals (e.g. wheat or barley);

*Microsphaera diffusa* (powdery mildew) on soybeans; *Monilinia* spp., e.g. *M. laxa*, *M. fructicola* and *M. fructigena* (bloom and twig blight, brown rot) on stone fruits and other rosaceous plants; *Mycosphaerella* spp. on cereals, bananas, soft fruits and ground nuts, such as e.g. *M. graminicola* (anamorph: *Septoria tritici*, *Septoria* blotch) on wheat or *M. fijiensis* (black Sigatoka disease) on bananas; *Peronospora* spp. (downy mildew) on cabbage (e.g. *P. brassicae*), rape (e.g. *P. parasitica*), onions (e.g. *P. destructor*), tobacco (*P. tabacina*) and soybeans (e.g. *P. manshurica*); *Phakopsora pachyrhizi* and *P. meibomiae* (soybean rust) on soybeans; *Phialophora* spp. e.g. on vines (e.g. *P. tracheiphila* and *P. tetraspora*) and soybeans (e.g. *P. gregata*: stem rot); *Phoma lingam* (root and stem rot) on rape and cabbage and *P. betae* (root rot, leaf spot and damping-off) on sugar beets; *Phomopsis* spp. on sunflowers, vines (e.g. *P. viticola*: can and leaf spot) and soybeans (e.g. stem rot: *P. phaseoli*, teleomorph: *Diaporthe phaseolorum*); *Physoderma maydis* (brown spots) on corn; *Phytophthora* spp. (wilt, root, leaf, fruit and stem root) on various plants, such as paprika and cucurbits (e.g. *P. capsici*), soybeans (e.g. *P. megasperma*, syn. *P. sojae*), potatoes and tomatoes (e.g. *P. infestans*: late blight) and broad-leaved trees (e.g. *P. ramorum*: sudden oak death); *Plasmodiophora brassicae* (club root) on cabbage, rape, radish and other plants; *Plasmopara* spp., e.g. *P. viticola* (grapevine downy mildew) on vines and *P. halstedii* on sunflowers; *Podosphaera* spp. (powdery mildew) on rosa¬ceous plants, hop, pome and soft fruits, e.g. *P. leucotricha* on apples; *Polymyxa* spp., e.g. on cereals, such as barley and wheat (*P. graminis*) and sugar beets (*P. betae*) and there¬by transmitted viral diseases; *Pseudocercosporella herpotrichoides* (eyespot, teleo¬morph: *Tapesia yallundae*) on cereals, e.g. wheat or barley; *Pseudoperonospora* (downy mildew) on various plants, e.g. *P. cubensis* on cucurbits or *P. humili* on hop; *Pseudopezicula tracheiphila* (red fire disease or 'rotbrenner', anamorph: *Phialophora*) on vines; *Puccinia* spp. (rusts) on various plants, e.g. *P. triticina* (brown or leaf rust), *P. strii¬formis* (stripe or yellow rust), *P. hordei* (dwarf rust), *P. graminis* (stem or black rust) or *P. recondita* (brown or leaf rust) on cereals, such as e.g. wheat, barley or rye, and asparagus (e.g. *P. asparagi*); *Pyrenophora* (anamorph: *Drechslera*) tritici-repentis (tan spot) on wheat or *P. teres* (net blotch) on barley; *Pyricularia* spp., e.g. *P. oryzae* (teleomorph: *Magnaporthe grisea*, rice blast) on rice and *P. grisea* on turf and cereals; *Pythium* spp. (damping-off) on turf, rice, corn, wheat, cotton, rape, sunflowers, soy¬beans, sugar beets, vegetables and various other plants (e.g. *P. ultimum* or *P. aphani¬dermatum*); *Ramularia* spp., e.g. *R. collo-cygni* (*Ramularia* leaf spots, Physiological leaf spots) on barley and *R. beticola* on sugar beets; *Rhizoctonia* spp. on cotton, rice, potatoes, turf, corn, rape, potatoes, sugar beets, vegetables and various other plants, e.g. *R. solani* (root and stem rot) on soybeans, *R. solani* (sheath blight) on rice or *R. cerealis* (*Rhizoctonia* spring blight) on wheat or barley; *Rhizopus stolonifer* (black mold, soft rot) on strawberries, carrots, cabbage, vines and tomatoes; *Rhynchosporium secalis* (scald) on barley, rye and triticale; *Sarocladium oryzae* and *S. attenuatum* (sheath rot) on rice; *Sclerotinia* spp. (stem rot or white mold) on vegetables and field crops, such as rape, sunflowers (e.g. *S. sclerotiorum*) and soybeans (e.g. *S. rolfsii* or *S. sclerotiorum*); *Septoria* spp. on various plants, e.g. *S. glycines* (brown spot) on soybeans, *S. tritici* (*Septoria* blotch) on wheat and *S.* (syn. *Stagonospora*) *nodorum* (*Stagonospora* blotch) on cereals; *Uncinula* (syn. *Erysiphe*) *necator* (powdery mildew, anamorph: *Oidium tuckeri*) on vines; *Setosphaeria* spp. (leaf blight) on corn (e.g. *S. turcicum*, syn. *Helminthosporium turcicum*) and turf;

Sphacelotheca spp. (smut) on corn, (e.g. *S. reiliana*: head smut), sorghum and sugar cane; *Sphaerotheca fuliginea* (powdery mildew) on cucurbits; *Spongospora subterranea* (powdery scab) on potatoes and thereby transmitted viral diseases; *Stagonospora* spp. on cereals, e.g. *S. nodorum* (*Stagonospora* blotch, teleomorph: *Leptosphaeria* [syn. *Phaeosphaeria*] nodorum) on wheat; *Synchytrium endobioticum* on potatoes (potato wart disease); *Taphrina* spp., e.g. *T. deformans* (leaf curl disease) on peaches and *T. pruni* (plum pocket) on plums; *Thielaviopsis* spp. (black root rot) on tobacco, pome fruits, vegetables, soybeans and cotton, e.g. *T. basicola* (syn. *Chalara elegans*); *Tilletia* spp. (common bunt or stinking smut) on cereals, such as e.g. *T. tritici* (syn. *T. caries*, wheat bunt) and *T. controversa* (dwarf bunt) on wheat; *Typhula incarnata* (grey snow mold) on barley or wheat; Uro¬cystis spp., e.g. *U. occulta* (stem smut) on rye; *Uromyces* spp. (rust) on vege¬tables, such as beans (e.g. *U. appendiculatus*, syn. *U. phaseoli*) and sugar beets (e.g. *U. betae*); *Ustilago* spp. (loose smut) on cereals (e.g. *U. nuda* and *U. avaenae*), corn (e.g. *U. maydis*: corn smut) and sugar cane; *Venturia* spp. (scab) on apples (e.g. *V. inaequalis*) and pears; and *Verticillium* spp. (wilt) on various plants, such as fruits and ornamentals, vines, soft fruits, vegetables and field crops, e.g. *V. dahliae* on straw¬berries, rape, potatoes and tomatoes.

The inventive mixtures and compositions are also suitable for controlling harmful fungi in the protection of stored products or harvest and in the protection of materials. The term "protection of materials" is to be understood to denote the protection of technical and non-living materials, such as adhesives, glues, wood, paper and paperboard, textiles, leather, paint dispersions, plastics, coiling lubricants, fiber or fabrics, against the infestation and destruction by harmful microorganisms, such as fungi and bacteria. As to the protection of wood and other materials, the particular attention is paid to the following harmful fungi: *Ascomycetes* such as *Ophiostoma* spp., *Ceratocystis* spp., *Aureobasidium* pullu¬lans, *Sclerophoma* spp., *Chaetomium* spp., *Humicola* spp., *Petriella* spp., *Trichurus* spp.; *Basidiomycetes* such as *Coniophora* spp., *Coriolus* spp., *Gloeophyllum* spp., *Lentinus* spp., *Pleurotus* spp., *Poria* spp., *Serpula* spp. and *Tyromyces* spp., *Deutero¬mycetes* such as *Aspergillus* spp., *Cladosporium* spp., *Penicillium* spp., *Trichorma* spp., *Alternaria* spp., *Paecilomyces* spp. and *Zygomycetes* such as *Mucor* spp., and in addition in the protection of stored products and harvest the following yeast fungi are worthy of note: *Candida* spp. and *Saccharomyces cerevisae*. In particular, the mixtures and compositions of the present invention are effective against plant pathogens in speciality crops such as vine, fruits, hop, vegetables and tabacco—see the above list.

Plant propagation materials may be treated with the polymeric, ionic compound comprising imidazolium groups and the fungicidal compositions according to the invention containing it prophylactically either at or before planting or transplanting. The invention also relates to agrochemical compositions comprising an auxiliary and at least one polymeric, ionic compound comprising imidazolium groups and at least compound V.

An agrochemical composition comprises a fungicidally effective amount of the at least one polymeric, ionic compound comprising imidazolium groups and the at least compound V. The term "effective amount" denotes an amount of the composition or of the compounds, which is sufficient for controlling harmful fungi on cultivated plants or in the protection of materials and which does not result in a substantial damage to the treated plants. Such an amount can vary in a broad range and is dependent on various factors, such as the fungal species to be controlled, the treated cultivated plant or material, the climatic conditions and the specific compounds used.

The polymeric, ionic compound comprising imidazolium groups can be converted into customary types of agrochemical compositions, e.g. solutions, emulsions, suspensions, dusts, powders, pastes, granules, pressings, capsules, and mixtures thereof. Examples for composition types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further compositions types are defined in the "Catalogue of pesticide formulation types and international coding system", Technical Monograph No. 2, 6th Ed. May 2008, CropLife International.

The compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e.g. toluene, paraffin, tetrahydronaphthalene, alkylated naphthalenes; alcohols, e.g. ethanol, propanol, butanol, benzylalcohol, cyclo¬hexanol; glycols; DMSO; ketones, e.g. cyclo¬hexanone; esters, e.g. lactates, carbonates, fatty acid esters, gamma-butyrolactone; fatty acids; phosphonates; amines; amides, e.g. N-methylpyrrolidone, fatty acid di¬methylamides; and mixtures thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharides, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emusifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulf¬onates, sulfates, phosphates, carboxylates, and mixtures thereof. Examples of sulf¬onates are alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides.

Examples of polymeric surfactants are home- or copolymers of vinylpyrrolidone, vinylalcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds which have a neglectable or even no pesticidal activity themselves, and which improve the biological performance of the polymeric, ionic compound comprising imidazolium groups on the target. Examples are surfactants, mineral or vegetable oils, and other auxilaries. Further examples are listed by Knowles, Adjuvants and additives, Agrow Reports DS256, T&F Informa UK, 2006, chapter 5.

Suitable thickeners are polysaccharides (e.g. xanthan gum, carboxymethylcellulose), anorganic clays (organically modified or unmodified), polycarboxylates, and silicates. Suitable bactericides are bronopol and isothiazolinone derivatives such as alkylisothiazolinones and benzisothiazolinones.

Suitable anti-freezing agents are ethylene glycol, propylene glycol, urea and glycerin. Suitable anti-foaming agents are silicones, long chain alcohols, and salts of fatty acids. Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants).

Suitable tackifiers or binders are polyvinylpyrrolidons, polyvinylacetates, polyvinyl alcohols, polyacrylates, biological or synthetic waxes, and cellulose ethers.

Examples for composition types and their preparation are (wherein active substances denote at least one polymeric, ionic compound comprising imidazolium groups and optionally compound V):

i) Water-Soluble concentrates (SL, LS)

10-60 wt % active substances and 5-15 wt % wetting agent (e.g. alcohol alkoxylates) are dissolved in water and/or in a water-soluble solvent (e.g. alcohols) ad 100 wt %. The active substance dissolves upon dilution with water.

ii) Dispersible Concentrates (DC)

5-25 wt % active substances and 1-10 wt % dispersant (e.g. polyvinylpyrrolidone) are dissolved in organic solvent (e.g. cyclohexanone) ad 100 wt %. Dilution with water gives a dispersion.

iii) Emulsifiable Concentrates (EC)

15-70 wt % active substances and 5-10 wt % emulsifiers (e.g. calcium dodecylbenzenesulfonate and castor oil ethoxylate) are dissolved in water-insoluble organic solvent (e.g. aromatic hydrocarbon) ad 100 wt %. Dilution with water gives an emulsion.

iv) Emulsions (EW, EO, ES)

5-40 wt % active substances and 1-10 wt % emulsifiers (e.g. calcium dodecylbenzenesulfonate and castor oil ethoxylate) are dissolved in 20-40 wt % water-insoluble organic solvent (e.g. aromatic hydrocarbon). This mixture is introduced into water ad 100 wt % by means of an emulsifying machine and made into a homogeneous emulsion. Dilution with water gives an emulsion.

v) Suspensions (SC, OD, FS)

In an agitated ball mill, 20-60 wt % active substances are comminuted with addition of 2-10 wt % dispersants and wetting agents (e.g. sodium lignosulfonate and alcohol ethoxylate), 0.1-2 wt % thickener (e.g. xanthan gum) and ad water ad 100 wt % to give a fine active substance suspension. Dilution with water gives a stable suspension of the active substance. For FS type composition up to 40 wt % binder (e.g. polyvinylalcohol) is added.

vi) Water-Dispersible Granules and Water-Soluble Granules (WG, SG)

50-80 wt % active substances are ground finely with addition of dispersants and wetting agents (e.g. sodium lignosulfonate and alcohol ethoxylate) ad 100 wt % and prepared as water-dispersible or water-soluble granules by means of technical appliances (e.g. extrusion, spray tower, fluidized bed). Dilution with water gives a stable dispersion or solution of the active substance.

vii) Water-Dispersible Powders and Water-Soluble Powders (WP, SP, WS)

50-80 wt % active substances are ground in a rotor-stator mill with addition of 1-5 wt % dispersants (e.g. sodium lignosulfonate), 1-3 wt % wetting agents (e.g. alcohol ethoxylate) and solid carrier (e.g. silica gel) ad 100 wt %. Dilution with water gives a stable dispersion or solution of the active substance.

viii) Gel (GW, GF)

In an agitated ball mill, 5-25 wt % active substances are comminuted with addition of 3-10 wt % dispersants (e.g. sodium lignosulfonate), 1-5 wt % thickener (e.g. carboxymethylcellulose) and water ad 100 wt % to give a fine suspension of the active substance. Dilution with water gives a stable suspension of the active substance.

iv) Microemulsion (ME)

5-20 wt % active substances are added to 5-30 wt % organic solvent blend (e.g. fatty acid dimethylamide and cyclohexanone), 10-25 wt % surfactant blend (e.g. alcohol ethoxylate and arylphenol ethoxylate), and water ad 100 wt %. This mixture is stirred for 1 h to produce spontaneously a thermodynamically stable microemulsion.

iv) Microcapsules (CS)

An oil phase comprising 5-50 wt % active substances, 0-40 wt % water insoluble organic solvent (e.g. aromatic hydrocarbon), 2-15 wt % acrylic monomers (e.g. methylmethacrylate, methacrylic acid and a di- or triacrylate) are dispersed into an aqueous solution of a protective colloid (e.g. polyvinyl alcohol). Radical polymerization initiated by a radical initiator results in the formation of poly(meth)acrylate microcapsules. Alternatively, an oil phase comprising 5-50 wt % of an active compound, 0-40 wt % water insoluble organic solvent (e.g. aromatic hydrocarbon), and an isocyanate monomer (e.g. diphenylmethene-4,4'-diisocyanatae) are dispersed into an aqueous solution of a protective colloid (e.g. polyvinyl alcohol). The addition of a polyamine (e.g. hexamethylenediamine) results in the formation of polyurea microcapsules. The monomers amount to 1-10 wt %. The wt % relate to the total CS composition.

ix) Dustable Powders (DP, DS)

1-10 wt % active substances are ground finely and mixed intimately with solid carrier (e.g. finely divided kaolin) ad 100 wt %.

x) Granules (GR, FG)

0.5-30 wt % active substances are ground finely and associated with solid carrier (e.g. silicate) ad 100 wt %. Granulation is achieved by extrusion, spray-drying or fluidized bed.

xi) Ultra-Low Volume Liquids (UL)

1-50 wt % active substances are dissolved in organic solvent (e.g. aromatic hydrocarbon) ad 100 wt %.

The compositions types i) to xi) may optionally comprise further auxiliaries, such as 0.1-1 wt % bactericides, 5-15 wt % anti-freezing agents, 0.1-1 wt % anti-foaming agents, and 0.1-1 wt % colorants.

The agrochemical compositions generally comprise between 0.01 and 95%, preferably between 0.1 and 90%, and in particular between 0.5 and 75%, by weight of active substance(s). The active substances are employed in a purity of from 90% to 100%, preferably from 95% to 100% (according to NMR spectrum).

Solutions for seed treatmenr (LS), suspoemulsions (SE), flowable concentrates (FS), powders for dry treatment (DS), water-dispersible powders for slurry treatment (WS), water-soluble powders (SS), emulsions (ES), emulsifiable concentrates (EC) and gels (GF) are usually employed for the purposes of treatment of plant propagation materials, particularly seeds. The compositions in question give, after two-to-tenfold dilution, active substance concentrations of from 0.01 to 60% by weight, preferably from 0.1 to 40%, in the ready-to-use preparations. Application can be carried out before or during sowing. Methods for applying or treating the polymeric, ionic compound comprising imidazolium groups and the optional compound V and compositions thereof, respectively, on to plant propagation material, especially seeds include dressing, coating, pelleting, dusting, soaking and in-furrow application methods of the propagation material. Preferably, the active compound(s) or the compositions thereof, respectively, are applied on to the plant propagation material by a method such that germination is not induced, e.g. by seed dressing, pelleting, coating and dusting.

When employed in plant protection, the amounts of active substances applied are, depending on the kind of effect desired, from 0.001 to 2 kg per ha, preferably from 0.005 to 2 kg per ha, more preferably from 0.05 to 0.9 kg per ha, in particular from 0.1 to 0.75 kg per ha.

In treatment of plant propagation materials such as seeds, e.g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seed) are generally required. When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material. Various types of oils, wetters, adjuvants, fertilizer, or micronutrients, and further pesticides (e.g. herbicides, insecticides, fungicides, growth regulators, safeners) may be added to the active substances or the compositions comprising them as premix or, if appropriate not until immediately prior to use (tank mix). These agents can be admixed with the compositions according to the invention in a weight ratio of 1:100 to 100:1, preferably 1:10 to 10:1.

The user applies the composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, individual components of the composition according to the invention such as parts of a kit or parts of a binary or ternary mixture may be mixed by the user himself in a spray tank and further auxiliaries may be added, if appropriate.

In the compositions according to the invention containing at least one compound V, the total weight ratio of polymeric, ionic compound(s) comprising imidazolium groups and compound(s) V generally depends from the properties of the active substances used, usually it is in the range of from 1:100 to 100:1, regularly in the range of from 1:80 to 80:1, preferably in the range of from 1:50 to 50:1, more preferably in the range of from 1:20 to 20:1, even more preferably in the range of from 1:10 to 10:1 and in particular in the range of from 1:4 to 4:1.

According to further embodiments of the compositions according to the invention containing at least one compound V, the total weight ratio of polymeric, ionic compound(s) comprising imidazolium groups and compound(s) V usually is in the range of from 100:1 to 1:1, regularly in the range of from 80:1 to 1:1, preferably in the range of from 50:1 to 1:1, more preferably in the range of from 20:1 to 1:1, even more preferably in the range of from 10:1 to 1:1 and in particular in the range of from 4:1 to 1:1.

According to further embodiments of the compositions according to the invention containing at least one compound V, the total weight ratio of polymeric, ionic compound(s) comprising imidazolium groups and compound(s) V usually is in the range of from 1:1 to 1:100, regularly in the range of from 1:1 to 1:80, preferably in the range of from 1:1 to 1:50, more preferably in the range of from 1:1 to 1:20, even more preferably in the range of from 1:1 to 1:10 and in particular in the range of from 1:1 to 1:4.

Any further active components are, if desired, added in a ratio of from 20:1 to 1:20 to the polymeric, ionic compound(s) comprising imidazolium groups.

In the mixtures and compositions, the compound ratios (e.g. polymeric, ionic compound(s) comprising imidazolium groups/compound V ratio) are advantageously chosen so as to produce a synergistic effect, i.e. in the fungicidal composition, the fungicidal use and method of the present invention the composition preferably contains the at least one imidazolium compound and the at least one compound V in synergistically effective amounts. This means that the relative amount, i.e. the weight ratio of the at least one imidazolium compound A and the at least one compound V in the composition, provides for an increased fungicidal efficacy on at least one harmful fungus which exceeds the additive fungicidal efficacy of the compounds of the composition as calculated from the fungicidal efficacy of the individual compounds at a given application rate. The calculation of the additive efficacies can be performed e.g. by Colby's formula (Colby, S. R. "Calculating synergistic and antagonistic responses of herbicide Combinations", Weeds, 15, 20-22, 1967). Synergism is present if the observed efficacy is greater than the calculated efficacy.

The term "synergistic effect" is also understood to refer to that defined by application of the Tammes method, (Tammes, P. M. L., "Isoboles, a graphic representation of synergism in pesticides", Netherl. J. Plant Pathol. 70, 1964).

To ensure synergism, the at least one imidazolium compound and the at least one compound V are preferably present in the compositions of the present invention in a total weight ratio as already indicated above, i.e. of from 100:1 to 1:100, more preferably from 80:1 to 1:80, even more preferably from 50:1 to 1:50, and in particular from 20:1 to 1:20.

The components can be used individually or already partially or completely mixed with one another to prepare the composition according to the invention. It is also possible for them to be packaged and used as combination such as a kit of parts.

The fungicidal action of the compositions according to the invention can be shown by the tests described below.

The active compounds, separately or jointly, are prepared as a stock solution comprising 25 mg of active compound which is made up to 10 ml using a mixture of acetone and/or DMSO and the emulsifier Uniperol® EL (wetting agent having an emulsifying and dispersing action based on ethoxylated alkylphenols) in a ratio by volume of solvent/emulsifier of 99:1. The mixture is then made up to 100 ml with water. This stock solution is diluted with the solvent/emulsifier/water mixture described to give the concentration of active compound stated below.

The visually determined percentages of infected leaf areas are converted into efficacies in % of the untreated control.

The efficacy (E) is calculated as follows using Abbot's formula:

$$E=(1-\alpha/\beta)\cdot 100$$

α corresponds to the fungicidal infection of the treated plants in % and
β corresponds to the fungicidal infection of the untreated (control) plants in %

An efficacy of 0 means that the infection level of the treated plants corresponds to that of the untreated control plants; an efficacy of 100 means that the treated plants were not infected.

The expected efficacies of active compound combinations were determined using Colby's formula (Colby, S. R. "Calculating synergistic and antagonistic responses of herbicide combinations", Weeds, 15, pp. 20-22, 1967) and compared with the observed efficacies.

$$E=x+y-x\cdot y/100 \quad \text{Colby's formula}$$

E expected efficacy, expressed in % of the untreated control, when using the mixture of the active compounds A and B at the concentrations a and b x efficacy, expressed in % of the untreated control, when using the active compound A at the concentration a
y efficacy, expressed in % of the untreated control, when using the active compound B at the concentration b In another aspect, the invention relates to a method for combating harmful fungi, which method comprises treating the fungi or materials, plants, parts thereof, the locus where the plants grow or are to grow or plants' propagation material to be protected from fungal attack with an effective amount of at least one polymeric, ionic compound comprising imidazolium groups (imidazolium compound), obtainable by reacting
a) at least one α-dicarbonyl compound,
b) at least one aldehyde,
c) at least one amino compound having at least two primary amino groups,
d) optionally an amino compound having only one primary amino group and
e) at least one protic acid,
and optionally subjecting the reaction product to an anion exchange,
where in the components a) and b) the aldehyde carbonyl groups may also be present as hemiacetal or acetal and the ketone carbonyl groups may also be present as hemiketal or ketal.

In another aspect, the invention relates to the use of at least one polymeric, ionic compound comprising imidazolium groups (imidazolium compound), obtainable by reacting
a) at least one α-dicarbonyl compound,
b) at least one aldehyde,
c) at least one amino compound having at least two primary amino groups,
d) optionally an amino compound having only one primary amino group and
e) at least one protic acid,
and optionally subjecting the reaction product to an anion exchange,
where in the components a) and b) the aldehyde carbonyl groups may also be present as hemiacetal or acetal and the ketone carbonyl groups may also be present as hemiketal or ketal;
for combating harmful fungi.

Preferably, the main chain of the at least one compound comprising imidazolium groups does not contain 1,4-bound phenylene rings; and/or the main chain of the at least one imidazolium compound apart from the nitrogen atoms of the imidazolium groups does not contain any quaternary nitrogen atoms that bear 4 residues that are different from hydrogen; and/or the amino compound having at least two primary amino groups is not 1,3-diamino-2-hydroxy-propane or 1,3-diamino-2-hydroxy-2-methyl-propane; and/or the polymer comprises at least 8 imidazolium rings.

In one preferred embodiment, the amino compound having at least two primary amino groups is not 1,3-diamino-2-hydroxy-propane or 1,3-diamino-2-hydroxy-2-methyl-propane.

In another embodiment, the polymer comprises at least 8, preferably at least 10 imidazolium rings.

In another embodiment, the main chain of the at least one compound comprising imidazolium groups does not contain 1,4-bound phenylene rings In another embodiment, the main chain of the at least one imidazolium compound apart from the nitrogen atoms of the imidazolium groups does not contain any quaternary nitrogen atoms that bear 4 residues that are different from hydrogen.

In one preferred embodiment, the amino compound having at least two primary amino groups is not 1,3-diamino-2-hydroxy-propane or 1,3-diamino-2-hydroxy-2-methyl-propane and the polymer comprises at least 8, preferably at least 10 imidazolium rings.

In particular, the polymer has one of the general or preferred meanings given above in context with the biocidal composition, and the fungicidal composition has one of the general or preferred meanings given above for the biocidal composition; i.e. the above-described biocidal composition is preferably a fungicidal composition.

In a specific embodiment, the composition contains at least one further agrochemically active compound V.

As regards suitable and preferred polymers, compositions, compounds V, fungi, plants and ways of using the polymers and compositions, reference is made to what has been said above.

Personal Care Composition

A further aspect of the invention is a personal care composition, comprising
A) at least one polymeric, ionic compound comprising imidazolium groups (imidazolium compound), obtainable by reacting
   a) at least one α-dicarbonyl compound,
   b) at least one aldehyde,
   c) at least one amino compound having at least two primary amino groups,
   d) optionally an amino compound having only one primary amino group and
   e) at least one protic acid,
   and optionally subjecting the reaction product to an anion exchange,
   where the main chain of the at least one compound comprising imidazolium groups does not contain 1,4-bound benzene rings, specifically does not contain benzene rings, and
   where in the components a) and b) the aldehyde carbonyl groups may also be present as hemiacetal or acetal and the ketone carbonyl groups may also be present as hemiketal or ketal,
C) optionally at least one cosmetically acceptable active ingredient, and
D) optionally at least one cosmetically acceptable auxiliary.

Preferably, the main chain of the at least one imidazolium compound apart from the nitrogen atoms of the imidazolium groups does not contain any quaternary nitrogen atoms that bear 4 residues that are different from hydrogen, either.

Suitable personal care compositions are cosmetic compositions and hygiene compositions. With regard to suitable and preferred embodiments of the imidazolium compound A), reference is made to the general definition of the imidazolium compound as defined above. Suitable and preferred embodiments of the compounds B) and C) are mentioned in the following.

Personal Care Composition Containing Imidazolium Compounds as Microbiocide

The personal care composition according to the invention can be a composition that is effective against various microorganisms. Thus, in a first variant, the personal care composition comprises at least one imidazolium compound as microbiocide. The personal care compositions according this variant contains at least one imidazolium compound A), alone or in combination with at least one further microbicidal compound B), present at a concentration effective to confer an antimicrobial effect on a person to whom it is applied. According to this variant, the imidazolium compound itself (=component A) may also act as cosmetically active ingredient. Accordingly, in such a composition the use of a further cosmetically acceptable active ingredient C) is only optional.

In a special embodiment, the invention relates to a personal care composition comprising
A) at least one imidazolium compound as defined above,
B) optionally at least one further microbicidal compound different from the compounds of component (A),
C) optionally at least one cosmetically acceptable active ingredient, and
D) optionally at least one cosmetically acceptable auxiliary, wherein the composition contains components A) and optionally B) in an antimicrobicidal effective amount.

An antimicrobicidal effective amount denotes an amount that is sufficient to reduce the cell population of an unwanted microorganism or several unwanted microorganisms under a predetermined threshold value.

The personal care composition may comprise at least one imidazolium compound A) as the sole antimicrobicidal effective component. Then, the personal care composition preferably comprises the at least one imidazolium compound A) in an amount of from 0.01 to 10 wt %, more preferably 0.05 to 5 wt %, in particular 0.1 to 1 wt %, based on the total weight of the composition. The personal care composition may also comprise at least one imidazolium compound A) and at least one further microbicidal compound B) different from the compounds A) as the antimicrobicidal effective components. Then, the personal care composition preferably comprises the sum of components A) and B) in an amount of from 0.01 to 10 wt %, more especially 0.05 to 5 wt %, in particular 0.1 to 1 wt %, based on the total weight of the composition.

Personal Care Composition Containing Imidazolium Compounds as Preservative

In a second variant, the personal care composition comprises at least one imidazolium compound as preservative. The personal care composition according to this variant contains at least one imidazolium compound A), alone or in combination with at least one further microbicidal compound B), present at a concentration effective to preserve the composition against microbes. Such compositions are usually non-toxic, cost-effective and shelf-stable over prolonged periods. In such a composition the imidazolium compound itself (=component A) usually does not act as cosmetically active ingredient. Thus, in the personal care composition according to this second variant the use of a further cosmetically acceptable active ingredient C) is usually mandatory.

A further aspect of the invention is a personal care composition comprising
A) at least one imidazolium compound as defined above,
B) optionally at least one further microbicidal compound different from the compounds of component (A),
C) optionally at least one cosmetically acceptable active ingredient, and
D) optionally at least one cosmetically acceptable auxiliary, wherein the composition contains components A) and optionally B) in a preservative effective amount.

A preservative effective amount denotes an amount that is sufficient to reduce the cell population of an unwanted microorganism under a predetermined threshold value to obtain shelf-stability over a certain period of time. Thus, a "preservative-effective amount" can be e.g. defined as an amount sufficient to reduce the cell population by three log orders of the five following microorganisms: *Staphylococcus aureus, Pseudomonas aeruginosa, Eschrechia coli, Candida albicans* and *Aspergillus niger*.

The personal care composition may comprise at least one imidazolium compound A) as the sole preservative effective component. Then, the personal care composition preferably comprises the at least one imidazolium compound A) in an amount of from 0.00001 to 10 wt %, more preferably 0.0001 to 5 wt %, in particular 0.001 to 1 wt %, based on the total weight of the composition. The personal care composition may also comprise at least one imidazolium compound A) and at least one further microbicidal compound B) different from the compounds A) as the preservative effective components. Then, the personal care composition preferably comprises the sum of components A) and B) in an amount of from 0.01 to 10 wt %, more especially 0.05 to 5 wt %, in particular 0.1 to 1 wt %, based on the total weight of the composition.

Personal Care Composition Containing Imidazolium Compounds to Perform a Function in the Final Product Different from the Function as Microbiocide or Preservative The imidazolium compounds according to the invention can also be advantageously employed to perform a function in the final product different from the function as microbiocide or preservative. The imidazolium compounds may perform this function as an alternative to or in addition to the function as microbiocide or preservative.

Suitable personal care compositions are:

skin-care preparations, e.g. skin-washing and cleansing preparations in the form of tablets, liquid soaps, bar soaps, syndets, washing gels, soapless detergents or washing pastes, bath preparations, e.g. liquid (foam baths, milks, oils, shower preparations) or solid bath preparations, e.g. bath cubes and bath salts;

skin-care preparations, e.g. skin emulsions, multi-emulsions, powders, sprays or skin oils;

cosmetic personal care preparations, e.g. facial make-up in the form of day creams or powder creams, face powder (loose or pressed), rouge or cream make-up, eye-care preparations, e.g. eyeshadow preparations, mascara, eyeliner, eye creams or eye-fix creams; lip-care preparations, e.g. lipsticks, lip gloss, lip contour pencils, nail-care preparations, such as nail varnish, nail varnish removers, nail hardeners or cuticle removers;

foot-care preparations, e.g. foot baths, foot powders, foot creams or foot balsams, special deodorants and antiperspirants or callus-removing preparations;

light-protective preparations, such as sun milks, lotions, creams or oils, sunblocks or tropicals, pre-tanning preparations or after-sun preparations;

skin-tanning preparations, e.g. self-tanning creams;

depigmenting preparations, e.g. preparations for bleaching the skin or skin-lightening preparations;

insect-repellents, e.g. insect-repellent oils, lotions, sprays or sticks;

deodorants, such as deodorant sprays, deodorant aerosols, pump-action sprays, deodorant gels, sticks or roll-ons, also water-free deodorant aerosols or sticks;

antiperspirants, e.g. antiperspirant sticks, creams or roll-ons, also water-free antiperspirant aerosols and water-free antiperspirant sticks;

preparations for cleansing and caring for blemished skin, e.g. synthetic detergents (solid or liquid), peeling or scrub preparations or peeling masks;

hair-removal preparations in chemical form (depilation), e.g. hair-removing powders, liquid hair-removing preparations, cream- or paste-form hair-removing preparations, hair-removing preparations in gel form or aerosol foams;

shaving preparations, e.g. shaving soap, foaming shaving creams, non-foaming shaving creams, foams and gels, pre-shave preparations for dry shaving, aftershaves or aftershave lotions;

fragrance preparations, e.g. fragrances (eau de Cologne, eau de toilette, eau de parfum, parfum de toilette, perfume), perfume oils or perfume creams;

cosmetic hair-treatment preparations, e.g. hair-washing preparations in the form of shampoos and conditioners, hair-care preparations, e.g. pretreatment preparations, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hairsetting preparations, hair foams, hairsprays, bleaching preparations, e.g. hydrogen peroxide solutions, lightening shampoos, bleaching creams, bleaching powders, bleaching pastes or oils, temporary, semi-permanent or permanent hair colorants, preparations containing self-oxidising dyes, or natural hair colorants, such as henna or camomile.

antidandruff preparations in the form of shampoos, conditioners, hair tonics, styling creams or gels or treatments packs, oral care preparations such as pastes, gels, powders, mouth washes and sprays.

A preferred embodiment is a personal care composition, comprising

A) at least one polymeric, ionic compound comprising imidazolium groups (imidazolium compound), obtainable by reacting
  a) at least one α-dicarbonyl compound,
  b) at least one aldehyde,
  c) at least one amino compound having at least two primary amino groups,
  d) optionally an amino compound having only one primary amino group and
  e) at least one protic acid,
  and optionally subjecting the reaction product to an anion exchange,
  where the main chain of the at least one compound comprising imidazolium groups does not contain 1,4-bound benzene rings; specifically does not contain benzene rings, and
  where in the components a) and b) the aldehyde carbonyl groups may also be present as hemiacetal or acetal and the ketone carbonyl groups may also be present as hemiketal or ketal, C) optionally at least one cosmetically acceptable active ingredient, and D) optionally at least one cosmetically acceptable auxiliary.

Preferably, the main chain of the at least one imidazolium compound apart from the nitrogen atoms of the imidazolium groups does not contain any quaternary nitrogen atoms that bear 4 residues that are different from hydrogen, either.

With regard to suitable and preferred embodiments of component A), reference is made to the afore-mentioned general definition of the imidazolium compounds employed according to the invention. With regard to suitable and preferred embodiments of cosmetically acceptable components C) and D), reference is made to the following general definition of those components.

Some appropriate personal care compositions include deodorants, antiperspirants, skin care products for facial, foot, hand and whole body uses, sun protection products, personal cleaning products, hair care products, feminine hygiene products, oral care products and decorative cosmetics such as lipsticks, mascara, facial makeup cremes and rouge.

Suitable cosmetic compositions may exist in a wide variety of forms, for example:

in the form of liquid preparations as a W/O, O/W, O/W/O, W/O/W or PIT emulsion and all kinds of microemulsions,
in the form of a gel,
in the form of an oil, a cream, milk or lotion,
in the form of a powder, a lacquer, a tablet or make-up,
in the form of a stick,
in the form of a spray (spray with propellant gas or pump-action spray) or an aerosol,
in the form of a foam, or
in the form of a paste.

The cosmetic compositions may be, for example, creams, gels, lotions, alcoholic and aqueous/alcoholic solutions, emulsions, wax/fat compositions, stick preparations, powders or ointments.

As water- and oil-containing emulsions (e.g. W/O, O/W, O/W/O and W/O/W emulsions or microemulsions) the preparations contain, for example, from 0.1 to 30% by weight, preferably from 0.1 to 15% by weight and especially from 0.5 to 10% by weight, based on the total weight of the composition, of one or more UV absorbers, from 1 to 60% by weight, especially from 5 to 50% by weight and preferably from 10 to 35% by weight, based on the total weight of the composition, of at least one oil component, from 0 to 30% by weight, especially from 1 to 30% by weight and preferably from 4 to 20% by weight, based on the total weight of the composition, of at least one emulsifier, from 10 to 90% by weight, especially from 30 to 90% by weight, based on the total weight of the composition, of water, and from 0 to 88.9% by weight, especially from 1 to 50% by weight, of further cosmetically acceptable adjuvants.

The cosmetic composition may also contain one or one more additional components C) and/or D), as described below.

Of special importance are cosmetic preparations for the hair, especially with the purpose of antidandruff treatment are the above-mentioned preparations for hair treatment, especially hair-washing preparations in the form of shampoos, hair conditioners, hair-care preparations, e.g. pretreatment preparations, hair tonics, styling creams, styling gels, pomades, hair rinses, treatment packs, intensive hair treatments, hair-straightening preparations, liquid hair-setting preparations, hair foams and hairsprays. Of special interest are hair-washing preparations in the form of shampoos.

A shampoo has, for example, the following composition:
from 0.01 to 5% by weight of the at least one component A),
12.0% by weight of sodium laureth-2-sulfate,
4.0% by weight of cocamidopropyl betaine,
3.0% by weight of sodium chloride, and
water ad 100%.

For example, especially the following hair-cosmetic formulations may be used:
a1) spontaneously emulsifying stock formulation, consisting of the antibacterial composition according to the above disclosure, PEG-6-C$_{10}$oxoalcohol and sorbitan sesquioleate, to which water and any desired quaternary ammonium compound, for example 4% minkamidopropyl dimethyl-2-hydroxyethylammonium chloride or Quaternium 80 is added;
a2) spontaneously emulsifying stock formulation consisting of the antibacterial composition according to the above disclosure, tributyl citrate and PEG-20-sorbitan monooleate, to which water and any desired quaternary ammonium compound, for example 4% minkamidopropyl dimethyl-2-hydroxyethylammonium chloride or Quaternium 80 is added;
b) quat-doped solutions of the antibacterial composition as disclosed above in butyl triglycol and tributyl citrate;
c) mixtures or solutions of the antibacterial composition as disclosed above with n-alkylpyrrolidone.

As used herein "cosmetically acceptable medium" means a medium which is non-toxic, non-irritating and otherwise suitable for contact with the surfaces of a human or other vertebrate body. Such surfaces include the hair, skin, mouth, anal, urethral and vaginal surfaces. Whether a composition is physiologically acceptable can be determined by tests well known to those of skill in the art.

A further aspect of the invention is a method of using the present personal care composition. The methods include contacting the personal care compositions with a part of the human body. In general, the method comprises applying the personal care composition to a body surface or part to be treated.

The term "applying" includes an appropriate action on the part of the user to contact the personal care composition to the body part. Applying includes, in some embodiments, spreading, spraying, squirting, wiping and brushing. The particular type of application depends on the body part to which the personal care composition is to be applied.

"Body part" means a part of body including the mouth and other epithelial surfaces of the body. Thus the term body part includes hair, skin and mouth, anus, urethra and vagina. In the case of the skin, the body part is often more specific. For example, in some embodiments the body part is the skin of the face, hand or foot. In other embodiments, the body part is the whole body. In other embodiments, for example where the personal care compositions are deodorants or antiperspirants, body part can be the underarms.

Preferably, the cosmetic composition comprises the components A) and, if present, B) in a fraction of from about 0.001 to 50% by weight, particularly preferably 0.01 to 30% by weight, in particular 0.05 to 20% by weight, based on the total weight of the composition.

Cosmetically Acceptable Components C) and D) (General Definition)

The components C) and D) of the cosmetic composition are preferably chosen from cosmetically acceptable carriers, emulsifiers, surfactants, perfume oils, rheology modifiers (thickeners), hair polymers, hair and skin conditioners, water-soluble or dispersible silicone-comprising polymers, bleachers, gelling agents, care agents, colorants, tinting agents, tanning agents, dyes, pigments, antidandruff agents, sunscreen agents, deodorizing active substances, vitamins, plant extracts, bodying agents, humectants, refatting agents, collagen, protein hydrolysates, lipids, antioxidants, antifoaming agents, antistatic agents, emollients, softeners, etc.

A comprehensive description of cosmetic auxiliaries is found in H. P. Fiedler, Lexikon der Hilfsstoffe für Pharmazie, Kosmetik and angrenzende Gebiete [Encyclopedia of Auxiliaries for Pharmaceuticals, Cosmetics and Related Fields], 4th edition, Aulendorff: ECV-Editio-Cantor-Verlag, 1996. A comprehensive description of cosmetic raw materials, auxiliaries and active substances, and also suitable formulations, are additionally found in K. Schrader, Grundlagen and Rezepturen der Kosmetika [Fundamental Principles and Formulations of Cosmetics], 2nd edition, Hüthig-Verlag, Heidelberg (1989).

A cosmetically acceptable medium comprises at least one cosmetically acceptable carrier. The cosmetic compositions preferably have a carrier component D) which is chosen from water, hydrophilic components, hydrophobic components and mixtures thereof.

Suitable hydrophilic carriers D) are, for example, mono-, di- or polyhydric alcohols having preferably 1 to 8 carbon atoms, such as ethanol, n-propanol, isopropanol, propylene glycol, glycerol, sorbitol, etc.

Suitable hydrophobic carriers D) are preferably chosen from
i) oils, fats, waxes,
ii) esters of $C_6$-$C_{30}$-monocarboxylic acids with mono-, di- or trihydric alcohols which are different from iii),
iii) saturated acyclic and cyclic hydrocarbons,
iv) fatty acids,
v) fatty alcohols,
vi) propellant gases,
and mixtures thereof.

Suitable silicone oils D) are volatile and non-volatile silicone oils. The term "volatile oil" means an oil capable of evaporating from the skin or the lips in less than one hour, and especially having a vapor pressure, at room temperature and atmospheric pressure, ranging from $10^{-3}$ to 300 mm Hg (0.13 Pa to 40,000 Pa).

Suitable silicone oils D) are for example, linear polydimethylsiloxanes, poly(methylphenylsiloxanes), optionally substituted with aliphatic and/or aromatic groups, which are optionally fluorinated, or with functional groups, such as hydroxyl, thiol and/or amine groups. Suitable silicone oils D) are also cyclic siloxanes. The number-average molecular weight of the polydimethylsiloxanes and poly(methylphenylsiloxanes) is preferably in a range from about 1000 to 150 000 g/mol. Preferred cyclic siloxanes have 4- to 8-membered rings. Suitable cyclic siloxanes are commercially available, for example, under the name cyclomethicone.

As volatile silicone oils that may be used in the invention, mention may be made of linear or cyclic silicones containing from 2 to 7 silicon atoms, these silicones optionally comprising alkyl or alkoxy groups containing from 1 to 10 carbon atoms. Mention may be made in particular of octamethylcyclotetrasiloxane, decamethylcyclopentasiloxane, dodecamethylcyclohexasiloxane, heptamethylhexyltrisiloxane, heptamethyloctyltrisiloxane, octamethyltrisiloxane and decamethyltetrasiloxane, and mixtures thereof. Among the non-volatile silicone oils that may be mentioned are non-volatile polydialkylsiloxanes, such as non-volatile polydimethylsiloxanes (PDMS); polydimethylsiloxanes comprising alkyl, alkoxy or phenyl groups, which are pendent or at the end of a silicone chain, these groups containing from 2 to 24 carbon atoms; phenyl silicones, for instance phenyl trimethicones, phenyl dimethicones, phenyl trimethyl-siloxy diphenylsiloxanes, diphenyl dimethicones, diphenyl methyldiphenyltrisiloxanes and polymethylphenylsiloxanes; polysiloxanes modified with fatty acids (especially of $C_8$-$C_{20}$), fatty alcohols (especially of $C_8$-$C_{20}$) or polyoxyalkylenes (especially polyoxy-ethylene and/or polyoxypropylene); amino polysiloxanes; polysiloxanes containing hydroxyl groups; fluoro polysiloxanes comprising a fluorinated group that is pendent or at the end of a silicone chain, containing from 1 to 12 carbon atoms, all or some of the hydrogen atoms of which are replaced with fluorine atoms; and mixtures thereof.

Preferred oil and fat components D) are chosen from paraffin and paraffin oils; vaseline; natural fats and oils, such as castor oil, soya oil, peanut oil, olive oil, sunflower oil, sesame oil, avocado oil, cocoa butter, almond oil, peach kernel oil, ricinus oil, cod-liver oil, pig fat, spermaceti, spermaceti oil, sperm oil, wheatgerm oil, macadamia nut oil, evening primrose oil, jojoba oil; fatty alcohols, such as lauryl alcohol, myristyl alcohol, cetyl alcohol, stearyl alcohol, oleyl alcohol, cetyl alcohol; fatty acids, such as myristic acid, stearic acid, palmitic acid, oleic acid, linoleic acid, linolenic acid and saturated, unsaturated and substituted fatty acids different therefrom; waxes, such as beeswax, carnauba wax, candililla wax, spermaceti, and mixtures of the abovementioned oil and fat components.

Suitable cosmetically and pharmaceutically compatible oil and fat components D) are described in Karl-Heinz Schrader, Grundlagen and Rezepturen der Kosmetika [Fundamentals and formulations of cosmetics], 2nd edition, Verlag Hüthig, Heidelberg, pp. 319-355, which is hereby incorporated by reference.

Suitable cosmetically active substances C) are, for example, skin and hair pigmentation agents, tanning agents, bleaches, keratin-hardening substances, antimicrobial active substances, photofilter active substances, repellent active substances, hyperemic substances, keratolytic and keratoplastic substances, antidandruff active substances, antiphlogistics, keratinizing substances, active substances which act as antioxidants and/or as free-radical scavengers, skin moisturizing or humectant substances, refatting active substances, deodorizing active substances, sebostatic active substances, plant extracts, antierythimatous or antiallergic active substances and mixtures thereof.

Artificially skin-tanning active substances C) which are suitable for tanning the skin without natural or artificial irradiation with UV rays are, for example, dihydroxyacetone, alloxan and walnut shell extract. Suitable keratin-hardening substances are generally active substances as are also used in antiperspirants, such as, for example, potassium aluminum sulfate, aluminum hydroxychloride, aluminum lactate, etc. Antimicrobial active substances are used in order to destroy microorganisms and/or to inhibit their growth and thus serve both as preservatives and also as deodorizing substance which reduces the formation or the intensity of body odor. These include, for example, customary preservatives known to the person skilled in the art, such as p-hydroxybenzoates, imidazolidinylurea, formaldehyde, sorbic acid, benzoic acid, salicylic acid, etc. Such deodorizing substances are, for example, zinc ricinoleate, triclosan, undecylenic acid alkylolamides, triethyl citrate, chlorhexidine etc. Suitable photofilter active substances are substances which absorb UV rays in the UV-B and/or UV-A region. Suitable UV filters are those specified above. Also suitable are p-aminobenzoic esters, cinnamic esters, benzophenones, camphor derivatives, and pigments which stop UV rays, such as titanium dioxide, talc and zinc oxide. Suitable repellent active substances are compounds which are able to keep or drive certain animals, in particular insects, away from people. These include, for example, 2-ethyl-1,3-hexanediol, N,N-diethyl-m-toluamide, etc. Suitable hyperemic substances which stimulate blood flow in the skin are, for example, essential oils, such as dwarf-pine, lavender, rosemary, juniper berry, horse chestnut extract, birch leaf extract, hay flower extract, ethyl acetate, camphor, menthol, peppermint oil, rosemary extract, eucalyptus oil, etc. Suitable keratolytic and keratoplastic substances are, for example, salicylic acid, calcium thioglycolate, thioglycolic acid and its salts, sulfur, etc. Suitable antidandruff active substances are, for example, sulfur, sulfur polyethylene glycol sorbitan monooleate, sulfur ricinol polyethoxylate, zinc pyrithione, aluminum pyrithione, etc. Suitable antiphlogistics, which counteract skin irritations, are, for example, allantoin, bisabolol, dragosantol, camomile extract, panthenol, etc.

The compositions according to the invention can comprise, as active substance C) at least one polymer. These include, very generally, anionic, cationic, amphoteric and neutral polymers.

Suitable anionic polymers C) for the personal care compositions according to the invention are generally all anionic polymers known for this application. The composition according to the invention preferably comprises at least one soluble or dispersed anionic polymer. The anionic polymers that may be employed include, but are not limited to, polymers comprising groups derived from carboxylic acids, sulfonic acids or phosphoric acids. Preferably, the anionic polymers have a number-average molecular mass in a range from 500 to 5 000 000.

The anionic polymers C) used in the personal care compositions according to the invention are preferably selected from:

A) Homo- or copolymers of acrylic or methacrylic acid or salts thereof. Examples are the products sold under the names VERSICOL® E or K by the company Allied Colloid and ULTRAHOLD® by BASF SE. Further preferred anionic polymers C) are the copolymers of acrylic acid and acrylamide and salts thereof. Examples are the products sold in the form of their sodium salt under the names RETEN® 421, 423 or 425 by the company Hercules. Further preferred anionic polymers C) are the sodium salts of polyhydroxycarboxylic acids;

B) Copolymers of acrylic or methacrylic acids with a monoethylenic monomer, such as ethylene, styrene, vinyl esters and acrylic or methacrylic acid esters, optionally grafted onto a polyalkylene glycol, such as polyethylene glycol and optionally crosslinked. Such polymers are described, for example, in French patent 1 222 944 and German patent application No. 2 330 956. Suitable are also copolymers whose polymer chain comprises acrylamide units that are optionally N-alkylated and/or hydroxyalkylated. Examples are the polymers described, e.g. in the Luxembourg patent applications 75370 and 75371 or sold under the name QUADRAMER® by the company American Cyanamid. Suitable are also copolymers of acrylic acid and at least one ($C_1$-$C_4$)alkyl methacrylate, the copolymer of methacrylic acid and ethyl acrylate sold under the name LUVIMER® MAE® by BASF SE; the terpolymer of tert-butyl acrylate, ethyl acrylate and methacrylic acid sold under the name LUVIMER® 100 P LUVIMER® 36 D and LUVIMER® 30 E by BASF SE, the copolymer of N-tert.-butylacrylamide, ethyl acrylate, acrylic acid (Ultrahold strong);

C) Copolymers derived from crotonic acid, such as those whose chain comprises vinyl acetate or propionate units and optionally other monomers, such as allylic or methallylic esters, vinyl ether or vinyl ester of a saturated, linear or branched carboxylic acid comprising a long hydrocarbon-based chain, such as those comprising at least 5 carbon atoms, it being possible for these polymers to be grafted and/or crosslinked, or alternatively a vinyl, allylic or methallylic ester of an [alpha]- or [beta]-cyclic carboxylic acid. Preferred copolymers of vinyl acetate, crotonic acid and optionally at least one further vinyl ester are the Luviset® trademarks of BASF SE. Such polymers are also described, inter alia, in French patents 1 222 944, 1 580 545, 2 265 782, 2 265 781, 1 564 110 and 2 439 798. Further commercial products falling within this category are the resins 28-29-30, 26-13-14 and 28-13-10 sold by National Starch;

D) Polymers derived from maleic, fumaric or itaconic acids or anhydrides with vinyl esters, vinyl ethers, vinyl halides, phenylvinyl derivatives or acrylic acid and its esters. The polymers of this category may be esterified. Such polymers are described e.g. in U.S. Pat. Nos. 2,047,398, 2,723,248, and 2,102,113 and GB patent 839 805. Suitable commercially available products are e.g. polymers sold under the names GANTREZ® AN or ES by the company ISP. Polymers also falling within this category are the copolymers of maleic, citraconic or itaconic anhydrides and of an allylic or methallylic ester optionally comprising an acrylamide or methacrylamide group, an [alpha]-olefin, acrylic or methacrylic esters, acrylic or methacrylic acid or vinylpyrrolidone in their chain, the anhydride functions being monoesterified or monoamidated. These polymers are described, for example, in French patents 2 350 384 and 2 357 241 by the applicant;

E) Polyacrylamides Comprising Carboxylate Groups;

F) Polymers comprising sulfonic groups are polymers comprising vinylsulfonic, styrenesulfonic, naphthalenesulfonic or acrylamidoalkylsulfonic units. These polymers can be chosen, for example, from: polyvinylsulfonic acid salts with a molecular weight in a range from 1000 to 100 000, and also copolymers with an unsaturated comonomer, such as acrylic or methacrylic acids and esters thereof, and also acrylamide or derivatives thereof, vinyl ethers and vinylpyrrolidone; polystyrenesulfonic acid salts, the sodium salts having a molecular weight in a range from 500 000 to 100 000, sold, respectively, under the names FLEXAN® 500 and FLEXAN® 130 by National Starch. These compounds are described in patent FR 2 198 719; and polyacrylamidesulfonic acid salts, such as those mentioned in U.S. Pat. No. 4,128,631 and, for example, polyacrylamidoethylpropanesulfonic acid sold under the name COSMEDIA POLYMER® HSP 1180 by Henkel.

Preferred examples of anionic polymers C) are homopolymers and copolymers of acrylic acid and methacrylic acid or salts thereof, copolymers of acrylic acid and acrylamide and salts thereof; sodium salts of polyhydroxycarboxylic acids, water-soluble or water-dispersible polyesters, polyurethanes, e.g. Luviset PUR® from BASF, and polyureas. Particularly suitable polymers are copolymers of t-butyl acrylate, ethyl acrylate, methacrylic acid (e.g. Luvimer® 100P), copolymers of ethyl acrylate and methacrylic acid (e.g. Luvimer® MAE), copolymers of N-tert-butylacrylamide, ethyl acrylate, acrylic acid (Ultrahold® 8, strong), copolymers of vinyl acetate, crotonic acid and if appropriate further vinyl esters (e.g. Luviset® grades), maleic anhydride copolymers, if appropriate reacted with alcohol, anionic polysiloxanes, e.g. carboxyfunctional ones, t-butyl acrylate, methacrylic acid (e.g. Luviskol® VBM), copolymers of acrylic acid and methacrylic acid with hydrophobic monomers, such as, for example, $C_4$-$C_{30}$-alkyl esters of (meth) acrylic acid, $C_4$-$C_{30}$-alkylvinyl esters, $C_4$-$C_{30}$-alkyl vinyl ethers and hyaluronic acid. Examples of anionic polymers are also vinyl acetate/crotonic acid copolymers, as are sold, for example, under the names Resyn® (National Starch) and Gafset® (GAF), and vinylpyrrolidone/vinyl acrylate copolymers obtainable, for example, under the trade name Luviflex® (BASF). Further suitable polymers are the vinylpyrrolidone/acrylate terpolymer obtainable under the name Luviflex® VBM-35 (BASF) and polyamides containing sodium sulfonate or polyesters containing sodium sulfonate. Also suitable are vinylpyrrolidone/ethyl methacrylate/methacrylic acid copolymers, as are sold by Stepan under the names Stepanhold-Extra and —R1, and the Carboset® grades from BF Goodrich. A further preferred example of an anionic polymer C) is a methyl methacrylate/methacrylic acid/acrylic acid/urethane acrylate copolymer. Those polymers are commercially available as Luviset Shape® (INCI Name: Polyacrylate-22) from BASF SE. Luviset Shape is designed e.g. for aqueous hair sprays to provide a fast-drying, non-tacky, long-lasting hold.

Suitable cationic polymers C) are polymers different from the imidazolium compounds according to the invention (=component A). The cationic polymer C) may be chosen in principle from all cationic polymers known to a person skilled in the art as suitable for cosmetic compositions. Cationic polymers for compositions for improving the cosmetic properties of the hair are for example those described in patent applications EP-A-0 337 354 FR-A-2 270 846, FR-2 383 660, FR-2 598 611, FR-2 470 596 and FR-2 519 863. For the purposes of the present invention, the term "cationic polymer" denotes any polymer comprising at least one cationic group or at least one cationogenic group that may be ionized into a cationic group. The at least one cationic polymer may be chosen from those containing units comprising primary, secondary, tertiary, and/or quaternary amine groups that either may form part of the main polymer chain or may be borne by a side substituent directly attached thereto.

Suitable cationic polymers C) are, for example:
(1) Homopolymers or copolymers derived from acrylic or methacrylic esters or amides and comprising at least one of the units of the following formulae:

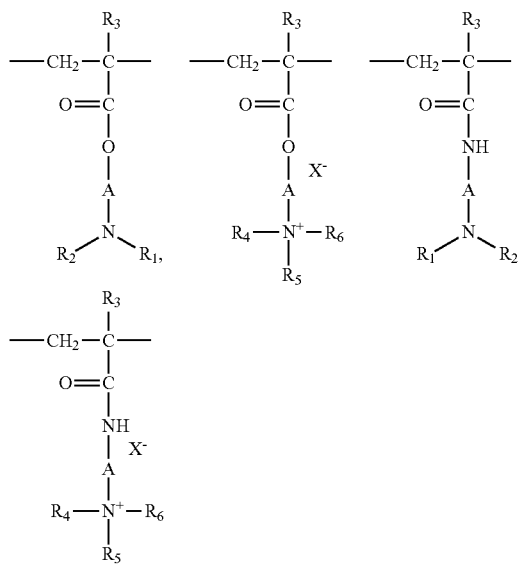

wherein:
$R_3$, which may be identical or different, is chosen from a hydrogen atom and a $CH_3$ radical;
A, which may be identical or different, is chosen from linear or branched alkyl groups comprising from 1 to 6 carbon atoms, for example from 2 to 3 carbon atoms, and hydroxyalkyl groups comprising from 1 to 4 carbon atoms;
$R_4$, $R_5$ and $R_6$, which may be identical or different, are chosen from alkyl groups comprising from 1 to 18 carbon atoms and a benzyl radical, and in at least one embodiment, $R_4$, $R_5$ and $R_6$, which may be identical or different, are chosen from alkyl groups comprising from 1 to 6 carbon atoms;
$R_1$ and $R_2$, which may be identical or different, are chosen from hydrogen and alkyl groups comprising from 1 to 6 carbon atoms, for example methyl or ethyl; and
$X^-$ is chosen from anions derived from a mineral or organic acid, such as a methosulfate anion, and halides, such as chloride or bromide.

The copolymers of group (1) may also comprise at least one unit derived from comonomers that may be chosen from the family of acrylamides, methacrylamides, diacetone acrylamides, acrylamides, and methacrylamides substituted on the nitrogen with lower ($C_1$-$C_4$)alkyls, acrylic or methacrylic acids or esters thereof, vinyllactams, such as vinylpyrrolidone or vinylcaprolactam, and vinyl esters.

Suitable members of group (1) are:
Copolymers of acrylamide and of dimethylaminoethyl methacrylate quaternized with dimethyl sulfate or with a dimethyl halide,
the copolymers of acrylamide and of methacryloyloxyethyltrimethylammonium chloride described, for example, in EP-A-0 080 976,
the copolymers of acrylamide and of methacryloyloxyethyltrimethylammonium methosulfate,
quaternized or nonquaternized vinylpyrrolidone/dialkylaminoalkyl acrylate or methacrylate copolymers, such as those described in FR patents 2 077 143 and 2 393 573,
dimethylaminoethyl methacrylate/vinylcaprolactam/vinylpyrrolidone terpolymers,
vinylpyrrolidone/methacrylamidopropyldimethylamine copolymers, and
quaternized vinylpyrrolidone/dimethylaminopropylmethacrylamide copolymers.
(2) Cationic polysaccharides, for example non-limiting mention may be made of cationic celluloses and cationic galactomannan gums. In at least one embodiment, the cationic polysaccharides are cellulose ether derivatives comprising quaternary ammonium groups, cationic cellulose copolymers or cellulose derivatives grafted with a water-soluble quaternary ammonium monomer and cationic galactomannan gums.
(3) Polymers comprising piperazinyl units and divalent alkylene or hydroxyalkylene radicals comprising straight or branched chains, optionally interrupted by oxygen, sulfur or nitrogen atoms or by aromatic or heterocyclic rings, and also the oxidation and/or quaternization products of these polymers.
(4) Water-soluble polyamino amides prepared, as non-limiting example, by polycondensation of an acidic compound with a polyamine; these polyamino amides can be cross-linked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound which is reactive with a bis-halohydrin, a bis-azetidinium, a bis-haloacyidiamine, a bis-alkyl halide, an epihalohydrin, a diepoxide or a bis-unsaturated derivative; the crosslinking agent being used in proportions ranging from 0.025 to 0.35 mol per amine group of the polyamino amide; these polyamino amides can be alkylated or, if they contain at least one tertiary amine function, they can be quaternized.
(5) Polyaminoamide derivatives resulting from the condensation of polyalkylene polyamines with polycarboxylic acids followed by alkylation with difunctional agents. Non-limiting mention may be made, for example, of adipic acid/dialkylamino-hydroxyalkyldialkylenetriamine polymers wherein the alkyl radical comprises from 1 to 4 carbon atoms, such as methyl, ethyl or propyl. Among these derivatives, non-limiting mention may be made of the adipic acid/dimethylaminohydroxypropyl/diethylenetriamine polymers.

(6) Polymers obtained by reaction of a polyalkylene polyamine comprising two primary amine groups and at least one secondary amine group with a dicarboxylic acid chosen from diglycolic acid and saturated aliphatic dicarboxylic acids comprising from 3 to 8 carbon atoms.

(7) Cyclopolymers of alkyldiallylamine or of dialkyldiallylammonium, such as the homopolymers or copolymers comprising, as main constituent of the chain, units corresponding to formula

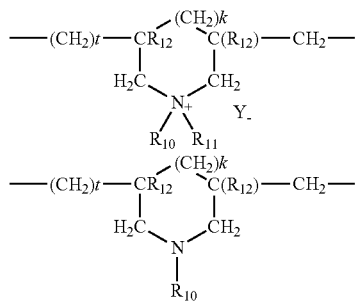

wherein
k and t are equal to 0 or 1, the sum k+t being equal to 1;
$R_{12}$ is chosen from a hydrogen atom and a methyl radical;
$R_{10}$ and $R_{11}$, which may be identical or different, are chosen from alkyl groups comprising from 1 to 6 carbon atoms, hydroxyalkyl groups wherein the alkyl group, for example, comprises from 1 to 5 carbon atoms, and lower ($C_1$-$C_4$) amidoalkyl groups, or $R_{10}$ and $R_{11}$, together with the nitrogen atom to which they are attached, are chosen from heterocyclic groups such as piperidyl or morpholinyl; and
$Y^-$ is an anion such as bromide, chloride, acetate, borate, citrate, tartrate, bisulfate, bisulfite, sulfate or phosphate.

Such polymers (7) are described, for example, in FR patent 2 080 759 and in its Certificate of Addition 2 190 406.

In at least one embodiment, $R_{10}$ and $R_{11}$, which may be identical or different, are chosen from alkyl groups comprising from 1 to 4 carbon atoms.

Among the polymers defined above, non-limiting mention may be made, for example, of the dimethyldiallylammonium chloride homopolymers sold under the name MERQUAT® 100 by the company Nalco (and its homologs of low weight-average molar mass) and copolymers of diallyldimethylammonium chloride and of acrylamide.

(8) Quaternary diammonium polymers containing repeating units corresponding to the formula (6):

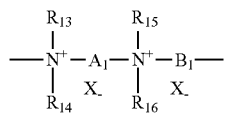

wherein:
$R_{13}$, $R^1a$, $R_{15}$ and $R_{16}$, which may be identical or different, are chosen from aliphatic, alicyclic or arylaliphatic radicals comprising from 1 to 20 carbon atoms, and lower hydroxyalkylaliphatic radicals such as hydroxyethyl, or $R_{13}$, $R_{14}$, $R_{15}$ and $R_{16}$, together or separately, constitute, with the nitrogen atoms to which they are attached, heterocycles optionally comprising a second heteroatom other than nitrogen, or $R_{13}$, $R_{14}$, $R_{15}$ and $R_{16}$ are chosen from a linear or branched ($C_1$-$C_6$)alkyl radical substituted with a nitrile, ester, acyl, or amide group, and a group —CO—O—$R_{17}$-D or —CO—NH—$R_{17}$-D, wherein $R_{17}$ is an alkylene and D is a quaternary ammonium group;

$A_1$ and $B_1$ are chosen from polymethylene groups comprising from 2 to 20 carbon atoms, wherein the polymethylene groups may be linear or branched, saturated or unsaturated, and wherein the polymethylene groups may comprise, linked to or intercalated in the main chain, at least one aromatic ring, at least one oxygen or sulfur atom, or sulfoxide, sulfone, disulfide, amino, alkylamino, hydroxyl, quaternary ammonium, ureido, amide or ester groups, and $X^-$ is an anion derived from a mineral or organic acid;
or $A_1$, $R_{13}$ and $R_{15}$ can form, with the two nitrogen atoms to which they are attached, a piperazine ring;
in addition, if $A_1$ is chosen from a linear or branched, saturated or unsaturated alkylene or hydroxyalkylene radical, Bi is chosen from polymethylene groups comprising from 2 to 20 carbon atoms, wherein the polymethylene groups may be linear or branched, saturated or unsaturated, and wherein the polymethylene groups may comprise, linked to or intercalated in the main chain, at least one aromatic ring, at least one oxygen or sulfur atom, sulfoxide, sulfone, disulfide, amino, alkylamino, hydroxyl, quaternary ammonium, ureido, amide or ester groups, and a group $(CH_2)_n$—CO-D-OC—$(CH_2)_n$—;
wherein D is chosen from:
a) a glycol residue of formula: —O—Z—O—, wherein Z is chosen from a linear or branched hydrocarbon-based radical, and a group corresponding to one of the following formulae:

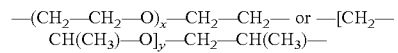

wherein x and y are integers ranging from 1 to 4, which is a defined and unique degree of polymerization or an average degree of polymerization;
b) a bis-secondary diamine residue, such as a piperazine derivative;
c) a bis-primary diamine residue of formula: —NH—Y—NH—, wherein Y is chosen from a linear or branched hydrocarbon-based-radical, and the divalent radical

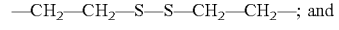

d) a ureylene group of formula: —NH—CO—NH—; and
n is an integer ranging from 1 to 20, for example from 1 to 10.

In at least one embodiment, $X^-$ is an anion such as chloride or bromide.

These polymers can have a number-average molar mass in a range from 1000 to 100 000.

In at least one embodiment, polymers that consist of repeating units corresponding to formula (a) are used:

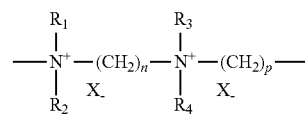

wherein
$R_1$, $R_2$, $R_3$ and $R_4$, which may be identical or different, are chosen from alkyl and hydroxyalkyl radicals comprising from 1 to 4 carbon atoms, n and p are integers ranging from 2 to 20, and $X^-$ is an anion derived from a mineral or organic acid.

In at least one embodiment, $R_1$, $R_2$, $R_3$ and $R_4$ are chosen from a methyl radical and n=3, p=6 and X=Cl. Such a polymer is known as hexadimethrine chloride according to the INCI (CTFA) nomenclature.

(9) Polyquaternary ammonium polymers comprised of units of formula (7):

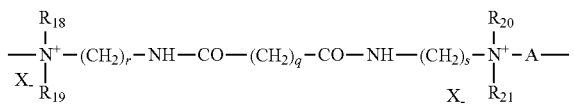

wherein:
$R_{18}$, $R_{19}$, $R_{20}$ and $R_{21}$, which may be identical or different, are chosen from a hydrogen atom, and methyl, ethyl, propyl, [beta]-hydroxyethyl, [beta]-hydroxypropyl and —CH$_2$CH$_2$(OCH$_2$CH$_2$)$_p$OH radicals, wherein p is equal to 0 or to an integer ranging from 1 to 6, with the proviso that $R_{18}$, $R_{19}$, $R^2o$ and $R_{21}$ do not simultaneously represent a hydrogen atom,
r and s, which may be identical or different, are integers ranging from 1 to 6,
q is an integer ranging from 1 to 34,
$X^-$ is an anion such as a halide,
A is chosen from a dihalide radical and —CH$_2$—CH$_2$—O—CH$_2$—CH$_2$—. In at least one embodiment, A is —CH$_2$—CH$_2$—O—CH$_2$—CH$_2$—.

Non-limiting examples of such compounds are described in patent application EP-A-122 324.

Non-limiting examples include the products MIRAPOL® A15, MIRAPOL® (R) AD1, MIRAPOL® AZ1 and MIRAPOL® 175 sold by the company Miranol.

(10) Quaternary polymers of vinyllactam (vinylpyrrolidone and/or vinylcaprolactam) and of vinylimidazole.

(11) Crosslinked polymers of methacryloyloxy(C$_1$-C$_4$)alkyltri(C$_1$-C$_4$)alkyl-ammonium salts, such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with a compound containing olefinic unsaturation, for example methylenebisacrylamide.

Other cationic polymers C) that can be used in the context of the disclosure are cationic proteins or cationic protein hydrolysates, polyalkyleneimines, for example non-limiting mention may be made of polyethyleneimines, polymers containing vinylpyridine or vinylpyridinium units, condensates of polyamines and of epichlorohydrin, quaternary polyureylenes and chitin derivatives.

Preferred cationic polymers C) are polymers with the INCI name Polyquaternium, e.g. copolymers of vinylpyrrolidone/N-vinylimidazolium salts (Luviquat® FC, Luviquat® HM, Luviquat® MS, Luviset Clear®, Luviquat Supreme®, Luviquat® Care), copolymers of N-vinylpyrrolidone/dimethylaminoethyl methacrylate, quaternized with diethyl sulfate (Luviquat® PQ 11), copolymers of N-vinylcaprolactam/N-vinylpyrrolidone/N-vinylimidazolium salts (Luviquat® Hold); cationic cellulose derivatives (Polyquaternium-4 and –10), acrylamido copolymers (Polyquaternium-7) and chitosan. Suitable cationic (quaternized) polymers are also Merquat® (polymer based on dimethyldiallylammonium chloride), Gafquat® (quaternary polymers which are formed by reacting polyvinylpyrrolidone with quaternary ammonium compounds), Polymer JR (hydroxyethylcellulose with cationic groups) and cationic polymers based on plants, e.g. guar polymers, such as the Jaguar® grades from Rhodia.

Suitable neutral polymers C) are e.g. polyvinylpyrrolidones, copolymers of N-vinylpyrrolidone and vinyl acetate and/or vinyl propionate, polysiloxanes, polyvinylcaprolactam and other copolymers with N-vinylpyrrolidone, polyethyleneimines and salts thereof, polyvinylamines and salts thereof, cellulose derivatives, polyaspartic acid salts and derivatives. These include, for example, Luviflex® Swing (partially saponified copolymer of polyvinyl acetate and polyethylene glycol, BASF).

Suitable polymers C) are also nonionic, water-soluble or water-dispersible polymers or oligomers, such as polyvinylcaprolactam, e.g. Luviskol® Plus (BASF), or polyvinylpyrrolidone and copolymers thereof, in particular with vinyl esters, such as vinyl acetate, e.g. Luviskol® VA 37 (BASF); polyamides, e.g. based on itaconic acid and aliphatic diamines, as are described, for example, in DE-A-43 33 238.

Suitable polymers C) are also amphoteric or zwitterionic polymers, such as the octylacrylamide/methyl methacrylate/tert-butylaminoethyl methacrylate/2-hydroxypropyl methacrylate copolymers obtainable under the names Amphomer® (National Starch), and zwitterionic polymers, as are disclosed, for example, in the German patent applications DE 39 29 973, DE 21 50 557, DE 28 17 369 and DE 37 08 451. Acrylamidopropyltrimethylammonium chloride/acrylic acid or methacrylic acid copolymers and alkali metal and ammonium salts thereof are preferred zwitterionic polymers. Further suitable zwitterionic polymers are methacroylethylbetaine/methacrylate copolymers, which are commercially available under the name Amersette® (AMERCHOL), and copolymers of hydroxyethyl methacrylate, methyl methacrylate, N,N-dimethylaminoethyl methacrylate and acrylic acid (Jordapon®).

Suitable polymers C) are also nonionic, anionic, cationic or amphoteric siloxane-containing, polymers. Suitable are in principle organomodified and non-organomodified silicones. Siloxane containing polymers are typical cosmetically acceptable agents that are beneficial to keratin material. The silicones that can be used in accordance with the invention may be soluble or insoluble in the composition. They may be in the form of oils, waxes, resins or gums. Non-limiting examples of the organopolysiloxanes are defined in greater detail in Walter Noll's "Chemistry and Technology of Silicones" (1968) Academic Press. They can be volatile or nonvolatile. With regard to volatile silicones, reference is made to the volatile silicone oils mentioned above. Volatile silicones are preferably chosen from those having a boiling point in a range from 60° C. to 260° C.

Examples of volatile silicones are:
(i) Cyclic silicones comprising from 3 to 7 and for example from 4 to 5 silicon atoms. These are, for example, but not limited to, octamethylcyclotetrasiloxane sold under the name Volatile Silicone 7207 by Union Carbide or SILBIONE® 70045 V 2 by Rhodia, decamethylcyclopentasiloxane sold under the name Volatile Silicone 7158 by Union Carbide, and SILBIONE® 70045 V 5 by Rhodia, and mixtures thereof.

Suitable are also cyclocopolymers of the dimethylsiloxane/methylalkylsiloxane type, such as Volatile Silicone FZ 3109 sold by the company Union Carbide, having the general chemical structure:

 with

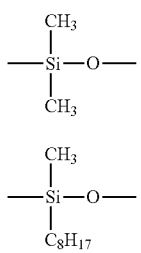

(D)

(D)'

Suitable are also mixtures of cyclic silicones with organosilicone compounds, such as the mixture of octamethylcyclotetrasiloxane and tetratrimethylsilylpentaerythritol (50/50) and the mixture of octamethylcyclotetrasiloxane and oxy-1,1'-bis(2,2,2',2',3,3'-hexa-trimethylsilyloxy)neopentane;

(ii) Linear volatile silicones comprising from 2 to 9 silicon atoms and having a viscosity of less than or equal to $5 \times 10^{-6}$ m$^2$/s at 25° C. A non-limiting example is decamethyltetrasiloxane sold under the name SH 200 by the company Toray Silicone. Silicones belonging to this category are also described in Todd & Byers "Volatile Silicone Fluids for Cosmetics", Cosmetics and Toiletries, Vol. 91, Jan. 76, pp. 27-32.

Further examples of nonvolatile silicones that are suitable as component C) include polyalkylsiloxanes, polyarylsiloxanes, polyalkylarylsiloxanes, silicone gums and resins, polyorganosiloxanes modified with organofunctional groups, and also mixtures thereof.

Organomodified silicones that can be used in accordance with the invention are silicones as defined above and comprising in their structure at least one organofunctional group attached via a hydrocarbon-based group.

Examples of organomodified silicones are polyorganosiloxanes comprising:

Polyethyleneoxy and/or polypropyleneoxy groups optionally comprising ($C_6$-$C_{24}$)alkyl groups. Such polyorganosiloxanes are commercially available, such as the products known as dimethicone copolyol sold by the company Dow Corning under the name DC 1248, SILWET® L 722, L 7500, L 77 and L 711 by the company Union Carbide, and the ($C_{12}$alkyl)methicone copolyol sold by the company Dow Corning under the name Q2 5200; suitable nonionic siloxane-containing polymers C) are also polyether siloxanes, such as the Tegopren® trademarks (Goldschmidt) or Belsil® trademarks (Wacker);

substituted or unsubstituted amine groups. Such polyorganosiloxanes with substituted or unsubstituted amine groups are commercially available, such as the products sold under the name GP 4 Silicone Fluid and GP 7100 by the company Genesee, or the products sold under the names Q2 8220 and Dow Corning 929 or 939 by the company Dow Corning. The substituted amine groups are, for example, ($C_1$-$C_4$)aminoalkyl groups;

thiol groups. Such polyorganosiloxanes with thiol groups are commercially available, e.g. the products sold under the names GP 72 A and GP 71 from Genesee;

alkoxylated groups. Such polyorganosiloxanes with alkoxylated groups are commercially available, such as the product sold under the name Silicone Copolymer F-755 by SWS Silicones and ABIL WAX® 2428, 2434 and 2440 by the company Goldschmidt;

hydroxylated groups. Such polyorganosiloxanes with alkoxylated groups are commercially available, e.g. the polyorganosiloxanes comprising a hydroxyalkyl function, described in French patent application FR-A-85/16334;

acyloxyalkyl groups. Such polyorganosiloxanes with acyloxyalkyl groups are commercially available, e.g. the polyorganosiloxanes described in U.S. Pat. No. 4,957,732;

anionic groups of the carboxylic acid type. Such polyorganosiloxanes with anionic groups of the carboxylic acid type are commercially available, e.g. the products described in patent EP 186 507 from the company Chisso Corporation;

anionic groups of the alkylcarboxylic type. Such polyorganosiloxanes with anionic groups of the alkylcarboxylic type are commercially available, e.g. those present in the product X-22-3701 E from the company Shin-Etsu;

2-hydroxyalkyl sulfonate groups;

2-hydroxyalkyl thiosulfate groups. Such polyorganosiloxanes with 2-hydroxyalkyl thiosulfate are commercially available, e.g. such as the products sold by the company Goldschmidt under the names ABIL® S201 and ABIL® S255; and hydroxyacylamino groups. Such polyorganosiloxanes with 2-hydroxyalkyl thiosulfate are commercially available, e.g. the polyorganosiloxanes described in patent application EP 342 834. Non-limiting mention may be made, for example, of the product Q2-8413 from the company Dow Corning.

The personal care compositions according to the invention may comprise as component C) at least one polyisobutene or poly(α-olefin), chosen from those that are well known in the art. A preferred product is Luvitol Lite (INCI Name: Hydrogenated Polyisobutene) from BASF SE. Polyisobutenes and poly(α-olefins) can be used advantageously as a hair and skin conditioner. E.g. Luvitol Lite provides on the skin a pleasant soft feeling without being oily. Polyisobutenes and poly(α-olefins) can also be used as a conditioner in hair products, such as shampoos and body washes, hair styling and conditioning applications. They contribute to properties, such as manageability, wet and dry comb, and shine. Finally, below is a simple example of Luvitol Lite's use in a shampoo type formula with more than 60% oil, which, I suspect, does not foam very much.

In addition to the abovementioned constituents, the personal care compositions according to the invention can also comprise at least one surface-active substance as component D). The surface-active substances include surfactants, dispersing agents and wetting agents.

Suitable are anionic, cationic, nonionic and amphoteric surfactants, including polymer surfactants and surfactants with heteroatoms in the hydrophobic group.

The following list of suitable and preferred surfactants is not limited to the application in personal care compositions but is applicable to all biocide compositions according to the invention.

Non-limiting examples of anionic surfactants useful in embodiments of the compositions of the present invention are disclosed in McCutcheon's, Detergents and Emulsifiers, North American edition (1990), published by The Manufacturing Confectioner Publishing Co.; McCutcheon's, Functional Materials, North American Edition (1992); and U.S. Pat. No. 3,929,678, to Laughlin et al., issued Dec. 30, 1975, all of which are incorporated herein by reference.

Non-limiting examples of anionic surfactants useful in embodiments of the compositions of the present invention are disclosed in McCutcheon's, Detergents and Emulsifiers, North American edition (1990), published by The Manufacturing Confectioner Publishing Co.; McCutcheon's, Functional Materials, North American Edition (1992); and U.S. Pat. No. 3,929,678, to Laughlin et al., issued Dec. 30, 1975, all of which are incorporated herein by reference.

Nonlimiting examples of anionic surfactants include alkyl and alkyl ether sulfates; sulfated monoglycerides; sulfonated olefins; alkyl aryl sulfonates; primary or secondary alkane sulfonates; alkyl sulfosuccinates; acyl taurates; acyl isethionates; alkyl glycerylether sulfonate; sulfonated methyl esters; sulfonated fatty acids; alkyl phosphates; acyl glutamates; acyl sarcosinates; alkyl sulfoacetates; acylated peptides; alkyl ether carboxylates; acyl lactylates; anionic fluorosurfactants; and mixtures thereof. Mixtures of anionic surfactants can be used effectively in some embodiments of the present disclosure.

Suitable anionic surfactants for use in personal care compositions according to the invention include alkyl sulfates and alkyl ether sulfates. Suitable components have the general formulae $R^{11}$—O—$SO_3$-M and $R^{11}$—($CH_2H_4$—O)$_x$—O—$SO_3$-M, wherein $R^{11}$ is a saturated or unsaturated, branched or unbranched alkyl group from about 8 to about 24 carbon atoms, x is 1 to 10, and M is a water-soluble cation such as ammonium, sodium, potassium, magnesium, triethanolamine, diethanolamine and monoethanolamine. The alkyl sulfates are typically made by the sulfation of monohydric alcohols (having from about 8 to about 24 carbon atoms) using sulfur trioxide or other known sulfation technique. The alkyl ether sulfates are typically made as condensation products of ethylene oxide and monohydric alcohols (having from about 8 to about 24 carbon atoms) and then sulfated. These alcohols can be derived from fats, for example, coconut oil or tallow, or can be synthetic. Specific examples of alkyl sulfates which are useful in some embodiments of inventive cleanser compositions are sodium, ammonium, potassium, magnesium, or TEA salts of lauryl or myristyl sulfate. Examples of alkyl ether sulfates include ammonium, sodium, magnesium, or TEA laureth-3 sulfate.

Another suitable class of anionic surfactants are sulfated monoglycerides of the general formula $R^{12}$—CO—O—$CH_2$—C(OH)H—$CH_2$—O—$SO_3$-M, wherein $R^{12}$ is a saturated or unsaturated, branched or unbranched alkyl group from about 8 to about 24 carbon atoms, and M is a water-soluble cation such as ammonium, sodium, potassium, magnesium, triethanolamine, diethanolamine and monoethanolamine. These are typically made by the reaction of glycerin with fatty acids (having from about 8 to about 24 carbon atoms) to form a monoglyceride and the subsequent sulfation of this monoglyceride with sulfur trioxide. An example of a sulfated monoglyceride is sodium cocomonoglyceride sulfate.

Other suitable anionic surfactants include olefin sulfonates of the general formula $R^{13}SO_3$-M, wherein $R^{13}$ is a mono-olefin having from about 12 to about 24 carbon atoms, and M is a water-soluble cation, such as ammonium, sodium, potassium, magnesium, triethanolamine, diethanolamine and monoethanolamine. These compounds can be produced by the sulfonation of -olefins by means of uncomplexed sulfur trioxide, followed by neutralization of the acid reaction mixture in conditions, such that any sulfones which have been formed in the reaction are hydrolyzed to give the corresponding hydroxyalkanesulfonate. An example of a sulfonated olefin is sodium C14/C16-olefin sulfonate.

Other suitable anionic surfactants are the linear alkylbenzene sulfonates of the general formula $R^{14}$—$C_6H_4$—$SO_3$-M, wherein $R^{14}$ is a saturated or unsaturated, branched or unbranched alkyl group from about 8 to about 24 carbon atoms, and M is a water-soluble cation such as ammonium, sodium, potassium, magnesium, triethanolamine, diethanolamine and monoethanolamine. These are formed by the sulfonation of linear alkyl benzene with sulfur trioxide. An example of this anionic surfactant is sodium dodecylbenzene sulfonate.

Further suitable anionic surfactants (in particular for the cleansing compositions) include primary or secondary alkane sulfonates of the form $R^{15}$-$SO_3$-M, wherein $R^{15}$ is a saturated or unsaturated, branched or unbranched alkyl chain from about 8 to about 24 carbon atoms, and M is a water-soluble cation such as ammonium, sodium, potassium, magnesium, triethanolamine, diethanolamine and monoethanolamine. These are commonly formed by the sulfonation of paraffins using sulfur dioxide in the presence of chlorine and ultraviolet light or another known sulfonation method. The sulfonation can occur in either the secondary or primary positions of the alkyl chain. An example of an alkane sulfonate useful herein is alkali metal or ammonium $C_{13}$-$C_{17}$ paraffin sulfonates.

Further suitable anionic surfactants are alkyl sulfosuccinates, which include disodium N-octadecylsulfosuccinamate; diammonium lauryl sulfosuccinate; tetrasodium N-(1,2-dicarboxyethyl)-N-octadecylsulfosuccinate; diamyl ester of sodium sulfosuccinic acid; dihexyl ester of sodium sulfosuccinic acid; and dioctyl esters of sodium sulfosuccinic acid.

Also useful are taurates which are based on taurine, which is also known as 2-aminoethanesulfonic acid. Examples of taurates include N-alkyltaurines, such as the one prepared by reacting dodecylamine with sodium isethionate, according to the teaching of U.S. Pat. No. 2,658,072 which is incorporated herein by reference in its entirety. Other examples of taurine derivatives that are useful in embodiments of the disclosure include the acyl taurines formed by the reaction of n-methyl taurine with fatty acids (having from about 8 to about 24 carbon atoms).

Further suitable anionic surfactants are acyl isethionates. The acyl isethionates typically have the formula $R^{16}$—CO—O—$CH_2$—$CH_2SO_3$-M, wherein $R^{16}$ is a saturated or unsaturated, branched or unbranched alkyl group having from about 10 to about 30 carbon atoms, and M is a cation. These are typically formed by the reaction of fatty acids (having from about 8 to about 30 carbon atoms) with an alkali metal isethionate. Nonlimiting examples of these acyl isethionates include ammonium cocoyl isethionate, sodium cocoyl isethionate, sodium lauroyl isethionate, and mixtures thereof.

Further suitable anionic surfactants are alkylglyceryl ether sulfonates of the form $R^{17}$—$OCH_2$—C(OH)H—$CH_2$—$SO_3$-M, wherein $R^{17}$ is a saturated or unsaturated, branched or unbranched alkyl group from about 8 to about 24 carbon atoms, and M is a water-soluble cation, such as ammonium, sodium, potassium, magnesium, triethanolamine, diethanolamine and monoethanolamine. These can be formed by the reaction of epichlorohydrin and sodium bisulfite with fatty alcohols (having from about 8 to about 24 carbon atoms) or other known methods. One example is sodium cocoglyceryl ether sulfonate.

Further suitable anionic surfactants are sulfonated fatty acids of the general formula $R^{18}$—$CH(SO_4)$—COOH and sulfonated methyl esters of the general formula $R^{18}$—CH($SO_4$)—CO—O—$CH_3$, where $R^{18}$ is a saturated or unsaturated, branched or unbranched alkyl group from about 8 to about 24 carbon atoms. These surfactants are generally formed by the sulfonation of fatty acids or alkyl methyl esters (having from about 8 to about 24 carbon atoms) with sulfur trioxide or by other known sulfonation techniques. Examples include alpha sulfonated coconut fatty acid and lauryl methyl ester.

Further suitable anionic surfactants are phosphates, such as monoalkyl-, dialkyl-, and trialkylphosphate salts formed by the reaction of phosphorous pentoxide with monohydric branched or unbranched alcohols having from about 8 to about 24 carbon atoms. In some embodiments, these anionic materials are also be formed by other known phosphation methods. An example from this class of surfactants is sodium mono or dilaurylphosphate.

Further suitable anionic surfactants are acyl glutamates corresponding to the formula $R^{19}$—CO—N(COOH)—$CH_2CH_2$—$CO_2$-M, wherein $R^{19}$ is a saturated or unsaturated, branched or unbranched alkyl or alkenyl group of about 8 to about 24 carbon atoms, and M is a water soluble cation. Nonlimiting examples of which include sodium lauroyl glutamate and sodium cocoyl glutamate.

Further suitable anionic surfactants are alkanoyl sarcosinates corresponding to the formula $R^{20}$—CON($CH_3$)—$CH_2CH_2$—$CO_2$-M, wherein $R^{20}$ is a saturated or unsaturated, branched or unbranched alkyl or alkenyl group of about 10 to about 20 carbon atoms, and M is a watersoluble cation. Nonlimiting examples of which include sodium lauroyl sarcosinate, sodium cocoyl sarcosinate, and ammonium lauroyl sarcosinate. Other anionic materials include alkyl ether carboxylates corresponding to the formula $R^{21}$—($OCH_2CH_2$)$_x$—$OCH_2$—$CO_2$-M, wherein $R^{21}$ is a saturated or unsaturated, branched or unbranched alkyl or alkenyl group of about 8 to about 24 carbon atoms, x is 1 to 10, and M is a water-soluble cation. Nonlimiting examples of which include sodium laureth carboxylate. Other anionic materials include acyl lactylates corresponding to the formula $R^{22}$—CO—[O—CH($CH_3$)—CO]$_x$—$CO_2$-M, wherein $R^{22}$ is a saturated or unsaturated, branched or unbranched alkyl or alkenyl group of about 8 to about 24 carbon atoms, x is 3, and M is a water-soluble cation, nonlimiting examples of which include sodium cocoyl lactylate. Other anionic materials include the carboxylates, nonlimiting examples of which include sodium lauroyl carboxylate, sodium cocoyl carboxylate, and ammonium lauroyl carboxylate. Anionic fluorosurfactants can also be used. A counter cation, M, counterbalances the negative charge of the anionic surfactant. Some especially suitable counter cations are sodium, potassium, ammonium, monoethanolamine, diethanolamine, and triethanolamine. An especially suitable counter cation is ammonium.

Suitable non-ionic surfactants for use in personal care compositions according to the invention are condensation products of ethylene oxide with various reactive hydrogen-containing compounds reactive therewith having long hydrophobic chains (for example aliphatic chains of about 12-20 carbon atoms) which condensation products ("ethoxamers") contain hydrophilic polyoxyethylene moieties, such as condensation products of poly(ethyleneoxide) with fatty acids, fatty alcohols, fatty amides, polyhydric alcohols (for example sorbitan monostearate) and polypropylene oxide (for example Pluronic a materials). Polyoxamers include for example block copolymers of polyoxyethylene and polyoxypropylene having an average molecular weight from about 3000 to 5000 and a preferred average molecular weight from about 3500 to 4000 and containing about 10 to 80% hydrophilic polyoxyethylene groups, by weight, of the block copolymer (for example Pluronic F127). Other non-ionic surfactants are for example alkyl polyglucosids, alcanolamides, ethers of e.g. fatty acids with ethylene oxid or polyethylenglycol, amine oxides e.g. cocamidopropyla amine oxid.

Suitable amphoteric surfactants for use in personal care compositions according to the invention are secondary or tertiary aliphatic amine derivatives, where the aliphatic chain can be linear or branched and contains at least 8 to 22 carbon atoms and one anionic group, such as carboxylate, sulfonate, sulfate, phosphate or phosphonate. Suitable amphoteric surfactants are also acyl/dialkyl ethylenediamines, such as acylamphoacetate, disodium acylamphodipropionate, sodium acylamphohydroxypropylsulfonate, disodium acylamphodiacetate, sodium acylamphopropionate, where acyl represents either an alkyl or alkenyl, mono- or polyunsaturated residue containing 5 to 29 carbon atoms. Suitable amphoteric surfactants are also N-alkyl amino acids or imino acids, such as aminopropyl alkylglutamide, alkylaminopropionic acid, sodium alkylimino propionate, alkyl glycinates and carboxyglycinates, e.g. sodium cocoglycinate. Suitable amphoteric surfactants are also $C_8$-$C_{18}$-betains, $C_8$-$C_{18}$-sulfobetains, $C_8$-$C_{24}$-alkylamido-$C_1$-$C_4$-alkylene betains, imidazoline carboxylates, alkylamphocarboxycarbonic acids, alkylamphocarbonic acid (for example lauroamphoglycinate) and N-alkyl-β-aminopropionate or N-alkyl-β-iminodi-propionate. Preferably, the amphoteric surfactant comprises $C_{10}$-$C_{20}$-alkylamido-$C_1$-$C_4$-alkylenbetaine and/or coco fatty acid amide propylbetaine.

Suitable thickening polymers useful herein as rheology modifier D) include anionic polymers, cationic polymers, amphoteric polymers and nonionic polymers. The thickening polymers useful herein include, for example, acrylic polymers, polyalkylene glycol polymers having a molecular weight of more than about 10 000, celluloses and derivatives thereof, such as hydroxyethyl cellulose, polyvinylpyrrolidone, polyvinyl alcohol, gums, such as guar gum and xanthan gum, carragenan, pectin, agar, quince seed (*Cyclonia oblonga* Mill), starch (rice, corn, potato, wheat), algae colloids (algae extract), dextran, succinoglucan, pulleran, carboxymethyl starch, methylhydroxypropyl starch, sodium alginate, and alginic acid propylene glycol esters. Neutralizing agents may be included to neutralize the anionic thickening agents described hereinabove. Nonlimiting examples of such neutralizing agents include sodium hydroxide, potassium hydroxide, ammonium hydroxide, monoethanolamine, diethanolamine, triethanolamine, diisopropanolamine, aminomethylpropanol, trimethamine, tetrahydroxypropyl ethylenediamine, and mixtures thereof.

Preferred thickening polymers useful herein as rheology modifier D) include acrylic polymers. Acrylic polymers useful herein include those comprising monomers selected from the group consisting of acrylic acid, salts of acrylic acid, derivatives of acrylic acid, methacrylic acid, salts of methacrylic acid, derivatives of methacrylic acid, and mixtures thereof. The derivatives include, for example, alkyl acrylate, acrylamide, alkyl methacrylate, and methacrylamide. Such acrylic polymers include, for example, cross linked acrylic acid polymers with the CTFA name Carbomer, sodium polyacrylate, polyethylacrylate, polyacrylamide, and acrylic acid/alkyl acrylate copolymers with the CTFA name Acrylates/$C_{10-30}$ Alkyl Acrylate Crosspolymer. Commercially available acrylic polymers highly useful herein include, for example, polyacrylamide with tradename Sepigel 305 available SEPPIC Inc., and Acrylates/$C_{10-30}$ Alkyl Acrylate Crosspolymer having tradenames Pemulen TR-I, Pemulen TR-2, Carbopol 1342, Carbopol 1382, and Carbopol ETD 2020, all available from B. F. Goodrich Company.

Suitable thickening polymers useful herein as rheology modifier D) include also so called associative polymers. Suitable associative polymers are mentioned in the following.

Preferred thickening polymers useful herein as rheology modifier D) are also the following products that are commercially available from BASF SE and Cognis corporation:

Rheocare TTA (2-methyl-2-propenoic acid polymer with butyl 2-propenoate and ethyl 2-propenoate, CAS-No. 31069-81-5), LUVIGEL® grades, inter alia LUVIGEL® advance (cross-linked cationic rheology modifier), LUVIGEL® EM (milky emulsion of sodium acrylates copolymer in caprylic/capric triglyceride and water) and LUVIGEL® STAR (non-ionic, electrolyte tolerant, polyurethane-based associative rheology modifier).

A cationic-compatible liquid rheology modifier that is especially suitable as component D) for the personal care compositions of the invention is a cationic polymer with the INCI name polyacrylate-1 crosspolymer. They are commercially available under the trade mark Carbopol Aqua CC from Noveon Inc. The Polyacrylate-1 Crosspolymer is the product of the polymerization of a mixture of monomers comprising (or constituted of):
a di($C_1$-$C_4$ alkyl)amino($C_1$-$C_6$ alkyl)methacrylate,
at least one (meth)acrylic acid $C_1$-$C_{30}$ alkyl ester,
a polyethoxylated $C_{10}$-$C_{30}$ alkyl methacrylate (20-25 mol of ethylene oxide unit),
a polyethylene glycol/polypropylene glycol 30/5 alkyl ether,
a hydroxyl($C_2$-$C_6$ alkyl)methacrylate, and
an ethylene glycol dimethacrylate.

The imidazolium compounds according to the invention can be employed advantageously in detergent cosmetic compositions employed for cleansing and caring the hair or the skin.

A first special embodiment of the invention is a cosmetic composition, comprising in a cosmetically acceptable medium
at least one imidazolium compound (=component A),
at least one surfactant and
at least one cosmetically acceptable active ingredient that is beneficial to keratin materials.

With regard to suitable and preferred embodiments of component A), reference is made to the aforementioned general definition of the imidazolium compounds employed according to the invention. The at least one imidazolium compound (=component A) may be used in combination with at least one further cationic polymer different from the compounds of component (A). With regard to suitable and preferred additional cationic polymers, reference is made to the cationic polymers mentioned before as component C).

With regard to suitable and preferred surfactants, reference is made to the surfactants mentioned before as component D). Suitable surfactants and in particular combinations of surfactants are disclosed in US 2009/0048132 A1 which is incorporated herein by reference.

The at least one cosmetically acceptable active ingredient that is beneficial to keratin materials is preferably selected from:
(1) hydrolyzed or nonhydrolyzed, modified or unmodified saccharides, oligosaccharides and polysaccharides,
(2) hydrolyzed or nonhydrolyzed, modified or unmodified amino acids, oligopeptides, peptides and proteins,
(3) branched or unbranched fatty acids and alcohols,
(4) animal, plant and mineral waxes,
(5) ceramides and pseudoceramides,
(6) hydroxylated organic acids,
(7) UV-screening agents,
(8) antioxidants and free-radical scavengers,
(9) chelating agents,
(10) antidandruff agents,
(11) seborrhea regulators,
(12) calmatives,
(13) cationic surfactants,
(14) organomodified and non-organomodified silicones,
(15) mineral, plant and animal oils,
(16) polyisobutenes and poly([alpha]-olefins),
(17) fatty esters, for example those comprising from 15 to 50 carbon atoms,
(18) soluble and dispersed anionic polymers, and
(19) soluble and dispersed nonionic polymers, and mixtures thereof.

Suitable compounds (1)-(19) are described in US 2009048132 A1 which is incorporated herein by reference.

A second special embodiment of the invention is a cosmetic composition comprising in a cosmetically acceptable medium
at least one imidazolium compound (=component A), and
at least one associative polymer.

Preferably, the composition according to the second special embodiment further comprises at least one surfactant. With regard to suitable and preferred surfactants, reference is made to the surfactants mentioned before as component D).

Preferably, the composition according to the second special embodiment further comprises at least one conditioning agent. Preferably, the at least one conditioning agent is chosen from silicones, cationic polymers other than the imidazolium compounds of the present disclosure, mineral, plant, and animal oils, ceramides, pseudoceramides, poly-α-olefins, fluoro oils, fluoro waxes, fluoro gums, carboxylic acid esters, etc. Preferably, the at least one conditioning agent is present in an amount ranging from 0.001% to 20% by weight, more preferably 0.01% to 10% by weight, based the total weight of the composition. In particular, the conditioner is a rinse-out or leave-in conditioner.

Preferably, the composition according to the second special embodiment is in the form of a foaming detergent composition or a conditioner. In particular, the foaming detergent composition is a shampoo, shower gel, makeup-removing product, or bubble bath.

With regard to suitable and preferred embodiments of component A), reference is made to the aforementioned general definition of the imidazolium compounds employed according to the invention. The at least one imidazolium compound (=component A) may be used in combination with at least one further cationic polymer different from the compounds of component (A). With regard to suitable and preferred additional cationic polymers, reference is made to the cationic polymers mentioned before as component C).

With regard to suitable and preferred associative polymers, reference is made to WO 2010/023411 A2 which is incorporated herein by reference. Suitable cationic associative polymers and anionic associative polymers are also disclosed in US 2009/0074692 A1 which is incorporated herein by reference. Preferred associative polymers can be obtained by polymerization of a monomer mixture comprising at least one associative vinyl monomer. Non-limiting examples of the at least one include (meth)acrylates of polyalkoxylated $C_8$-$C_{30}$ fatty alcohols and mixtures thereof. Preferred associative vinyl monomers are polyethoxylated cetyl(meth)acrylates, polyethoxylated cetearyl(meth)acrylates, polyethoxylated stearyl(meth)acrylates, polyethoxylated arachidyl(meth)acrylates, polyethoxylated behenyl (meth)acrylates, and polyethoxylated lauryl(meth)acrylates. The polyalkoxylated portion of the associative monomer comprises preferably from 10 to 80, such as from 15 to 40, and such as from 20 to 35 alkylene oxide units, selected from ethylene oxide, propylene oxide and mixtures thereof. Preferably, the polyalkoxylated portion of the associative monomer comprises from 10 to 80, more preferably from 15 to 40, and in particular from 20 to 35 ethylene oxide units.

In a preferred embodiment, the at least one associative polymer is selected from anionic associative polymers. Preferably, the composition comprises the at least associative polymer in an amount of from 1 to 50 wt %, more preferably of from 2 to wt %, based on the total weight of the composition.

A third special embodiment is an antidandruff composition, comprising in a cosmetically acceptable medium
  at least one imidazolium compound (=component A), and
  optionally at least one antidandruff agent different from the imidazolium compound.

With regard to suitable and preferred embodiments of component A), reference is made to the aforementioned general definition of the imidazolium compounds employed according to the invention. The at least one imidazolium compound (=component A) may be used in combination with at least one further cationic polymer different from the compounds of component (A). With regard to suitable and preferred additional cationic polymers, reference is made to the cationic polymers mentioned before as component C).

Preferably, the composition according to the third special embodiment further comprises at least one surfactant. With regard to suitable and preferred surfactants, reference is made to the surfactants mentioned before as component D). The surfactant is generally present in the composition according to the third special embodiment in an amount ranging from 0.1% to 60% by weight approximately, preferably from 3% to 40% and even more preferably from 5% to 30%, relative to the total weight of the composition.

The antidandruff agent which is different from the imidazolium compounds are chosen in particular from:
1) Pyridinethione salts, in particular the calcium, magnesium, barium, strontium, zinc, cadmium, tin and zirconium salts. The zinc salt of pyridinethione is particularly preferred. The zinc salt of pyridinethione is sold in particular under the name ZINC OMADINE by the company OLIN.
2) 1-Hydroxy-2-pyrrolidone derivatives represented by formula (IV):

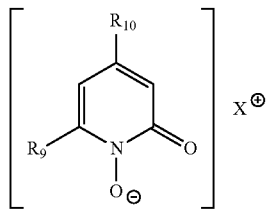

wherein:
  $R_9$ is chosen from an alkyl group containing from 1 to 17 carbon atoms, an alkenyl group containing from 2 to 17 carbon atoms, a cycloalkyl group containing from 5 to 8 carbon atoms, a bicycloalkyl group containing from 7 to 9 carbon atoms, a cycloalkyl(alkyl) group, an aryl group wherein the aryl may have as possible substituents a halogen group, a nitro group, and a cyano group, an aralkyl group wherein the alkyl contains from 1 to 4 carbon atoms, an arylalkenyl group wherein the alkenyl contains from 2 to 4 carbon atoms, an aryloxy-alkyl wherein the alkyl contains from 1 to 4 carbon atoms, arylmercaptoalkyl group wherein the alkyl contains from 1 to 4 carbon atoms, a furylalkenyl group wherein the alkenyl contains from 2 to 4 carbon atoms or wherein the furyl contains from 2 to 4 carbon atoms, an alkoxy group containing from 1 to 4 carbon atoms, a nitro group, a cyano group and a halogen atom;
  $R_{10}$ is chosen from a hydrogen atom, a ($C_1$-$C_4$) alkyl group, a ($C_2$-$C_4$) alkenyl group, a halogen atom, a phenyl group, and a benzyl group; and
  $X^+$ is chosen from a quaternized organic base, an alkali metal ion, alkaline-earth metal ion, and an ammonium ion.

Compounds of formula (IV) are, for example, 1-hydroxy-4-methyl-2-pyridone, 1-hydroxy-6-methyl-2-pyridone, 1-hydroxy-4,6-dimethyl-2-pyridone, 1-hydroxy-4-methyl-6-(2,4,4-trimethylpentyl)-2-pyridone, 1-hydroxy-4-methyl-6-cyclohexyl-2-pyridone, 1-hydroxy-4-methyl-6-(methylcyclohexyl)-2-pyridone, 1-hydroxy-4-methyl-6-(2-bicyclo (2,2,1) heptyl)-2-pyridone, 1-hydroxy-4-methyl-6-(4-methylphenyl)-2-pyridone, 1-hydroxy-4-methyl-6-(1-(4-nitrophenoxy)butyl)-2-pyridone, 1-hydroxy-4-methyl-6-(4-cyanophenoxymethyl)-2-pyridone, 1-hydroxy-4-methyl-6-(phenyl-sulphonylmethyl)-2-pyridone or 1-hydroxy-4-methyl-6-(4-bromobenzyl)-2-pyridone.

The compounds of formula (IV) can be used in the form of salts with organic or inorganic bases. Examples of organic bases are, in particular, alkanolamines of low molecular weight, such as ethanolamine, diethanolamine, N-ethylethanolamine, triethanolamine, diethylaminoethanol and 2-amino-2-methylpropanediol; non-volatile bases, such as ethylenediamine, hexamethylenediamine, cyclohexylamine, benzylamine and N-methylpiperazine; quaternary ammonium hydroxides, such as trimethylbenzyl hydroxide; guanidine and its derivatives, and in particular its alkyl derivatives. Examples of inorganic bases are, in particular, alkali metal salts, such as sodium and potassium salts; ammonium salts, alkaline-earth metal, salts such as magnesium and calcium salts; salts of divalent, trivalent or tetravalent cationic metals, such as zinc, aluminium or zirconium. The alkanolamines, ethylenediamine and inorganic bases, such as the alkali metal salts are preferred.

In a particularly preferred embodiment, in the compound of formula (IV) $R_9$ is a radical

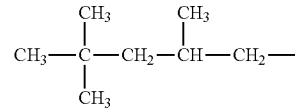

$R_{10}$ is a methyl group, and
$X^+$ is $N+H_3CH_2CH_2OH$.
This compound (IV) is commercially available under the name OCTOPIROX (1-hydroxy-4-methyl-6-(2,4,4-trimethylpentyl)-2-pyridone, monoethanolamine salt).
3) 2,2'-Dithiobis(pyridine N-oxide) of formula (V):

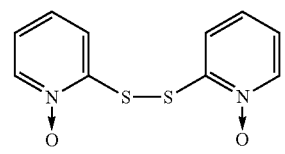 [SMILES: [O-][n+]1ccccc1SSc1cccc[n+]1[O-]]

The compounds of formula (V) can be introduced into the composition in the form of inorganic salts. An example of an inorganic salt is magnesium sulphate.

4) Trihalocarbamides of formula (VI) below:

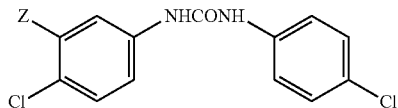

wherein:
Z is a halogen atom, such as chlorine, or a ($C_1$-$C_4$) trihaloalkyl group, such as $CF_3$.

5) Triclosan, represented by formula (VII):

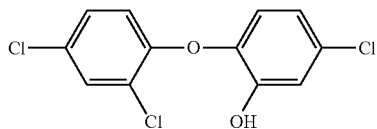

6) Azo compounds, such as climbazole, ketoconazole, clotrinazole, econazole, isoconazole and miconazole;
7) Antifungal polymers, such as amphotericin B or nystatin;
8) Selenium sulphide;
9) Other antidandruff agents are sulphur in its various forms, cadmium sulphide, allantoin, coal tars or wood tars and derivatives thereof, in particular cade oil, salicylic acid, undecylenic acid, fumaric acid and allylamines, such as terbinafine.

Zinc Omadoine, Octopirox and selenium sulphide are particularly preferred.

Preferably, the at least imidazolium compound and the additional antidandruff agent(s) are present in an amount ranging from 0.01% to 10% by weight and more particularly from 0.1 to 5% by weight, based on the total weight of the composition.

A fourth special embodiment is a composition for the treatment of acne and cutaneous disorders linked to hyperseborrhoea, comprising in a cosmetically acceptable medium at least one imidazolium compound (=component A).

With regard to suitable and preferred embodiments of component A), reference is made to the aforementioned general definition of the imidazolium compounds employed according to the invention. Suitable formulations are disclosed in WO 03/000221 A1 which is incorporated herein by reference.

A fifth special embodiment is a hair dye composition, comprising in a cosmetically acceptable medium
at least one imidazolium compound (=component A), and
at least one cationic dye.

With regard to suitable and preferred embodiments of component A), reference is made to the aforementioned general definition of the imidazolium compounds employed according to the invention. Suitable hair dye formulations are disclosed in FR 2912908 A1 which is incorporated herein by reference. It was surprisingly found that advantageous properties are obtained, if the cationic polymers used in the hair dye compositions according to this document are replaced completely or partly by at least one imidazolium compound employed according to the invention.

A sixth special embodiment is a cosmetic composition for treating a keratinous substrate, comprising in a cosmetically acceptable medium
at least one imidazolium compound (=component A), as defined above and in the following, and
at least one fatty quaternary amine.

With regard to suitable and preferred embodiments of component A), reference is made to the aforementioned general definition of the imidazolium compounds employed according to the invention.

The at least one fatty quaternary amine is preferably selected from compounds containing from about 6 to about 22 carbon atoms. The anion of the quaternary agent can be a common ion, such as chloride, ethosulfate, methosulfate, acetate, bromide, lactate, nitrate, phosphate, or tosylate and mixtures thereof. The long chain alkyl groups can include additional or replaced carbon or hydrogen atoms or ether linkages. Other substitutions on the quaternary nitrogen can be hydrogen, benzyl or short chain alkyl or hydroxyalkyl groups, such as methyl, ethyl, hydroxymethyl or hydroxyethyl, hydroxypropyl or combinations thereof.

Examples of fatty quaternary amines include, but are not limited to: Behentrimonium chloride, Cocotrimonium chloride, Cethethyldimonium bromide, Dibehenyldimonium chloride, Dihydrogenated tallow benzylmonium chloride, disoyadimonium chloride, Ditallowedimonium chloride, Hydroxycetyl hydroxyethyl dimonium chloride, Hydroxyethyl Behenamidopropyl dimonium chloride, Hydroxyethyl Cetyldimonium chloride, Hydroxyethyl tallowedimonium chloride, myristalkonium chloride, PEG-2 Oleamonium chloride, PEG-5 Stearmonium chloride, PEG-15 cocoyl quaternium 4, PEG-2 stearalkonium 4, lauryltrimonium chloride; Quaternium-16; Quaternium-18, lauralkonium chloride, olealkonium chloride, cetylpyridinium chloride, Polyquaternium-5, Polyquaternium-6, Polyquaternium-7, Polyquaternium-10, Polyquaternium-22, Polyquaternium-37, Polyquaternium-39, Polyquaternium-47, cetyl trimonium chloride, dilauryldimonium chloride, cetalkonium chloride, dicetyldimonium chloride, soyatrimonium chloride, stearyl octyl dimonium methosulfate, behentrimonium methosulfate (18-MEA), stearalkonium chloride, and mixtures thereof. Other quaternary ammonium compounds are listed in the CTFA Cosmetic Ingredient Handbook, First Edition, on pages 41-42, incorporated herein by reference.

A preferred fatty quaternary amine is Incroquat® Behenyl 18-MEA, which is a mixture of behentrimonium methosulfate, $C_{10\text{-}40}$ isoalkylamidopropylethyldimonium ethosulfate (Quaternium-33) and cetyl alcohol, commercially available from Croda, Inc.

The amount of the at least one fatty quaternary amine in the composition according to the sixth special embodiment is preferably in a range from 0.001% to 2% by weight, more preferably from 0.01% to 1.0% by weight, in particular from 0.1% to 0.5% by weight, based on the total weight of the composition.

Preferably, the composition according to the sixth special embodiment further comprises at least one surfactant. With regard to suitable and preferred surfactants, reference is made to the surfactants mentioned before as component D). Preferably at least one nonionic surfactant is employed. The amount of surfactant in the composition according to the sixth special embodiment is preferably in a range from 0.5% to 20% by weight, more preferably from 1.0% to 5.0% by weight, based on the total weight of the composition.

Preferably, the composition according to the sixth special embodiment further comprises at least one ceramide. Ceramides may be used in the composition for moisturizing the fiber and maintaining cuticle integrity. Ceramides are available by extraction from natural sources, or as synthetic ceramides and pseudoceramides. Preferred ceramides are e.g. 2-oleamido-1,3-octanediol and Ceramide II from Quest. Mixtures of ceramides are suitable, such as Ceramides LS from Laboratories Serobiologiques. The amount of ceramide in the composition according to the sixth special embodiment is preferably in a range from 0.001% to 0.5% by weight, more preferably from 0.01% to 0.5% by weight, in particular from 0.01% to 0.1% by weight, based on the total weight of the composition.

Preferably, the composition according to the sixth special embodiment is substantially anhydrous. The term "substantially anhydrous" means that the composition is either completely free of water or contains no appreciable amount of water, preferably no more than 5% by weight, and more preferably no more than 1% by weight, based on the weight of the composition.

Suitable formulations are disclosed in US 2008/0131391 which is incorporated herein by reference. It was surprisingly found that advantageous properties are obtained, if the quaternary ammonium polymers a) used in the compositions according to this document are replaced completely or partly by at least one imidazolium compound (=component a) according to the invention.

A seventh special embodiment is a cosmetic composition for treating a keratinous substrate, comprising in a cosmetically acceptable medium
  at least one imidazolium compound (=component A), as defined above and in the following, and
  at least one alkoxysilanes with solubilizing functional groups.

With regard to suitable and preferred embodiments of component A), reference is made to the aforementioned general definition of the imidazolium compounds employed according to the invention. Suitable alkoxysilanes and formulations are disclosed in FR 2910276 A1 which is incorporated herein by reference.

Home Care Composition

A further aspect of the invention is a home care composition comprising
A) at least one imidazolium compound as defined above,
B) optionally at least one further microbicidal compound different from the compounds of component (A),
C) optionally at least one active ingredient and/or auxiliary.

The home care composition according to the invention can be a composition that is effective against various microorganisms. According to this variant, the imidazolium compound itself may act as active ingredient. Accordingly, in such a composition the use of a further active ingredients and/or auxiliaries C) is only optional.

The home care composition according to the invention can also be a composition that contains at least one imidazolium compound (component A) as preservative. Accordingly, in such a composition the use of a further component B) and/or C) is usually mandatory.

A typical home care composition according to the invention contains at least one imidazolium compound A), optionally at least one further microbicidal compound B), and at least one further component C), selected from non-ionic surfactants, anionic surfactants, amphoteric surfactants, water, alcohols and a combination thereof. The home care compositions can include additional components C), such as enzymes, bleaches, whiteners, color care agents, fabric softeners, suds suppressors, dispersants, dye transfer inhibitors, chelating agents, aerosol propellants, gelling agents, thickening agents and a combination thereof.

The home care composition according to the invention can be formulated in a variety of ways and may include a hydrophilic phase, a hydrophobic phase and optionally at least one emulsifying agent. The home care composition may be in the form of a liquids, semi-solid, paste, gel, bar, tablet, spray, foam, powder or granules.

For the purpose of the invention the term "home care composition" means a composition for use in the general environment of human beings and is further described in the following. Home care compositions are generally nontoxic when applied in the vicinity of human beings, for example to fabrics and other items used by humans, when applied to surfaces used by, or in the vicinity of, humans, or when applied to spaces occupied by humans.

A further aspect of the invention is a method of using a home care composition, as defined above and in the following, by applying the composition to an article, surface or space. Exemplary articles, surfaces and spaces include clothes, furniture fabrics, rugs and carpets, draperies, dishes and cooking utensils, grills, ovens, and other items used by humans. The term "surface" includes hard surfaces in the human environment, such as floors, glass surfaces (such as glass windows, doors and countertops), other counter surfaces, bath, toilet bowl, sink and other bathroom surfaces. The term "space" includes the interior portion of buildings occupied by humans, including the air contained therein.

Advantageously, a home care composition comprising at least one imidazolium compound A) possesses effective antimicrobial preservative properties. Further, a home care composition comprising at least one imidazolium compound A) also confers an antimicrobial effect on articles, surfaces or spaces to which it is applied. Home care compositions according to the invention include:
  surface cleaning compositions (for example, glass, floor, counter, bath, toilet bowl, sink, appliance and furniture cleaning compositions);
  deodorants (for example, solid, liquid and spray deodorants air and/or surface deodorants);
  disinfectants (for example, spray and solid air disinfectants (including gel); and spray, solid, liquid and paste surface disinfectants);
  waxes and other surface protecting and/or polishing compositions;
  laundry compositions (for example detergents, fabric softeners and whiteners); and
  rug shampoos.

Preferably, the home care composition comprises the components A) and, if present, B) in a fraction of from about 0.001 to 50% by weight, particularly preferably 0.01 to 30% by weight, in particular 0.1 to 20% by weight, based on the total weight of the composition.

Pharmaceutical Composition

A further aspect of the invention is a pharmaceutical composition comprising
A) at least one imidazolium compound as defined above,
B) optionally at least one further microbicidal compound different from the compounds of component (A),
C) optionally at least one pharmaceutically acceptable active ingredient, and
D) optionally at least one pharmaceutically acceptable excipient.

The pharmaceutical composition according to the invention can be a composition that is effective against various microorganisms. According to this variant, the imidazolium compound itself may act as pharmaceutically active ingredient. Accordingly, in such a composition the use of a further pharmaceutically acceptable active ingredient C) is only optional.

The pharmaceutical composition according to the invention can also be a composition that contains at least one imidazolium compound (component A) as preservative. Accordingly, in such a composition the use of a further pharmaceutically acceptable active ingredient C) is usually mandatory.

Preferably, the pharmaceutical composition comprises the components A) and, if present, B) in a fraction of from about 0.001 to 50% by weight, particularly preferably 0.01 to 30% by weight, in particular 0.1 to 20% by weight, based on the total weight of the composition.

The pharmaceutical composition of the invention is suitable for administering in principle any type of active pharmaceutical ingredient C). These include benzodiazepines, antihypertensives, vitamins, cytostatics, in particular taxol, anesthetics, neuroleptics, antidepressants, antibiotics, antimycotics, fungicides, chemotherapeutics, urologics, thrombocyte aggregation inhibitors, sulfonamides, spasmolytics, hormones, immunoglobulins, sera, thyroid therapeutic agents, psychopharmacological agents, antiparkinsonians and other antihyperkinetic agents, ophthalmics, neuropathy preparations, calcium metabolism regulators, muscle relaxants, narcotics, antilipemics, hepatic therapeutic agents, coronary agents, cardiacs, immunotherapeutics, regulatory peptides and their inhibitors, hypnotics, sedatives, gynecological agents, antigouts, fibrinolytic agents, enzyme preparations and transport proteins, enzyme inhibitors, emetics, circulation-promoting agents, diuretics, diagnostics, corticoids, cholinergics, bile duct therapeutics, antiasthmatics, broncholytics, beta-receptor blockers, calcium antagonists, ACE inhibitors, antiarteriosclerotics, antiinflammatories, anticoagulants, antihypotensives, antihypoglycemics, antihypertonics, antifibrinolytics, antiepileptics, antiemetics, antidotes, antidiabetics, antiarrhythmics, antianemics, antiallergics, anthelmintics, analgesics, analeptics, aldosterone antagonists and slimming agents Examples of suitable active ingredients C) are: acarbose, non-steroidal antirheumatics, cardiac glycosides, acetylsalicylic acid, virustatics, aclarubicin, acyclovir, cisplatin, actinomycin, alpha- and beta-sympathomimetics, allopurinol, alosetron, alprostadil, prostaglandins, amantadine, ambroxol, amlodipine, methotrexate, 5-aminosalicylic acid, amitriptyline, amlodipine, amoxicillin, anastrozole, atenolol, atorvastatin, azathioprine, balsalazide, beclomethasone, betahistine, bezafibrate, bicalutamide, diazepam and diazepam derivatives, budesonide, bufexamac, buprenorphine, methadone, calcium salts, potassium salts, magnesium salts, candesartan, carbamazepine, captopril, cefalosporins, celetoxib, cetirizine, chenodeoxycholic acid, ursodeoxycholic acid, theophylline and theophylline derivatives, trypsins, cimetidine, clarithromycin, clavulanic acid, clindamycin, clobutinol, clonidine, cotrimoxazole, codeine, caffeine, vitamin D and derivatives of vitamin D, colestyramine, cromoglicic acid, coumarin and coumarin derivatives, cysteine, cytarabine, cyclophosphamide, ciclosporin, cyproterone, cytarabine, dapiprazole, desogestrel, desonide, dihydralazine, diltiazem, ergot alkaloids, dimenhydrinate, dimethyl sulfoxide, dimethicone, dipyridamole, domperidone and domperidone derivatives, donepzil, dopamine, doxazosin, doxorubicin, doxylamine, dapiprazole, benzodiazepines, diclofenac, glycoside antibiotics, desipramine, econazole, ACE inhibitors, enalapril, ephedrine, epinephrine, epoetin and epoetin derivatives, morphinans, calcium antagonists, irinotecan, modafinil, orlistat, peptide antibiotics, phenyloin, riluzoles, risedronate, sildenafil, topiramate, macrolide antibiotics, esomeprazole, estrogen and estrogen derivatives, progestogen and progestogen derivatives, testosterone and testosterone derivatives, androgen and androgen derivatives, ethenzamide, etofenamate, etofibrate, fenofibrate, etofylline, etoposide, famciclovir, famotidine, felodipine, fenofibrate, fentanyl, fenticonazole, gyrase inhibitor, fluconazole, fludarabine, flunarizine, fluorouracil, fluoxetine, flurbiprofen, ibuprofen, flutamide, fluvastatin, follitropin, formoterol, fosfomicin, furosemide, fusidic acid, galantamine, gallopamil, ganciclovir, gemfibrozil, gentamicin, ginkgo, St John's wort, glibenclamide, urea derivatives as oral antidiabetics, glucagon, glucosamine and glucosamine derivatives, glutathione, glycerol and glycerol derivatives, hypothalamus hormones, goserelin, guanethidine, halofantrine, haloperidol, heparin and heparin derivatives, hyaluronic acid, hydralazine, hydrochlorothiazide and hydrochlorothiazide derivatives, salicylates, hydroxyzine, idarubicin, ifosfamide, imipramine, indometacin, indoramine, insulin, interferons, iodine and iodine derivatives, isoconazole, isoprenaline, glucitol and glucitol derivatives, itraconazole, ketoconazole, ketoprofen, ketotifen, lacidipine, lansoprazole, levodopa, levomethadone, thyroid hormones, lipoic acid and lipoic acid derivatives, lisinopril, lisuride, lofepramine, lomustine, loperamide, loratadine, maprotiline, mebendazole, mebeverine, meclozine, mefenamic acid, mefloquine, meloxicam, mepindolol, meprobamate, meropenem, mesalazine, mesuximide, metamizole, metformin, methotrexate, methylphenidate, methylprednisolone, metixen, metoclopramide, metoprolol, metronidazole, mianserin, miconazole, minocycline, minoxidil, misoprostol, mitomycin, mizolastine, moexipril, morphine and morphine derivatives, evening primrose, nalbuphine, naloxone, tilidine, naproxen, narcotine, natamycin, neostigmine, nicergoline, nicethamide, nifedipine, niflumic acid, nimodipine, nimorazole, nimustine, nisoldipine, adrenaline, and adrenaline derivatives, norfloxacin, novaminsulfone, noscapine, nystatin, ofloxacin, olanzapine, olsalazine, omeprazole, omoconazole, ondansetron, orlistat, oseltamivir, oxaceprol, oxacillin, oxiconazole, oxymetazoline, pantoprazole, paracetamol, paroxetine, penciclovir, oral penicillins, pentazocine, pentifylline, pentoxifylline, perphenazine, pethidine, plant extracts, phenazone, pheniramine, barbituric acid derivatives, phenylbutazone, phenyloin, pimozide, pindolol, piperazine, piracetam, pirenzepine, piribedil, piroxicam, pramipexol, pravastatin, prazosin, procaine, promazine, propiverine, propranolol, propyphenazone, prostaglandins, protionamide, proxyphylline, quetiapine, quinapril, quinaprilate, ramipril, ranitidine, reproterol, reserpine, ribavirin, rifampicin, risperidone, ritonavir, ropinirol, rosiglitazone, roxatidine, roxithromycin, ruscogenin, rutoside and rutoside derivatives, sabadilla, salbutamol, salmeterol, scopolamine, selegiline, sertaconazole, sertindole, sertraline, silicates, simvastatin, sitosterol, sotalol, spaglumic acid, sparfloxacin, spectinomycin, spiramycin, spirapril, spironolactone, stavudine, streptomycin, sucralfate, sufentanil, sulbactam, sulfonamides, sulfasalazine, sulpiride, sultamicillin, sultiam, sumatriptan, suxamethonium chloride, tacrine, tacrolimus, taliolol, tamoxifen, taurolidine, tazarotene, tegaserod, temazepam, teniposide, tenoxicam, terazosin, terbinafine, terbutaline, terfenadine, terlipressin, tertatolol, tetracyclines, tetryzoline, theobromine, theophylline, butizine, thiamazole, phenothiazines, thiotepa, tiagabine, tiapride, propionic acid derivatives, ticlopidine, timolol, timidazole, tioconazole, tioguanine, tioxolone, tiropramide, tizanidine, tolazoline, tolbutamide, tolcapone, tolnaftate, tolperisone, topotecan, torasemide, antiestrogens, tramadol, tramazoline, trandolapril, tranylcypromine, trapidil, trazodone, triamcinolone and triamcinolone derivatives, triamterene, trifluperidol, trifluridine, trimethoprim, trimipramine, tripelennamine, triprolidine, trifosfamide, tromantadine, trometamol, tropalpin, troxerutin, tulobuterol, tyramine, tyrothricin, urapidil, ursodeoxycholic acid, chenodeoxycholic acid, valaciclovir, valdecoxib, valproic acid, vancomycin, vecuronium chloride, venlafaxine, verapamil, vidarabine, vigabatrine, viloxazine, vinblastine, vincamine, vincristine, vindesine, vinorelbine, vinpocetine, viquidil, warfarin, xantinol nicotinate, xipamide, zafirlukast, zalcitabine, zanamivir, zidovudine, zolmitriptan, zolpidem, zopiclone, zotepine and the like.

The active ingredients can, if desired, also be used in the form of their pharmaceutically acceptable salts or derivatives, and in the case of chiral active ingredients it is possible to employ both optically active isomers and racemates or mixtures of diastereoisomers. The compositions of the invention can, if desired, also comprise two or more active pharmaceutical ingredients.

The formulation base of pharmaceutical compositions of the invention preferably comprises pharmaceutically acceptable excipients D). Pharmaceutically acceptable excipients are those known to be usable in the area of pharmacy, food technology and adjacent sectors, in particular the excipients listed in relevant pharmacopeias (e.g. DAB, Ph. Eur., BP, USP, JP) and others, whose properties do not stand in the way of physiological use.

Suitable excipients D) may be: lubricants, wetting agents, emulsifying and suspending agents, antioxidants, anti-irritants, chelating agents, emulsion stabilizers, film formers, gel formers, odor-masking agents, resins, hydrocolloids, solvents, solubilizers, neutralizers, permeation promoters, pigments, colorants, stabilizers, disintegrants, dessicants, opacifiers, thickeners, waxes, plasticizers, flavors, sweeteners, excipients to reduce permeation etc. An arrangement concerning this is based on specialist knowledge as described for example in Fiedler, H. P. Lexikon der Hilfsstoffe für Pharmazie, Kosmetik and angrenzende Gebiete, 4th edition, Aulendorf: ECV-Editio-Cantor-Verlag, 1996.

Plant Protection Composition

A further aspect of the invention is a plant protection composition comprising
A) at least one imidazolium compound as defined above,
B) optionally at least one further microbicidal compound different from the compounds of component (A),
C) optionally at least one active substance for plant protection, and
D) optionally at least one auxiliary.

The plant protection composition according to the invention can be a composition that is effective against various microorganisms. According to this variant, the imidazolium compound itself may act as active ingredient. Accordingly, in such a composition the use of a further active substance for plant protection C) is only optional. Preferably, the plant protection composition in which the imidazolium compound itself acts as active ingredient is a fungicidal composition. Such compositions have been described in detail above.

The plant protection composition according to the invention can however also be a composition that contains at least one imidazolium compound (component A) as preservative. Accordingly, in such a composition the use of at least one further active substance for plant protection C) is usually mandatory.

The pharmaceutical composition of the invention is suitable in principle any type of active substance for plant protection C). Examples of at least one active substance for plant protection are described in the following.

Examples of fungicidal active substances C) comprise:
acylalanines, such as benalaxyl, metalaxyl, ofurace or oxadixyl;
amine derivatives, such as aldimorph, dodine, dodemorph, fenpropimorph, fenpropidin, guazatine, iminoctadine, spiroxamine or tridemorph;
anilinopyrimidines, such as pyrimethanil, mepanipyrim or cyprodinil;
antibiotics, such as cycloheximide, griseofulvin, kasugamycin, natamycin, polyoxin and streptomycin;
azoles, such as bitertanol, bromoconazole, cyproconazole, difenoconazole, diniconazole, epoxiconazole, fenbuconazole, fluquinconazole, flusilazole, flutriafol, hexaconazole, imazalil, ipconazole, metconazole, myclobutanil, penconazole, propiconazole, prochloraz, prothioconazole, tebuconazole, tetraconazole, triadimefon, triadimenol, triflumizole or triticonazole;
2-methoxybenzophenones, such as those disclosed in EP-A 897 904 by the general formula (I), e.g. metrafenone;
dicarboximides, such as iprodione, myclozolin, procymidone or vinclozolin;
dithiocarbamates, such as ferbam, nabam, maneb, mancozeb, metam, metiram, propineb, polycarbamate, thiram, ziram or zineb;
heterocyclic compounds, such as anilazine, benomyl, boscalid, carbendazim, carboxin, oxycarboxin, cyazofamid, dazomet, dithianon, famoxadone, fenamidone, fenarimol, fuberidazole, flutolanil, furametpyr, isoprothiolane, mepronil, nuarimol, picobenzamid, probenazole, proquinazid, pyrifenox, pyroquilon, quinoxyfen, silthiofam, thiabendazole, thifluzamide, thiophanate-methyl, tiadinil, tricyclazole or triforine;
nitrophenyl derivatives, such as binapacryl, dinocap, dinobuton or nitrothal-isopropyl;
phenylpyrroles, such as fenpiclonil or fludioxonil;
unclassified fungicides, such as acibenzolar-S-methyl, benthiavalicarb, carpropamid, chlorothalonil, cyflufenamid, cymoxanil, diclomezine, diclocymet, diethofencarb, edifenphos, ethaboxam, fenhexamid, fentin acetate, fenoxanil, ferimzone, fluazinam, fosetyl, fosetyl-aluminum, iprovalicarb, hexachlorobenzene, metrafenone, pencycuron, propamocarb, phthalide, tolclofos-methyl, quintozene or zoxamide;
strobilurins, such as those disclosed in WO 03/075663 by the general formula (I), for example azoxystrobin, dimoxystrobin, fluoxastrobin, kresoxim-methyl, metominostrobin, orysastrobin, picoxystrobin, pyraclostrobin and trifloxystrobin;
sulfenic acid derivatives, such as captafol, captan, dichlofluanid, folpet or tolylfluanid;
cinnamamides and analogous compounds, such as dimethomorph, flumetover or flumorph;
6-aryl-[1,2,4]triazolo[1,5-a]pyrimidines, such as those disclosed, e.g., in WO 98/46608, WO 99/41255 or WO 03/004465, in each case by the general formula (I);
amide fungicides, such as cyflufenamid and (Z)—N-[α-(cyclopropylmethoxyimino)-2,3-difluoro-6-(difluoromethoxy)benzyl]-2-phenylacetamide.

Examples of herbicides C) comprise:
1,3,4-thiadiazoles, such as buthidazole and cyprazole;
amides, such as allidochlor, benzoylprop-ethyl, bromobutide, chlorthiamid, dimepiperate, dimethenamid, diphenamid, etobenzanid, flamprop-methyl, fosamine, isoxaben, metazachlor, monalide, naptalam, pronamide or propanil;
aminophosphoric acids, such as bilanafos, buminafos, glufosinate-ammonium, glyphosate or sulfosate;
aminotriazoles, such as amitrole, or anilides, such as anilofos or mefenacet;

aryloxyalkanoic acid, such as 2,4-D, 2,4-DB, clomeprop, dichlorprop, dichlorprop-P, fenoprop, fluoroxypyr, MCPA, MCPB, mecoprop, mecoprop-P, napropamide, naproanilide or triclopyr;

benzoic acids, such as chloramben or dicamba;

benzothiadiazinones, such as bentazon;

bleachers, such as clomazone, diflufenican, fluorochloridone, flupoxam, fluridone, pyrazolate or sulcotrione;

carbamates, such as carbetamide, clorbufam, chlorpropham, desmedipham, phenmedipham or vernolate;

quinolinecarboxylic acids, such as quinclorac or quinmerac;

dichloropropionic acids, such as dalapon;

dihydrobenzofurans, such as ethofumesate;

dihydrofuran-3-ones, such as flurtamone;

dinitroanilines, such as benefin, butralin, dinitramine, ethalfluralin, fluchloralin, isopropalin, nitralin, oryzalin, pendimethalin, prodiamine, profluralin, trifluralin;

dinitrophenols, such as bromofenoxim, dinoseb, dinoseb acetate, dinoterb, DNOC or minoterb acetate;

diphenyl ethers, such as acifluorfen-sodium, aclonifen, bifenox, chlornitrofen, difenoxuron, ethoxyfen, fluorodifen, fluoroglycofen-ethyl, fomesafen, furyloxyfen, lactofen, nitrofen, nitrofluorfen or oxyfluorfen;

dipyridyls, such as cyperquat, difenzoquat metilsulfate, diquat or paraquat dichloride;

imidazoles, such as isocarbamid;

imidazolinones, such as imazamethapyr, imazapyr, imazaquin, imazethabenzmethyl, imazethapyr, imazapic or imazamox;

oxadiazoles, such as methazole, oxadiargyl or oxadiazone;

oxiranes, such as tridiphane;

phenols, such as bromoxynil or ioxynil;

phenoxyphenoxypropionic acid esters, such as clodinafop, cyhalofop-butyl, diclofop-methyl, fenoxaprop-ethyl, fenoxaprop-P-ethyl, fenthiaprop-ethyl, fluazifop-butyl, fluazifop-P-butyl, haloxyfop-ethoxyethyl, haloxyfop-methyl, haloxyfop-P-methyl, isoxapyrifop, propaquizafop, quizalofop-ethyl, quizalofop-P-ethyl or quizalofop-P-tefuryl;

phenylacetic acids, such as chlorfenac;

phenylpropionic acids, such as chlorphenprop-methyl;

ppi-active substances (ppi=preplant incorporated), such as benzofenap, flumiclorac-pentyl, flumioxazin, flumipropyn, flupropacil, pyrazoxyfen, sulfentrazone or thidiazimin;

pyrazoles, such as nipyraclofen;

pyridazines, such as chloridazon, maleic hydrazide, norflurazon or pyridate;

pyridinecarboxylic acids, such as clopyralid, dithiopyr, picloram or thiazopyr;

pyrimidyl ethers, such as pyrithiobac acid, pyrithiobac-sodium, KIH-2023 or KIH-6127;

sulfonamides, such as flumetsulam or metosulam;

triazolecarboxamides, such as triazofenamide;

uracils, such as bromacil, lenacil or terbacil;

furthermore benazolin, benfuresate, bensulide, benzofluor, bentazon, butamifos, cafenstrole, chlorthal-dimethyl, cinmethylin, dichlobenil, endothall, fluorbentranil, mefluidide, perfluidone, piperophos, topramezone and prohexadione-calcium;

sulfonylureas, such as amidosulfuron, azimsulfuron, bensulfuron-methyl, chlorimuron-ethyl, chlorsulfuron, cinosulfuron, cyclosulfamuron, ethametsulfuron-methyl, flazasulfuron, halosulfuron-methyl, imazosulfuron, metsulfuron-methyl, nicosulfuron, primisulfuron, prosulfuron, pyrazosulfuron-ethyl, rimsulfuron, sulfometuron-methyl, thifensulfuron-methyl, triasulfuron, tribenuron-methyl, triflusulfuron-methyl or tritosulfuron;

plant protection active substances of the cyclohexenone type, such as alloxydim, clethodim, cloproxydim, cycloxydim, sethoxydim and tralkoxydim. Very particularly preferred herbicidal active substances of the cyclohexenone type are: tepraloxydim (cf. AGROW, No. 243, 11.3.95, page 21, caloxydim) and 2-(1-[2-{4-chlorphenoxy}propyloxyimino]butyl)-3-hydroxy-5-(2H-tetrahydrothio-pyran-3-yl)-2-cyclohexen-1-one, and of the sulfonylurea type is: N-(((4-methoxy-6-[trifluoromethyl]-1,3,5-triazin-2-yl)amino)carbonyl)-2-(trifluoromethyl)benzenesulfonamide.

Examples of insecticides C) comprise:

organophosphates, such as acephate, azinphos-methyl, chlorpyrifos, chlorfenvinphos, diazinon, dichlorvos, dimethylvinphos, dioxabenzofos, dicrotophos, dimethoate, disulfoton, ethion, EPN, fenitrothion, fenthion, isoxathion, malathion, methamidophos, methidathion, methyl parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, pirimiphos-ethyl, pyraclofos, pyridaphenthion, sulprophos, triazophos, trichlorfon, tetrachlorvinphos or vamidothion;

carbamates, such as alanycarb, benfuracarb, bendiocarb, carbaryl, carbofuran, carbosulfan, fenoxycarb, furathiocarb, indoxacarb, methiocarb, methomyl, oxamyl, pirimicarb, propoxur, thiodicarb or triazamate;

pyrethroids, such as bifenthrin, cyfluthrin, cycloprothrin, cypermethrin, deltamethrin, esfenvalerate, etofenprox, fenpropathrin, fenvalerate, cyhalothrin, lambda-cyhalothrin, permethrin, silafluofen, tau-fluvalinate, tefluthrin, tralomethrin, alpha-cypermethrin or zeta-cypermethrin;

arthropodal growth regulators: a) chitin synthesis inhibitors, e.g. benzoylureas, such as chlorfluazuron, diflubenzuron, flucycloxuron, flufenoxuron, hexaflumuron, lufenuron, novaluron, teflubenzuron, triflumuron, buprofezin, diofenolan, hexythiazox, etoxazole or clofentezine; b) ecdysone antagonists, such as halofenozide, methoxyfenozide or tebufenozide; c) juvenile hormone mimics, such as pyriproxyfen, methoprene or fenoxycarb; d) lipid biosynthesis inhibitors such as spirodiclofen;

neonicotinoids, such as flonicamid, clothianidin, dinotefuran, imidacloprid, thiamethoxam, nitenpyram, nithiazine, acetamiprid or thiacloprid;

additional unclassified insecticides, such as abamectin, acequinocyl, acetamiprid, amitraz, azadirachtin, bensultap, bifenazate, cartap, chlorfenapyr, chlordimeform, cyromazine, diafenthiuron, dinotefuran, diofenolan, emamectin, endosulfan, ethiprole, fenazaquin, fipronil, formetanate, formetanate hydrochloride, gamma-HCH, hydramethylnon, imidacloprid, indoxacarb, isoprocarb, metolcarb, pyridaben, pymetrozine, spinosad, tebufenpyrad, thiamethoxam, thiocyclam, XMC and xylylcarb;

N-phenylsemicarbazones, such as those disclosed in EP-A 462 456 by the general formula (1), especially compounds of the general formula (A)

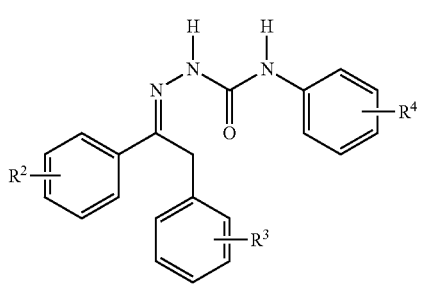 (A)

in which $R^2$ and $R^3$ represent, independently of one another, hydrogen, halogen, CN, $C_1$-$C_4$ alkyl, $C_1$-$C_4$ alkoxy, $C_1$-$C_4$ haloalkyl or $C_1$-$C_4$ haloalkoxy and $R^4$ represents $C_1$-$C_4$ alkoxy, $C_1$-$C_4$ haloalkyl or $C_1$-$C_4$ haloalkoxy, e.g. compound IV, in which $R^2$ represents 3-$CF_3$, $R^3$ represents 4-CN and $R^4$ represents 4-$OCF_3$.

Useable growth regulators C) are, e.g., chlormequat chloride, mepiquat chloride, prohexadione-calcium or the group of the gibberellins. These include, e.g. the gibberellin $GA_1$, $GA_3$, $GA_4$, $GA_5$ and $GA_7$, and the like, and the corresponding exo-16,17-dihydrogibberellins, and also the derivatives thereof, e.g. the esters with $C_1$-$C_4$ carboxylic acids, The exo-16,17-dihydro-$GA_5$ 13-acetate is preferred according to the invention.

Antimicrobial Polymer Composition or Coating Composition

The imidazolium compounds employed according to the invention are in particular suitable to provide antimicrobial polymers and coating compositions, for example compositions for medical applications. The polymer compositions and coating compositions show an outstanding antimicrobial activity. Thus, in a further aspect, the invention provides an antimicrobial polymer composition or coating composition, wherein the polymer composition or the coating comprises an effective antimicrobial amount of at least one polymeric, ionic compound comprising imidazolium groups (component A), as defined above.

Preferably, the polymer composition or coating composition comprises at least one imidazolium compound in an amount of from about 0.001 to about 15.0 weight percent, more preferably 0.01 to 10.0 weight percent, based on the total weight of the polymer composition or the coating composition.

A further aspect of the invention is a polymer composition or coating composition, comprising
A) at least one imidazolium compound as defined above,
B) optionally at least one further microbicidal compound different from the compounds of component (A),
C) optionally at least one polymer and/or at least one polymerizable compound, and
D) optionally at least one additive.

With regard to suitable and preferred compounds of the components A) and B), reference is made to the aforementioned description of suitable and preferred embodiments of those components.

The employed polymers may be in any form, for example fibers, films or molded parts. They may be for example woven or nonwoven polymer fabrics.

Suitable polymers C) may be selected from:
1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE), linear low density polyethylene (LLDPE), branched low density polyethylene (BLDPE) and medium density polyethylene (MDPE).

Polyolefins, i.e. the polymers of monoolefins exemplifiedin the preceding paragraph, preferably polyethylene and polypropylene, can be prepared by different, and especially by the following, methods:
a) radical polymerization (normally under high pressure and at elevated temperature).
b) catalytic polymerization using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either p- or s-coordinated. These metal complexes may be in the free form or fixed on substrates, typically on activated magnesium chloride, titanium(III) chloride, alumina or silicon oxide. These catalysts may be soluble or insoluble in the polymerization medium. The catalysts can be used by themselves in the polymerization or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).
3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidenenorbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.
4. Hydrocarbon resins (for example C5-C9) including hydrogenated modifications thereof (e.g. tackifiers) and mixtures of polyalkylenes and starch.
5. Polystyrene, poly(p-methylstyrene), poly(a-methylstyrene).

6. Copolymers of styrene or [alpha-methylstyrene with dienes or acrylic derivatives, for example styrene/butadiene, styrene/unsaturated ester, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

7. Graft copolymers of styrene or [alpha-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, SAN, MBS, ASA or AES polymers.

8. Halogen-containing polymers such as polychloroprene, chlorinated rubbers, chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bis-glycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine andisophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides and polybenzimidazoles.

18. Polyesters derived from dicarboxylic acids and diols and/or from hydroxycarboxylic acids or the corresponding lactones, for example polyethylene terephthalate, polytrimethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS. Polyesters and polyester copolymers as defined in U.S. Pat. No. 5,807,932 (column 2, line 53), incorporated herein by reference.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, polyisocyanates or epoxy resins.

26. Crosslinked epoxy resins derived from polyepoxides, for example from bis glycidyl ethers or from cycloaliphatic diepoxides.

27. Natural polymers such as cellulose, rubber, gelatin and chemically modified homologous derivatives thereof, for example cellulose acetates, cellulose propionates and cellulose butyrates, or the cellulose ethers, such as methyl cellulose; as well as rosins and their derivatives.

28. Blends of the aforementioned polymers (polyblends), for example PP/EPDM, Polyamide/-EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO.

29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.
30. Aqueous emulsions of natural or synthetic rubber, e.g. natural latex or latices of carboxylated styrene/butadiene copolymers.
31. Polysiloxanes such as the soft, hydrophilic polysiloxanes described, for example, in U.S. Pat. No. 4,259,467; and the hard polyorganosiloxanes described, for example, in U.S. Pat. No. 4,355,147.
32. Silicone elastomers, for example liquid silicone rubbers (LSR). Liquid Silicone Rubbers are available from Dow Chemical and are described for example in U.S. Pat. Nos. 6,569,536; 6,420,038; 6,297,291; 6,218,466; 6,130,272; 5,994,461; 5,989,719; 5,973,030; 5,908,888; 5,880,199; 5,877,256; 5,859,094; 5,789,084 and 5,661,210. The disclosures of these U.S. patents are incorporated by reference.
33. Polyketimines in combination with unsaturated acrylic polyacetoacetate resins or with unsaturated acrylic resins. The unsaturated acrylic resins include the urethane acrylates, polyether acrylates, vinyl or acryl copolymers with pendant unsaturated groups and the acrylated melamines. The polyketimines are prepared from polyamines and ketones in the presence of an acid catalyst.
34. Radiation curable compositions containing ethylenically unsaturated monomers or oligomers and a polyunsaturated aliphatic oligomer.
35. Epoxymelamine resins such as light-stable epoxy resins crosslinked by an epoxy functional coetherified high solids melamine resin such as LSE-4103 (Monsanto).

Included also are thermoplastic olefin (TPO), thermoplastic elastomers, polyetherimide, polymethylpentene, polyphenylene ether, polyphenylene sulfide, polysulfone or polytetrafluoroethylene (PTFE).

Some polymers of specific technical interest include:
Polysulfone (PSF)
Polyethersulfone (PES)
Polyphenylsulfone (PPS)
Polyvinylidene Fluoride (PVDF)
Polypropylene (PP)
Polyethylene (PE)
Cellulose, Cellulose acetates (CA), Cellulose nitrate
Polyamide (PA)
Polyacrylonitrile (PAN)
Polytetrafluoroethylene (PTFE)
Polycarbonate (PC)
Polymethylmethacrylate (PMMA).

In particular, the present polymers are those that are typically employed in medical applications, for example polyurethanes, polycarbonate, liquid silicone rubbers, polyethylene, polypropylene, polyethylene/polypropylene copolymers or polymer composites.

Polymer composites are for instance natural products composites, for example a natural product mixed with a thermoplastic polymer such as a polyolefin. Such composites are disclosed in published U.S. app. No. 20040235983, the disclosure of which is hereby incorporated by reference.

Natural products are for instance wood flour, flax, hemp, jute, kenaf or rice husk. The thermoplastic polymer is for instance polyethylene or polypropylene.

A preferred polymer composition or coating composition according to the invention additionally contains, for example, one or more components D) selected from antioxidants, light stabilizers (such as UV absorbers and/or sterically hindered amines, phosphites, phosphonites), metal deactivators, nucleating agents, fillers, plasticisers, pigments, flameproofing agents, antistatic agents, lubricants, emulsifiers, rheology additives, catalysts, flow-control agents, optical brighteners, blowing agents and combinations thereof.

The employed components D), in particular the antioxidants, light stabilizers, and metal deactivators, preferably have a high migration fastness and temperature resistance.

Suitable antioxidants D) are selected from the following classes:

1. Alkylated monophenols, for example 2,6-di-tert-butyl-4-methylphenol, 2-tert-butyl-4,6-di-methylphenol, 2,6-di-tert-butyl-4-ethylphenol, etc;
2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol, etc;
3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis(3,5-di-tert-butyl-4-hydroxyphenyl)adipate, etc;
4. Tocopherols;
5. Hydroxylated thiodiphenyl ethers, for example 2, 2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol), 4,4'-bis(2,6-dimethyl-4-hydroxyphenyl)-disulfide, etc;
6. Alkylidenebisphenols, for example 2, 2'-methylenebis(6-tert-butyl-4-methylphenol), 2,2' methylenebis(6-tert-butyl-4-ethylphenol), 2,2'-methylenebis[4-methyl-6-(α-methylcyclohexyl)-phenol, 1,1-bis-(3,5-dimethyl-2-hydroxyphenyl)butane, 2,2-bis(3,5-di-tert-butyl-4-hydroxyphenyl)propane, 2,2-bis(5-tert-butyl-4-hydroxy-2-methylphenyl)-4-n-dodecylmercaptobutane, 1,1,5,5-tetra-(5-tert-butyl-4-hydroxy-2-methylphenyl)pentane, etc;
7. O-, N- and S-benzyl compounds, for example 3, 5,3',5'-tetra-tert-butyl-4,4'-dihydroxydibenzyl ether, octadecyl-4-hydroxy-3,5-dimethylbenzylmercapto-acetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)-dithioterephthalate, bis (3,5-di-tert-butyl-4-hydroxybenzyl)sulfide, isooctyl-3,5-di-tert-butyl-4-hydroxybenzylmercaptoacetate, etc;
8. Hydroxybenzylated malonates, for example dioctadecyl-2,2-bis(3,5-di-tert-butyl-2-hydroxybenzyl)malonate, di-octadecyl-2-(3-tert-butyl-4-hydroxy-5-methylbenzyl)-malonate, didodecylmercaptoethyl-2,2-bis(3,5-di-tert-butyl-4-hydroxybenzyl)-malonate, bis[4-(1,1,3,3-tetramethylbutyl)phenyl-2,2-bis(3,5-di-tert-butyl-4-hydroxybenzyl)malonate, etc;
9. Aromatic hydroxybenzyl compounds, for example 1, 3,5-tris(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)-phenol, etc;
10. Triazine compounds, for example 2,4-bis(octylmercapto)-6-(3,5-di-tert-butyl-4-hydroxy-anilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris-(3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris-(3,5-di-tert-butyl-4-hydroxyphenylethyl)-1,3,5-triazine, 1,3,5-tris(3,5-di-tert-butyl-4-hyphenylpropionyl)-hexahydro-1,3,5-triazine, 1,3,5-tris(3,5-dicyclohexyl-4-hydroxybenzyl)isocyanurate, etc.
11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl-3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid, etc;
12. Acylaminophenols, for example 4-hydroxylauranilide, 4-hydroxystearanilide, octyl N-(3,5-di-tert-butyl-4-hydroxyphenyl)carbamate, etc;
13. Esters of β-(3,5-di-tert-butyl-4-hydroxyphenyl)propionic acid with mono- or polyhydric alcohols;
14. Esters of β-(5-tert-butyl-4-hydroxy-3-methylphenyl) propionic acid with mono- or polyhydric alcohols;
15. Esters of β-(3,5-dicyclohexyl-4-hydroxyphenyl)propionic acid with mono- or polyhydric alcohols;
16. Esters of 3,5-di-tert-butyl-4-hydroxyphenyl acetic acid with mono- or polyhydric alcohols;
    Suitable mono- or polyhydric alcohols for compounds 13.) to 16.) are methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis-(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2octane.
17. Amides of β-(3,5-di-tert-butyl-4-hydroxyphenyl)propionic acid e.g. N,N'-bis(3,5-di-tert-butyl-4-hydroxyphenylpropionyl)hexamethylenediamide, N,N'-bis(3,5-di-tert-butyl-4-hydroxy-phenylpropionyl) trimethylenediamide, N,N'-bis(3,5-di-tert-butyl-4-hydroxyphenylpropionyl)hydrazide, N,N'-bis[2-(3-(3,5-di-tert-butyl-4-hydroxy-phenylpropionyloxy) ethyloxamide (Naugard(R)XL-1, supplied by Uniroyal).
18. Ascorbic Acid (Vitamin C)
19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl) diphenylamine, N,N'-dimethyl-N,N'-di-sec-butyl-p-phenylenediamine, diphenylamine, N-allyldiphenylamine, 4-isopropoxydiphenyl-amine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butyl-aminophenol, 4-butyrylaminophenol, 4-nonanoylaminophenol, 4-dodecanoylaminophenol, 4-octadecanoylaminophenol, bis(4-methoxy-phenyl) amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)aminoethane, 1,2-bis(phenyl-amino)propane, (o-tolyl)biguanide, bis[4-(1',3'-dimethylbutyl)phenylamine, tert-octylated N-phenyl-1-naphthylamine, a mixture of mono- and dialkylated tert-butyl/tert-octyldiphenylamines, a mixture of mono- and dialkylated nonyldiphenylamines, a mixture of mono- and dialkylated dodecyldiphenylamines, a mixture of mono- and dialkylatedisopropyl/isohexyldiphenylamines, a mixture of mono- and dialkylated tert-butyldiphenylamines, 2,3-dihydro-3,3-dimethyl-4H-1,4-benzothiazine, phenothiazine, a mixture of mono- and dialkylated tert-butyl/tert-octylphenothiazines, a mixture of mono- and dialkylated tert-octyl-phenothiazines, N-allylphenothiazine, N,N,N',N'-tetraphenyl-1,4-diaminobut-2-ene.

Suitable light stabilizers (UV absorbers) and metal deactivators are selected, for example, from groups a) to s):
a) 4,4-diarylbutadienes,
b) cinnamic esters,
c) benzotriazoles,
d) hydroxybenzophenones,
e) diphenylcyanoacrylates,
f) oxamides,
g) 2-phenyl-1,3,5-triazines;
h) antioxidants,
i) nickel compounds,
j) sterically hindered amines,
k) metal deactivators,
l) phosphites and phosphonites,
m) hydroxylamines,
n) nitrones,
o) amine oxides,
p) benzofuranones and indolinones,
q) thiosynergists,
r) peroxide scavengers, and
s) basic costabilizers.

The antimicrobial compounds A), optional B) and optional additives D) may be added to at least one polymer and/or at least one polymerizable compound C) individually or mixed with one another. If desired, the individual components can be mixed with one another before incorporation into the polymer or polymerizable composition for example by dry blending.

The incorporation of the biocides of the invention can be carried out by known methods, such as dry blending in the form of a powder or wet mixing in the form of solutions, dispersions or suspensions for example in an inert solvent, water or oil. The biocides of the invention may be incorporated, for example, before or after molding or also by applying the dissolved or dispersed biocide (or an additive mixture containing the biocide) to the polymer material or the polymerisable composition, with or without subsequent evaporation of the solvent or the suspension/dispersion agent. They may be added directly into the processing apparatus (e.g. extruders, internal mixers, etc), e.g. as a dry mixture or powder or as solution or dispersion or suspension.

The incorporation can be carried out e.g. in any heatable container equipped with a stirrer, e.g. in a closed apparatus such as a kneader, mixer or stirred vessel. The incorporation is preferably carried out in an extruder or in a kneader. The processing may take place in an inert atmosphere or in the presence of oxygen.

The addition of biocide (or an additive mixture containing the biocide) to the polymer substrate can be carried out in all customary mixing machines in which the polymer is melted and mixed with the additives. Suitable machines are known to those skilled in the art. They are predominantly mixers, kneaders and extruders.

Processing includes extrusion, co-kneading, pultrusion, compression molding, sheet extrusion, thermoforming, injection molding or rotational molding. The process is preferably carried out in an extruder by introducing the additives during processing.

Particularly preferred processing machines are single-screw extruders, contrarotating and corotating twin-screw extruders, rotomolding devices, planetary-gear extruders, ring extruders or cokneaders. It is also possible to use processing machines provided with at least one gas removal compartment to which a vacuum can be applied.

Suitable extruders and kneaders are described, for example, in Handbuch der Kunststoffextrusion, Vol. 1 Grundlagen, Editors F. Hensen, W. Knappe, H. Potente, 1989, pp. 3-7, ISBN:3-446-14339-4 (Vol. 2 Extrusionsanlagen 1986, ISBN 3-446-14329-7).

The biocide (or an additive mixture containing the biocide) can also be added to the polymer in the form of a masterbatch ("concentrate") which contains the components in a concentration of, for example, about 1% to about 40% and preferably about 2% to about 20% by weight incorporated in a polymer. The polymer must not necessarily be identical to the polymer where the additives are added finally. In such operations, the polymer can be used in the form of powder, granules, solutions, suspensions or in the form of latices. Incorporation can take place prior to or during the shaping operation, or by applying the dispersed compound to the polymer, with or without subsequent evaporation of the solvent. A further possibility for incorporating the biocide of the invention (or an additive mixture containing the biocide) into polymer substrates is to add them before, during or directly after the polymerization of the corresponding monomers or prior to crosslinking. In this context the additives of the invention can be added as it is or else in encapsulated form (for example in waxes, oils or polymers).

The polymers containing the biocide (or an additive mixture containing the biocide) described herein can be used for the production of moldings, rotomolded articles, injection molded articles, blow molded articles, profiles, films, woven and nonwoven fabrics, and the like.

When the polymer composition or coating composition according to the invention is used in the medical sector, it is for example a catheter, hose, tube, valve, articles for urology, bone cement, fabric, toothbrushes, silicone plastics, films, textiles, diapers and the like.

The coating composition according to the invention usually contains a film forming binder.

The binder can in principle be any binder which is customary in industry, for example those described in Ullmann's Encyclopedia of Industrial Chemistry, 5th Edition, Vol. A18, pp. 368-426, VCH, Weinheim 1991. In general, it is a film forming binder based on a thermoplastic or thermosetting resin, predominantly on a thermosetting resin. Examples thereof are alkyd, acrylic, acrylic alkyd, polyester, phenolic, melamine, epoxy and polyurethane resins and mixtures thereof. The binder can be a cold-curable or hot-curable binder; the addition of a curing catalyst may be advantageous. Suitable catalysts which accelerate curing of the binder are described, for example, in Ullmann's Encyclopedia of Industrial Chemistry, Vol. A18, p. 469, VCH Verlagsgesellschaft, Weinheim 1991.

The coating compositions according to the invention are for example employed as a top coat for plastics or metal or as a wood coating.

Examples of coatings compositions containing specific binders are:

1. paints based on cold- or hot-crosslinkable alkyd, acrylate, polyester, epoxy or melamine resins or mixtures of such resins, if desired with addition of a curing catalyst;
2. two-component polyurethane paints based on hydroxyl-containing acrylate, polyester or polyether resins and aliphatic or aromatic isocyanates, isocyanurates or polyisocyanates;
3. one-component polyurethane paints based on blocked isocyanates, isocyanurates or polyisocyanates which are deblocked during baking, if desired with addition of a melamine resin;
4. one-component polyurethane paints based on a tri-salkoxycarbonyltriazine crosslinker and a hydroxyl group containing resin such as acrylate, polyester or polyether resins;
5. one-component polyurethane paints based on aliphatic or aromatic urethaneacrylates or polyurethaneacrylates having free amino groups within the urethane structure and melamine resins or polyether resins, if necessary with curing catalyst;
6. two-component paints based on (poly)ketimines and aliphatic or aromatic isocyanates, isocyanurates or polyisocyanates;
7. two-component paints based on (poly)ketimines and an unsaturated acrylate resin or a polyacetoacetate resin or a methacrylamidoglycolate methyl ester;
8. two-component paints based on carboxyl- or amino-containing polyacrylates and polyepoxides;
9. two-component paints based on acrylate resins containing anhydride groups and on a polyhydroxy or polyamino component;
10. two-component paints based on acrylate-containing anhydrides and polyepoxides;
11. two-component paints based on (poly)oxazolines and acrylate resins containing anhydride groups, or unsaturated acrylate resins, or aliphatic or aromatic isocyanates, isocyanurates or polyisocyanates;
12. two-component paints based on unsaturated polyacrylates and polymalonates;
13. thermoplastic polyacrylate paints based on thermoplastic acrylate resins or externally crosslinking acrylate resins in combination with etherified melamine resins;
14. paint systems based on siloxane-modified or fluorine-modified acrylate resins.

The coating compositions may also comprise further components, examples being solvents, pigments, dyes, plasticizers, stabilizers, thixotropic agents, drying catalysts and/or levelling agents. Examples of possible components are those described in Ullmann's Encyclopedia of Industrial Chemistry, 5th Edition, Vol. A18, pp. 429-471, VCH, Weinheim 1991.

Possible drying catalysts or curing catalysts are, for example, organometallic compounds, amines, amino-containing resins and/or phosphines. Examples of organometallic compounds are metal carboxylates, especially those of the metals Pb, Mn, Co, Zn, Zr or Cu, or metal chelates, especially those of the metals Al, Ti or Zr, or organometallic compounds, such as organotin compounds, for example.

Examples of metal carboxylates are the stearates of Pb, Mn or Zn, the octoates of Co, Zn or Cu, the naphthenates of Mn and Co or the corresponding linoleates, resinates or tallates.

Examples of metal chelates are the aluminium, titanium or zirconium chelates of acetylacetone, ethyl acetylacetate, salicylaldehyde, salicylaldoxime, o-hydroxyaceto-phenone or ethyl trifluoroacetylacetate, and the alkoxides of these metals.

Examples of organotin compounds are dibutyltin oxide, dibutyltin dilaurate or dibutyltin dioctoate.

Examples of amines are, in particular, tertiary amines, for example tributylamine, triethanolamine, N-methyldiethanolamine, N-dimethylethanolamine, N-ethylmorpholine, N-methylmorpholine or diazabicyclooctane (triethylenediamine) and salts thereof. Further examples are quaternary ammonium salts, for example trimethylbenzyl-ammonium chloride.

Amino-containing resins are simultaneously binder and curing catalyst. Examples thereof are amino-containing acrylate copolymers.

The curing catalyst used can also be a phosphine, for example triphenylphosphine.

The coating compositions can also be radiation-curable coating compositions. In this case, the binder essentially comprises monomeric or oligomeric compounds containing ethylenically unsaturated bonds, which after application are cured by actinic radiation, i.e. converted into a crosslinked, high molecular weight form. Where the system is UV-curing, it generally contains a photoinitiator as well. Corresponding systems are described in the above mentioned publication Ullmann's Encyclopedia of Industrial Chemistry, 5th Edition, Vol. A18, pages 451-453.

The coating compositions according to the invention can be applied to any desired substrates, for example to metal, wood, plastic, ceramic materials or plastic wood composites.

The coating compositions according to the invention are also suitable for protecting a wood surface. In this case, the coating compositions can be applied in form of a varnish, paint, etc or by impregnation. A further aspect of the invention is a method for providing antimicrobial activity to a wood surface which method comprises applying a present coatings composition, especially a varnish, paint, stain or impregnation on wood. The coating composition may be applied by impregnation or as base coat (primer) or top coat.

If the coating composition is employed for protecting a wood surface, preferably a solvent is used, selected e.g. from the group consisting of aliphatic hydrocarbons, cycloaliphatic hydrocarbons, aromatic hydrocarbons, alcohols, ethers, esters, ketones, glycols, glycol ethers, glycol esters, polyglycols or mixtures thereof. Preferably, in this case the binder is selected from the group consisting of alkyd resins, modified alkyd resins, autocrosslinking or non-autocrosslinking acrylic resins, polyester resins, drying oils, phenolic resins, nitrocellulose or mixtures thereof.

Other additives like fungicides or insecticides are possible. Suitable components are known to the skilled artisan.

Any coating composition suitable for coating wood may be used as a top coat. It will normally contain a binder, dissolved or dispersed in an organic solvent or in water or a mixture of water and solvent. The binder may typically be a surface coating resin which dries in the air or hardens at room temperature. Exemplary of such binders are nitrocellulose, polyvinyl acetate, polyvinyl chloride, unsaturated polyester resins, polyacrylates, polyurethanes, epoxy resins, phenolic resins, and especially alkyd resins. The binder may also be a mixture of different surface coating resins. Provided the binders are curable binders, they are normally used together with a hardener and/or accelerator.

The top coat may also be a radiation-curable, solvent-free formulation of photopolymerizable compounds. Illustrative examples are mixtures of acrylates or methacrylates, unsaturated polyester/styrene mixtures or mixtures of other ethylenically unsaturated monomers or oligomers.

The top coat may contain a soluble dye and/or a pigment and/or a filler. The pigment may be an organic, inorganic or metallic pigment. The pigments may be opaque or transparent, such as for example transparent iron oxides. The filler may be typically kaolin, calcium carbonate or aluminium silicate. Preferably, the top coat is a clear varnish, i.e. it contains no undissolved components.

The present invention is particularly useful for the following applications: in home applications, such as furniture, wood floors, chipboards or timber work; outdoor applications, such as fences, construction parts, wooden fronts, window frames and the like.

The present coatings compositions may be applied to the substrates by the customary methods, for example by brushing, spraying, pouring, dipping or electrophoresis; see also Ullmann's Encyclopedia of Industrial Chemistry, 5th Edition, Vol. A18, pp. 491-500.

Depending on the binder system, the coatings may be cured at room temperature or by heating. The coatings may for example be cured at 50 to 150° C., and, e.g. in the case of powder coatings or coil coatings, even at higher temperatures.

The coating compositions can comprise an organic solvent or solvent mixture in which the binder is soluble. The coating compositions can otherwise be an aqueous solution or dispersion. The vehicle can also be a mixture of organic solvent and water. The coating composition may be a high-solids paint or can be solvent-free (e.g. a powder coating material). Powder coatings are, for example, those described in Ullmann's Encyclopedia of Industrial Chemistry, 5th Ed., A18, pages 438-444. The powder coating material may also have the form of a powder-slurry (dispersion of the powder preferably in water).

The pigments can be inorganic, organic or metallic pigments. The present coatings compositions may contain no pigments and may be used as a clearcoat.

The following examples illustrate the invention without restricting it.

EXAMPLES

A) Biocide Compositions

Determination of the Minimum Inhibitory Concentration (MIC):

The effects of the biocidal compositions comprising an imidazolium polymer were tested in Minimum Inhibitory Concentration tests against *Staphylococcus aureus* and *Pseudomonas aeruginosa* as exemplary members of the harmful microorganisms mentioned above. The MIC measurements were performed following a procedure described by J. M. Andrews, J. Antimicrobial Chemotherapy, (2001) 48, Suppl. S1, 5-16 based on the commendations of the British Society for Antimicrobial Chemotherapy.

For pre-cultivation of the bacteria, *Staphylococcus aureus* ATCC 29213 and *Pseudomonas aeruginosa* ATCC 27853 were streaked onto IsoSensitest agar plates, respectively, and incubated at 37° C. overnight. Single colonies were used to inoculate 50 mL of IsoSensitest broth in 250 mL of baffled Erlenmeyer flasks at 190 rpm and 37° C. for 15 hours, respectively. Then, 50 mL of IsoSensitest broth were inoculated with the precultures to a final optical density of OD=0.1, respectively.

Stock solutions of the biocidal composition comprising an imidazolium polymer were prepared at 10 mg/mL and 1 mg/mL in deionized water. Dilution series (log 2, from 4096 μg/mL to 0.25 μg/mL) with deionized water were made. Concentrations from 4096 μg/mL to 8 μg/mL were made using the 10 mg/mL stock solution; Concentrations from 4 μg/mL to 0.25 μg/mL were made using the 1 mg/mL stock solution. 75 μl quantities of each dilution were added to 8 wells of a 96 well microtiter-plate, respectively. Then, 75 μl of the bacterial suspension with an optical density of OD=0.1 were added to the wells. Wells charged with 75 μl of water and 75 μl of non-inoculated IsoSensitest broth served as sterile control. Wells charged with 75 μl of water and 75 μl of bacterial suspension served as positive control for unrestricted growth. The microtiter-plates were incubated for 24 hours at 37° C. and 750 rpm and the growth of microorganisms was determined by measuring the optical density. The optical density was measured in a time frame from 1.5 h to 24 h. As Minimum Inhibitory Concentration, these concentrations were determined, where no growth could be observed after 24 h (OD smaller than 0.1). As a control, three known antibiotics were chosen (J. M. Andrews, J. Antimicrobial Chemotherapy, (2001), 48, Suppl. S1, 5-16) to offer a comparison of the biocidal composition comprising an imidazolium polymer with known antibiotics.

TABLE 1

Imidazolium polymers and their biological activity:

| No. | Diamine | Acid | Repeating unit of the imidazolium polymer | MIC *Staphylococcus aureus* ATCC 29213 = DSM 2569 [μg/mL] | MIC *Pseudomonas aeruginosa* ATCC 27853 = DSM 1117 [μg/mL] |
|---|---|---|---|---|---|
| 1 | 1,4-Butanediamine | Acetic acid | imidazolium-butylene repeating unit with acetate counterion | 4 | 4 |
| 2 | 1,4-Butanediamine | Phosphoric acid | imidazolium-butylene repeating unit with $H_2PO_4^-$ counterion | 4 | 2 |
| 3 | 1,4-Butanediamine | Methane sulfonic acid | imidazolium-butylene repeating unit with methanesulfonate counterion | 16 | 8 |
| 4 | 1,4-Butanediamine | Sulfuric acid | imidazolium-butylene repeating unit with $HSO_4^-$ counterion | 2 | 2 |
| 5 | 1,4-Butanediamine | Hexanoic acid | imidazolium-butylene repeating unit with hexanoate counterion | 8 | 4 |
| 6 | 1,4-Butanediamine | Octanoic acid | imidazolium-butylene repeating unit with octanoate counterion | 8 | 8 |

TABLE 1-continued

Imidazolium polymers and their biological activity:

| No. | Diamine | Acid | Repeating unit of the imidazolium polymer | MIC Staphylococcus aureus ATCC 29213 = DSM 2569 [µg/mL] | MIC Pseudomonas aeruginosa ATCC 27853 = DSM 1117 [µg/mL] |
|---|---|---|---|---|---|
| 7 | 1,4-Butane-diamine | Adipic acid | 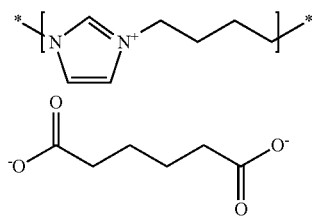 | 32 | 16 |
| 8 | 1,4-Butane-diamine | Terephthalic acid | 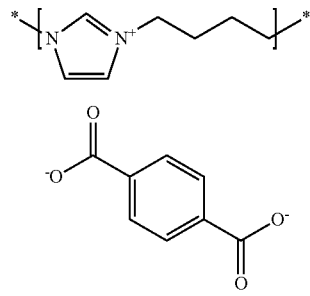 | 4 | 4 |
| 9 | 1,5-Pentane-diamin | Acetic acid | 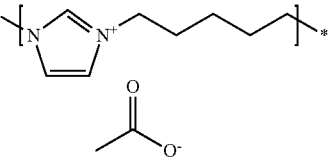 | 4 | 8 |
| 10 | 1,6-Hexane-diamin | Acetic acid | 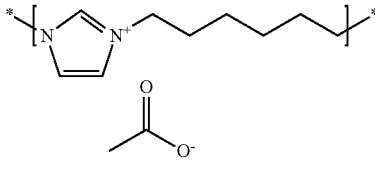 | 8 | 64 |
| 11 | 1,6-Hexane-diamin | Methane sulfonic acid | 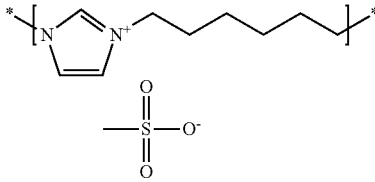 | 8 | 16 |
| 12 | 1,6-Hexane-diamin | [2-(2-methoxy-ethoxy)-ethoxy]-acetic acid | 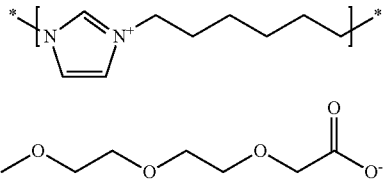 | 4 | 8 |
| 13 | 1,12-Dodecane-diamine | Acetic acid | 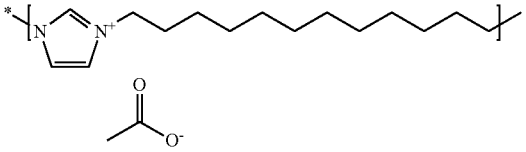 | 8 | 32 |

TABLE 1-continued

Imidazolium polymers and their biological activity:

| No. | Diamine | Acid | Repeating unit of the imidazolium polymer | MIC Staphylococcus aureus ATCC 29213 = DSM 2569 [μg/mL] | MIC Pseudomonas aeruginosa ATCC 27853 = DSM 1117 [μg/mL] |
|---|---|---|---|---|---|
| 14 | Poly(vinyl-formamid-co-vinylamine) ca. 50% hydrolysis grade | Acetic acid | | — | 128 |
| 15 | 1,8-Diamino-3,6-dioxaoctane | Acetic acid | *−[imidazolium−CH₂CH₂−O−CH₂CH₂−O−CH₂CH₂]−* ; CH₃COO⁻ | 16 | 16 |
| 17 | 1,8-Diamino-3,6-dioxaoctane | Sulfuric acid | *−[imidazolium−CH₂CH₂−O−CH₂CH₂−O−CH₂CH₂]−* ; HSO₄⁻ | 32 | 16 |
| 18 | Tris(2-aminoethylamine) 0.5 parts + 1,6-hexanediamine 0.5 parts | Acetic acid | | 32 | — |
| 19 | Tris(2-aminoethylamine) 0.5 parts + 1,6-hexanediamine 1 part | Acetic acid | | 64 | |
| 20 | Tris(2-aminoethylamine) 0.3 parts + 1,6-hexanediamine 1 part | Acetic acid | | 16 | — |
| 21 | Tris(2-aminoethylamine) 0.5 parts + 1,4-butanediamine 0.5 parts | Acetic acid | | 32 | — |
| 22 | Tris(2-aminoethylamine) 0.3 parts + 1,4-butanediamine 1 parts | Acetic acid | | 64 | — |
| 23 | Tris(2-aminoethylamine) 0.7 parts | Acetic acid | | 64 | — |
| 24 | Tris(2-aminoethylamine) 0.5 parts + ethylene diamine 0.5 parts | Acetic acid | | 64 | — |

TABLE 2

Known biocidal polymers and their biological activity

| No. | Comparative polymers | structure of the prior art polymer | MIC Staphylococcus aureus ATCC 29213 = DSM 2569 [µg/mL] | MIC Pseudomonas aeruginosa ATCC 27853 = DSM 1117 [µg/mL] |
|---|---|---|---|---|
| C1 | Poly(vinylformamid-co-vinylamine) >90% hydrolysis grade | | 256 | 256 |
| C2 | 1,3-Dibutyl-imidazolium acetate | [structure: 1,3-dibutylimidazolium with CH₃COO⁻] | 2048 | 4096 |

TABLE 3

Known antibiotics and their biological activity as control

| No. | Control antibiotics | MIC Staphylococcus aureus ATCC 29213 = DSM 2569 [µg/mL] | MIC Pseudomonas aeruginosa ATCC 27853 = DSM 1117 [µg/mL] |
|---|---|---|---|
| Control 1 | Cephalexine | 4 | >4096 |
| Control 2 | Tetracycline | 1 | 32 |
| Control 3 | Nalidixic acid | 64 | 1024 |

B) Cosmetic Compositions

The active materials (AM) are given in percentages.

Examples 1 to 4 (Shampoo Compositions)

In g AM

| | example no. | | | |
|---|---|---|---|---|
| | 1 | 2 | 3 | 4 |
| Cocoglucoside [1] | 5 | 5 | 5 | 5 |
| Cocoamidopropyl betaine [2] | 5.4 | 5.4 | 5.4 | 5.4 |
| Sodium lauryl ether (5 OE) carboxylate [3] | 3 | 3 | 3 | 3 |
| Sodium lauryl ether sulfate [4] | 4 | 4 | 4 | 4 |
| Imidazolium compound according to example 1, 2, 3, 4, 5, 6, 7, 8, 9, 10, 11, 12, 13, 14, 15, 16, 17, 18, 19, 20, 21, 22, 23, 24 | 0.4 | 0.4 | 0.4 | 0.4 |
| Polydimethylsiloxane (Dimethicone) [5] | 2.6 | 1 | 0.5 | 0.1 |
| Preserving agent | qs | qs | qs | qs |
| Fragrance | qs | qs | qs | qs |
| Citric acid | qs | qs | qs | qs |
| pH | 6.5 | 6.5 | 6.5 | 6.5 |
| Water qs | 100 g | 100 g | 100 g | 100 g |

[1] PLANTACARE ® 818 UP sold by Cognis
[2] DEHYTO ® AB 30 sold by Cognis
[3] AKYPO ® RLM 45 CA sold by KAO
[4] TEXAPON ® N 702 sold by Cognis
[5] DC 200 Fluid 60000 CS sold by Dow Corning Example 5 (Hair Conditioner with Anionic Associative Polymer)

| | |
|---|---|
| Imidazolium compound according to example 1, 2, 3, 4, 5, 6, 7, 8, 9, 10, 11, 12, 13, 14, 15, 16, 17, 18, 19, 20, 21, 22, 23, 24 | 1 g |
| Methacrylic acid/ethyl acrylate/oxyethylenated (25 EO) behenyl methacrylate terpolymer as an aqueous emulsion (20 wt %) [1] | 0.1 g AM |
| Chlorhexidine digluconate solution | 0.2 g |
| Methyl p-hydroxybenzoate | 0.3 g |
| Lactic acid qs | pH 4.0 +− 0.2 |
| Cetylstearyl alcohol [2] | 5 g |
| Water qs | 100 g |

[1] sold under the trade name Aculyn 28 by Rohm & Haas
[2] sold under the trade name Lanette O OR by the company Cognis The obtained hair conditioner composition was stable and viscous. When applied to wet hair after shampooing, it could be easily applied, had a good spreadability and good washout properties. The treated hair was smooth and shiny.

Example 6 (Antidandruff Shampoo Composition)

| | |
|---|---|
| Sodium lauryl ether sulphate (2.2 EO) | 17 g AM |
| Cocoylbetaine as an aqueous 30% solution (DEHYTON AB 30 from Henkel) | 2.5 g AM |
| Terpolymer of methacrylamidopropyl-trimethylammonium chloride, acrylic acid and stearyl methacrylate (49 mol %/49 mol %/2 mol %) | 1 g AM |
| Sodium cetostearyl sulphate | 0.75 g |
| Coconut acid monoisopropanolamide | 0.6 g |
| Imidazolium compound according to example 1, 2, 3, 4, 5, 6, 7, 8, 9, 10, 11, 12, 13, 14, 15, 16, 17, 18, 19, 20, 21, 22, 23, 24 | 0.5 g |
| Preserving agents, fragrance | qs |
| Water qs | 100 g |

Example 7 (Cream for Treatment of Acne and Hyperseborrhoea)

| | |
|---|---|
| Imidazolium compound according to example 1, 2, 3, 4, 5, 6, 7, 8, 9, 10, 11, 12, 13, 14, 15, 16, 17, 18, 19, 20, 21, 22, 23, 24 | 1.00% |
| Sorbitane tristearate | 1.00% |
| perfume | 0.30% |

-continued

| | |
|---|---|
| crosslinked acrylic acid homopolymer | 0.40% |
| xanthane gum | 0.50% |
| copolymer of ethylene glycol dimethacrylate/lauryl methacrylate | 1.00% |
| cyclopenta dimethylsiloxane | 6.00% |
| glycerine | 3.00% |
| mixture of cetyl/stearyl alcohol, ethoxylated stearyl alcohol (6 EO and 32 EO) | 4.00% |
| demineralized water qs | 100 |

Example 8 (Mineral Oil)

| | |
|---|---|
| oleth-5 | 5.00 |
| cetyl alcohol (and) behentrimonium methosulfate (and) Quaternium-33 | 1.00 |
| 2-oleamido-1,3-octadecandiol | 0.10 |
| oleth-20 | 5.00 |
| Imidazolium compound according to example 1, 2, 3, 4, 5, 6, 7, 8, 9, 10, 11, 12, 13, 14, 15, 16, 17, 18, 19, 20, 21, 22, 23, 24 | 0.50 |

Example 9 (Foam Conditioner)

| | [%] |
|---|---|
| Imidazolium compound according to example 1, 2, 3, 4, 5, 6, 7, 8, 9, 10, 11, 12, 13, 14, 15, 16, 17, 18, 19, 20, 21,22, 23, 24 | 20.00 |
| Cremophor A 25 (Ceteareth 25/BASF) | 0.2 |
| Comperlan KD (Coamide DEA/Henkel) | 0.1 |
| Water | 69.7 |
| Propane/butane | 10.0 |

Further additive: perfume, preservative . . .

Preparation: Weigh in and dissolve with stirring. Bottle and add propellant gas.

Example 10 (Hair Gel)

| | [%] |
|---|---|
| Phase 1: | |
| Imidazolium compound according to example 1, 2, 3, 4, 5, 6, 7, 8, 9, 10, 11, 12, 13, 14, 15, 16, 17, 18, 19, 20, 21, 22, 23, 24 | 12.00 |
| Water, dist. | 37.00 |
| Aminomethylpropanol (38% strength solution) | 1.0 |
| Further additive: preservative, soluble ethoxylated silicone, perfume . . . | |
| Phase 2: | |
| Aculyn 28 (1% strength aqueous suspension) | 50.00 |

Preparation:

Phases 1 and 2 are weighed in and homogenized separately. Phase 2 is then slowly stirred into phase 1. An essentially clear, stable gel forms.

Example 11 (Hair Gel)

| | [%] |
|---|---|
| Phase 1: | |
| Imidazolium compound according to example 1, 2, 3, 4, 5, 6, 7, 8, 9, 10, 11, 12, 13, 14, 15, 16, 17, 18, 19, 20, 21, 22, 23, 24 | 12.00 |
| Water, dist. | 30.00 |
| Further additive: preservative, soluble ethoxylated silicone, perfume . . . | |
| Phase 2: | |
| Natrosol HR 250 (5% strength solution) Hydroxyethylcellulose (Hercules) | 50.00 |

Preparation:

Phases 1 and 2 are weighed in and homogenized separately. Phase 2 is then slowly stirred into phase 1. An essentially clear, stable gel forms.

C) Fungicidal Activity

The following polymers F1 to F27 were prepared according to the procedures described in WO 2010/0725721. C1 is a comparative example.

The α-dicarbonyl compound a) used was glyoxal, the aldehyde b) used was a formaldehyde source and the diamine c) used is indicated in the table.

Polymers F28 and F29 were prepared as follows:

F28: 1,4-Diaminobutane (1.1 mol) and glyoxal (1.1 mol) were added at room temperature simultaneously dropwise to benzaldehyde (1.1 moles) in of acetic acid (4.3 mol). The mixture was heated for three hours to reflux. Water was distilled off to give the polymer as a dark oil.

$^1$H-NMR (D$_2$O) δ=7.86-7.15 (m, 1H); 4.31-4.18 (m, 0.3H); 3.31-2.99 (m, 0.5H); 2.05 (s, 1.6H); 2.01-1.83 (m, 0.8H).

F29: The polymer was prepared in analogy to polymer F28, using however dodecanal as aldehyde.

$^1$H-NMR (D$_2$O) δ=7.61-7.48 (m, 1H); 4.32-4.15 (m, 2.2H); 3.10-2.96 (m, 2.5H); 2.04 (s, 21H); 2.01-1.86 (m, 3.3H); 1.81-1.65 (m, 3.2H); 1.47-1.14 (m, 12H).

$M_w$ is the weight-average molecular weight as obtained by GPC (gel permeation chromatography/size exclusion chromatography) using 0.02 mol/l formic acid+0.2 mol/l KCl in water as elution agent and pullulan standard (linear polymaltotriose and maltohexose; from PSS, Germany), or using hexafluoroisopropanol+0.05% potassium trifluoroacetate in water as elution agent and PMMA standard. PDI is the polydispersity $M_w/M_n$ ($M_n$=number-average molecular weight).

| No. | amine | repeating units | $M_w$ | PDI |
|---|---|---|---|---|
| F1 | 1,4-diamino-butane | [imidazolium structure with HSO$_4^-$] | 30000 | 8 |

-continued
| No. | amine | repeating units | $M_w$ | PDI |
|---|---|---|---|---|
| F2 | 1,4-diamino-butane | 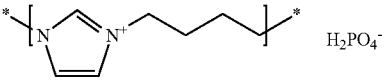 H$_2$PO$_4^-$ | | |
| F3 | 1,4-diamino-butane | 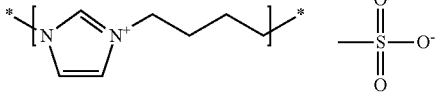 | | |
| F4 | 1,6-diamino-hexane | 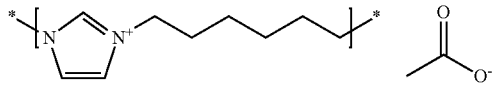 | | |
| F5 | 1,4-diamino-butane | 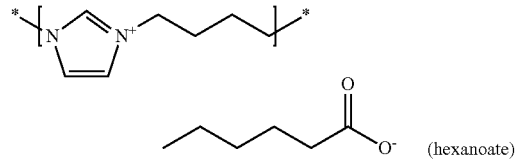 (hexanoate) | | |
| F6 | 1,6-diamino-hexane | 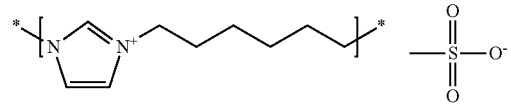 | 10700 | 5.4 |
| F7 | 2,6-diamino-hexanoic acid | 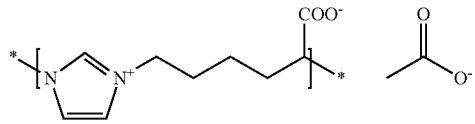 | 10200 | 4.3 |
| F8 | 1,6-diamino-hexane | 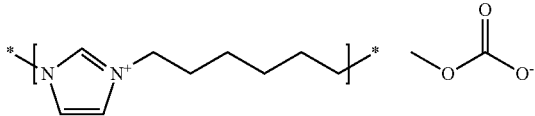 | 19600 | 12.3 |
| F9 | NH$_2$—(CH$_2$)$_3$—(OCH$_2$CH$_2$O)—(CH$_2$)$_3$—NH$_2$ | 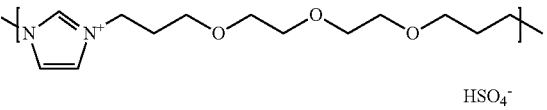 HSO$_4^-$ | | |
| F10 | NH$_2$—[(CH$_2$)$_2$O]$_2$—(CH$_2$)$_2$—NH$_2$ | 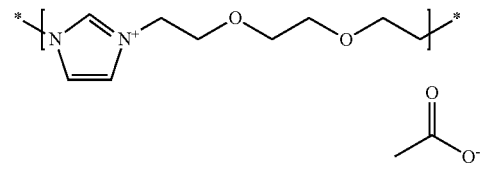 | | |
| F11 | NH$_2$—[(CH$_2$)$_2$O]$_2$—(CH$_2$)$_2$—NH$_2$ | 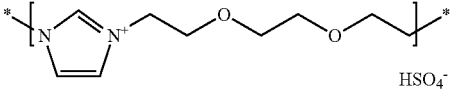 HSO$_4^-$ | | |
| F12 | 1,4-diamino-butane | 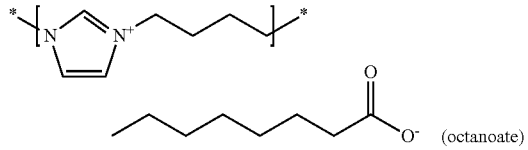 (octanoate) | 10000 | 7.2 |

-continued
| No. | amine | repeating units | $M_w$ | PDI |
|---|---|---|---|---|
| F13 | 1,4-diamino-butane | 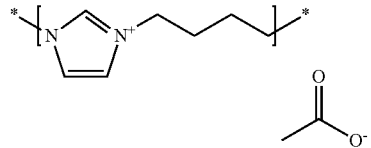 | 13200 | 6.4 |
| F14 | 1,6-diamino-hexane | 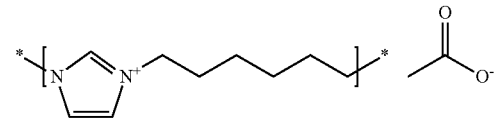 | | |
| F15 | 1,4-diamino-butane | 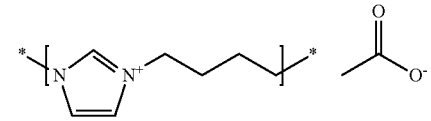 | 38500 | 2.5 |
| F16 | 1,12-diamino-dodecane | 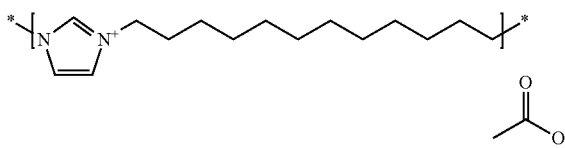 | 70000 | 2.5 |
| F17 | 1,4-diamino-butane | 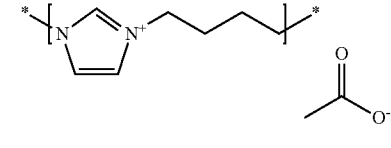 | 2310 | |
| F18 | 1,4-diamino-butane | 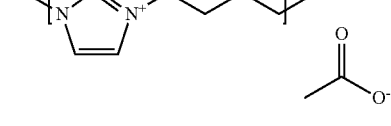 | 112000 | |
| F19 | 1,4-diamino-butane | 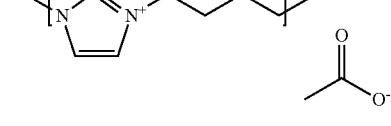 | 40000 | |
| F20 | 1,4-diamino-butane | 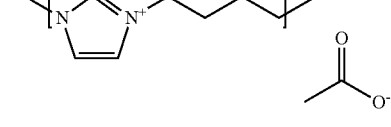 | 8770 | |
| F21 | 80% 1,4-diamino-butane + 20% $CH_3CH_2C-(OCH_2CH_2-CH(CH_3)NH_2)_3$ | anion: acetate | 3000 | |
| F22 | see F21 | anion: acetate | 14000 | |
| F23 | Bis(4-amino-cyclohexyl)-methane | 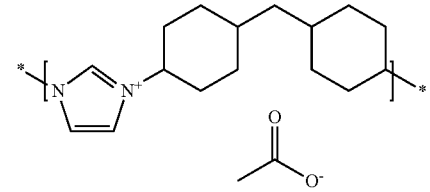 | 12000 | |
| F24 | 1,8-diamino-octane | 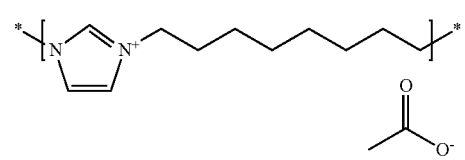 | 43000 | |

-continued

| No. | amine | repeating units | $M_w$ | PDI |
|---|---|---|---|---|
| F25 | 1,6-diamino-hexane | 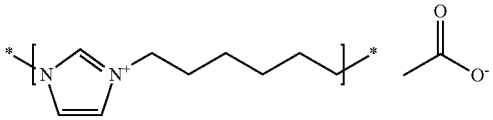 | 70000 | |
| F26 | 3-amino-methylbenzyl-amine | 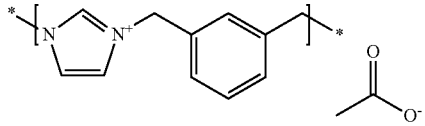 | 20000 | |
| F27 | isophoron-diamine | 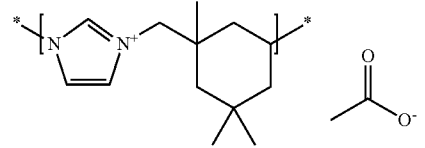 | 49800 | |
| F28 | 1,4-diamino-butane | 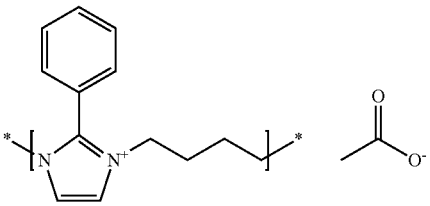 | 1200 | 1.9 |
| F29 | 1,4-diamino-butane | 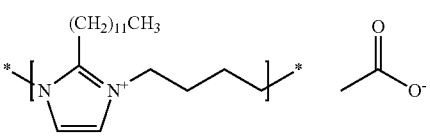 | | |
| C1 | 1,4-diamino-2-hydroxy-propane | 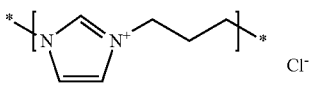 | | |

C.1) Green House Tests

The spray solutions were prepared in several steps:

The stock solutions were prepared: a mixture of acetone and/or dimethylsulfoxide and the wetting agent/emulsifier Wettol, which is based on ethoxylated alkylphenoles, in a relation (volume) solvent-emulsifier of 99 to 1 was added to 25 mg of the active compound to give a total of 5 ml. Water was then added to total volume of 100 ml. This stock solution was diluted with the described solvent-emulsifier-water mixture to the given concentration.

C.1.1) Preventative Fungicidal Control of *Botrytis cinerea* on Leaves of Green Pepper Young seedlings of green pepper were grown in pots to the 4 to 5 leaf stage. These plants were sprayed to run-off with an aqueous suspension, containing the concentration of active ingredient or their mixture mentioned in the table below. The next day the plants were inoculated with an aqueous biomalt solution containing the spore suspension of *Botrytis cinerea*. Then the plants were immediately transferred to a humid chamber. After 5 days at 22 to 24° C. and a relative humidity close to 100% the extent of fungal attack on the leaves was visually assessed as % diseased leaf area.

The untreated control showed 90% disease.

Plants treated with 250 ppm of compounds F1 and F13, respectively, had at most 40% diseased leaf area. Plants treated with 250 ppm of compound C1 showed 90% diseased leaf area.

Plants treated with 500 ppm of compounds F1, F5, F8, F11, F18, F20 and F26, respectively, had at most 7% diseased leaf area.

C.1.2) Protective Control of Soy Bean Rust on Soy Beans Caused by *Phakopsora Pachyrhizi*

Leaves of pot-grown soy bean seedlings were sprayed to run-off with an aqueous suspension, containing the concentration of active ingredient or their mixture as described below. The plants were allowed to air-dry. The trial plants were cultivated for 1 day in a greenhouse chamber at 23-27° C. and a relative humidity between 60 and 80%. Then the plants were inoculated with spores of *Phakopsora pachyrhizi*. To ensure the success the artificial inoculation, the plants were transferred to a humid chamber with a relative humidity of about 95% and 20 to 24° C. for 24 h. The trial plants were cultivated for fourteen days in a greenhouse chamber at 23-27° C. and a relative humidity between 60 and 80%. The extent of fungal attack on the leaves was visually assessed as % diseased leaf area.

The untreated control showed 70% diseased leaf area.

Plants treated with 250 ppm of compounds F1 and F15, respectively, had at most 30% diseased leaf area. Plants treated with 250 ppm of compound C1 showed 70% diseased leaf area.

Plants treated with 500 ppm of compounds F2, F3, F4, F5, F10, F13, F14, F21, F22, F23, F24 and F25, respectively, had at most 20% diseased leaf area.

C.1.3) Control of Late Blight on Tomatoes Caused by *Phytophthora infestans*

Young seedlings of tomato plants were grown in pots. These plants were sprayed to run-off with an aqueous suspension, containing the concentration of active ingredient or their mixture mentioned in the table below. The next day, the treated plants were inoculated with an aqueous suspension of sporangia of *Phytophthora infestans*. After inoculation, the trial plants were immediately transferred to a humid chamber. After 6 days at 18 to 20° C. and a relative humidity close to 100% the extent of fungal attack on the leaves was visually assessed as % diseased leaf area.

The untreated control showed 90% diseased leaf area.

Plants treated with 500 ppm of compounds F1, F8, F11, F15, F16, F18, F22, F23, F24, F25 and F26, respectively, had at most 20% diseased leaf area.

C.2) Microtests

The active compounds were formulated separately as a stock solution having a concentration of 10000 ppm in dimethyl sulfoxide.

C.2.1) Activity against the grey mold *Botrytis cinerea* in the microtiterplate test (Botrci)

The stock solutions were mixed according to the ratio, pipetted onto a micro titer plate (MTP) and diluted with water to the stated concentrations. A spore suspension of *Botrci cinerea* in an aqueous biomalt or yeast-bactopeptone-sodiumacetate solution was then added. The plates were placed in a water vapor-saturated chamber at a temperature of 18° C. Using an absorption photometer, the MTPs were measured at 405 nm 7 days after the inoculation.

The measured parameters were compared to the growth of the active compound-free control variant (100%) and the fungus-free and active compound-free blank value to determine the relative growth in % of the pathogens in the respective active compounds.

C.2.2) Activity Against the Late Blight Pathogen *Phytophthora infestans* in the Microtiter Test (Phytin)

The stock solutions were mixed according to the ratio, pipetted onto a micro titer plate (MTP) and diluted with water to the stated concentrations. A spore suspension of *Phytophtora infestans* containing a pea juice-based aqueous nutrient medium or DDC medium was then added. The plates were placed in a water vapor-saturated chamber at a temperature of 18° C. Using an absorption photometer, the MTPs were measured at 405 nm 7 days after the inoculation.

The measured parameters were compared to the growth of the active compound-free control variant (100%) and the fungus-free and active compound-free blank value to determine the relative growth in % of the pathogens in the respective active compounds.

C.2.3) Activity Against Leaf Blotch on Wheat Caused by *Septoria tritici* (Septtr)

The stock solutions were mixed according to the ratio, pipetted onto a micro titer plate (MTP) and diluted with water to the stated concentrations. A spore suspension of *Septoria tritici* in an aqueous biomalt or yeast-bactopeptone-glycerine solution was then added. The plates were placed in a water vapor-saturated chamber at a temperature of 18° C. Using an absorption photometer, the MTPs were measured at 405 nm 7 days after the inoculation.

The measured parameters were compared to the growth of the active compound-free control variant (100%) and the fungus-free and active compound-free blank value to determine the relative growth in % of the pathogens in the respective active compounds.

| Compound no. | Growth (%) at 32 pm Botrci | Growth (%) at 32 pm Phytin | Growth (%) at 32 pm Septtr |
|---|---|---|---|
| F1 | | | 0 |
| F3 | | | 0 |
| F4 | | | 0 |
| F5 | | | 0 |
| F6 | 0 | 1 | 0 |
| F8 | | | 0 |
| F11 | | | 0 |
| F12 | 0 | 0 | 0 |
| F13 | | | 0 |
| F15 | | | 0 |
| F16 | | | 2 |

C.3) Microtests with Mixtures of Active Compounds

The active compounds were formulated separately as a stock solution having a concentration of 10000 ppm in dimethyl sulfoxide.

C.3.1) Activity Against the Late Blight Pathogen *Phytophthora infestans* in the Microtiter Test (Phytin)

The stock solutions were mixed according to the ratio, pipetted onto a micro titer plate (MTP) and diluted with water to the stated concentrations. A spore suspension of *Phytophtora infestans* containing a pea juice-based aqueous nutrient medium or DDC medium was then added. The plates were placed in a water vapor-saturated chamber at a temperature of 18° C. Using an absorption photometer, the MTPs were measured at 405 nm 7 days after the inoculation.

The measured parameters were compared to the growth of the active compound-free control variant (100%) and the fungus-free and active compound-free blank value to determine the relative growth in % of the pathogens in the respective active compounds. These percentages were converted into efficacies.

The expected efficacies of active compound mixtures were determined using Colby's formula [R. S. Colby, "Calculating synergistic and antagonistic responses of herbicide combinations", Weeds 15, 20-22 (1967)] and compared with the observed efficacies.

| Active compound/ active mixture | Concentration (ppm) | Mixture | Observed efficacy | Calculated efficacy according to Colby (%) | Synergism (%) |
|---|---|---|---|---|---|
| F15 | 1 | — | 46 | | |
| Pyraclostrobin | 0.063 | — | 24 | | |
| Epoxiconazole | 0.25 | — | 11 | | |
| Azole* | 4 | — | 20 | | |
| Fluxapyroxad | 0.063 | — | 12 | | |
| F15 Pyraclostrobin | 1 0.063 | 16:1 | 87 | 59 | 28 |
| F15 Epoxiconazole | 1 0.25 | 4:1 | 86 | 52 | 34 |
| F15 Azole* | 1 4 | 1:4 | 91 | 57 | 34 |
| F15 Fluxapyroxad | 1 0.063 | 16:1 | 84 | 53 | 31 |

C.3.2) Activity Against the Grey Mold *Botrytis cinerea* in the Microtiterplate Test (Botrci)

The stock solutions were mixed according to the ratio, pipetted onto a micro titer plate (MTP) and diluted with water to the stated concentrations. A spore suspension of *Botrci cinerea* in an aqueous biomalt or yeast-bactopeptone-sodiumacetate solution was then added. The plates were placed in a water vapor-saturated chamber at a temperature of 18° C. Using an absorption photometer, the MTPs were measured at 405 nm 7 days after the inoculation.

| Active compound/ active mixture | Concentration (ppm) | Mixture | Observed efficacy | Calculated efficacy according to Colby (%) | Synergism (%) |
|---|---|---|---|---|---|
| F15 | 1 | — | 18 | | |
| Pyraclostrobin | 0.016 | — | 0 | | |
| Epoxiconazole | 0.063 | — | 34 | | |
| Azole* | 1 | — | 15 | | |
| Fluxapyroxad | 0.016 | — | 13 | | |
| F15 Pyraclostrobin | 1 0.016 | 63:1 | 69 | 18 | 51 |
| F15 Epoxiconazole | 1 0.063 | 16:1 | 99 | 45 | 54 |
| F15 Azole* | 1 1 | 1:1 | 100 | 30 | 70 |
| F15 Fluxapyroxad | 1 0.016 | 63:1 | 98 | 28 | 70 |

C.3.3) Activity Against Rice Blast *Pyricularia Oryzae* in the Microtiterplate Test (Pyrior)

The stock solutions were mixed according to the ratio, pipetted onto a micro titer plate (MTP) and diluted with water to the stated concentrations. A spore suspension of *Pyricularia oryzae* in an aqueous biomalt or yeast-bactopeptone-glycerine solution was then added. The plates were placed in a water vapor-saturated chamber at a temperature of 18° C. Using an absorption photometer, the MTPs were measured at 405 nm 7 days after the inoculation.

| Active compound/ active mixture | Concentration (ppm) | Mixture | Observed efficacy | Calculated efficacy according to Colby (%) | Synergism (%) |
|---|---|---|---|---|---|
| F15 | 4 | — | 8 | | |
|  | 1 | — | 0 | | |
| F19 | 4 | — | 14 | | |
|  | 1 | — | 5 | | |
| Azole* | 16 | — | 65 | | |
| Epoxiconazole | 0.25 | — | 5 | | |
| F15 Azole* | 1 16 | 1:16 | 96 | 65 | 31 |
| F15 Epoxiconazole | 4 0.25 | 16:1 | 66 | 12 | 54 |
| F19 Azole* | 1 16 | 1:16 | 86 | 67 | 19 |
| F19 Epoxiconazole | 4 0.25 | 16:1 | 36 | 18 | 18 |

C.3.4) Activity Against Leaf Blotch on Wheat Caused by *Septoria tritici* (Septtr)

The stock solutions were mixed according to the ratio, pipetted onto a micro titer plate (MTP) and diluted with water to the stated concentrations. A spore suspension of *Septoria tritici* in an aqueous biomalt or yeast-bactopeptone-glycerine solution was then added. The plates were placed in a water vapor-saturated chamber at a temperature of 18° C. Using an absorption photometer, the MTPs were measured at 405 nm 7 days after the inoculation.

| Active compound/ active mixture | Concentration (ppm) | Mixture | Observed efficacy | Calculated efficacy according to Colby (%) | Synergism (%) |
|---|---|---|---|---|---|
| F19 | 0.016 | — | 0 | | |
| F24 | 0.063 | — | 1 | | |
| Pyraclostrobin | 0.001 | — | 38 | | |
| Azole* | 4 | — | 40 | | |
|  | 0.25 | — | 4 | | |
| F19 Pyraclostrobin | 0.016 0.001 | 16:1 | 63 | 38 | 25 |
| F24 Azole* | 0.063 0.25 | 1:4 | 33 | 4 | 29 |

Azole* = 2-[rel-(2S;3R)-3-(2-chlorophenyl)-2-(2,4-difluorophenyl)-oxiranylmethyl]-2H-[1,2,4]triazole-3-thiol

The invention claimed is:

1. A biocide composition comprising an ionic polymer produced by a process comprising polymerizing
   a) at least one α-dicarbonyl compound,
   b) at least one aldehyde,
   c) at least one amino compound having at least two primary amino groups, and
   d) optionally an amino compound having only one primary amino group in the presence of
   e) at least one protic acid,
   to provide a polymer product;
   and optionally subjecting the reaction product to an anion exchange,
   the ionic polymer having a weight average molecular weight of from 2000 to 200,000, and has a dispersity PDI of 1.1 to 20,
   where in the components a) and b) the aldehyde carbonyl groups may also be present as hemiacetal or acetal and the ketone carbonyl groups may also be present as hemiketal or ketal;
   where the main chain of the at least one compound comprising imidazolium groups does not contain 1,4-bound phenylene rings;
   where the amino compound having at least two primary amino groups is not 1,3-diamino-2-hydroxy-propane or 1,3-diamino-2-hydroxy-2-methyl-propane; and
   where the polymer comprises at least 10 repeat units each comprising an imidazolium ring;
   and at least one carrier and/or at least one auxiliary agent.

2. The composition as claimed in claim 1, wherein the main chain of the at least one imidazolium compound apart from the nitrogen atoms of the imidazolium groups does not contain any quaternary nitrogen atoms that bear 4 residues that are different from hydrogen.

3. The composition as claimed in claim 1, wherein component a) comprises or consists of glyoxal or a hemiacetal or acetal thereof.

4. The composition as claimed in claim 1, wherein component b) comprises or consists of a formaldehyde source or an aldehyde of formula $R^3$—CHO, where $R^3$ is selected from $C_1$-$C_{20}$-alkyl, a group —$CH_2[O$—$CH_2CH_2]_x$—$OR^a$, wherein x is 1, 2, 3, 4, 5 or 6 and $R^a$ is hydrogen or $C_1$-$C_4$-alkyl; and phenyl which may be substituted by 1, 2, 3, 4 or 5 radicals selected from $C_1$-$C_{20}$-alkyl, $C_1$-$C_6$-haloalkyl, $C_1$-$C_{20}$-alkoxy, $C_1$-$C_6$-haloalkoxy and NR'R", where R' and R'R" are, independently of each other, selected from hydrogen and C1-C6-alkyl; or comprises or consists of a formaldehyde source.

5. The composition as claimed in claim 1, wherein component c) is selected from
amines of the formula 1

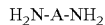   (1)

wherein
A is a divalent aliphatic, alicyclic, aliphatic-alicyclic, aromatic or araliphatic radical, where the aliphatic moieties in the aforementioned aliphatic, aliphatic-alicyclic or araliphatic radicals may be interrupted by one or more nonadjacent groups which are selected from —O—, —S— and —N($R^b$)—, where $R^b$ is selected from hydrogen, $C_1$-$C_{20}$-alkyl and a group [$CH_2CH_2$—O]$_y$—$R^c$, wherein y is 1, 2, 3, 4, 5 or 6 and $R^c$ is hydrogen or $C_1$-$C_4$-alkyl; where alicyclic or aromatic moieties in the aforementioned alicyclic, aliphatic-alicyclic, aromatic or araliphatic radicals may be substituted by 1, 2, 3 or 4 radicals selected from $C_1$-$C_{20}$-alkyl, $C_1$-$C_{20}$-alkoxy, a radical of the formula
—O—[$CH_2CH_2O$]$_z$—$R^d$, where $R^d$ is hydrogen or $C_1$-$C_4$-alkyl and z is 1, 2, 3, 4, 5 or 6;
carboxyl and carboxylate, and where the aliphatic moieties in the aforementioned aliphatic, aliphatic-alicyclic or araliphatic radicals may be substituted by 1, 2, 3 or 4 radicals selected from $C_1$-$C_{20}$-alkoxy, a radical of the formula —O—[$CH_2CH_2O$]$_z$—$R^d$, where $R^d$ is hydrogen or $C_1$-$C_4$-alkyl and z is 1, 2, 3, 4, 5 or 6, carboxyl and carboxylate; with the proviso that the aromatic or araliphatic radicals do not contain 1,4-bound phenylene rings;
amines of the formula 2

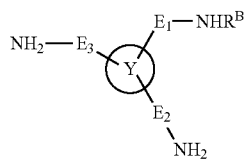   (2)

in which
Y is $CR^C$, N, $C_2$-$C_6$-alkyl or $C_3$-$C_6$-cycloalkyl;
$E_1$, $E_2$ and $E_3$, independently of each other, are a single bond, $C_1$-$C_{10}$-alkylene, —$NR^D$—$C_2$-$C_{10}$-alkylene or —O—$C_1$-$C_{10}$-alkylene, with the proviso that $E_1$, $E_2$ and $E_3$ are not a single bond and are not —$NR^D$—C2-$C_{10}$-alkylene when Y is N;
$R^C$ is H, $C_1$-$C_4$-alkyl, $C_2$-$C_4$-hydroxyalkyl or $C_1$-$C_4$-alkoxy; and
$R^B$ and $R^D$, independently of each other, are H, $C_1$-$C_4$-alkyl, $C_2$-$C_4$-hydroxyalkyl or $C_1$-$C_4$-alkoxy and
mixtures thereof.

6. The composition as claimed in claim 5, wherein
the divalent aliphatic radicals A are selected from linear and branched $C_1$-$C_{30}$-alkylene which may be interrupted by one or more nonadjacent groups which are selected from —O—, —S— and —N($R^b$)—, where $R^b$ is selected from hydrogen, $C_1$-$C_{20}$-alkyl and a group [$CH_2CH_2$—O]$_y$—$R^c$, wherein y is 1, 2, 3, 4, 5 or 6 and $R^c$ is hydrogen or $C_1$-$C_4$-alkyl; and/or may be substituted by 1, 2, 3 or 4 radicals selected from $C_1$-$C_{20}$-alkoxy, a radical of the formula —O—[$CH_2CH_2O$]$_z$—$R^d$, where $R^d$ is hydrogen or $C_1$-$C_4$-alkyl and z is 1, 2, 3, 4, 5 or 6, carboxyl and carboxylate;

the divalent alicyclic radicals A are selected from $C_5$-$C_8$-cycloalkylene which may carry 1, 2, 3 or 4 $C_1$-$C_4$-alkyl radicals;
the divalent aliphatic-alicyclic radicals A are selected from $C_1$-$C_4$-alkylene-$C_5$-$C_8$-cycloalkylene, $C_5$-$C_8$-cycloalkylene-$C_1$-$C_4$-alkylene-$C_5$-$C_8$-cycloalkylene and $C_1$-$C_4$-alkylene-$C_5$-$C_8$-cycloalkylene-$C_1$-$C_4$-alkylene, with the cycloalkylene radicals possibly carrying 1, 2, 3 or 4 $C_1$-$C_4$-alkyl radicals;
the divalent aromatic radicals A are selected from 1,2-phenylene, 1,3-phenylene, naphthylene and biphenylene, with the phenylene radicals possibly carrying 1, 2, 3 or 4 radicals selected from $C_1$-$C_{20}$-alkyl, $C_1$-$C_{20}$-alkoxy and a radical of the formula —O—[$CH_2CH_2O$]$_z$—$R^d$, where $R^d$ is hydrogen or $C_1$-$C_4$-alkyl and z is 1, 2, 3, 4, 5 or 6; or
the divalent araliphatic radicals A are selected from phenylene-$C_1$-$C_4$-alkylene, phenylene-$C_1$-$C_4$-alkylene-phenylene and $C_1$-$C_4$-alkylene-phenylene-$C_1$-$C_4$-alkylene, with the phenylene radicals possibly carrying 1, 2, 3 or 4 radicals selected from $C_1$-$C_{20}$-alkyl, $C_1$-$C_{20}$-alkoxy and a radical of the formula
—O—[$CH_2CH_2O$]$_z$—$R^d$, where $R^d$ is hydrogen or $C_1$-$C_4$-alkyl and z 1, 2, 3, 4, 5 or 6.

7. The composition as claimed in claim 5, wherein component c) is selected from the group consisting of
compounds of the formula $H_2N$—($CH_2$)$_m$—$NH_2$, wherein m is an integer of 3 to 20, where a $CH_2$ group may be substituted by a carboxyl or carboxylate group;
compounds of the formula $NH_2$—[B—X—]$_k$—B—$NH_2$; in which X is O, each B independently is $C_2$-$C_6$-alkylene; and k is an integer from 1 to 100;
bis(4-aminocyclohexyl)methane, bis(3-aminocyclohexyl)methane, isophoronediamine, 1,1-bis(aminomethyl)cyclohexane, 1,2-bis(aminomethyl)cyclohexane, 1,3-bis(aminomethyl)cyclohexane, 1,4-bis(aminomethyl)cyclohexane, aminopropylcyclohexylamine, 3(4)-aminomethyl-1-methylcyclohexylamine;
3-aminomethyl-benzylamine;
amines of the formula 2,

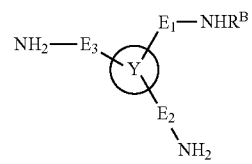   (2)

wherein Y is $CR^C$, where $R^C$ is H or $C_1$-$C_4$-alkyl, and $E_1$, $E_2$ and $E_3$, independently of each other, are —O—$C_1$-$C_6$-alkylene; and
mixtures thereof.

8. The composition as claimed in claim 1, wherein component c) is a mixture of amino compounds, comprising at least one amine with two primary amino groups and at least one amine with more than two primary amino groups.

9. The composition as claimed in claim 1, wherein component c) is a polyvinylamine polymer, polyalkylenimine, polyamidoamine or a mixtures thereof.

10. The composition as claimed in claim 1, wherein the at least one protic acid e) is not a hydrohalic acid and the imidazolium compound does essentially not comprise anions of a hydrohalic acid.

11. The composition as claimed in claim 1, wherein the anions of the at least one protic acid e) and/or the anions of the imidazolium compound are selected from the group consisting of:
the group of carboxylates and polybasic carboxylic acids,
the group of sulfates, sulfites and sulfonates, and
the group of phosphates.

12. The composition as claimed in claim 1, wherein the anions of the at least one protic acid e) and/or the anions of the imidazolium compound are selected from the group consisting of formate, acetate, propionate, butyrate, pentanoate, hexanoate, heptanoate, octanoate, glycolate (hydroxyacetate), adipate, succinate, phthalate, terephthalate, methoxyacetate, $(C_1\text{-}C_4\text{-alcoxy})(CH_2CH_2O)_xCH_2COO^-$ with x being 1-4, benzoate, hydrogenphosphate, sulfate, hydrogensulfate and methanesulfonate.

13. The composition as claimed in claim 1, where in case that the composition is a crop protection composition, the anions of the at least one protic acid e) and/or the anions of the imidazolium compound are additionally selected from the group consisting of chloride, bromide and iodide.

14. The composition as claimed in claim 1, wherein the composition is
a plant protection composition;
a personal care composition,
a home care composition,
a composition used for industrial or institutional or hospital disinfection,
a material protection composition or
a pharmaceutical composition.

15. A method for combating harmful organisms or for protecting human beings, animals, materials or processes from the effects of these harmful organisms, wherein the habitat of the harmful organism or the human being, animal or material to be protected is brought into contact with a biocide composition or the biocide composition is employed in said process, wherein the biocide composition is as claimed in claim 1.

16. The method according claim 15 wherein the harmful organism is selected from the group consisting of bacteria and fungi.

17. The method for combating harmful fungi, which method comprises treating the fungi or materials, plants, parts thereof, the locus where the plants grow or are to grow or plants' propagation material to be protected from fungal attack with an effective amount of the composition as claimed in claim 1.

18. A process for combating harmful fungi which comprises contacting the fungi with the biocide as claimed in claim 1.

19. The biocide composition as claimed in claim 1, wherein the carrier and auxiliary agent is selected from the group consisting of further microbicidal compounds, solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

20. The biocide composition as claimed in claim 1, comprising the carrier is a fatty alcohols.

21. The biocide composition as claimed in claim 19, wherein said further microbicidal compound is selected from the group consisting of isothiazolones, activated halogen compounds, formaldehyde release compounds, phenolic compounds, aldehydes, acids, esters, biphenyls, urea derivatives, O-acetals, O-formals, N-acetals, N-formals, benzamidines, phthalimides, pyridine derivatives, quaternary ammonium and phosphonium compounds, amines, amphoteric compounds, dithiocarbamates, compounds containing active oxygen, inorganic salts, organic metal salts, and mixtures thereof.

22. The biocide composition as claimed in claim 21, wherein the further microbicidal compound is selected from the group consisting of 2-bromo-2-nitropropane-1,3-diol; 2-(hydroxymethyl)-2-nitro-1,3-propanediol; 5-chloro-2-methyl-2H-isothiazol-3-one; 2-methyl-2H-isothiazol-3-one; 1,2-benzisothiazol-3(2H)-one; 2-n-octyl-2H-isothiazol-3-one; 4,5-dichloro-2-octyl-2H-isothiazol-3-one; 2 butyl-benzo-[d]isothiazol-3-one; dibromodicyanobutane; [beta]-bromo-[beta]-nitrostyrene; 7a-ethyldihydro-1H,3H,5H-oxazolo[3,4-c]oxazole; tetrahydro-1,3,4,6-tetrakis (hydroxymethyl)-imidazo[4,5 d]imidazole-2,5(1H,3H)-dione; 1,3-dimethyl-5,5-dimethylhydantoin; diazolidinyl ureas; imidazolidinyl ureas; N'-(3,4-dichlorophenyl)-N,N-dimethyl urea; 3,3'-methylene¬bis(5 methyl-oxazolidine); 2-sodiumsulfidopyridine-N-oxide and its metal salts; dibromonitritopropionamide; tetrakishydroxymethylphosphonium salts; ortho-phenylphenol; salts of ortho-phenylphenol; 1-(3-chloroallyl)-3,5,7-triaza-1-azodiadamantane salts; 5-chloro-2-(2,4-dichlorophenoxy)phenol; 3,4,4' trichlorocarbanilide; o-benzo-p-chlorophenol; p-hydroxybenzoates; 2-(thiocyanomethylthio) benzothiazole; 3,5-dimethyl-1,3,5-thiadiazinane-2-thione; 2,4 dichlorobenzyl alcohol; chlorothalonil; methylenebis(thiocyanate); peracetic acid; 4,4-dimethyl-oxazolidine; phenoxyethanol; phenoxypropanol; 2,6-dimethyl-m-dioxan-4-ol-acetate; glutaraldehyde; glyoxal; ortho-phthalaldehyde; 4-(2-nitrobutyl)-morpholine; 1,3,5-tris-(2-hydroxyethyl)-1,3,5-hexahydrotriazine; benzalkoniumchloride; polyhexamethylenebiguanide salts;
poly(oxyethylene(dimethylimino)ethylene(dimethylimino)-ethylene dichloride; chlorhexidine gluconate; chloroisocyanurates; 1-bromo-3-chloro-5,5-dimethylhydantoin; polyvinylamines; polyethylene imines; IPBC; terbutryn; ziram; zineb; dichlofluanid; trichlofuanid; folpet; metal dihexa-2,4-dienoate; tebuconazole; 3 benzo(b)thien-2-yl-5,6-dihydro-1,4,2-oxathiazine-4-oxide; pyrithiones; thiram; cybutryne; MBT; carbendazim; diuron; chlorotoluron; fluorometuron; thiabendazole; metazachlor; CuSCN; and dicopper oxide.

23. The biocide composition as claimed in claim 22, wherein the further microbicidal compound is selected from the group consisting of phenoxyethanol, glutaraldehyde and glyoxal.

24. The biocide composition as claimed in claim 19, comprising a surfactant which is selected from the group consisting of cationic, nonionic and amphoteric surfactants.

25. The biocide composition as claimed in claim 24, comprising a nonionic surfactant which is selected from the group consisting of alkoxylates, N-substituted fatty acid amides, amine oxides, esters, sugar-based surfactants, and polymeric surfactants.

26. The biocide composition as claimed in claim 24, comprising a nonionic surfactant which is selected from the group consisting of alkylpolyglucosides, homopolymers and copolymers of vinylpyrrolidone, alcohols which have been alkoxylated with 1 to 50 equivalents of ethylene oxide and/or propylene oxide, amines which have been alkoxylated with 1 to 50 equivalents of ethylene oxide and/or propylene oxide, and condensation products of poly(ethyleneoxide) with fatty acids, fatty alcohols, fatty amides, polyhydric alcohols, and polypropylene oxide.

27. The biocide composition as claimed in claim 1, comprising at least one cosmetically acceptable carrier and further comprising a component selected from the group consisting of emulsifiers, surfactants, perfume oils, rheology modifiers (thickeners), hair polymers, hair and skin conditioners, water-soluble or dispersible silicone-comprising polymers, bleachers, gelling agents, care agents, colorants, tinting agents, tanning agents, dyes, pigments, antidandruff agents, sunscreen agents, deodorizing active substances, vitamins, plant extracts, bodying agents, humectants, refatting agents, collagen, protein hydrolysates, lipids, antioxidants, antifoaming agents, antistatic agents, emollients, and softeners.

28. The composition as claimed in claim 1, wherein the carrier is at least one cosmetically acceptable carrier and further comprising a cationic polymer selected from the following groups:

homopolymers or copolymers derived from acrylic or methacrylic esters or amides and comprising at least one of the units of the following formulae:

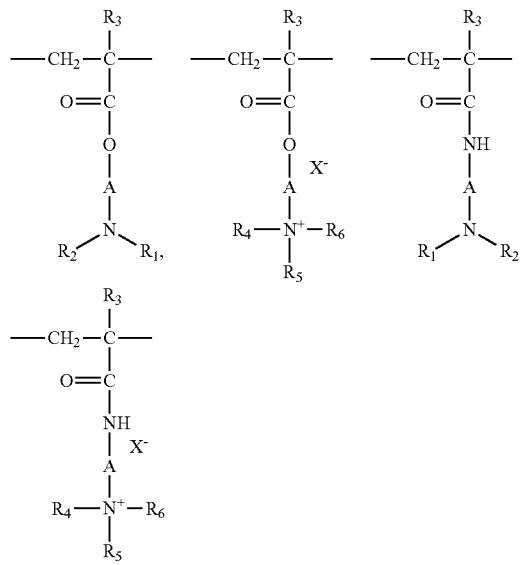

wherein $R_3$, which may be identical or different, is chosen from a hydrogen atom and a $CH_3$ radical;

A, which may be identical or different, is chosen from linear or branched alkyl groups comprising from 1 to 6 carbon atoms, and hydroxyalkyl groups comprising from 1 to 4 carbon atoms;

$R_4$, $R_5$ and $R_6$, which may be identical or different, are chosen from alkyl groups comprising from 1 to 18 carbon atoms and a benzyl radical, and in at least one embodiment, $R_4$, $R_5$ and $R_6$, which may be identical or different, are chosen from alkyl groups comprising from 1 to 6 carbon atoms;

$R_1$ and $R_2$, which may be identical or different, are chosen from hydrogen and alkyl groups comprising from 1 to 6 carbon atoms; and $X^-$ is chosen from anions derived from a mineral or organic acid, and halides;

cationic polysaccharides;

polymers comprising piperazinyl units and divalent alkylene or hydroxyalkylene radicals comprising straight or branched chains, optionally interrupted by oxygen, sulfur or nitrogen atoms or by aromatic or heterocyclic rings, and oxidation and/or quaternization products of these polymers;

water-soluble polyamino amides;

polyaminoamide derivatives resulting from the condensation of polyalkylene polyamines with polycarboxylic acids followed by alkylation with difunctional agents;

polymers obtained by reaction of a polyalkylene polyamine comprising two primary amine groups and at least one secondary amine group with a dicarboxylic acid chosen from diglycolic acid and saturated aliphatic dicarboxylic acids comprising from 3 to 8 carbon atoms;

cyclopolymers of alkyldiallylamine or of dialkyldiallylammonium, the homopolymers or copolymers comprising, as main constituent of the chain, units corresponding to one or both of the formulae

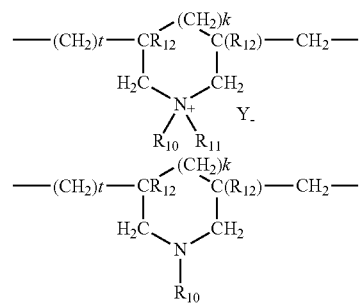

wherein k and t are equal to 0 or 1, the sum k+t being equal to 1;

$R_{12}$ is chosen from a hydrogen atom and a methyl radical;

$R_{10}$ and $R_{11}$, which may be identical or different, are chosen from alkyl groups comprising from 1 to 6 carbon atoms, hydroxyalkyl groups wherein the alkyl group, for example, comprises from 1 to 5 carbon atoms, and lower ($C_1$-$C_4$) amidoalkyl groups, or $R_{10}$ and $R_{11}$, together with the nitrogen atom to which they are attached, are chosen from heterocyclic groups; and $Y^-$ is an anion which is bromide, chloride, acetate, borate, citrate, tartrate, bisulfate, bisulfite, sulfate or phosphate;

quaternary diammonium polymers containing repeating units corresponding to the following formula (6)

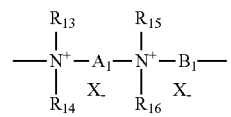

wherein $R_{13}$, $R_{14}$, $R_{15}$ and $R_{16}$, which may be identical or different, are chosen from aliphatic, alicyclic or arylaliphatic radicals comprising from 1 to 20 carbon atoms, and lower hydroxyalkylaliphatic radicals such as hydroxyethyl, or $R_{13}$, $R_{14}$, $R_{15}$ and $R_{16}$, together or separately, constitute, with the nitrogen atoms to which they are attached, heterocycles optionally comprising a second heteroatom other than nitrogen, or $R_{13}$, $R_{14}$, $R_{15}$ and $R_{16}$ are chosen from a linear or branched ($C_1$-$C_6$)alkyl radical substituted with a nitrile, ester, acyl, or amide group, and a group —CO—O—$R_{17}$-D or —CO—NH—$R_{17}$-D, wherein $R_{17}$ is an alkylene and D is a quaternary ammonium group;

$A_1$ and $B_1$ are chosen from polymethylene groups comprising from 2 to 20 carbon atoms, wherein the polymethylene groups may be linear or branched, saturated or unsaturated, and wherein the polymethylene groups may comprise, linked to or intercalated in the main chain, at least one aromatic ring, at least one oxygen or sulfur atom, or sulfoxide, sulfone, disulfide, amino, alkylamino, hydroxyl, quaternary ammonium, ureido, amide or ester groups, and $X^-$ is an anion derived from a mineral or organic acid;

or $A_1$, $R_{13}$ and $R_{15}$ can form, with the two nitrogen atoms to which they are attached, a piperazine ring;

in addition, if $A_1$ is chosen from a linear or branched, saturated or unsaturated alkylene or hydroxyalkylene radical, $B_1$ is chosen from polymethylene groups comprising from 2 to 20 carbon atoms, wherein the polymethylene groups may be linear or branched, saturated or unsaturated, and wherein the polymethylene groups may comprise, linked to or intercalated in the main chain, at least one aromatic ring, at least one oxygen or sulfur atom, sulfoxide, sulfone, disulfide, amino, alkylamino, hydroxyl, quaternary ammonium, ureido, amide or ester groups, and a group $(CH_2)_n$—CO-D-OC—$(CH_2)_n$—;

wherein D is chosen from
a) a glycol residue of formula: —O—Z—O—, wherein Z is chosen from a linear or branched hydrocarbon-based radical, and a group corresponding to one of the following formulae:

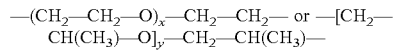

—$(CH_2$—$CH_2$—O$)_x$—$CH_2$—$CH_2$— or —[$CH_2$—CH($CH_3$)—O]$_y$—$CH_2$—CH($CH_3$)— wherein x and y are integers ranging from 1 to 4, which is a defined and unique degree of polymerization or an average degree of polymerization;

b) a bis-secondary diamine residue;
c) a bis-primary diamine residue of formula: —NH—Y—NH—, wherein Y is chosen from a linear or branched hydrocarbon-based-radical, and the divalent radical —$CH_2$—$CH_2$—S—S—$CH_2$—$CH_2$—; and
d) a ureylene group of formula: —NH—CO—NH—; and wherein n is an integer ranging from 1 to 20;
polyquaternary ammonium polymers comprised of units of the following formula (7)

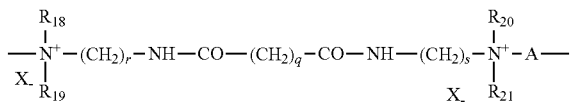

wherein
$R_{18}$, $R_{19}$, $R_{20}$ and $R_{21}$, which may be identical or different, are chosen from a hydrogen atom, and methyl, ethyl, propyl, [beta]-hydroxyethyl, [beta]-hydroxypropyl and —$CH_2CH_2$(O$CH_2CH_2)_p$OH radicals, wherein p is equal to 0 or to an integer ranging from 1 to 6, with the proviso that $R_{18}$, $R_{19}$, $R_{20}$ and $R_{21}$ do not simultaneously represent a hydrogen atom,
r and s, which may be identical or different, are integers ranging from 1 to 6,
q is an integer ranging from 1 to 34,
$X^-$ is an anion,
A is chosen from a dihalide radical and —$CH_2$—$CH_2$—O—$CH_2$—$CH_2$—;

quaternary polymers of vinyllactam;
crosslinked polymers of methacryloyloxy($C_1$-$C_4$)alkyltri ($C_1$-$C_4$)alkyl-ammonium salts;
cationic proteins and cationic protein hydrolysates;
polyalkyleneimines;
polymers containing vinylpyridine or vinylpyridinium units;
condensates of polyamines and of epichlorohydrin; and
quaternary polyureylenes and chitin derivatives.

29. The composition as claimed in claim 1, comprising at least one cosmetically acceptable carrier and further comprising at least one cosmetically acceptable active ingredient that is beneficial to keratin materials and is selected from the group consisting of:
(1) hydrolyzed or nonhydrolyzed, modified or unmodified saccharides, oligosaccharides and polysaccharides,
(2) hydrolyzed or nonhydrolyzed, modified or unmodified amino acids, oligopeptides, peptides and proteins,
(3) branched or unbranched fatty acids and alcohols,
(4) animal, plant and mineral waxes,
(5) ceramides and pseudoceramides,
(6) hydroxylated organic acids,
(7) UV-screening agents,
(8) antioxidants and free-radical scavengers,
(9) chelating agents,
(10) antidandruff agents,
(11) seborrhea regulators,
(12) calmatives,
(13) cationic surfactants,
(14) organomodified and non-organomodified silicones,
(15) mineral, plant and animal oils,
(16) polyisobutenes and poly([alpha]-olefins),
(17) fatty esters, for example those comprising from 15 to 50 carbon atoms,
(18) soluble and dispersed anionic polymers, and
(19) soluble and dispersed nonionic polymers, and mixtures thereof.

30. The composition as claimed in claim 1, for treating a keratinous substrate, comprising at least one cosmetically acceptable carrier and further comprising at least one fatty quaternary amine.

31. The composition of claim 30, wherein the fatty quaternary amine is selected from the group consisting of Behentrimonium chloride, Cocotrimonium chloride, Cethethyldimonium bromide, Dibehenyldimonium chloride, Dihydrogenated tallow benzylmonium chloride, disoyadimonium chloride, Ditallowedimonium chloride, Hydroxycetyl hydroxyethyl dimonium chloride, Hydroxyethyl Behenamidopropyl dimonium chloride, Hydroxyethyl Cetyldimonium chloride, Hydroxyethyl tallowedimonium chloride, myristalkonium chloride, PEG-2 Oleamonium chloride, PEG-5 Stearmonium chloride, PEG-15 cocoyl quaternium 4, PEG-2 stearalkonium 4, lauryltrimonium chloride; Quaternium-16; Quaternium-18, lauralkonium chloride, olealkonium chloride, cetylpyridinium chloride, Polyquaternium-5, Polyquaternium-6, Polyquaternium-7, Polyquaternium-10, Polyquaternium-22, Polyquaternium-37, Polyquaternium-39, Polyquaternium-47, cetyl trimonium chloride, dilauryldimonium chloride, cetalkonium chloride, dicetyldimonium chloride, soyatrimonium chloride, stearyl octyl dimonium methosulfate, behentrimonium methosulfate (18-MEA), stearalkonium chloride, and a mixture of behentrimonium methosulfate and $C_{10}$-$C_{40}$ isoalkylamidopropylethyldimonium ethosulfate and cetyl alcohol.

32. The composition as claimed in claim 1, comprising an additional component selected from enzymes, bleaches, whiteners, color care agents, fabric softeners, suds suppressors, dispersants, dye transfer inhibitors, chelating agents, aerosol propellants, gelling agents, or thickening agents.

33. The composition as claimed in claim 1, comprising a surfactant which is selected from polyelectrolytes.

34. The composition as claimed in claim 33, wherein the polyelectrolyte is selected from alkali salts of polyacrylic acid.

35. The composition as claimed in claim 1, wherein the polymer has a dispersity PDI of 1.5 to 15.

36. The composition as claimed in claim 1, wherein the polymer the weight average molecular weight Mw for the polymeric ionic compound from 4,000 to 200,000.

37. A biocide composition, comprising at least one polymeric, ionic compound comprising imidazolium groups (imidazolium compound) which consists essentially of at least 10 repeat units of the general formula (IV)

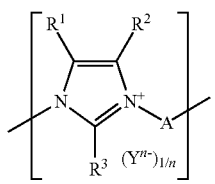
(IV)

wherein
R$^1$ and R$^2$ are independently hydrogen and in each case unsubstituted or substituted C$_1$-C$_{20}$-alkyl, C$_1$-C$_{20}$-alkoxy, C$_1$-C$_{20}$-alkylthio, C$_3$-C$_8$-cycloalkyl, C$_3$-C$_8$-cycloalkoxy, C$_3$-C$_8$-cycloalkylthio, aryl, aryloxy and arylthio,
R$^3$ is hydrogen, C$_1$-C$_{20}$-alkyl, C$_3$-C$_8$-cycloalkyl, optionally substituted aryl and a group —CH$_2$—[O—CH$_2$CH$_2$—]$_x$—OR$^a$, wherein x is 1, 2, 3, 4, 5 or 6 and R$^a$ is hydrogen or C$_1$-C$_4$-alkyl, wherein the aryl may be substituted by 1, 2, 3, 4 or 5 radicals selected from C$_1$-C$_{20}$-alkyl, C$_1$-C$_6$-haloalkyl, C$_1$-C$_{20}$-alkoxy, C$_1$-C$_6$-haloalkoxy and NR'R", where R' and R'R" are, independently of each other, selected from hydrogen and C$_1$-C$_6$-alkyl,
each A is independently a divalent aliphatic, alicyclic, aliphatic-alicyclic, aromatic or araliphatic radical, where the aliphatic moieties in the aforementioned aliphatic, aliphatic-alicyclic or araliphatic radicals may be interrupted by one or more nonadjacent groups which are selected from —O—, —S— and —N(R$^b$)—, where R$^b$ is selected from hydrogen, C$_1$-C$_{20}$-alkyl and a group —[CH$_2$CH$_2$—O—]$_y$—R$^c$, wherein y is 1, 2, 3, 4, 5 or 6 and R$^c$ is hydrogen or C$_1$-C$_4$-alkyl; where alicyclic or aromatic moieties in the aforementioned alicyclic, aliphatic-alicyclic, aromatic or araliphatic radicals may be substituted by 1, 2, 3 or 4 radicals selected from C$_1$-C$_{20}$-alkyl, C$_1$-C$_{20}$-alkoxy, a radical of the formula —O—[CH$_2$CH$_2$O]$_z$—R$^d$, where R$^d$ is hydrogen or C$_1$-C$_4$-alkyl and z is 1, 2, 3, 4, 5 or 6; carboxyl and carboxylate, and where the aliphatic moieties in the aforementioned aliphatic, aliphatic-alicyclic or araliphatic radicals may be substituted by 1, 2, 3 or 4 radicals selected from C$_1$-C$_{20}$-alkoxy, a radical of the formula —O—[CH$_2$CH$_2$O]$_z$—R$^d$, where R$^d$ is hydrogen or C$_1$-C$_4$-alkyl and z is 1, 2, 3, 4, 5 or 6, carboxyl and carboxylate; with the proviso that the aromatic or araliphatic radicals do not contain 1,4-bound phenylene rings;
and does not contain 1,4-bound phenylene units and is not 2-hydroxy-propane-1,3-diyl or 2-hydroxy-2-methyl-propane-1,3-diyl; and where one CH$_2$ group may be substituted by a carboxyl or carboxylate group; a group —[B—X—]$_k$—B— in which each X independently is O or S, each B independently is C$_2$-C$_6$-alkylene; and k is an integer from 1 to 100; and a group of one of the following formulae

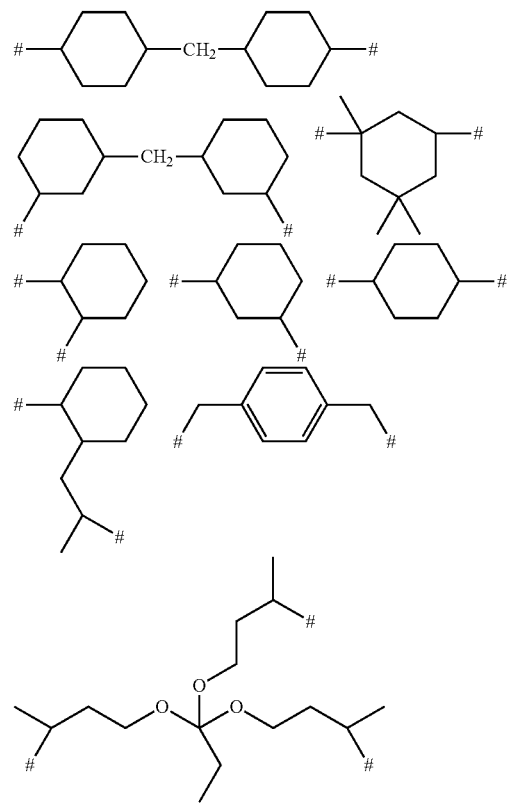

where # is the attachment point to the imidazolium ring; and
Y$^{n-}$ is an n-valent anion;
and at least one carrier and/or at least one auxiliary agent and
wherein the polymeric ionic compound has a weight average molecular weight of from 2000 to 200,000 and has a dispersity PDI of 1.1 to 20.

38. The composition as claimed in claim 37, wherein the polymer has a dispersity PDI of 1.5 to 15.

39. A cosmetic composition comprising
the biocide composition as claimed in claim 1,
at least one surfactant and
at least one cosmetically acceptable active ingredient that is beneficial to keratin materials.

* * * * *